(12) United States Patent
Li et al.

(10) Patent No.: US 10,329,577 B2
(45) Date of Patent: Jun. 25, 2019

(54) METHODS OF MODULATING SEED AND ORGAN SIZE IN PLANTS

(71) Applicants: Institute of Genetics and Developmental Biology, Beijing (CN); PLANT BIOSCIENCE LIMITED, Norwich Norfolk (GB)

(72) Inventors: Yunhai Li, Beijing (CN); Tian Xia, Beijing (CN); Na Li, Beijing (CN); Jack Dumenil, Norwich Norfolk (GB); Michael Bevan, Norwich Norfolk (GB)

(73) Assignees: Institute of Genetics and Developmental Biology Chinese Academy of Sciences, Beijing (CN); Plant Bioscience Limited, Norwich (GB)

( * ) Notice: Subject to any disclaimer, the term of this patent is extended or adjusted under 35 U.S.C. 154(b) by 249 days.

(21) Appl. No.: 14/912,045

(22) PCT Filed: Jul. 30, 2014

(86) PCT No.: PCT/EP2014/066427
§ 371 (c)(1),
(2) Date: Feb. 12, 2016

(87) PCT Pub. No.: WO2015/022192
PCT Pub. Date: Feb. 19, 2015

(65) Prior Publication Data
US 2016/0194651 A1    Jul. 7, 2016

(30) Foreign Application Priority Data

Aug. 14, 2013  (WO) ................ PCT/CN2013/081457

(51) Int. Cl.
*C12N 15/82* (2006.01)
*C07K 14/415* (2006.01)
*C12N 9/00* (2006.01)

(52) U.S. Cl.
CPC ........ *C12N 15/8261* (2013.01); *C07K 14/415* (2013.01); *C12N 9/93* (2013.01); *C12Y 603/02019* (2013.01); *Y02A 40/146* (2018.01)

(58) Field of Classification Search
None
See application file for complete search history.

(56) References Cited

U.S. PATENT DOCUMENTS

2011/0247094 A1* 10/2011 Allen .................. C07K 14/415
800/275

OTHER PUBLICATIONS

Van Daele et al, Plant Biotechnology Journal, 2012, vol. 10, pp. 488-500. (Year: 2012).*
Li et al, Genes & Development, 2008, vol. 22, pp. 1331-1336, cited in the IDS filed Feb. 12, 2016. (Year: 2008).*
Krizek, Beth A, "Making bigger plants: key regulators of final organ size", Current Opinion in Plant Biology (2009) vol. 12, pp. 17-22 Jan. 1, 2009.
Du, Liang et al., The Ubiquitin Receptor DA1 Regulates Seed and Organ Size by Modulating the Stability of the Ubiquitin-Specific Protease UBP15/SOD2 in *Arabidopsis*, vol. 26 pp. 665-677 Feb. 1, 2014.
Xia, Tian, The Ubiquitin Receptor DA1 Interacts with the E3 Ubiquitin Ligase DA2 to Regulate Seed and Organ Size in *Arabidopsis*, THe Plant Cell, vol. 25, pp. 3347-3359 Sep. 1, 2013.
Disch, Sabine, The E3 Ubiquitin Ligase Big Brother Controls *Arabidopsis* Organ Size in a Dosage-Dependent Manner, Current Biology, vol. 16, pp. 272-279 Feb. 7, 2006.
Guerra Davide et al, Identification of a Protoen Network Interacting with TdRF1, a Wheat RING Ubiquitin Ligase with a Protective Role against Cellular Dehydration, vol. 2/1/2012.
European Patent Office, "International Searching Report and Written Opinion", issued in connection to International Application No. PCT/EP2014/066427, dated Oct. 30, 2014, 15 pages Oct. 30, 2014.
Li, Yunhai et al., Contol of final seed and organ size by the DA1 gene family in *Arabidopsis thaliana*, Genes Dev., vol. 22, pp. 1331-1336, 2008.
Xia, Tian, et al., "DA2 acts synergistically with DA1 to regulate plant seed and organ size", Plant Molecular Biology and Modern Agriculture—Abstracts of Papers of National Plant Biology Seminar, Publication date: Jul. 18, 2010.

* cited by examiner

*Primary Examiner* — Eileen B O Hara
(74) *Attorney, Agent, or Firm* — McKee, Voorhees & Sease, PLC

(57) ABSTRACT

This invention relates to a plant E3 ubiquitin ligase (termed DA2) which acts synergistically with DA1 to control seed and organ size. Methods of increasing plant yield are provided that comprise reducing the expression or activity of DA2 in a plant that is deficient in DA1 expression or activity. Plants with increased yield and methods of producing such plants are also provided.

20 Claims, 18 Drawing Sheets

Specification includes a Sequence Listing.

METHODS OF MODULATING SEED AND ORGAN SIZE IN PLANTS

FIELD OF INVENTION

This invention relates to methods of altering the size of the seeds and organs of plants, for example to improve plant yield.

BACKGROUND OF INVENTION

The size of seeds and organs is an agronomically and ecologically important trait that is under genetic control (Alonso-Blanco, C. *PNAS* USA 96, 4710-7 (1999); Song, X. J. *Nat Genet* 39, 623-30 (2007); Weiss, J. *Int J Dev Biol* 49, 513-25 (2005); Dinneny, J. R. *Development* 131, 1101-10 (2004); Disch, S. *Curr Biol* 16, 272-9 (2006); *Science* 289, 85-8 (2000); Horiguchi, G. *Plant J* 43, 68-78 (2005); Hu, Y *Plant J* 47, 1-9 (2006); Hu, Y. *Plant Cell* 15, 1951-61 (2003); Krizek, B. A. *Dev Genet* 25, 224-36 (1999); Mizukami, Y. *PNAS* USA 97, 942-7 (2000); Nath, U. *Science* 299, 1404-7 (2003); Ohno, C. K. *Development* 131, 1111-22 (2004); Szecsi, J. *Embo J* 25, 3912-20 (2006); White, D. W. *PNAS USA* 103, 13238-43 (2006); Horvath, B. M. *Embo J* 25, 4909-20 (2006); Garcia, D. *Plant Cell* 17, 52-60 (2005). The final size of seeds and organs is constant within a given species, whereas interspecies seed and organ size variation is remarkably large, suggesting that plants have regulatory mechanisms that control seed and organ growth in a coordinated and timely manner. Despite the importance of seed and organ size, however, little is known about the molecular and genetic mechanisms that control final organ and seed size in plants.

The genetic regulation of seed size has been investigated in plants, including in tomato, soybean, maize, and rice, using quantitative trait locus (QTL) mapping. To date, in the published literature, two genes (Song, X. J. *Nat Genet* 39, 623-30 (2007); Fan, C. Theor. Appl. Genet. 112, 1164-1171 (2006)), underlying two major QTLs for rice grain size, have been identified, although the molecular mechanisms of these genes remain to be elucidated. In *Arabidopsis*, eleven loci affecting seed weight and/or length in crosses between the accessions Ler and Cvi, have been mapped {Alonso-Blanco, 1999 supra}, but the corresponding genes have not been identified. Recent studies have revealed that AP2 and ARF2 are involved in control of seed size. Unfortunately, however, ap2 and arf2 mutants have lower fertility than wild type (Schruff, M. C. Development 137, 251-261 (2006); Ohto, M. A. PNAS USA 102, 3123-3128 (2005); Jofuku, K. D. PNAS USA 102, 3117-3122 (2005)). In addition, studies using mutant plants have identified several positive and negative regulators that influence organ size by acting on cell proliferation or expansion {Krizek, B. A. *Dev Genet* 25, 224-36 (1999); Mizukami, Y. *Proc Natl Acad Sci USA* 97, 942-7 (2000); Nath, U. *Science* 299, 1404-7 (2003); Ohno, C. K. *Development* 131, 1111-22 (2004); Szecsi, J. *Embo J* 25, 3912-20 (2006); White, D. W. *PNAS USA* 103, 13238-43 (2006); Horvath, B. M. *Embo J* 25, 4909-20 (2006); Garcia, D. *Plant Cell* 17, 52-60 (2005). Horiguchi, G. *Plant J* 43, 68-78 (2005); Hu, Y *Plant J* 47, 1-9 (2006) Dinneny, J. R. *Development* 131, 1101-10 (2004)).

Several factors involved in ubiquitin-related activities have been known to influence seed size. A growth-restricting factor, DA1, is a ubiquitin receptor and contains two ubiquitin interaction motifs (UIMs) that bind ubiquitin in vitro, and da1-1 mutant forms large seeds by influencing the maternal integuments of ovules (Li et al., 2008). Mutations in an enhancer of da1-1 (EOD1), which encodes the E3 ubiquitin ligase BIG BROTHER (BB) (Disch et al., 2006; Li et al., 2008), synergistically enhance the seed size phenotype of da1-1, indicating that DA1 acts synergistically with EOD1/BB to control seed size. In rice, a quantitative trait locus (QTL) for GRAIN WIDTH AND WEIGHT2 (GW2), encoding an E3 ubiquitin ligase, controls grain size by restricting cell division (Song et al., 2007). A GW2 homologue in wheat has been identified (Ta-GW2; Bednarek et al 2012). An unknown protein encoded by rice qSW5/GW5 is required to limit grain size in rice (Shomura et al., 2008; Weng et al., 2008). GW5 physically interacts with polyubiquitin in a yeast two-hybrid assay, suggesting that GW5 may be involved in the ubiquitin-proteasome pathway (Weng et al., 2008). However, it is not clear whether these two factors act in maternal and/or zygotic tissues in rice.

Identification of further factors that control the final size of both seeds and organs will not only advance understanding of the mechanisms of size control in plants, but may also have substantial practical applications for example in improving crop yield and plant biomass for generating biofuel.

SUMMARY OF INVENTION

The present inventors have identified a plant E3 ubiquitin ligase (termed DA2) which regulates the final size of seeds and organs by restricting cell proliferation in the integuments of developing seeds. DA2 was unexpectedly found to act synergistically with DA1 and independently of EOD1 to control seed and organ size. The targeting of DA2 and DA1 and/or EOD1 may therefore be useful in improving plant yield.

An aspect of the invention provides a method of increasing the yield of a plant comprising;
  reducing the expression or activity of a DA2 polypeptide within cells of the plant,
  wherein the plant is deficient in DA1 expression or activity.

Another aspect of the invention provides a method of increasing the yield of a plant comprising;
  reducing the expression or activity of a DA2 polypeptide within cells of the plant,
  wherein the plant is deficient in EOD1 expression or activity.

Another aspect of the invention provides a method of increasing the yield of a plant comprising;
  reducing the expression or activity of a DA2 polypeptide within cells of said plant,
  wherein the plant is deficient in DA1 and EOD1 expression or activity.

Another aspect of the invention provides a method of increasing the yield of a plant comprising;
  reducing or abolishing the expression or activity of a DA2 polypeptide within cells of said plant, and;
  i) reducing or abolishing the expression or activity of a DA1 polypeptide within said cells,
  ii) reducing or abolishing the expression or activity of EOD1 within said cells, and/or
  iii) expressing a dominant-negative DA polypeptide within said cells.

Another aspect of the invention provides a method of producing a plant with an increased yield comprising:
  providing a plant cell that is deficient in the expression or activity of DA1, EOD1 or both DA1 and EOD1, incorporating a heterologous nucleic acid which abolishes or suppresses the expression or activity of a DA2 polypeptide into the plant cell by means of transformation, and;

regenerating the plant from one or more transformed cells.

DETAILED DESCRIPTION OF EMBODIMENTS OF THE INVENTION

Figure 1:
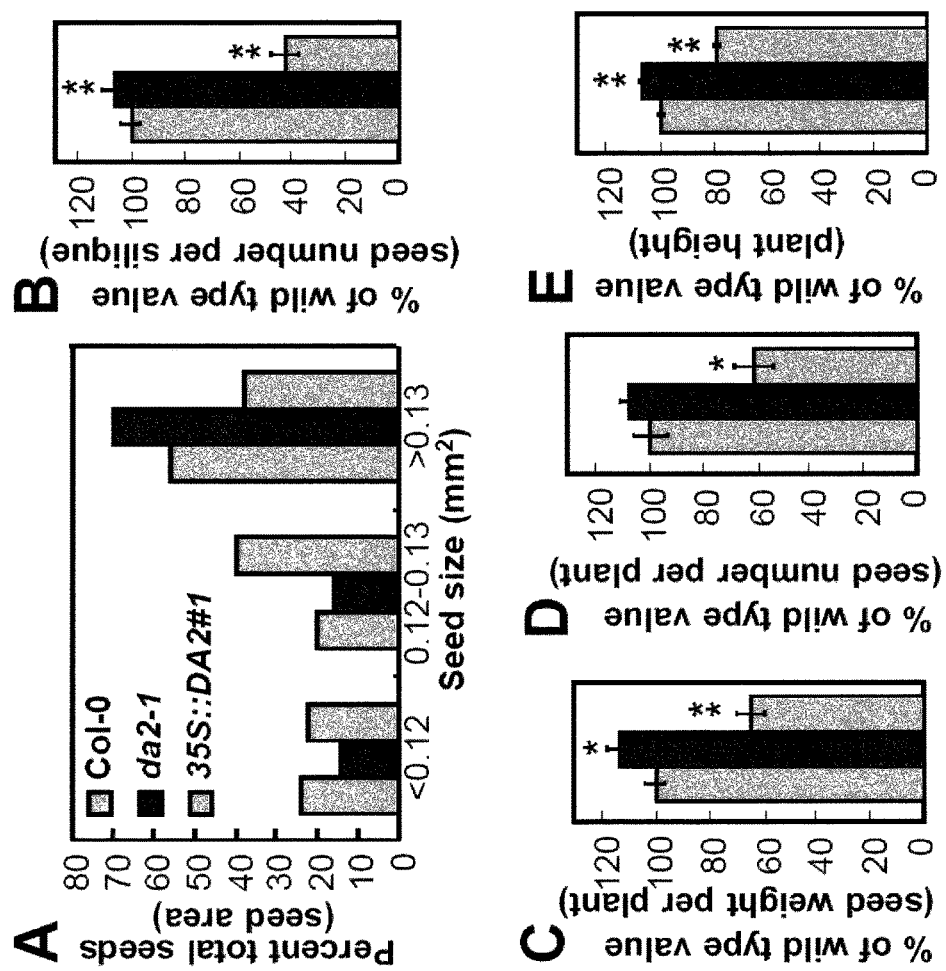
FIG. 1 shows seed and organ size in the da2-1 mutant. 1A shows the projective area of Col-0, da2-1 and 35S::DA2#1 seeds. The seeds were classified into three groups (>0.13, 0.12-0.13 and <0.12 mm2). Values for each group are expressed as a percentage of the total seed number analyzed. 1B shows the seed number per silique for Col-0, da2-1 and 35S::DA2#1. Siliques (from the fourth silique to the tenth silique) on main stem were used to measure seed number per silique. 1C shows seed weight per plant for Col-0, da2-1 and 35S::DA2#1. 1D shows seed number per plant for Col-0, da2-1 and 35S::DA2#1. 1E shows the height of Col-0, da2-1 and 35S::DA2#1 plants. Values (B-E) are given as mean±SE relative to the wild-type value, set at 100%. **, P<0.01 and *, P<0.05 compared with the wild type (Student's t-test). Bars: F, 1 cm; G, 1 mm

This invention relates to methods of altering plant traits which affect yield, such as seed and organ size, by altering the expression or activity of the plant E3 ubiquitin ligase DA2 in combination with the alterations in the expression or activity of DA1 and/or EOD1. Preferably, the expression or activity of DA2 and DA1 is altered in the plant.

The expression or activity DA2 expression may be altered before, at the same time, or after alteration of DA1 and/or EOD1 expression or activity. For example, in some embodiments, the expression or activity of a DA2 polypeptide may be altered in one or more plant cells which already have one of; altered DA1 expression or activity, altered EOD1 expression or activity, or altered DA1 and EOD1 expression or activity.

Provided herein are methods of increasing the yield of plant, for example by increasing organ or seed size, that comprise providing a plant that is deficient in DA1 and/or EOD1 expression or activity and reducing the expression of DA2 in one or more cells of the plant. In other embodiments, the expression or activity of DA1 and/or EOD1 may be reduced in one or more plant cells which have reduced expression or activity of a DA2 polypeptide.

Other methods may comprise reducing the expression of DA2 in one or more cells of the plant and reducing the expression or activity of DA1, EOD1 or both DA1 and EOD1 in one or more cells.

Also provided herein are methods of producing a plant with increased yield relative to wild-type plant that comprise;
(a) incorporating into a plant cell by means of transformation
 (i) a first heterologous nucleic acid which reduces the expression of a DA2 polypeptide,
 (ii) a second heterologous nucleic acid which reduces the expression of one of a DA1 polypeptide and a EOD1 polypeptide, and optionally,
 (iii) a third heterologous nucleic acid which reduces the expression of the other of a DA1 polypeptide and a EOD1 polypeptide, and
(b) regenerating the plant from one or more transformed cells.

Other methods of producing a plant with increased yield may comprise:
providing a plant cell that is deficient in DA1 and/or EOD1 expression or activity, preferably DA1 activity,
incorporating a heterologous nucleic acid which reduces the activity or expression of a DA2 polypeptide into the plant cell by means of transformation, and;
regenerating the plant from the transformed cell.

Following regeneration, a plant with reduced activity or expression of a DA2 polypeptide and reduced activity or expression of DA1 and/or EOD1 relative to the wild type plant may be selected.

The combination of reduced DA2 expression and reduced DA1 and/or EOD1 expression synergistically increase the size of the seeds and/or organs of the plant, thereby increasing the plant yield.

One or more yield-related traits in the plant may be improved by the combination of reduced DA2 expression or activity and reduced DA1 and/or EOD1 expression or activity. For example, one or more of life-span, organ size and seed size may be increased in the plant relative to control or wild-type plants in which expression of the DA2 polypeptide has not been reduced.

Expression or activity of DA2, DA1 or EOD1 may be reduced in the methods described herein by at least 50% relative to the wild-type plant, at least 60%, at least 70%, at least 80%, at least 90%, at least 95% or at least 98%. In some preferred embodiments, expression or activity is reduced to zero or substantially zero (i.e. expression or activity is abolished).

Methods of the invention comprise altering the expression or activity of a DA2 polypeptide in one or more cells of a plant.

DA2 polypeptides are E3 ubiquitin ligases found in plants. DA2 polypeptides whose expression or activity is reduced as described herein may comprise a RING domain (Stone, S. L. et al. (2005)), preferably a C5HC2, C5NC2 or C5TC2 RING domain. A suitable RING domain may consist of the amino acid sequence of SEQ ID NO: 1;

```
                                              (SEQ ID NO: 1)
C(X)₂C(X)₁₁CC(X)₄CX₂CX₇(H/N/T)X₆CX₂C.
```

For example, a suitable RING domain may consist of the amino acid sequence of SEQ ID NO: 2;

```
                                              (SEQ ID NO: 2)
CPICFL(Y/F)YPSLNRS(K/R)CC(S/M/T/A)K(G/S)ICTECFL (Q/R)MK(P/N/S/V/T/N)(T/P)(H/N/T)(T/S)(A/T/C)(R/Q/

K)PTQCP(F/Y)C
```

In some embodiments, the H/N/T residue at position 33 in the RING domain of SEQ ID NO: 2 may be T or N.

In some preferred embodiments, a DA2 polypeptide may comprise a RING domain having an amino acid sequence shown in Table 1 (SEQ ID NOS: 3-19), for example *Arabidopsis* DA2 (SEQ ID NO: 11), *Arabidopsis* DAL2 (SEQ ID NO: 13) or Rice GW2 (SEQ ID NO: 7) or a variant thereof. For example a RING domain may have the amino acid sequence of residues 59 to 101 of SEQ ID NO: 20 (Pt_GI-224061326.pro), residues 59 to 101 of SEQ ID NO: 21 (Rc_GI-255578534.pro), residues 59 to 101 of SEQ ID NO: 22 (Vv_GI-147817790.pro), residues 59 to 101 of SEQ ID NO: 23 (Gm_GI-356549538.pro), residues 59 to 101 of SEQ ID NO: 24 (At_GI-18411948.pro), residues 61 to 103 of SEQ ID NO: 25 (Ta_GI 408743661.pro), residues 61 to 103 of SEQ ID NO: 26 (Hv_GI-164371454.pro), residues 61 to 103 of SEQ ID NO: 27 (Bd_GI-357140854.pro), residues 62 to 104 of SEQ ID NO: 28 (Os_GI-115445269.pro), residues 63 to 105 of SEQ ID NO: 29 (Sb_GI-242064618.pro), residues 65 to 107 of SEQ ID NO: 30 (Zm_GI-220961719.pro), residues 61 to 103 of SEQ ID NO: 31 (Ta_GI-408743658.pro), residues 43 to 85 of SEQ ID NO: 32 (Bd_GI-357125256.pro), residues 62 to 104 of SEQ ID NO: 33 (Os_GI-218197613.pro), residues 62 to 104 of SEQ ID NO: 34 (Zm_GI-260935347.pro) or residues 62 to 104 of SEQ ID NO: 35 (Sb_GI-242092026.pro).

Further suitable RING domain sequences may be identified using standard sequence analysis techniques as described herein (e.g. Simple Modular Architecture Research Tool (SMART); EMBL Heidelberg, DE).

DA2 polypeptides may further comprise a first consensus domain. The first consensus domain may be located upstream (i.e. on the N terminal side) of the RING domain. A suitable first consensus domain may consist of the amino acid sequence of SEQ ID NO: 36.

```
                                              (SEQ ID NO: 36)
Q(Q/Absent)GLY(P/M/N/V/Q/L/V/E)(H/S/N)(P/K/R)D(I/

V)D(L/I/H/V/Q)(K/R)KL(R/K)(R/K)LI(V/L)(E/D)(A/S/T)

KLAPC
```

In some preferred embodiments, a DA2 polypeptide may comprise a first consensus domain of a DA2 amino acid sequence shown in Table 2, for example residues 20 to 45 of SEQ ID NO: 20, residues 20 to 45 of SEQ ID NO: 21, residues 20 to 45 of SEQ ID NO: 22, residues 20 to 45 of SEQ ID NO: 23, residues 20 to 45 of SEQ ID NO: 24, residues 21 to 46 of SEQ ID NO: 25, residues 21 to 46 of SEQ ID NO: 26, residues 21 to 46 of SEQ ID NO: 27, residues 21 to 46 of SEQ ID NO: 28, residues 21 to 46 of SEQ ID NO: 29, residues 21 to 46 of SEQ ID NO: 30, residues 21 to 46 of SEQ ID NO: 31, residues 4 to 29 of SEQ ID NO: 32, residues 23 to 48 of SEQ ID NO: 33, residues 23 to 48 of SEQ ID NO: 34 or residues 23 to 48 of SEQ ID NO: 35.

A DA2 polypeptide may further comprise a second consensus domain. The second consensus domain may be located downstream (i.e. on the C terminal side) of the RING domain. The second consensus domain may consist of the amino acid sequence of SEQ ID NO: 37.

```
                                              (SEQ ID NO: 37)
(N/S)YAVEYRG(V/G)K(T/S)KEE(K/R)(G/S)(V/T/I/F/L/M)

EQ(L/I/V/F)EEQ(R/L/K)VIEA(Q/K)(I/M)RMR(H/Q)(K/Q)

(E/A).
```

In some preferred embodiments, a DA2 polypeptide may comprise a second consensus domain of an DA2 amino acid sequence shown in Table 2, for example residues 106 to 141 of SEQ ID NO: 20, residues 106 to 141 of SEQ ID NO: 21, residues 106 to 141 of SEQ ID NO: 22, residues 106 to 141 of SEQ ID NO: 23, residues 106 to 141 of SEQ ID NO: 24, residues 107 to 143 of SEQ ID NO: 25, residues 107 to 143 of SEQ ID NO: 26, residues 107 to 143 of SEQ ID NO: 27, residues 108 to 144 of SEQ ID NO: 28, residues 109 to 145 of SEQ ID NO: 29, residues 111 to 147 of SEQ ID NO: 30, residues 107 to 143 of SEQ ID NO: 31, residues 90 to 125 of SEQ ID NO: 32, residues 108 to 143 of SEQ ID NO: 33, residues 108 to 143 of SEQ ID NO: 34 or residues 108 to 143 of SEQ ID NO: 35.

Further examples of suitable first and second domain sequences may be identified using standard sequence analysis techniques as described herein (e.g. Simple Modular Architecture Research Tool (SMART); EMBL Heidelberg, DE).

In some preferred embodiments, a DA2 polypeptide whose expression or activity is reduced as described herein may comprise a RING Domain of SEQ ID NO: 2, first consensus domain of SEQ ID NO: 36 and a second consensus domain of SEQ ID NO: 37.

For example, a DA2 polypeptide may comprise any combination of RING domain sequence, first consensus domain sequence and second consensus domain sequence as set out above.

A suitable DA2 polypeptide may comprise an amino acid sequence of any one of SEQ ID NOS 20 to 35 as set out in Table 2 or may be variant of one of these sequences. In some preferred embodiments, a DA2 polypeptide may comprise the amino acid sequence of SEQ ID NO: 28 or 33 (OsGW2), SEQ ID NO: 24 (AtDA2), SEQ ID NO: 25 or SEQ ID NO: 31 (TaGW2) or may be a variant of any one of these sequences which has E3 ubiquitin ligase activity.

A DA2 polypeptide which is a variant of any one of SEQ ID NOS: 20 to 35 or other reference DA2 sequence may comprise an amino acid sequence having at least 20%, at least 30%, at least 40%, at least 50%, at least 60%, at least 70%, at least 80%, at least 90%, at least 95%, or at least 98% sequence identity to the reference DA2 sequence.

A DA2 polypeptide which is a variant of any one of SEQ ID NOS: 20 to 35 may further comprise a RING domain having the sequence of SEQ ID NO: 2 a first consensus domain having the sequence of SEQ ID NO: 36 and a second consensus domain having the sequence of SEQ ID NO: 37. Examples of suitable sequences are set out above. In some preferred embodiments, a DA2 polypeptide may comprise the RING domain, first consensus domain and second consensus domain of any one of SEQ ID NOS: 20 to 35.

A nucleic acid encoding a DA2 polypeptide may comprise a nucleotide sequence set out in a database entry selected from the group consisting of JN896622.1 GI:408743658 (TaGW2-A); and JN896623.1 GI:408743660 (TaGW2-B) or may be variant of one of these sequences.

In some preferred embodiments, a nucleic acid encoding a DA2 polypeptide may comprise the nucleotide sequence encoding AtDA2, AtDAL2, OsGW2, TaGW2-A or TaGW2-B or may be a variant of any one of these DA2 sequences which encodes a polypeptide which has DA2 activity.

DA2 polypeptides and encoding nucleic acids may be identified in any plant species of interest, in particular a crop plant, such as wheat, barley, maize, rice, soybean, and another agricultural plants, using routine sequence analysis techniques.

Reduction in DA2 expression or activity in a plant is shown herein to synergistically enhance the effect on yield-associated traits in plants of mutations that reduce the activity or expression of DA1. In preferred embodiments, methods described herein may comprise reducing DA2 expression in a plant that is deficient in DA1 expression or activity or reducing both DA1 and DA2 expression in a plant.

DA1 polypeptides are ubiquitin receptors found in plants and are described in detail in Li et al (2008), Wang, et al (2012) and WO2009/047525. DA1 polypeptides whose expression or activity is reduced as described herein may comprise a LIM domain, a conserved C terminal domain and one or more UIM domains.

A LIM domain comprises two Zn finger motifs and may have the amino acid sequence (SEQ ID NO:38);

C(X)$_2$C(X)$_{16\text{-}23}$(H/C)(X)$_{2/4}$(C/H/E)(X)$_2$C(X)$_2$
C(X)$_{14\text{-}21}$(C/H)(X)$_{2/1/3}$(C/H/D/E)X where X is any amino acid and Zn coordinating residues are underlined.

The Zn coordinating residues in the LIM domain may be C, H, D or E, preferably C.

In some preferred embodiments, a LIM domain may comprise CXXC, HXXCXXCXXC and HxxC motifs, where X is any amino acid. For example, a LIM domaim may comprise the amino acid sequence (SEQ ID NO:39);

C(X)$_2$C(X)$_{16\text{-}23}$(H)(X)$_2$(C)(X)$_2$C(X)$_2$C(X)$_{14\text{-}21}$H(X)$_2$
CX where X is any amino acid and Zn coordinating residues are underlined In some embodiments, a LIM domain may comprise the amino acid sequence of the AtDA1 LIM domain;

CAGCNMEIGHGRFLNCLNSLWHPECFRCYGCSQPISEYEFSTSGNYPFHK
ACY
(SEQ ID NO: 40; Zn coordinating residues are underlined)

Other LIM domains include the LIM domain of an DA1 amino acid sequence shown in Table 3, for example residues 141 to 193 of SEQ ID NO: 41 (Si_GI-514815267.pro), residues 123 to 175 of SEQ ID NO: 42 (Bd_GI-357157184.pro), residues 155 to 207 of SEQ ID NO: 43 (Br_DA1b.pro), residues 172 to 224 of SEQ ID NO: 44 (Br_DA1a.pro), residues 172 to 224 of SEQ ID NO: 45 (At_GI-15221983.pro), residues 117 to 169 of SEQ ID NO: 46 (Tc_GI-508722773.pro), residues 117 to 169 of SEQ ID NO: 47 (Gm_GI-356564241.pro), residues 121 to 173 of SEQ ID NO: 48 (Gm_GI-356552145.pro), residues 119 to 171 of SEQ ID NO: 49 (Vv_GI-302142429.pro), residues 122 to 174 of SEQ ID NO: 50 (Vv_GI-359492104.pro), residues 125 to 177 of SEQ ID NO: 51 (Sl_GI-460385048.pro), residues 516 to 568 of SEQ ID NO: 52 (Os_GI-218197709.pro), residues 124 to 176 of SEQ ID NO: 53 (OsGI–115466772.pro), residues 150 to 202 of SEQ ID NO: 54 (Bd_GI-357160893.pro), residues 132 to 184 of SEQ ID NO: 55 (Bd_GI-357164660.pro), residues 124 to 176 of SEQ ID NO: 56 (Sb_GI-242092232.pro), residues 147 to 199 of SEQ ID NO: 57 (Zm_GI-212275448.pro), residues 190 to 242 of SEQ ID NO: 58 (At_GI-240256211.pro), residues 162 to 214 of SEQ ID NO: 59 (At_GI-145360806.pro), residues 1240 to 1291 of SEQ ID NO: 60 (At_GI-22326876.pro), residues 80 to 122 of SEQ ID NO: 61 (At_GI-30698242.pro), residues 347 to 402 of SEQ ID NO: 62 (At_GI-30698240.pro), residues 286 to 341 of SEQ ID NO: 63 (At_GI-15240018.pro) or residues 202 to 252 of SEQ ID NO: 64 (At_GI-334188680.pro).

LIM domain sequences may be identified using standard sequence analysis techniques (e.g. Simple Modular Architecture Research Tool (SMART); EMBL Heidelberg, DE).

In addition to a LIM domain, a DA1 protein may further comprise a carboxyl terminal region having an amino acid sequence at least 20%, at least 30%, at least 40%, at least 50%, at least 60%, at least 70%, at least 80%, at least 90%, at least 95%, or at least 98% amino acid identity to the sequence of residues 198 to 504 of SEQ ID NO: 41, residues 180 to 487 of SEQ ID NO: 42, residues 212 to 514 of SEQ ID NO: 43, residues 229 to 532 of SEQ ID NO: 44, residues 229 to 532 of SEQ ID NO: 45, residues 174 to 478 of SEQ ID NO: 46, residues 174 to 474 of SEQ ID NO: 47, residues 178 to 478 of SEQ ID NO: 48, residues 176 to 462 of SEQ ID NO: 49, residues 179 to 482 of SEQ ID NO: 50, residues 182 to 486 of SEQ ID NO: 51, residues 573 to 878 of SEQ ID NO: 52, residues 181 to 486 of SEQ ID NO: 53, residues 207 to 512 of SEQ ID NO: 54, residues 189 to 491 of SEQ ID NO: 55, residues 181 to 486 of SEQ ID NO: 56, residues 204 to 508 of SEQ ID NO: 57, residues 247 to 553 of SEQ ID NO: 58, residues 219 to 528 of SEQ ID NO: 59, residues 1296 to 1613 of SEQ ID NO: 60, residues 128 to 450 of SEQ ID NO: 61, residues 404 to 702 of SEQ ID NO: 62, residues 343 to 644 of SEQ ID NO: 63 or residues 256 to 587 of SEQ ID NO: 64.

The carboxyl terminal region of the DA1 protein may comprise the metallopeptidase motif HEMMH (SEQ ID NO: 65).

The carboxyl terminal region may further comprise a EK(X)$_8$R(X)$_4$SEEQ (SEQ ID NO: 66) or EK(X)$_8$R(X)$_4$SEQ (SEQ ID NO: 67) motif positioned between the LIM domain and HEMMH motif.

In addition to a LIM domain and a conserved carboxyl terminal region, a DA1 protein may comprise a UIM1 domain and a UIM2 domain. The UIM1 and UIM2 domains may be located between the N terminal and the LIM domain of the DA1 protein.

A UIM1 domain may consist of the sequence of SEQ ID NO: 68 and a UIM2 domain may consist of the sequence of SEQ ID NO: 69.

```
                                              (SEQ ID NO: 68)
         p---pLpbAl pb.Sbp-.pp p (SEQ ID NO: 69)
         p---pLpbAl pb.Sbp-spp p
``` wherein;

p is a polar amino acid residue, for example, C, D, E, H, K, N, Q, R, S or T;

b is a big amino acid residue, for example, E, F, H, I, K, L, M, Q, R, W or Y;

s is a small amino acid residue, for example, A, C, D, G, N, P, S, T or V;

l is an aliphatic amino acid residue, for example, I, L or V;

• is absent or is any amino acid, and

− is any amino acid.

Further examples of UIM1 and UIM2 domain sequences may be identified using standard sequence analysis techniques as described herein (e.g. Simple Modular Architecture Research Tool (SMART); EMBL Heidelberg, DE).

In some preferred embodiments, a DA1 polypeptide may comprise;

a LIM domain of SEQ ID NO: 39, a C terminal region having at least 20% sequence identity to residues 229 to 532 of SEQ ID NO: 45 or the equivalent region of any one of SEQ NOS 41 to 44 or 46 to 64, as set out above and comprising a EK(X)$_8$R(X)$_4$SEEQ or EK(X)$_8$R(X)$_4$SEQ motif and a HEMMH motif, a UIM domain of SEQ ID NO:66, and a UIM domain of SEQ ID NO:67.

A DA1 protein may comprise an amino acid sequence of a plant DA1 protein shown in Table 3 (SEQ ID NOS: 41 to 64) or may be a homologue or variant of one of these sequences which has DA1 activity. For example, a DA1 polypeptide may comprise an amino acid sequence shown in Table 3 (SEQ ID NOS: 41 to 64) or may be variant of one of these sequences which has DA1 activity.

For example, a DA1 polypeptide may comprise an amino acid sequence of AtDA1, AtDAR1, AtDAR2, AtDAR3, AtDAR4, AtDAR5, AtDAR6, AtDAR7, BrDA1a, BrDA1b, BrDAR1, BrDAR2, BrDAR3-7, BrDAL1, BrDAL2, BrDAL3, OsDA1, OsDAR2, OsDAL3, OsDAL5, PpDAL1, PpDAL2, PpDAL3, PpDAL4, PpDAL5, PpDAL6, PpDAL7, PpDAL8, SmDAL1, SmDAL2 or ZmDA1, preferably AtDA1, AtDAR1 BrDA1a, BrDA1b, OsDA1 or ZmDA1 or a homologue or variant of one of these sequences.

In some preferred embodiments, a DA1 polypeptide may comprise the amino acid sequence of AtDA1 (AT1G19270; NP_173361.1 GI: 15221983) or may be variant of this sequence which has DA1 activity.

Other DA1 protein sequences which include the characteristic features set out above may be identified using standard sequence analysis tools. A skilled person is readily able to identify nucleic acid sequences encoding DA1 proteins in any plant species of interest.

A DA1 protein in a plant species of interest may have an amino acid sequence which is a variant of a DA1 protein reference amino acid sequence set out herein.

A DA1 polypeptide which is a variant of a reference DA1 sequence, such as any one of SEQ ID NOS 41 to 64, may comprise an amino acid sequence having at least 20%, at least 30%, at least 40%, at least 50%, at least 60%, at least 70%, at least 80%, at least 90%, at least 95%, or at least 98% sequence identity to the reference sequence.

Particular amino acid sequence variants that occur in a plant species may differ from a reference sequence set out herein by insertion, addition, substitution or deletion of 1 amino acid, 2, 3, 4, 5-10, 10-20 20-30, 30-50, or more than 50 amino acids.

In some embodiments, a DA1 polypeptide which is a variant of the AtDA1 sequence of SEQ ID NO: 45 may comprise a UIM1 domain having the sequence QENEDIDRAIALSLLEENQE (SEQ ID NO: 70) and a UIM2 domain having the sequence DEDEQIARALQESMVVGNSP (SEQ ID NO: 71).

A DA1 polypeptide which is a variant of AtDA1 sequence of SEQ ID NO: 45 may comprise a LIM domain having the sequence:

```
                                              (SEQ ID NO: 72)
ICAGCNMEIGHGRFLNCLNSLWHPECFRCYGCSQPISEYEFSTSGNYPFH

KAC
```

A nucleic acid encoding a DA1 polypeptide may comprise a nucleotide sequence set out in a database entry selected from the group consisting of NM_101785.3 GI:42562170 (AtDA1); NM_001057237.1 GI:115454202 (OsDA1); BT085014.1 GI: 238008663 (ZmDA1) or may be variant of one of these sequences which encodes an active DA1 polypeptide.

In some preferred embodiments, a nucleic acid encoding a DA1 polypeptide may comprise the nucleotide sequence of AtDA1 (NM_101785.3 GI: 42562170), ZmDA1 (BT085014.1 GI: 238008663), OsDA1 (NM_001057237.1 GI:115454202) or may be a variant of any one of these sequences which encodes a polypeptide which retains DA1 activity.

DA1 polypeptides and encoding nucleic acids may be identified in plant species, in particular crop plants, such as wheat, barley, maize, rice, and another agricultural plants, using routine sequence analysis techniques.

In some preferred embodiments, DA1 activity in one or more cells of a plant may be reduced by expression of a dominant-negative DA1 polypeptide in the one or more cells (see for example Li et al (2008); WO2009/047525; Wang et al 2012). A plant expressing a dominant-negative DA1 polypeptide may have a da1-1 phenotype.

A dominant negative allele of a DA1 polypeptide may comprise a DA1 polypeptide having a mutation, e.g. a substitution or deletion, at a a conserved R residue that is located at position 358 of the *A. thaliana* DA1 amino acid sequence, position 333 of the *Z. mays* DA1 amino acid sequence or the equivalent position in another DA1 amino acid sequence. For example, a dominant negative allele of a DA1 polypeptide may comprise a mutation of the conserved R residue at a position equivalent to position 358 of the *A. thaliana* DA1 amino acid sequence or position 333 of the *Z. mays* DA1 amino acid sequence. In preferred embodiments, the conserved R residue may be substituted for K.

The conserved R residue that is located at a position in a DA1 amino acid sequence which is equivalent to position 358 of SEQ ID NO: 45 of *A. thaliana* DA1 or position 333 of the *Z. mays* DA1 of SEQ ID NO: 57 is located at the position within the DA1 amino acid sequence which corresponds to R333 of SEQ ID NO:57 and R358 of SEQ ID NO:45 i.e. it is in the same position relative to the other motifs and domains of the DA1 protein. The conserved R residue is located between the LIM domain and the HEMMH peptidase motif of the C terminal region and is completely conserved in the same sequence context in DA1 proteins. The conserved R residue may be contained in a EK(X)$_8$R(X)$_4$SEEQ (SEQ ID NO: 66) or EK(X)$_8$R(X)$_4$SEQ (SEQ ID NO: 67) motif within the C terminal region.

The conserved R residue may be identified by aligning these conserved C terminal regions using standard sequence analysis and alignment tools and is identified with an arrow in the sequences of Table 3.

Nucleic acid which encodes a dominant negative allele of a DA protein may be produced by any convenient technique. For example, site directed mutagenesis may be employed on a nucleic acid encoding a DA1 polypeptide to alter the conserved R residue at the equivalent position to R358 of *A. thaliana* DA1 or R333 of the *Zea mays* DA1, for example to K. Reagents and kits for in vitro mutagenesis are commercially available.

In some embodiments, a nucleic acid encoding a dominant-negative DA1 polypeptide as described herein may be operably linked to a heterologous regulatory sequence, such as a promoter, for example a constitutive, inducible, tissue-specific or developmental specific promoter. The nucleic acid encoding the dominant-negative DA1 polypeptide may be comprised in one or more vectors. For example, the mutated nucleic acid encoding the dominant-negative allele of a DA1 protein may be further cloned into an expression vector and expressed in plant cells as described below to alter the plant phenotype.

In other embodiments, a mutation may be introduced into an endogenous DA1 nucleic acid in a plant, such that the DA1 polypeptide encoded by the mutant DA1 nucleic acid has dominant-negative activity.

Nucleic acid encoding a dominant-negative DA1 polypeptide may be expressed in the same plant species or variety from which it was originally isolated or in a different plant species or variety (i.e. a heterologous plant).

Reduction or abolition of DA2 expression in a plant is also shown herein to enhance the effect of mutations that reduce the expression or activity of EOD1 on yield-associated traits in plants.

Methods described herein may comprise reducing DA2 expression or activity in a plant that is deficient in EOD1 expression or activity or reducing both DA2 and EOD1 expression or activity in a plant. In preferred embodiments, the plant may also be deficient in DA1 activity or the method may additionally comprise reducing or abolishing DA1 expression in the plant EOD1 polypeptides are E3 ubiquitin ligases found in plants and are described in detail in Disch et al. (2006), Li et al (2008) and WO2009/047525.

An EOD1 polypeptide whose expression or activity is reduced as described herein may comprise an EOD domain. A suitable EOD domain may consist of the amino acid sequence of SEQ ID NO: 73;

(SEQ ID NO: 73)
(E/K)RCVICQ(L/M)(K/R/G/T/E)Y(K/R)(R/I)(G/K)(D/N/E)

-continued
(R/Q/K/L)Q(I/M/V)(K/N/T/A)L(L/P)C(K/S)H(V/A)YH(S/
T/G/A)(E/Q/D/S/G)C(I/G/T/V)(S/T)(K/R)WL(G/T/S)INK
(V/I/A/K)CP(V/I)C In some preferred embodiments, an EOD1 polypeptide may comprise a EOD domain having an amino acid sequence of residues 195 to 237 of SEQ ID NO: 74 (Zm_GI-223973923.pro), residues 195 to 237 of SEQ ID NO: 75 (Sb_GI-242042045.pro), residues 195 to 237 of SEQ ID NO: 76 (Zm_GI-226496789.pro), residues 218 to 260 of SEQ ID NO: 77 (Os_GI-222624282.pro), residues 196 to 238 of SEQ ID NO: 78 (Os_GI-115451045.pro), residues 197 to 239 of SEQ ID NO: 79 (Bd_GI-357113826.pro), residues 193 to 235 of SEQ ID NO: 80 (Sl_GI-460410949.pro), residues 187 to 229 of SEQ ID NO: 81 (Rc_GI-255582236.pro), residues 150 to 192 of SEQ ID NO: 82 (Pt_GI-224059640.pro), residues 194 to 236 of SEQ ID NO: 83 (Gm_GI-356548935.pro), residues 194 to 236 of SEQ ID NO: 84 (Gm_GI-356544176.pro), residues 194 to 236 of SEQ ID NO: 85 (Vv_GI-359487286.pro), residues 189 to 231 of SEQ ID NO: 86 (Tc_GI-508704801.pro), residues 192 to 234 of SEQ ID NO: 87 (Pp_GI-462414664.pro), residues 190 to 232 of SEQ ID NO: 88 (Cr_GI-482561003.pro), residues 195 to 237 of SEQ ID NO: 89 (At_GI-22331928.pro) or residues 195 to 237 (Sl_GI-460370551.pro) of SEQ ID NO: 90, as shown in Table 4.

Further suitable EOD domain sequences may be identified using standard sequence analysis techniques as described herein (e.g. Simple Modular Architecture Research Tool (SMART); EMBL Heidelberg, DE).

A EOD1 polypeptide whose expression or activity is reduced as described herein may comprise an amino acid sequence of any one of SEQ ID NOS 74 to 90 as set out in Table 4. In some preferred embodiments, a EOD1 polypeptide may comprise the amino acid sequence of SEQ ID NO: 89 (AtEOD1) or SEQ ID NOS: 77 or 78 (OsEOD1) or may be a variant of this sequence which retains E3 ubiquitin ligase activity.

A EOD1 polypeptide which is a variant of any one of SEQ ID NOS: 74 to 90 or other reference EOD1 sequence may comprise an amino acid sequence having at least 20%, at least 30%, at least 40%, at least 50%, at least 60%, at least 70%, at least 80%, at least 90%, at least 95%, or at least 98% sequence identity to the reference EOD1 sequence.

A EOD polypeptide which is a variant of any one of SEQ ID NOS: 74 to 90 may further comprise a EOD domain having the sequence of SEQ ID NO: 73. Examples of suitable sequences are set out above.

A nucleic acid encoding a EOD1 polypeptide may comprise a nucleotide sequence set out in a database entry selected from the group consisting of XM_002299911.1 GI:224059639 (PtEOD1); XM_002531864.1 GI:255582235 (RcEOD1); XM_002279758.2 GI:359487285 (VvEOD1); XM_003542806.1 GI:356548934 (GmEOD1a); XM_003540482.1 GI:356544175 (GmEOD1b); XM_002468372.1 GI:242042044 (SbEOD1); NM_001147247.1 GI:226496788 (ZmEOD1); or NP_001030922.1 GI: 79316205 (AtEOD1; At3g63530) or may be variant of one of these sequences.

In some preferred embodiments, a nucleic acid encoding a EOD1 polypeptide may comprise the nucleotide sequence encoding AtEOD1 or OsEOD1 or may be a variant of any one of these sequences which encodes a polypeptide which has EOD1 activity.

EOD1 polypeptides and encoding nucleic acids whose expression or activity is reduced as described herein may be readily identified in any plant species of interest, in particular a crop plant, such as wheat, barley, maize, rice, and another agricultural plants, using routine sequence analysis techniques.

DA2 mutation in plants is also shown herein to synergistically enhance the effect of combinations of DA1 and EOD1 mutations on yield-associated traits in plants.

The methods described herein are not limited to particular plant species and expression or activity of DA2, DA1 and/or EOD1 may be reduced in any plant species of interest, as described herein.

An DA1, DA2 or EOD1 polypeptide in a plant species of interest may have an amino acid sequence which is a variant of a respective DA1, DA2 or EOD1 reference amino acid sequence set out herein. A DA1, DA2 or EOD1 polypeptide which is a variant of a reference sequence set out herein, may comprise an amino acid sequence having at least 20%, at least 30%, at least 40%, at least 50%, at least 60%, at least 70%, at least 80%, at least 90%, at least 95%, or at least 98% sequence identity to the reference sequence.

Particular amino acid sequence variants that occur in a plant species may differ from a reference sequence set out herein by insertion, addition, substitution or deletion of 1 amino acid, 2, 3, 4, 5-10, 10-20 20-30, 30-50, or more than 50 amino acids.

A DA1, DA2 or EOD1 nucleic acid in a plant species of interest may have a nucleotide sequence which is a variant of a respective DA1, DA2 or EOD1 reference nucleotide sequence set out herein. For example, variant nucleotide sequence may be a homologue, or allele of a reference DA1, DA2 or EOD1 sequence set out herein, and may differ from the reference DA1, DA2 or EOD1 nucleotide sequence by one or more of addition, insertion, deletion or substitution of one or more nucleotides in the nucleic acid, for example 2, 3, 4, 5-10, 10-20 20-30, 30-50, or more than 50, leading to the addition, insertion, deletion or substitution of one or more amino acids in the encoded polypeptide. Of course, changes to the nucleic acid that make no difference to the encoded amino acid sequence are included. A DA1, DA2 or EOD1 encoding nucleic acid may comprise a sequence having at least 20% or at least 30% sequence identity with the reference nucleic acid sequence, preferably at least 40%, at least 50%, at least 60%, at least 65%, at least 70%, at least 80%, at least 90%, at least 95% or at least 98%. Sequence identity is described above.

Sequence similarity and identity are commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm (Nucl. Acids Res. (1997) 25 3389-3402) may be used.

Sequence comparison may be made over the full-length of the relevant sequence described herein.

Suitable variant amino acid and nucleotide sequences can be identified in any plant species of interest using standard sequence analysis techniques.

A DA1, DA2 or EOD1 nucleotide sequence which is a variant of a reference DA1, DA2 or EOD1 nucleic acid sequence set out herein, may selectively hybridise under stringent conditions with this nucleic acid sequence or the complement thereof.

Stringent conditions include, e.g. for hybridization of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

An alternative, which may be particularly appropriate with plant nucleic acid preparations, is a solution of 5×SSPE (final 0.9 M NaCl, 0.05M sodium phosphate, 0.005M EDTA pH 7.7), 5×Denhardt's solution, 0.5% SDS, at 50° C. or 65° C. overnight. Washes may be performed in 0.2×SSC/0.1% SDS at 65° C. or at 50-60° C. in 1×SSC/0.1% SDS, as required.

Nucleic acids as described herein may be wholly or partially synthetic. In particular, they may be recombinant in that nucleic acid sequences which are not found together in nature (do not run contiguously) have been ligated or otherwise combined artificially. Alternatively, they may have been synthesised directly e.g. using an automated synthesiser.

The expression of a DA2 nucleic acid and a DA1 and/or EOD1 nucleic acid may reduced or abolished in one or more cells of a plant by any convenient technique.

Methods for reducing the expression or activity of a DA2 polypeptide and a DA1 and/or EOD1 polypeptide in a plant are well-known in the art and are described in more detail below. In some embodiments, the expression of active DA2, DA1 and/or EOD1 polypeptide may be reduced, preferably abolished, by introducing a mutation into the nucleic acid sequence in a plant cell which encodes the polypeptide or which regulate the expression of such a nucleic acid sequence. The mutation may disrupt the expression or function of the DA2, DA1 and/or EOD1 polypeptide. Suitable mutations include knock-out and knock-down mutations. In some embodiments, a mutation may produce a dominant-negative allele of DA1. A plant may then be regenerated from the mutated cell. The nucleic acids may be mutated by insertion or deletion of one or more nucleotides. Techniques for the mutagenesis, inactivation or knockout of target genes are well-known in the art (see for example In Vitro Mutagenesis Protocols; Methods in Molecular Biology (2nd edition) Ed Jeff Braman; Sambrook J et al. 2012. Molecular Cloning: A Laboratory Manual (4th Edition) CSH Press; Current Protocols in Molecular Biology; Ed Ausubel et al (2013) Wiley). In some embodiments, mutations may be introduced into a target EOD1, DA2 or DA1 gene by genome editing techniques, for example RNA guided nuclease techniques such as CRISPR, Zinc-finger nucleases (ZFNs) and transactivator-like effector nucleases (TALENs) (Urnov, F. D. et al *Nature reviews. Genetics* 11, 636-646 (2010); Joung, J. K. et al. *Nature reviews. Molecular cell biology* 14, 49-55 (2013); Gasiunas, G. et al *PNAS USA* 109, E2579-2586 (2012); Cong, L. et al. *Science* 339, 819-823 (2013)).

Sequence mutations which reduce the expression or activity may include a deletion, insertion or substitution of one or more nucleotides, relative to the wild-type nucleotide sequence, a gene amplification or an increase or decrease in methylation, for example hypermethylation. The one or more mutations may be in a coding or non-coding region of the nucleic acid sequence. Mutations in the coding region of the gene encoding the component may prevent the translation of full-length active protein i.e. truncating mutations, or allow the translation of full-length but inactive or impaired function protein i.e. mis-sense mutations. Mutations or epigenetic changes, such as methylation, in non-coding regions of the gene encoding the component, for example, in a regulatory element, may prevent transcription of the gene. A nucleic acid comprising one or more sequence mutations may encode a variant polypeptide which has reduced or abolished activity or may encode a wild-type polypeptide which has little or no expression within the cell, for example through the altered activity of a regulatory element. A nucleic acid comprising one or more sequence mutations may have one, two, three, four or more mutations relative to the unmutated sequence.

For example, the activity of EOD1 may be reduced, preferably abolished, by introducing a mutation, such as a deletion, insertion or substitution, at a position corresponding to position 44 of SEQ ID NO: 89, for example, an A to T substitution. A position in a EOD1 polypeptide sequence which is equivalent to position 44 of SEQ ID NO: 89 may be identified using standard sequence analysis and alignment tools, as shown in Table 4.

DA2, DA1 and EOD1 coding sequences may be identified in any plant species of interest using standard sequence analysis techniques, for example by comparison with the reference sequences set out herein.

Mutations suitable for abolishing expression of an active DA2, DA1 and/or EOD1 polypeptide will be readily apparent to the skilled person.

In some preferred embodiments, a mutation that reduces or abolishes DA2 expression or activity may be introduced into a plant cell that expresses a dominant negative DA1 polypeptide and optionally comprises either i) a heterologous nucleic acid that encodes an EOD1 suppressor nucleic acid or ii) a mutation that reduces EOD1 expression or activity.

In some embodiments, the expression of a DA1, DA2 and/or EOD1 polypeptide may be reduced in a plant cell by expressing a heterologous nucleic acid which encodes or transcribes a suppressor nucleic acid, for example a suppressor RNA or RNAi molecule, within cells of said plant. The suppressor RNA suppresses the expression of its target polypeptide (i.e. DA1, DA2 or EOD1) in the plant cells.

Nucleic acids as described herein may be wholly or partially synthetic. In particular, they may be recombinant in that nucleic acid sequences which are not found together in nature (do not run contiguously) have been ligated or otherwise combined artificially. Alternatively, they may have been synthesised directly e.g. using an automated synthesiser.

The nucleic acid may of course be double- or single-stranded, cDNA or genomic DNA, or RNA. The nucleic acid may be wholly or partially synthetic, depending on design. Naturally, the skilled person will understand that where the nucleic acid includes RNA, reference to the sequence shown should be construed as reference to the RNA equivalent, with U substituted for T.

"Heterologous" indicates that the gene/sequence of nucleotides in question or a sequence regulating the gene/sequence in question, has been introduced into said cells of the plant or an ancestor thereof, using genetic engineering or recombinant means, i.e. by human intervention. Nucleotide sequences which are heterologous to a plant cell may be non-naturally occurring in cells of that type, variety or species (i.e. exogenous or foreign) or may be sequences which are non-naturally occurring in that sub-cellular or genomic environment of the cells or may be sequences which are non-naturally regulated in the cells i.e. operably linked to a non-natural regulatory element.

The suppression of the expression of a target polypeptide in plant cells is well-known in the art. A suitable suppressor nucleic acid may be a copy of all or part of the target DA1, DA2 and/or EOD1 gene inserted in antisense or sense orientation or both relative to the DA1, DA2 and/or EOD1 gene, to achieve reduction in expression of the target gene. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of this approach may be found in WO95/34668 (Biosource); Angell & Baulcombe (1997) The EMBO Journal 16, 12:3675-3684; and Voinnet & Baulcombe (1997) Nature 389: pg 553.

In some embodiments, the suppressor nucleic acid may be a sense suppressor of expression of the DA1, DA2 and/or EOD1 polypeptide.

A suitable sense suppressor nucleic acid may be a double stranded RNA (Fire A. et al Nature, Vol 391, (1998)). dsRNA mediated silencing is gene specific and is often termed RNA interference (RNAi). RNAi is a two-step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction (Zamore P. D. Nature Structural Biology, 8, 9, 746-750, (2001)

siRNAs (sometimes called microRNAs) down-regulate gene expression by binding to complementary RNAs and either triggering mRNA elimination (RNAi) or arresting mRNA translation into protein. siRNA may be derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complementary target sequences without RNA cleavage and degrade mRNAs bearing fully complementary sequences.

Accordingly, the present invention provides the use of RNAi sequences based on the DA1, DA2 and/or EOD1 nucleic acid sequence for suppression of the expression of the DA1, DA2 and/or EOD1 polypeptide. For example, an RNAi sequence may correspond to a fragment of a reference DA2, DA1 or EOD1 nucleotide sequence set out herein or may be a variant thereof.

siRNA molecules are typically double stranded and, in order to optimise the effectiveness of RNA mediated down-regulation of the function of a target gene, it is preferred that the length and sequence of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA sequences which are transcribed from DNA, but are not translated into protein. A DNA sequence that codes for a miRNA is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed on John et al, PLoS Biology, 11(2), 1862-1879, 2004.

Typically, the RNA molecules intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such as siRNA finder (Ambion). siRNA and miRNA sequences can be synthetically produced and added exogenously to cause gene downregulation or produced using expression systems (e.g. vectors). In a preferred embodiment, the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5' overhangs, e.g. of one or two (ribo) nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complementary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of DA1, DA2 and/or EOD1. For example, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of a reference DA2, DA1 or EOD1 nucleotide sequence set out herein or a variant thereof.

In other embodiments, the suppressor nucleic acid may be an anti-sense suppressor of expression of the DA1, DA2 and/or EOD1 polypeptide. In using anti-sense sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) Nature 334, 724-726; Zhang et al, (1992) The Plant Cell 4, 1575-1588, English et al., (1996) The Plant Cell 8, 179-188. Antisense technology is also reviewed in Bourque, (1995), Plant Science 105, 125-149, and Flavell (1994) PNAS USA 91, 3490-3496.

An anti-sense suppressor nucleic acid may comprise an anti-sense sequence of at least 10 nucleotides from a nucleotide sequence is a fragment of a reference DA2, DA1 or EOD1 nucleotide sequence set out herein or a variant thereof.

It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mis-match between the sequence used and the target gene. Effectively, the homology should be sufficient for the down-regulation of gene expression to take place.

A suppressor RNA molecule may comprise 10-40 nucleotides of the sense or anti-sense strand of a nucleic acid sequence which encodes DA2, DA1 and/or EOD1 polypeptide.

Suppressor nucleic acids may be operably linked to heterologous promoters, for example tissue-specific or inducible promoters. For example, integument and seed specific promoters can be used to specifically down-regulate two or more DA1, DA2 and/or EOD1 nucleic acids in developing ovules and seeds to increase final seed size.

In some preferred embodiments, DA2 suppressor nucleic acid may be expressed in a plant cell with a nucleic acid encoding a dominant negative DA1 polypeptide and optionally an EOD1 suppressor nucleic acid.

Nucleic acid encoding the suppressor nucleic acid and/or a dominant-negative DA1 polypeptide may be comprised in one or more vectors.

Nucleic acid encoding the suppressor nucleic acid(s) as described herein and/or dominant-negative DA1 polypeptide may be operably linked to a heterologous regulatory sequence, such as a promoter, for example a constitutive, inducible, tissue-specific or developmental specific promoter as described above.

Nucleic acid encoding suppressor nucleic acid(s) as described herein and/or dominant negative DA1 polypeptides may be contained on a nucleic acid construct or vector. The construct or vector is preferably suitable for transformation into and/or expression within a plant cell. A vector is, inter alia, any plasmid, cosmid, phage or Agrobacterium binary vector in double or single stranded linear or circular form, which may or may not be self-transmissible or mobilizable, and which can transform prokaryotic or eukaryotic host, in particular a plant host, either by integration into the cellular genome or exist extrachromasomally (e.g. autonomous replicating plasmid with an origin of replication).

Specifically included are shuttle vectors by which is meant a DNA vehicle capable, naturally or by design, of replication in two different organisms, which may be selected from *Actinomyces* and related species, bacteria and eukaryotic (e.g. higher plant, mammalia, yeast or fungal) cells.

A construct or vector comprising nucleic acid as described above need not include a promoter or other regulatory sequence, particularly if the vector is to be used to introduce the nucleic acid into cells for recombination into the genome.

Constructs and vectors may further comprise selectable genetic markers consisting of genes that confer selectable phenotypes such as resistance to antibiotics such as kanamycin, hygromycin, phosphinotricin, chlorsulfuron, methotrexate, gentamycin, spectinomycin, imidazolinones, glyphosate and d-amino acids.

Those skilled in the art can construct vectors and design protocols for recombinant gene expression, for example in a microbial or plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook et al, 2001, Cold Spring Harbor Laboratory Press and *Protocols in Molecular Biology*, Second Edition, Ausubel et al. eds. John Wiley & Sons, 1992. Specific procedures and vectors previously used with wide success upon plants are described by Bevan, Nucl. Acids Res. (1984) 12, 8711-8721), and Guerineau and Mullineaux, (1993) Plant transformation and expression vectors. In: Plant Molecular Biology Labfax (Croy RRD ed) Oxford, BIOS Scientific Publishers, pp 121-148.

When introducing a chosen gene construct into a cell, certain considerations must be taken into account, well known to those skilled in the art. The nucleic acid to be inserted should be assembled within a construct that contains effective regulatory elements that will drive transcription. There must be available a method of transporting the construct into the cell. Once the construct is within the cell membrane, integration into the endogenous chromosomal material either will or will not occur. Finally, the target cell type is preferably such that cells can be regenerated into whole plants.

It is desirable to use a construct and transformation method which enhances expression of the nucleic acid encoding the suppressor nucleic acid or dominant negative DA1 polypeptide. Integration of a single copy of the gene into the genome of the plant cell may be beneficial to minimize gene silencing effects. Likewise, control of the complexity of integration may be beneficial in this regard. Of particular interest in this regard is transformation of plant cells utilizing a minimal gene expression construct according to, for example, EP Patent No. EP1407000B1, herein incorporated by reference for this purpose.

Techniques well known to those skilled in the art may be used to introduce nucleic acid constructs and vectors into plant cells to produce transgenic plants with the properties described herein.

*Agrobacterium* transformation is one method widely used by those skilled in the art to transform plant species. Production of stable, fertile transgenic plants is now routine in the art (see for example Toriyama, et al. (1988) *Bio/Technology* 6, 1072-1074; Zhang, et al. (1988) *Plant Cell Rep.* 7, 379-384; Zhang, et al. (1988) *Theor Appl Genet* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, *Manila, Philippines* 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828; Nilsson, O. et al (1992) *Transgenic Research* 1, 209-220).

Other methods, such as microprojectile or particle bombardment (U.S. Pat. No. 5,100,792, EP-A-444882, EP-A-434616), electroporation (EP 290395, WO 8706614), microinjection (WO 92/09696, WO 94/00583, EP 331083, EP 175966, Green et al. (1987) *Plant Tissue and Cell Culture*, Academic Press), direct DNA uptake (DE 4005152, WO 9012096, U.S. Pat. No. 4,684,611), liposome mediated DNA uptake (e.g. Freeman et al. *Plant Cell Physiol.* 29: 1353 (1984)) or the vortexing method (e.g. Kindle, *PNAS U.S.A.* 87: 1228 (1990d)) may be preferred where *Agrobacterium* transformation is inefficient or ineffective, for example in some gymnosperm species. Physical methods for the transformation of plant cells are reviewed in Oard, 1991, *Biotech. Adv.* 9: 1-11.

Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, Methods for *Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Following transformation, a plant cell with reduced DA2 expression and reduced DA1 and/or EOD1 expression or activity may be identified and/or selected. A plant may be regenerated from the plant cell.

A plant with reduced DA2 activity or expression that is also deficient in the expression or activity of DA1, EOD1 or both DA1 and EOD1, as described above may be sexually or asexually propagated or grown to produce off-spring or descendants. Off-spring or descendants of the plant regenerated from the one or more cells may be sexually or asexually propagated or grown. The plant or its off-spring or descendents may be crossed with other plants or with itself.

The DA1, DA2 and/or EOD1 amino acid or nucleic acid sequence may be employed as a molecular marker to determine the expression or activity of one or more of the DA1, DA2 and/or EOD1 polypeptides in a plant before, during or after growing or sexually or asexually propagated as set out above. A method may comprise:

providing a population of plants,
determining the amount of expression of an DA1, DA2 and/or EOD1 polypeptide in one or more plants in the population, and
identifying one or more plants in the population with reduced expression of the DA1, DA2 and/or EOD1 polypeptide relative to other members of said population.

The population of plants may be produced as described above.

In some embodiments, a method may comprise:
crossing a first and a second plant to produce a population of progeny plants;
determining the expression of one or more of DA1, DA2 and EOD1 polypeptides in the progeny plants in the population, and
identifying a progeny plant in the population in which expression of the DA1, DA2 and/or EOD1 polypeptide is reduced relative to controls.

One or both of the first and second plants may be produced as described above.

A progeny plant in which expression of the DA2 and DA1 and/or EOD1 polypeptide is reduced relative to controls (e.g. other members of the population) may display increased seed and/or organ size relative to the controls and may have higher plant yields.

In some embodiments, DA1 and EOD1 amino acid or nucleic acid sequences may be employed as a molecular marker to determine the expression or activity of one or more of the DA1 and/or EOD1 polypeptides in a plant in order to identify a plant or plant cell deficient in DA1 and/or EOD1 in which expression or activity of a DA2 polypeptide may be reduced as described above. A method may comprise:

providing a population of plants,
determining the amount of expression of an DA1 and/or EOD1 polypeptide in one or more plants in the population, and
identifying one or more plants in the population with reduced expression of the DA1 and/or EOD1 polypeptide relative to other members of said population.

DA2 expression or activity may be reduced in the identified plants as methods described above.

A plant or progeny plant may be identified by i) measuring the amount of DA1, DA2 and/or EOD1 polypeptide in one or more cells of the plant ii) measuring the amount of DA1, DA2 and/or EOD1 mRNA in one or more cells of the plant or iii) sequencing the nucleic acid encoding the DA1, DA2 and/or EOD1 polypeptide in one or more cells of the plant and identifying the presence of one or more mutations.

The identified plants may be further propagated or crossed, for example, with other plants having reduced DA1, DA2 and/or EOD1 expression or self-crossed to produce inbred lines. The expression or activity of a DA1, DA2 and/or EOD1 polypeptide in populations of progeny plants may be determined and one or more progeny plants with reduced expression or activity of DA1, DA2 and/or EOD1 identified.

In some embodiments, the amount of expression of DA1, DA2 and/or EOD1 may be determined at the protein level. A method may comprise:

providing a population of plants,
determining the amount of DA1, DA2 and/or EOD1 polypeptide in one or more plants of said population, and
identifying one or more plants in the population with reduced amount of an DA1, DA2 and/or EOD1 polypeptide relative to other members of said population.

Conveniently, immunological techniques, such as Western blotting, may be employed, using antibodies which bind to the DA1, DA2 or EOD1 polypeptide and show little or no binding to other antigens in the plant. For example, the amount of an DA1, DA2 and/or EOD1 polypeptide in a plant cell may be determined by contacting a sample comprising the plant cell with an antibody or other specific binding member directed against the DA1, DA2 or EOD1 polypeptide, and determining binding of the DA1, DA2 or EOD1 polypeptide to the sample. The amount of binding of the specific binding member is indicative of the amount of DA1, DA2 or EOD1 polypeptide which is expressed in the cell.

The amount of DA1, DA2 and/or EOD1 polypeptide may be determined in one or more cells of the plant, preferably cells from an above-ground portion or tissue of the plant, such as the vasculature and primary and secondary meristems in the shoot.

In other embodiments, the expression of the DA1, DA2 or EOD1 polypeptide may be determined at the nucleic acid level. For example, the amount of nucleic acid encoding a DA1, DA2 or EOD1 polypeptide may be determined. A method of producing a plant having increased yield related traits may comprise:

providing a population of plants,
determining the level or amount of nucleic acid, for example mRNA, encoding the DA1, DA2 or EOD1 polypeptide in a cell of one or more plants of said population, and,
identifying one or more plants in the population with reduced amount of an DA1, DA2 or EOD1 encoding nucleic acid relative to other members of said population.

The level or amount of encoding nucleic acid in a plant cell may be determined for example by detecting the amount of transcribed encoding nucleic acid in the cell. This may be performed using standard techniques such as Northern blotting or RT-PCR.

Alternatively, the presence of sequence variations which affect the expression or activity of a DA1, DA2 or EOD1 polypeptide may be determined. Another method of producing a plant having increased growth and/or biomass may comprise:

providing a population of plants,
determining the presence of one or more sequence variations, for example, polymorphisms, mutations or regions of hypermethylation, in a nucleic acid encoding an DA1, DA2 and/or EOD1 polypeptide in a cell in one or more plants of said population,
wherein said one or more sequence variations which reduce the expression or activity of the encoded DA1, DA2 and/or EOD1 polypeptide, and
identifying one or more plants in the population with one or more sequence variations which reduce the expression or activity of DA1, DA2 and/or EOD1 relative to other members of said population.

DA1, DA2 and/or EOD1 polypeptides and encoding nucleic acid are described in more detail above.

The presence of one or more sequence variations in a nucleic acid may be determined by detecting the presence of the variant nucleic acid sequence in one or more plant cells or by detecting the presence of the variant polypeptide which is encoded by the nucleic acid sequence. Preferred nucleic acid sequence variation detection techniques include ARMS™-allele specific amplification, OLA, ALEX™, COPS, Taqman, Molecular Beacons, RFLP, and restriction site based PCR and FRET techniques.

Numerous suitable methods for determining the amount of a nucleic acid encoding an DA1, DA2 or EOD1 polypeptide, or the presence or absence of sequence variation in a nucleic acid encoding an DA1, DA2 or EOD1 polypeptide, in a plant cell, are available in the art (see for example (see for example Molecular Cloning: a Laboratory Manual: 3rd edition, Sambrook & Russell (2001) Cold Spring Harbor Laboratory Press NY; Current Protocols in Molecular Biology, Ausubel et al. eds. John Wiley & Sons (1992); DNA Cloning, The Practical Approach Series (1995), series eds. D. Rickwood and B. D. Hames, IRL Press, Oxford, UK and PCR Protocols: A Guide to Methods and Applications (Innis, et al. 1990. Academic Press, San Diego, Calif.)). Many current methods for the detection of sequence variation are reviewed by Nollau et al., Clin. Chem. 43, 1114-1120, 1997; and in standard textbooks, for example "Laboratory Protocols for Mutation Detection", Ed. by U. Landegren, Oxford University Press, 1996 and "PCR", $2^{nd}$ Edition by Newton & Graham, BIOS Scientific Publishers Limited, 1997.

Preferred polypeptide sequence variation techniques include immunoassays, which are well known in the art e.g. A Practical Guide to ELISA by D M Kemeny, Pergamon Press 1991; Principles and Practice of Immunoassay, $2^{nd}$ edition, C P Price & D J Newman, 1997, published by Stockton Press in USA & Canada and by Macmillan Reference in the United Kingdom.

In some embodiments, nucleic acid or an amplified region thereof may be sequenced to identify or determine the presence of polymorphism or mutation therein. A polymorphism or mutation may be identified by comparing the sequence obtained with the known sequence of DA1, DA2 or EOD1, for example as set out in sequence databases. Alternatively, it can be compared to the sequence of the corresponding nucleic acid from control cells. In particular, the presence of one or more polymorphisms or mutations that cause reduction but not total abrogation of function may be determined. Sequencing may be performed using any one of a range of standard techniques. Sequencing of an amplified product may, for example, involve precipitation with isopropanol, resuspension and sequencing using a TaqFS+ Dye terminator sequencing kit (e.g. from GE Healthcare UK Ltd UK). Extension products may be electrophoresed on an ABI 377 DNA sequencer and data analysed using Sequence Navigator software.

A progeny plant identified as having reduced DA1, DA2 and/or EOD1 expression may be tested for increased or enhanced yield related traits, such as increased seed or organ size, relative to controls.

The identified progeny plant may be further propagated or crossed, for example with the first or second plant (i.e. backcrossing) or self-crossed to produce inbred lines.

The identified progeny plant may be tested for seed size, organ size and/or plant yield relative to controls.

A plant produced as described herein may be deficient in DA2 expression or activity and may be further deficient in DA1 expression or activity, EOD1 expression or activity or both DA1 and EOD1 expression or activity.

The expression or activity of DA2, DA1 and EOD1 may be reduced or abolished in the plant by mutation or one or more nucleotides in the plant coding sequence and/or by the expression of a heterologous nucleic acid encoding a suppressor nucleic acid. In some preferred embodiments, the activity of DA1 may be reduced or abolished in the plant by expression of a heterologous nucleic acid encoding a dominant-negative DA1 polypeptide.

A plant may thus comprise heterologous nucleic acid which encodes a suppressor nucleic acid, such as an siRNA or shRNA, which reduces the expression of one or more of DA1, DA2 and EOD1 or which encodes a dominant negative DA1 polypeptide.

Any combination of mutations, suppressor nucleic acids may be employed in a plant as described herein. For example, a plant may comprise i) a mutation which reduces DA2 activity or expression, a heterologous nucleic acid encoding a suppressor nucleic acid which reduces EOD1 expression and a heterologous nucleic acid encoding a nucleic acid which encodes a dominant-negative DA1 polypeptide; ii) a heterologous nucleic acid encoding a suppressor nucleic acid which reduces DA2 expression or expression, a mutation which reduces EOD1 expression and a heterologous nucleic acid encoding a nucleic acid which encodes a dominant-negative DA1 polypeptide iii) heterologous nucleic acids encoding suppressor nucleic acids which reduce EOD1 and DA2 expression and a heterologous nucleic acid encoding a nucleic acid which encodes a dominant-negative DA1 polypeptide, or iv) mutation which reduce EOD1 and DA2 activity or expression and a heterologous nucleic acid encoding a nucleic acid which encodes a dominant-negative DA1 polypeptide.

In other embodiments, a plant may comprise i) a mutation which reduces DA2 activity or expression, a heterologous nucleic acid encoding a suppressor nucleic acid which reduces DA1 expression ii) a heterologous nucleic acid encoding a suppressor nucleic acid which reduces DA2 expression or expression, a mutation which reduces DA1 expression iii) heterologous nucleic acids encoding suppressor nucleic acids which reduce DA1 and DA2 expression, iv) mutations which reduce DA1 and DA2 activity or expression or v) a mutation which reduces DA2 activity or expression or a heterologous nucleic acid encoding a suppressor nucleic acid which reduces DA2 expression and a heterologous nucleic acid encoding a nucleic acid which encodes a dominant negative DA1 polypeptide.

Heterologous nucleic acids encoding the dominant-negative DA1 polypeptide and/or suppressor nucleic acids may be on the same or different expression vectors and may be incorporated into the plant cell by conventional techniques.

Examples of suitable plants for use in accordance with any aspect of the invention described herein include monocotyledonous and dicotelydonous higher plant, for example an agricultural or crop plant, such as a plant selected from the group consisting of *Lithospermum erythrorhizon, Taxus* spp, tobacco, cucurbits, carrot, vegetable *brassica*, melons, capsicums, grape vines, lettuce, strawberry, oilseed *brassica*, sugar beet, wheat, barley, maize, rice, soyabeans, peas, sorghum, sunflower, tomato, potato, pepper, *chrysanthemum*, carnation, linseed, hemp and rye.

A plant produced as described above may be sexually or asexually propagated or grown to produce off-spring or descendants. Off-spring or descendants of the plant regenerated from the one or more cells may be sexually or asexually propagated or grown. The plant or its off-spring or descendents may be crossed with other plants or with itself.

Another aspect of the invention provides a transgenic plant having reduced or abolished expression or activity of DA2 polypeptide within one or more cells thereof, wherein the plant is deficient in the expression or activity of DA1, EOD1 or both DA1 and EOD1.

The plant may comprise an exogenous nucleic acid which reduces or abolishes the expression or activity of one or more of DA2, DA1 and EOD1. In some embodiments, the transgenic plant may express a dominant negative DA1 polypeptide that reduces the activity of DA1.

In some embodiments, the plant may have reduced or abolished expression of DA1, DA2 and EOD1 or may have reduced or abolished expression of DA2 and EOD1 and may express a dominant negative DA1.

In addition to a plant produced by a method described herein, the invention encompasses any clone of such a plant, seed, selfed or hybrid progeny and descendants, and any part or propagule of any of these, such as cuttings and seed, which may be used in reproduction or propagation, sexual or asexual. Also encompassed by the invention is a plant which is a sexually or asexually propagated off-spring, clone or descendant of such a plant, or any part or propagule of said plant, off-spring, clone or descendant.

A suitable plant may be produced by a method described above.

The plant may have increased yield relative to control wild-type plants (i.e. identical plants in which the expression or activity of DA2 and optionally DA1 and/or EOD1 has not been reduced). For example, the mass of seeds (e.g. grain) or other plant product per unit area may be increased relative to control plants.

For example, one or more yield-related traits in the plant may be improved. Yield-related traits may include life-span, organ size and seed size.

A yield related trait may be improved, increased or enhanced in the plant relative to control plants in which expression of the nucleic acid encoding the DA2 polypeptide is not abolished or reduced (i.e. identical plants in which the expression of DA2 and optionally DA1 and/or EOD1 has not been reduced or abolished).

A plant according to the present invention may be one which does not breed true in one or more properties. Plant varieties may be excluded, particularly registrable plant varieties according to Plant Breeders Rights.

DA1 is shown herein to physically interact with DA2 in vivo. Compounds that disrupt or interfere with the interaction may be useful in increasing seed or organ size and improving plant yield.

A method of identifying a compound that increase plant yield may comprise;
 determining the effect of a test compound on the binding of a DA2 polypeptide to a DA1 polypeptide,
 a reduction or abolition of binding being indicative that the compound may be useful in increasing plant yield.

DA1 and DA2 polypeptides are described in more detail above.

The DA1 and DA2 polypeptides may be isolated or may be expressed recombinant or endogenously in a plant cell.

A compound that reduces or abolises DA1/DA2 binding may be useful in the treatment of plants to increase yield.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Other aspects and embodiments of the invention provide the aspects and embodiments described above with the term "comprising" replaced by the term "consisting of" and the aspects and embodiments described above with the term "comprising" replaced by the term "consisting essentially of".

All documents mentioned in this specification are incorporated herein by reference in their entirety for all purposes.

The contents of all database entries mentioned in this specification are also incorporated herein by reference in their entirety for all purposes. This includes the versions of any sequences which are current at the filing date of this application.

EXPERIMENTS

1. Methods
1.1 Plant Materials and Growth Conditions

*Arabidopsis* ecotype Columbia (Col-0) was the wild type line used. All mutants were in the Col-0 background. da2-1 (SALK_150003) was obtained from *Arabidopsis* Stock Centre NASC and ABRC collections. The T-DNA insertion was confirmed by PCR and sequencing. Seeds were surface-sterilized with 100% isopropanol for 1 min and 10% (v/v) household bleach for 10 min, washed at least three times with sterile water, stratified at 4° C. for 3d in the dark, dispersed on GM medium with 0.9% agar and 1% glucose, and then grown at 22° C. Plants were grown under long-day condition (16 h light/8 h dark) at 22° C.

1.2 Constructs and Transformation

The pDA2:DA2 construct was made by using a PCR-basedGateway system. The 1960 bp promoter sequence of DA2 was amplified using the primers DA2proGW-F and DA2proGW-R. PCR products were then cloned to the pCRS/GW/TOPO TA cloning vector (Invitrogen). The DA2 CDS was amplified and the PCR products were then cloned to the AscI and KpnI sites of the Gateway vector pMDC110 to get the DA2CDS-pMDC110 plasmid. The DA2 promoter was then subcloned to the DA2CDS-pMDC110 by LR reaction to generate the pDA2:DA2 construct. The plasmid pDA2:DA2 was introduced into the da2-1 mutant plants using *Agrobacterium tumefaciens* GV3101 and transformants were selected on hygromycin (3 μg/ml) containing medium.

The 35S:DA2 construct was made using a PCR-based Gateway system. PCR products were subcloned into the pCR8/GW/TOPO TA cloning vector (invitrogen) using TOPO enzyme. The DA2 gene was then subcloned into Gateway Binary Vector pMDC32 containing the 35S promoter (Curtis and Grossniklaus, 2003). The plasmid 35S:DA2 was introduced into Col-0 plants using *Agrobacterium tumefaciens* GV3101 and transformants were selected on hygromycin (30 μg/ml)-containing medium.

The 1960 bp promoter sequence of DA2 was amplified and the PCR products were cloned to the pGEM-T vector (Promaga) using T4 DNA ligase and sequenced. The DA2 promoter was then inserted into the SacI and NcoI sites of the binary vector pGreen-GUS (Curtis and Grossniklaus, 2003) to generate the transformation plasmid pDA2:GUS. The plasmid pDA2:GUS was introduced into Col-0 plants using *Agrobacterium tumefaciens* GV3101 and transformants were selected on kanamycin (50 μg/ml)-containing medium. The 35S:GW2 construct was made using a PCR-based Gateway system. PCR products were subcloned into the pCR8/GW/TOPO TA cloning vector (invitrogen) using TOPO enzyme. The GW2 gene was then subcloned into Gateway Binary Vector pMDC32 containing the 35S promoter (Curtis and Grossniklaus, 2003). The plasmid 35S: GW2 was introduced into Col-0 plants using *Agrobacterium tumefaciens* GV3101 and transformants were selected on hygromycin (30 µg/ml)-containing medium.

1.3 Morphological and Cellular Analysis

Average seed weight was determined by weighing mature dry seeds in batches of 500 using an electronic analytical balance (METTLER MOLEDO AL104 CHINA). The weights of five sample batches were measured for each seed lot. Seeds were photographed under a Leica microscope (LEICA S8APO) using a Leica CCD (DFC420) and seed size were measured by using Image J software. Area measurements of petals (stage 14), leaves, and cotyledons were made by scanning organs to produce a digital image, and then calculating area, length and width by using Image J software. Leaf, petal and embryo cell sizes were measured from DIC images. Biomass accumulation in flowers (stage 14) was measured by weighing organs.

1.4 GUS Staining

Samples (pDA2:GUS) were stained in a solution of 1 mM X-gluc, 100 mM Na3PO4 buffer, 3 mM each K3Fe(CN)6/K4Fe(CN)6, 10 mM EDTA, and 0.1% Nodidet-P40, and incubated at room temperature for 6 hours. After GUS staining chlorophyll was removed using 70% ethanol.

1.5 RNA Isolation, RT-PCR, and Quantitative Real-time RT-PCR Analysis

Total RNA was extracted from *Arabidopsis* roots, stems, leaves, seedlings and inflorescences using an RNeasy Plant Mini kit (TIANGEN, China). Reverse transcription (RT)-PCR was performed as described (Li et al., 2006). cDNA samples were standardized on actin transcript amount using the primers ACTIN2-F and ACTIN2-R. Quantitative real-time RT-PCR analysis was performed with a lightcycler 480 engine (Roche) using the lightcycler 480 SYBR Green Master (Roche). ACTIN7 mRNA was used as an internal control, and relative amounts of mRNA were calculated using the comparative threshold cycle method.

1.6 E3 Ubiquitin Ligase Activity Assay

The coding sequence of DA2 was cloned into BamH I and PstI sites of the pMAL-C2 vector to generate the construct MBP-DA2. The mutated DA2 (DA2C59S and DA2N91L) were generated by following the instruction manual of multi-site directed mutagenesis kit (Stratagene).

Bacterial lysates expressing MBP-DA2 and mutated MBP-DA2 were prepared from *E. coli* BL21 induced with 0.4 mM IPTG for 2 hours. Bacteria were lysed in TGH lysis buffer (50 mM HEPES [pH 7.5], 150 mM NaCl, 1.5 mM MgCl2, 1 mM EGTA, 1% Triton X-100, 10% glycerol, and protease inhibitor cocktail [Roche]) and sonicated. The lysates were cleared by centrifugation and incubated with amylose resin (New England Biolabs) at 4° C. for 30 min. Beads were washed by column buffer (20 mM Tris pH7.4, 200 mM NaCl, 1 mM EDTA) and equilibrated by reaction buffer (50 mM Tris pH7.4, 20 mM DTT, 5 mM MgCl2, 2 mM ATP). 110 ng E1 (Boston Biochem), 170 ng E2 (Boston Biochem), 1 µg His-ubiquitin (Sigma-Aldrich), and 2 µg DA2-MBP or mutated DA2-MBP fusion protein was incubated in a 20 µl reaction buffer for 2 hours at 30° C.

Polyubiquitinated proteins were detected by immunoblotting with an antibody against His (Abmart) and an antibody against MBP (New England Biolabs).

1.7 In Vitro Protein-protein Interaction

The coding sequences of DA1, da1-1, and DA1 derivatives containing specific protein domains were cloned into BamH I and Not I sites of the pGEX-4T-1 vector to generated GST-DA1, GST-DA1R358K, GST-DA1-UIM, and GST-DA1-LIM+C constructs, and EcoRI and XhoI sites of the pGEX-4T-1 vector to generate GST-DA1-LIM and GST-DA1-C constructs.

To test protein-protein interaction, bacterial lysates containing approximately 15 µg of MBP-DA2 fusion proteins were combined with lysates containing approximately 30 µg of GST-DA1, GST-DA1R358K, GST-DA1-UIM, GST-DA1-LIM, GST-DA1-LIM+C or GST-DA1-C fusion proteins. 20 µl amylose resin (New England Biolabs) was added into each combined solution with continued rocking at 4° C. for 1 hour. Beads were washed times with TGH buffer, and the isolated proteins were separated on a 10% SDS-polyacryamide gel and detected by western blot analysis with anti-GST (Abmart) and anti-MBP antibodies (Abmart), respectively.

1.8 Co-immunoprecipitation

The coding sequence of DA1 and DA1-C was cloned into KpnI and BamHI sites of the pCAMBIA1300-221-Myc vector to generate the transformation plasmid 35S::Myc-DA1 and 35S::Myc-DA1-C. PCR products were subcloned into the pCR8/GW/TOPO TA cloning vector (invitrogen) using TOPO enzyme. The DA2 gene was then subcloned into Gateway Binary Vector pMDC43 containing the 35S promoter and the GFP gene (Curtis and Grossniklaus, 2003). PCR products were subcloned into the pCR8/GW/TOPO TA cloning vector (invitrogen) using TOPO enzyme. The PEX10 gene were then subcloned into Gateway Binary Vector pH7FWG2 containing the 35S promoter and the GFP gene.

*Nicotiana benthamiana* leaves were transformed by injection of *Agrobacterium tumefaciens* GV3101 cells harboring 35S:Myc-DA1 and 35S:GFP-DA2 plasmids as previously described (Voinnet et al., 2003). Total protein was extracted with extraction buffer (50 mM Tris/HCl, pH 7.5, 150 mM NaCl, 20% glycerol, 2% Triton X-100, 1 mM EDTA, 1× complete protease inhibitor cocktail (Roche) and MG132 20 ug/ml) and incubated with GFP-Trap-A (Chromotek) for 1 hour at 4° C. Beads were washed 3 times with wash buffer (50 mM Tris/HCl, pH 7.5, 150 mM NaCl, 0.1% Triton X-100, and 1× complete protease inhibitor cocktail (Roche)). The immunoprecipitates were separated in 10% SDS-polyacryamide gel and detected by western blot analysis with anti-GFP (Beyotime) and anti-Myc (Abmart) antibodies, respectively.

1.9 Accession Numbers

*Arabidopsis* Genome Initiative locus identifiers for *Arabidopsis* genes mentioned herein are as follows: At1g19270 (NP_173361.1 GI: 15221983) (DA1), At4g36860 (NP_195404.6 GI:240256211) (DAR1), At1g78420 (NP_001185425.1 GI:334183988) (DA2), At1g17145 (NP_564016.1 GI:18394446) (DA2L), and At3g63530 (NP_001030922.1 GI: 79316205) (EOD1/BB).

2. Results 2.1 the Da2-1 Mutant Produces Large Seeds

Figure 10:
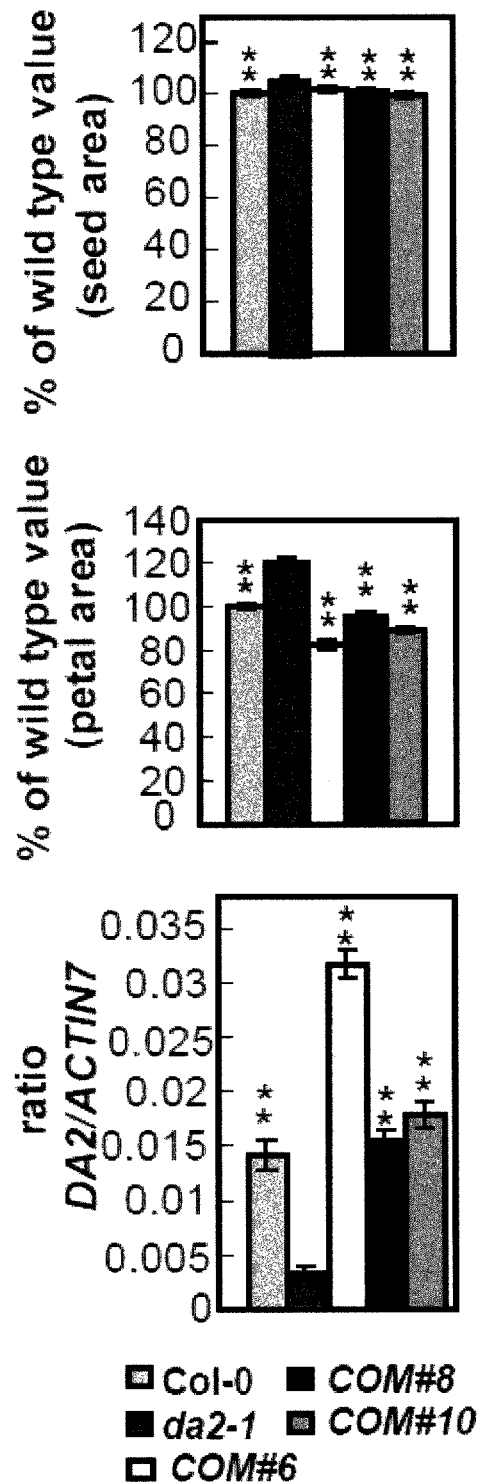
FIG. 10 shows the projective area of Col-0, da2-1, COM#6, COM#8, and COM#10 seeds (upper panel), where COM is da2-1 transformed with the DA2 coding sequence driven by its own promoter; petal area of Col-0, da2-1, COM#6, COM#8, and COM#10 plants (middle panel) and quantitative real-time RT-PCR analysis of the DA2 gene expression in Col-0, da2-1, COM#6, COM#8, and COM#10 seedlings (lower panel). Values (D and E) are given as mean±SE relative to the da2-1 values, set at 100%. **, P<0.01 compared with the da2-1 mutant (Student's t-test).
Figure 15:
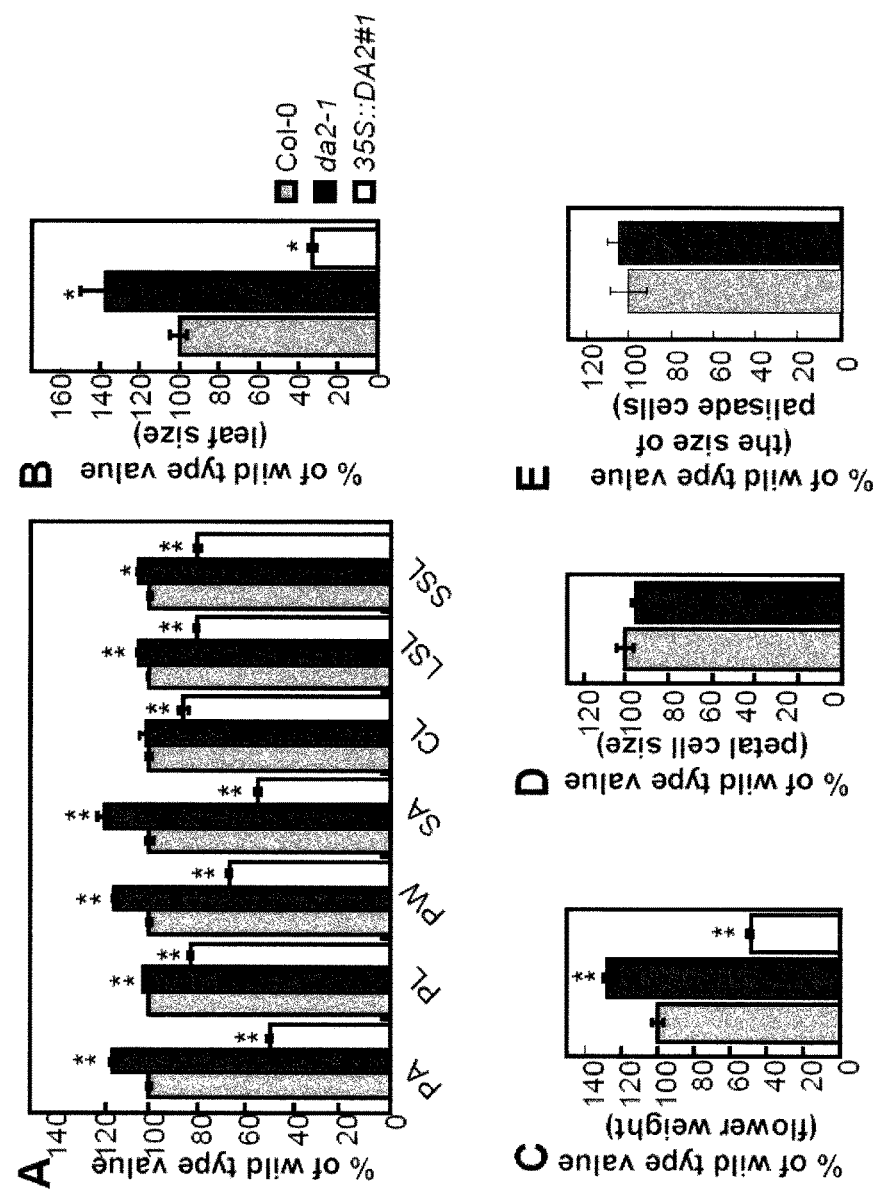
FIG. 15 shows that da2-1 mutants display increased organ size. 15A shows petal length (PL), petal width (PW), petal area (PA), sepal area (SA), carpel length (CL), long stamen length (LSL) and short stamen length (SSL) of Col-0, da2-1 and 35S:DA2#1 plants. 15B shows fifth leaf area of Col-0, da2-1 and 35S:DA2#1 plants. 15C shows weight of Col-0, da2-1 and 35S:DA2#1 flowers. 15D shows the size of adaxial epidermal cells in the maximal width region of Col-0 and da2-1 petals. 15E shows the size of palisade cells in the fifth leaves of Col-0 and da2-1. The opened flowers (stage 14) were used to measure the size of petals (15A), flower weight (C) and the size of epidermal cells (15D). Values (A-E) are given as mean±SE relative to the respective wild-type values, set at 100%. **, P<0.01 compared with the wild type (Student's t-test).

To further understand the mechanisms of ubiquitin-mediated control of seed size, we collected the publicly available T-DNA insertion lines of some predicted ubiquitin ligase genes that were expressed in *Arabidopsis* ovules and/or seeds in several microarray studies and investigated their seed growth phenotypes. From this screen, we identified several T-DNA insertion mutants with altered seed size. We designated one of these mutants da-2-1, referring to the order of discovery for large seed size mutants (DA means "large" in Chinese). Seeds produced by da2-1 were larger and heavier than the wild-type seeds (FIGS. 1A, 3C and 3D). Seed number per silique and seed yield per plant in da2-1 were slightly higher than those in wild type (FIGS. 1B and 10). By contrast, total number of seeds per plant in da2-1 was not significantly increased, compared with that in wild type (FIG. 1D). The da2-1 plants were higher than wild-type plants at the mature stage (FIG. 1E). In addition, da2-1 mutant plants formed large flowers and leaves as well as increased biomass compared with wild-type plants (FIG. 2; FIG. 15). The increased size of da2-1 mutant petals and leaves was not caused by larger cells (FIG. 15), indicating that it is the number of petal and leaf cells that is higher.

2.2 DA2 Acts Synergistically with DA1 to Control Seed Size, but does so Independently of EOD1

Figure 3:
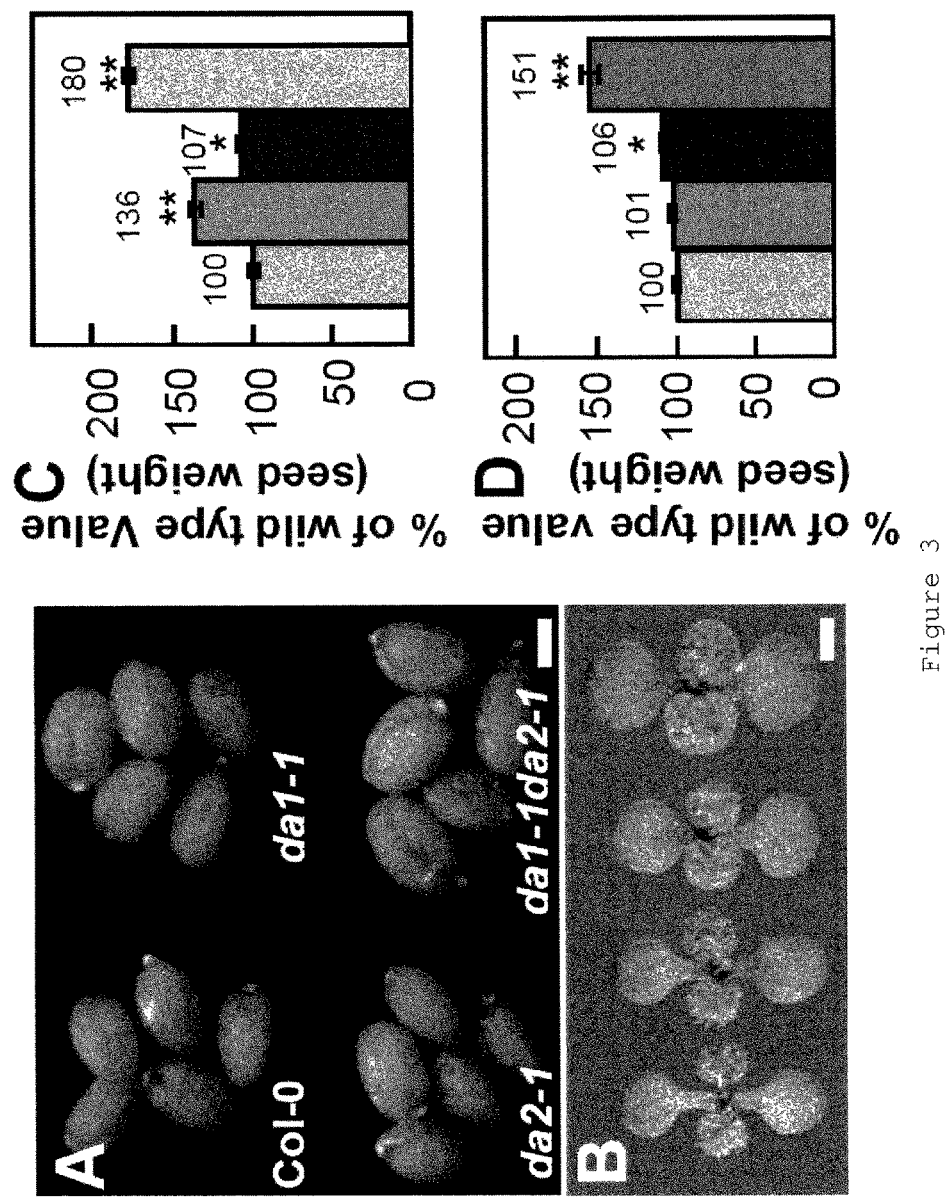
FIG. 3 shows that DA1 and DA2 act synergistically to control seed size. 3A shows dry seeds of Col-0, da1-1, da2-1 and da1-1 da2-1. 3B shows 10-day-old seedlings of Col-0, da2-1, da1-1 and da1-1 da2-1 (from left to right). 3C shows Seed weight of Col-0, da1-1, da2-1 and da1-1 da2-1. 3D shows seed weight of Col-0, da1-ko1, da2-1 and da1-ko1 da2-1. Values are given as mean±SE relative to the respective wild-type values, set at 100%. **, P<0.01 and *, P<0.05 compared with the wild type (Student's t-test). Bars: A, 0.1 mm; B, 1 m
Figure 4:
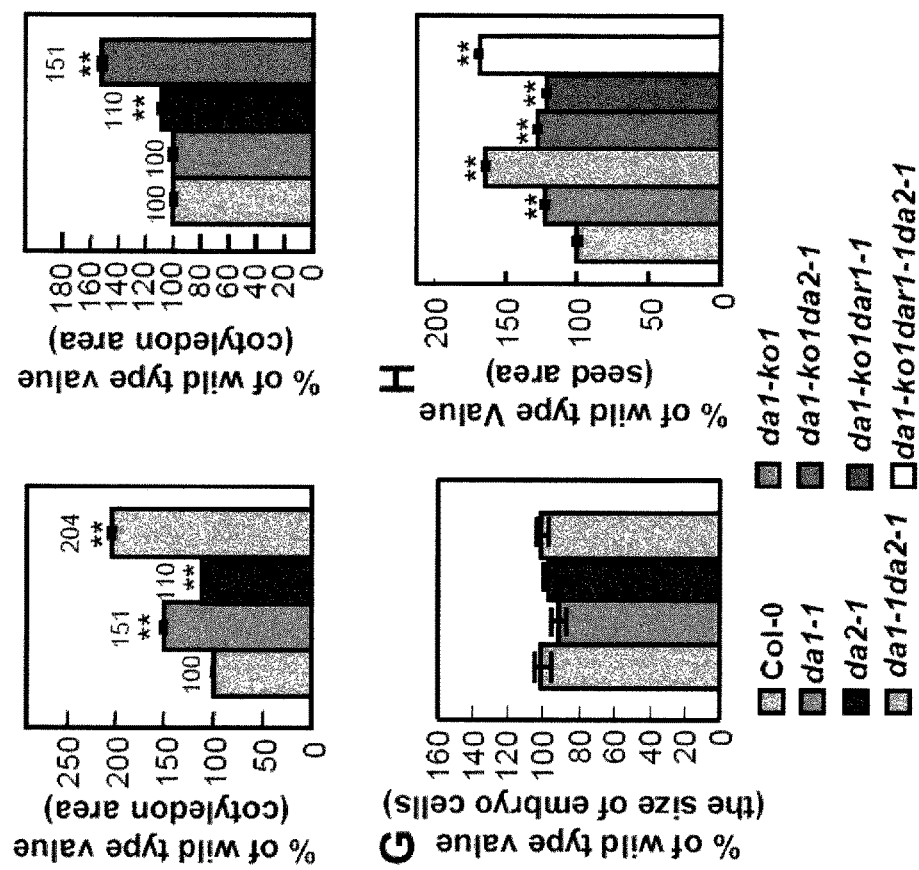
FIG. 4 shows that DA1 and DA2 act synergistically to control seed size. Upper left panel shows cotyledon area of 10-day-old Col-0, da1-1, da2-1 and da1-1 da2-1 seedlings. Upper right panel shows cotyledon area of 10-day-old Col-0, da1-ko1, da2-1 and da1-ko1 da2-1 seedlings. Lower left panel shows the average area of palisade cells in cotyledons of Col-0, da1-1, da2-1 and da1-1 da2-1 embryos. Lower right panel shows projective area of Col-0, da1-1, da1-1 da2-1, da1-ko1 da2-1, da1-ko1 dar1-1 and da1-ko1 dar1-1 da2-1 seeds. Values are given as mean±SE relative to the respective wild-type values, set at 100%. **, P<0.01 and *, P<0.05 compared with the wild type (Student's t-test). Bars: A, 0.1 mm; B, 1 m

The da2-1 mutant showed a weak but similar seed size phenotype to da1-1 (Li et al., 2008), providing indication that DA1 and DA2 could function in a common pathway. To test for a genetic interaction between DA1 and DA2, we generated a da1-1 da2-1 double mutant and determined its seed size. Although the da2-1 mutant had slightly larger and heavier seeds than wild type (FIGS. 1A, 3C and 3D), the da2-1 mutation synergistically enhanced the seed size and weight phenotypes of da1-1 (FIGS. 3A and 3C), revealing a synergistic genetic interaction between DA1 and DA2 in seed size. The changes in seed size were reflected in the size of the embryos and resulting seedlings (FIG. 3B). We further measured cotyledon area of 10-d-old seedlings. A synergistic enhancement of cotyledon size of da1-1 by the da2-1 mutation was also observed (FIGS. 3B and 4). The mutant protein encoded by the da1-1 allele has a negative activity toward DA1 and a DA1-related protein (DAR1), the most closely-related family member (Li et al., 2008).

Figure 16:
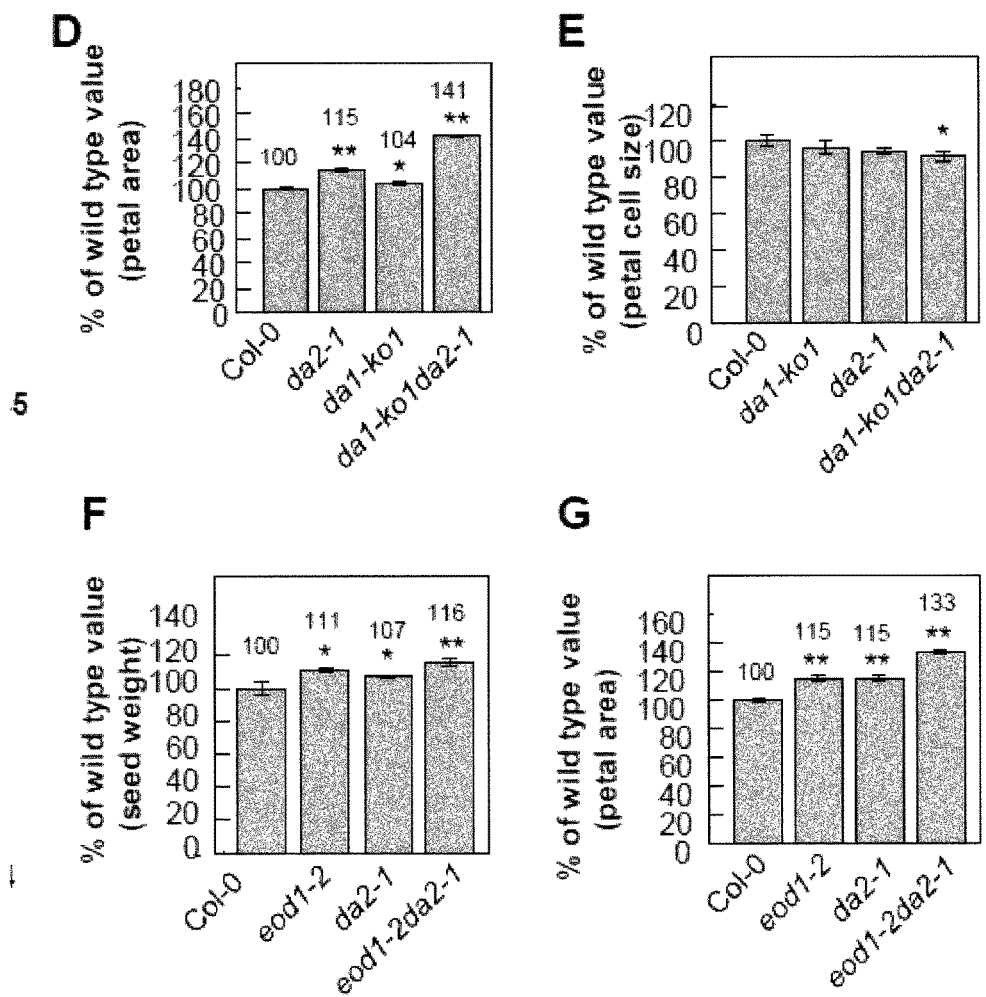
FIG. 16 shows that DA1 and DA2 act synergistically to control seed size. 16D shows the petal area of Col-0, da1-ko1, da2-1 and da1-ko1da2-1 flowers. 16E shows the size of adaxial epidermal cells in the maximal width region of Col-0, da1-ko1, da2-1 and da1-ko1da2-1 petals. 16F shows seed weight of Col-0, eod1-2, da2-1 and eod1-2 da2-1. 16G shows petal area of Col-0, eod1-2, da2-1 and eod1-2 da2-1. The opened flowers (stage 14) were used to measure the size of petals (16D and 16G) and the size of epidermal cells (16E). Values (16D-G) are given as mean±SE relative to the respective wild-type values, set at 100%. **, P<0.01 and *, P<0.05 compared with the wild type (Student's t-test). Bar: 0.1 mm.
Figure 17:
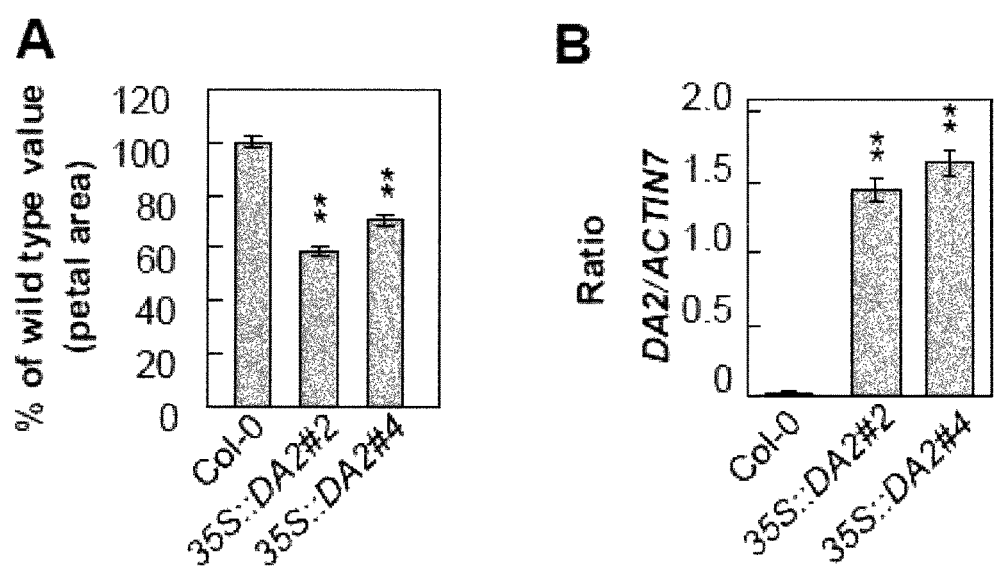
FIG. 17 shows that overexpression of DA2 restricts organ growth. 17A shows that petal area of Col-0, 35S:DA2#2 and 35S:DA2#4. 17B shows expression levels of DA2 in Col-0, 35S:DA2#2 and 35S:DA2#4 seedlings. Values (A and B) are given as mean±SE relative to Col-0 values, set at 100%. **, P<0.01 compared with the wild type (Student's ttest).

Double da1-ko1 dar1-1 T-DNA insertion mutants exhibited the da1-1 phenotypes, while da1-ko1 and dar1-1 single mutants did not show an obvious seed size phenotype (Li et al., 2008). As da1-1 and da2-1 act synergistically to increase seed size, one would expect that the da1-ko1 might synergistically enhance the phenotypes of da2-1. To test this, we generated the da1-ko1 da2-1 double mutant. As shown in FIG. 3D, the seed size and weight phenotypes of da2-1 were also synergistically enhanced by the da1-ko1 mutation. We further measured cotyledon area of 10-d-old seedlings. The da1-ko1 mutation synergistically enhanced the cotyledon size phenotype of da2-1 (FIG. 4 top right). Similarly, a synergistic enhancement of petal size of da2-1 by the da1-ko1 mutation was also observed (FIG. 16D). These results further demonstrate the synergistic effects of the simultaneous disruption of both DA1 and DA2.

We further measured the size of embryo cells and petal epidermal cells. Cell size in da1-1 da2-1 and da1-ko1 da2-1 double mutants was not increased, compared with that measured in their parental lines (FIG. 4 lower left; FIG. 16E), providing indication that DA1 and DA2 act synergistically to restrict cell proliferation processes.

The da1-1 da2-1 double mutant had larger seeds than da1-ko1 da2-1 double mutants (FIGS. 3C, 3D and 4), which is consistent with our previous report that the da1-1 allele had stronger phenotypes than da1-ko1 (Li et al., 2008). The size of da1-1 seeds was similar to that of da1-ko1 dar1-1 double mutant seeds because the da1-1 allele has a negative activity toward DA1 and DAR1 (FIG. 4 lower right) (Li et al., 2008). Therefore, one would expect that the size of da1-1 da2-1 double mutant seeds might be similar to that of da1-ko1 dar1-1 da2-1 triple mutant seeds. We therefore generated a da1-ko1 dar1-1 da2-1 triple mutant and investigated its seed size. As shown in FIG. 4, the size of da1-ko1 dar1-1 da2-1 triple mutant seeds was comparable with that of da1-1 da2-1 double mutant seeds, but larger than that of da1-ko1 da2-1 double mutant seeds. Thus, these genetic analyses further support that the da1-1 allele has a negative effect on both DA1 and DAR1 (Li et al., 2008).

We have previously identified an enhancer of da1-1 (EOD1), which is allelic to BIG BROTHER (BB) (Disch et al., 2006; Li et al., 2008). The eod1 mutations synergistically enhanced the seed size phenotype of da1-1 (Li et al., 2008). Similarly, the seed size and weight phenotypes of da2-1 were synergistically enhanced by da1-1 and da1-ko1 (FIGS. 3A,3C and 3D). We therefore asked whether DA2 and EOD1 could function in a common pathway. To determine genetic relationships between DA2 and EOD1, we analyzed an eod1-2 da2-1 double mutant. The genetic interaction between eod1-2 and da2-1 was essentially additive for both seed weight and petal size compared with their parental lines (FIG. 16), providing indication that DA2 functions to influence seed and organ growth separately from EOD1.

2.3 DA2 Acts Maternally to Influence Seed Size

Figure 6:
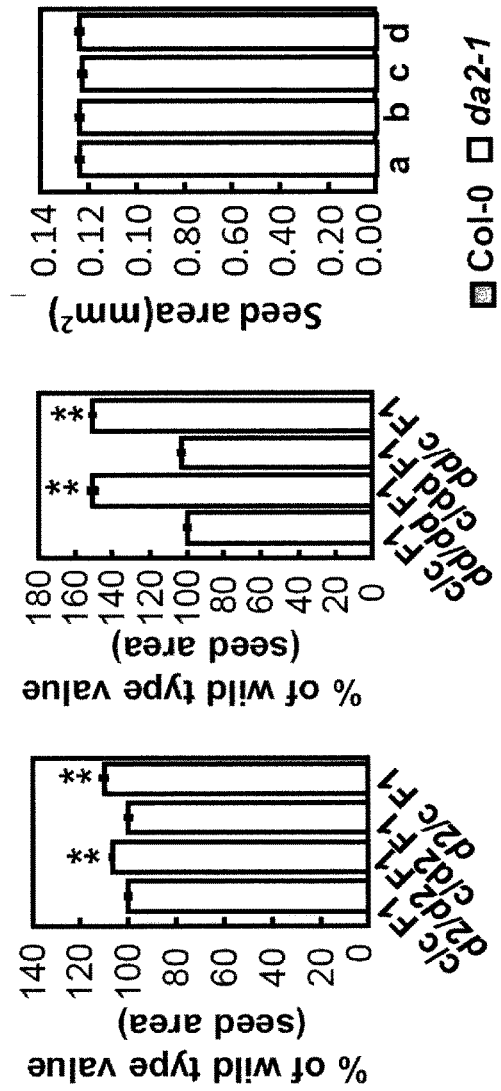
FIG. 6 shows (left panel) the projective area of Col-0× Col-0 (c/c) F1, da2-1×da2-1 (d2/d2) F1, Col-0×da2-1 (c/d2) F1, and da2-1×Col-0 (d2/c) F1 seeds and (middle panel) the projective area of Col-0×Col-0 (c/c) F1, da1-ko1 da2-1× da1-ko1 da2-1 (dd/dd) F1, Col-0×da1-ko1 da2-1 (c/dd) F1, da1-ko1 da2-1×Col-0 (dd/c) F1 seeds. Right panel shows projective seed area after pollination of da1-ko1/+da2-1/+ plants with da1-ko1 da2-1 double mutant pollen leading to the development of da1-ko1/+da2-1/+ (a), da1-ko1/+da2-1da2-1 (b), da1-ko1/da1-ko1 da2-1/+ (c) and da1-ko1 da2-1 (d) embryos within da1-ko1/+da2-1/+ seed coats. Projective area of individual seeds from da1-ko1/+da2-1/+ plants fertilized with da1-ko1 da2-1 double mutant pollen was measured. These seeds were further genotyped for da1-ko1 and da2-1 mutations. The data shows that da1-ko1 and da2-1 mutations are not associated with variation in the size of these seeds (P>0.05, Student's t-test). Values are given as mean±SE relative to the respective wild-type values, set at 100%. **, P<0.01 compared with the wild type (Student's t-test). Bars: A-D, 0.5 mm.

Considering that the size of seeds is affected by the maternal and/or zygotic tissues, we asked whether DA2 functions maternally or zygotically. To test this, we performed reciprocal cross experiments between wild type and da2-1. As shown in FIG. 6, the effect of da2-1 on seed size was observed only when maternal plants are homozygous for the da2-1 mutation. Seeds produced by maternal da2-1 plants, regardless of the genotype of the pollen donor, were consistently larger than those produced by maternal wild-type plants. This result indicates that da2-1 can act maternally to influence seed size. We have previously demonstrated that DA1 also functions maternally to control seed size (Li et al. 2008). As the da1-ko1 mutation synergistically enhanced the seed size phenotype of da2-1 (FIG. 3D), we further conducted reciprocal cross experiments between wild type and da1-ko1 da2-1 double mutant. Similarly, the effect of da1-ko1 da2-1 on seed size was observed only when da1-ko1 da2-1 acted as the maternal plant (FIG. 6).

Pollinating da1-ko1/+da2-1/+ plants with da1-ko1 da2-1 double mutant pollen leads to the development of da1-ko1 da2-1, da1-ko1/da1-ko1 da2-1/+, da1-ko1/+da2-1da2-1 and da1-ko1/+da2-1/+ embryos within da1-ko1/+da2-1/+ seed coats. We further measured the size of individual seeds from da1-ko1/+da2-1/+ plants fertilized with da1-ko1 da2-1 double mutant pollen and genotyped da1-ko1 and da2-1 mutations. Our results show that da1-ko1 and da2-1 mutations are not associated with variation in the size of these seeds (FIG. 6). Together, these analyses indicate that the embryo and endosperm genotypes for DA1 and DA2 do not affect seed size, and DA1 and DA2 are required in sporophytic tissue of the mother plant to control seed growth.

2.4 DA2 Acts Synergistically with DA1 to Affect Cell Proliferation in the Maternal Integuments The reciprocal crosses showed that DA1 and DA2 function maternally to determine seed size (FIG. 6) (Li et al., 2008). The integuments surrounding the ovule are maternal tissues and form the seed coat after fertilization, which may physically restrict seed growth. Several studies showed that the integument size of ovules determines seed size (Schruff et al., 2006; Adamski et al., 2009). We therefore asked whether DA1 and DA2 act through the maternal integuments to control seed size. To test this, we investigated mature ovules from wild type, da1-1, da2-1 and da1-1 da2-1 at 2 days after emasculation. The size of da1-1 ovules was dramatically larger than that of wild-type ovules (FIGS. 5 and 7), consistent with our previous findings (Li et al., 2008).

Figure 5:
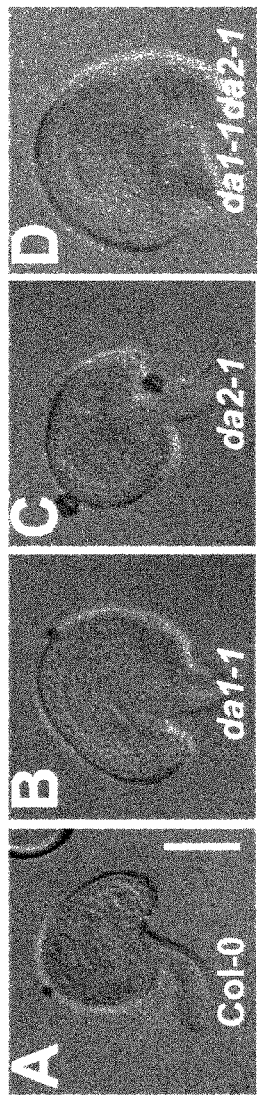
FIG. 5 shows that DA1 and DA2 act synergistically to control cell proliferation in maternal integuments of developing seeds. (5A-5D) show mature Ovules of Col-0, da1-1, da2-1 and da1-1 da2-1 respectively. The da1-1 mutation synergistically enhances the ovule size of da1-1.
Figure 7:
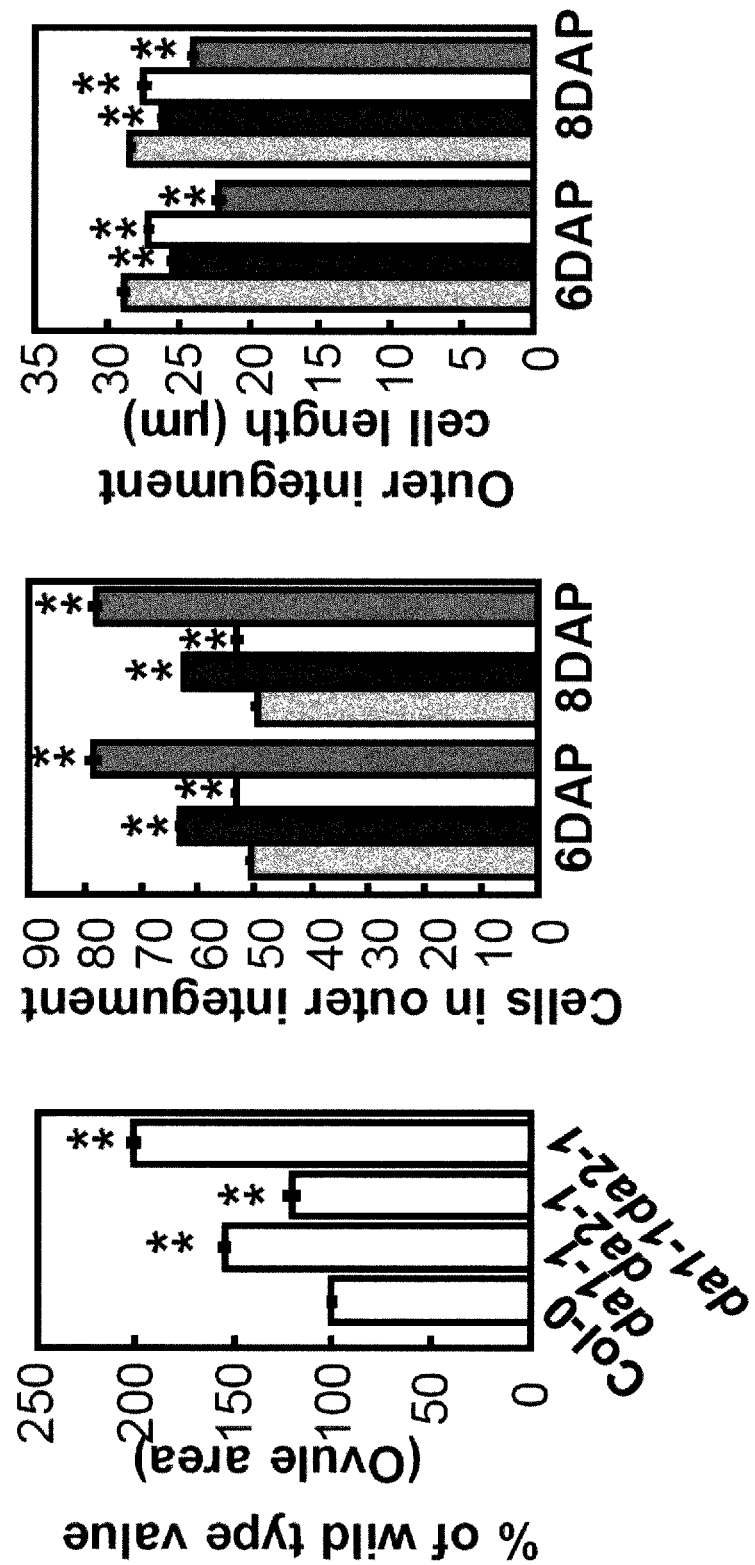
FIG. 7 shows (left panel) the projective area of Col-0, da1-1, da2-1 and da1-1 da2-1 mature ovules; (middle panel) the number of cells in the outer integuments of Col-0, da1-1, da2-1 and da1-1 da2-1 seeds at 6 DAP and 8 DAP; and (right panel) the average length of cells in the outer integuments of Col-0, da1-1, da2-1 and da1-1 da2-1 seeds at 6 DAP and 8 DAP calculated from the outer integument length and cell number for individual seeds.

The da2-1 ovules were also larger than wild-type ovules (FIGS. 5, and 7). The da2-1 mutation synergistically enhanced the ovule size phenotype of da1-1, consistent with their synergistic interactions in seed size.

We investigated the outer integument cell number of developing seeds in wild type, da1-1, da2-1 and da1-1 da2-1 at 6 DAP and 8 DAP. In wild-type seeds, the number of outer integument cells at 6 DAP was similar to that at 8 DAP (FIG. 7 middle panel), indicating that cells in the outer integuments of wild-type seeds completely stop division at 6 DAP. Similarly, cells in the outer integuments of da1-1, da2-1 and da1-1 da2-1 seeds completely stopped cell proliferation at 6 DAP. The number of outer integument cells in da1-1 and da2-1 seeds was significantly increased compared with that in wild-type seeds (FIG. 7). The da2-1 mutation synergistically enhanced the outer integument cell number of da1-1. We further investigated the outer integument cell length of wild-type, da1-1, da2-1 and da1-1 da2-1 seeds at 6 and 8 days after pollination. Cells in da1-1, da2-1 and da1-1 da2-1 outer integuments were significantly shorter than those in wild-type outer integuments (FIG. 7 right panel), providing indication of a compensation mechanism between cell proliferation and cell expansion in the integuments. Thus, these results show that DA2 acts synergistically with DA1 to restrict cell proliferation in the maternal integuments.

2.5 DA2 Encodes a Functional E3 Ubiquitin Ligase

Figure 8:
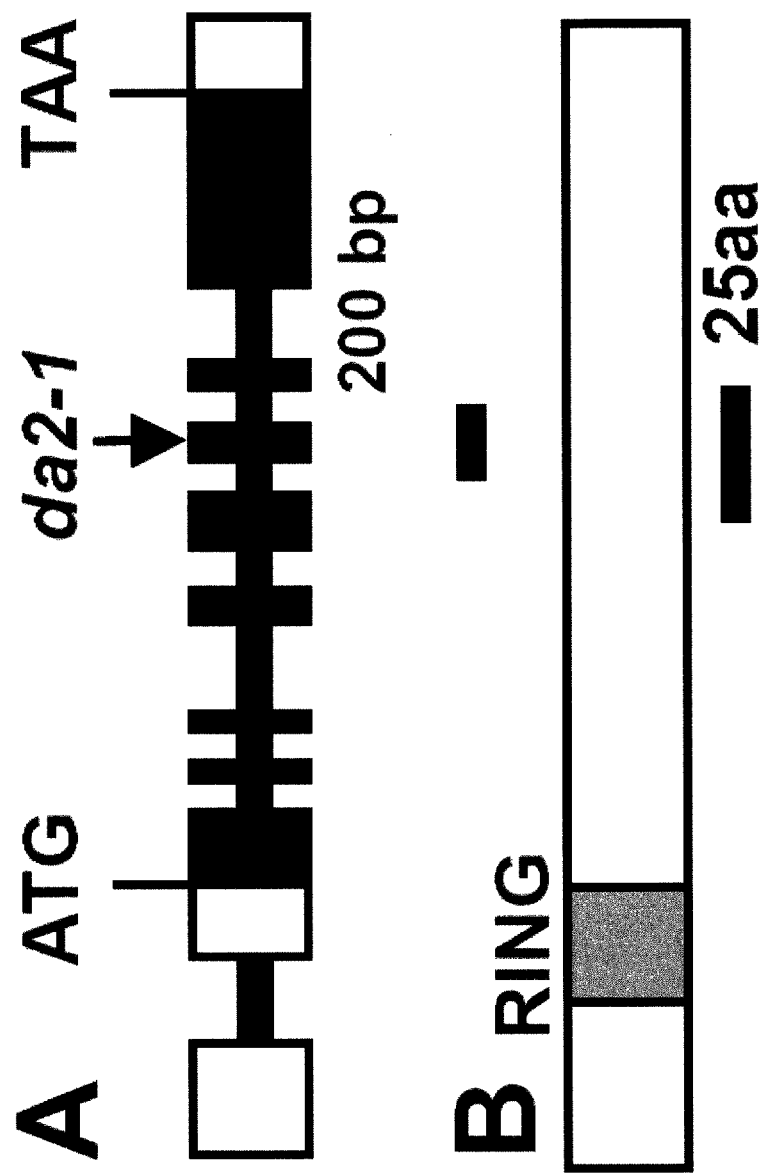
FIG. 8A shows the DA2 gene structure. The start codon (ATG) and the stop codon (TAA) are indicated. Closed boxes indicate the coding sequence, open boxes indicate the 5' and 3' untranslated regions, and lines between boxes indicate introns. The T-DNA insertion site (da2-1) in the DA2 gene is shown.
FIG. 8B shows that the DA2 protein contains a predicted RING domain.

The da2-1 mutation was identified with T-DNA insertion in the seventh exon of the gene At1g78420 (FIG. 8A). The T-DNA insertion site was further confirmed by PCR using T-DNA specific and flanking primers and sequencing PCR products. The full-length mRNA of At1g78420 could not be detected by semi-quantitative RT-PCR in da2-1 mutant. We expressed the At1g78420 CDS under the control of its own promoter in da2-1 plants and isolated 62 transgenic plants. Nearly all transgenic lines exhibited complementation of da2-1 phenotypes (FIG. 10), indicating that At1g78420 is the DA2 gene.

Figure 2:
FIG. 2 shows 4-d-old plants (F) of Col-0 (left), da2-1 (middle) and 35S::DA2#1 (right) and flowers (G) of Col-0 (top), da2-1 (middle) and 35S::DA2#1 (bottom).

To further characterize DA2 function, in particular gain of function phenotypes, we expressed the coding region of DA2 under the control of the CaMV 35S promoter in wild-type plants and isolated 77 transgenic plants. Overexpression of DA2 caused decreases in seed size, seed yield per plant and seed number per plant (FIGS. 1A, 1C and 1D). In addition, most transgenic plants overexpressing DA2 had small flowers and leaves, short siliques, reduced plant height as well as decreased biomass compared with wild type (FIGS. 1E, 2 and 15). These results further support the role of DA2 in limiting seed and organ growth.

Figure 9:
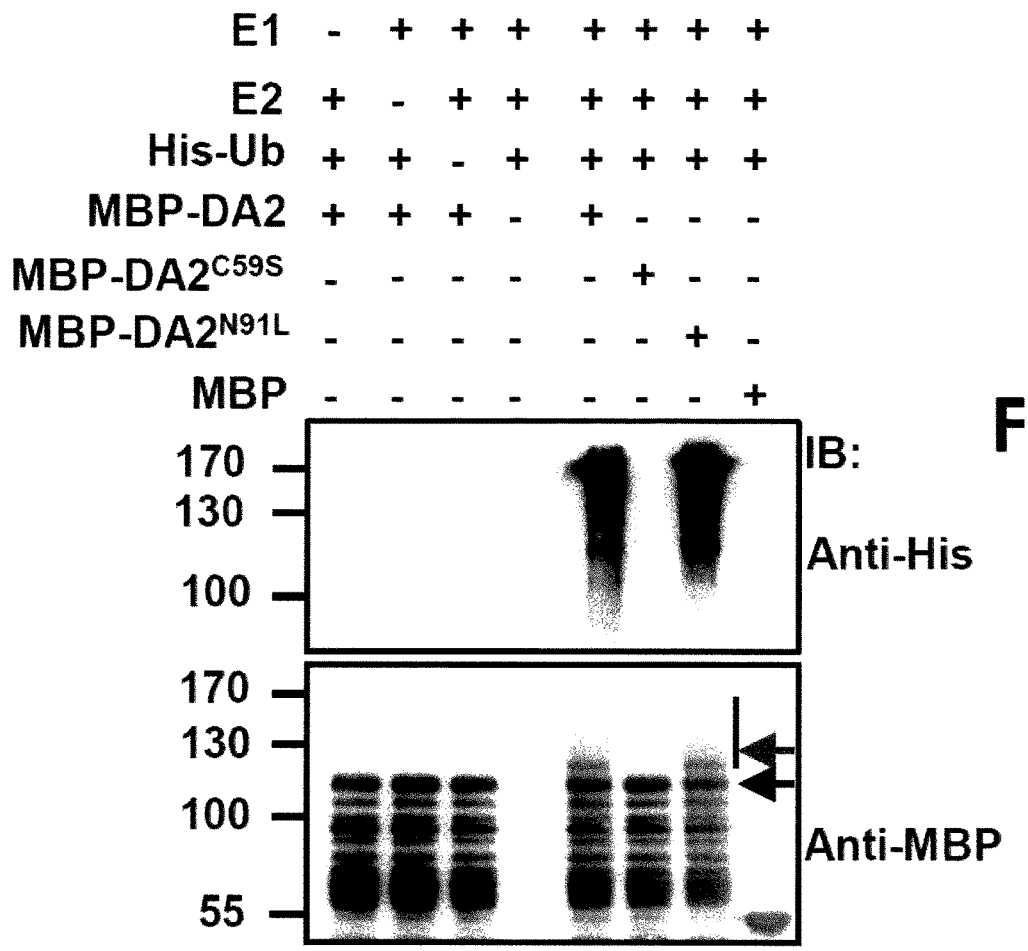
FIG. 9 shows E3 ubiquitin ligase activity of DA2. MBP-DA2 and mutated DA2 (MBP-DA2C59S and MBP-DA2N91L) fusion proteins were assayed for E3 ubiquitin ligase activity in the presence of E1, E2 and His-ubiquitin (His-Ub). Ubiquitinated proteins were detected by immunoblotting (IB) with anti-His antibody (Anti-His) and anti-MBP antibody (Anti-MBP), respectively. The lower arrow indicates MBP-DA2 proteins, and the upper arrow shows ubiquitinated MBP-DA2 proteins.

The DA2 gene is predicted to encode a 402-amino-acid protein containing one predicted RING domain (59-101) (FIG. 8B; Table 1). To investigate whether DA2 has E3 ubiquitin ligase activity, we expressed DA2 in *Escherichia coli* as a fusion protein with maltose binding protein (MBP) and purified MBP-DA2 protein from the soluble fraction. In the presence of an E1 ubiquitin activating enzyme, an E2 conjugating enzyme, His-ubiquitin and MBP-DA2, a polyubiquitination signal was observed by western blot using an anti-His antibody (FIG. 9, fifth lane from the left). The anti-MBP blot analysis also showed that MBP-DA2 was ubiquitinated (FIG. 9, fifth lane from the left). However, in the absence of any of E1, E2, His-ubiquitin or MBP-DA2, no polyubiquitination was detected (FIG. 9, first to fourth lanes from the left), demonstrating that DA2 is a functional E3 ubiquitin ligase. The RING motif is essential for the E3 ubiquitin ligase activity of RING finger proteins (Xie et al., 2002). Therefore, we tested whether an intact RING finger domain was required for DA2 E3 ligase activity. A single amino acid substitution allele was produced by mutagenizing Cysteine-59 to Serine (C59S), as this mutation is predicted to disrupt the RING domain (Tables 1 and 2). An in vitro ubiquitination assay indicated that the E3 ligase activity was abolished in the C59S mutant of DA2 (FIG. 9, sixth lane from the left), indicating that an intact RING domain is required for DA2 E3 ubiquitin ligase activity. We further overexpressed DA2 C59S (35S:DA2C59S) in wild-type Col-0 plants and isolated 69 transgenic plants. The seed size of transgenic plants was comparable with that of wild-type plants although transgenic plants had high expression levels of DA2 C59S, indicating that the DA2 C59S mutation affects the function of DA2 in seed growth.

Three RING types, RING-H2, RING-HCa and RING-HCb, and five modified RING types, RING-C2, RING-v, RING-D, RING-S/T and RING-G have been described in *Arabidopsis* (Stone et al., 2005). A new type of RING domain (C5HC2) found in rice GW2 has been proposed (Song et al., 2007). Although the spacing of the cysteines in the predicted RING domain of DA2 was similar to that in the RING domain (C5HC2) of rice GW2, the RING domain of DA2 lacked a conserved histidine residue that was replaced by an asparagine residue (Asn-91) (Tables 1 and 2). This amino acid substitution was also observed in the predicted RING domain of DA2 homologs in dicots, such as soybean and oilseed rape (Table 1). We therefore asked whether this asparagine residue (Asn-91) is crucial for its E3 ubiquitin ligase activity. A single amino acid substitution allele was produced by mutagenizing Asn-91 to Leucine (N91L). An in vitro ubiquitination assay showed that the N91L mutant of DA2 had the E3 ligase activity (FIG. 9, the seventh lane from the left), suggesting that Asn-91 may not be required for DA2 E3 ligase activity. These results suggest that the RING domain of DA2 might be a variant of that found in GW2. We further overexpressed DA2 N91L (35S: DA2N91L) in wild-type plants and isolated 26 transgenic plants. The seeds of transgenic plants were smaller than wild-type seeds, suggesting that the DA2 N91L could restrict seed growth.

2.6 Homologs of *Arabidopsis* DA2

Figure 18:
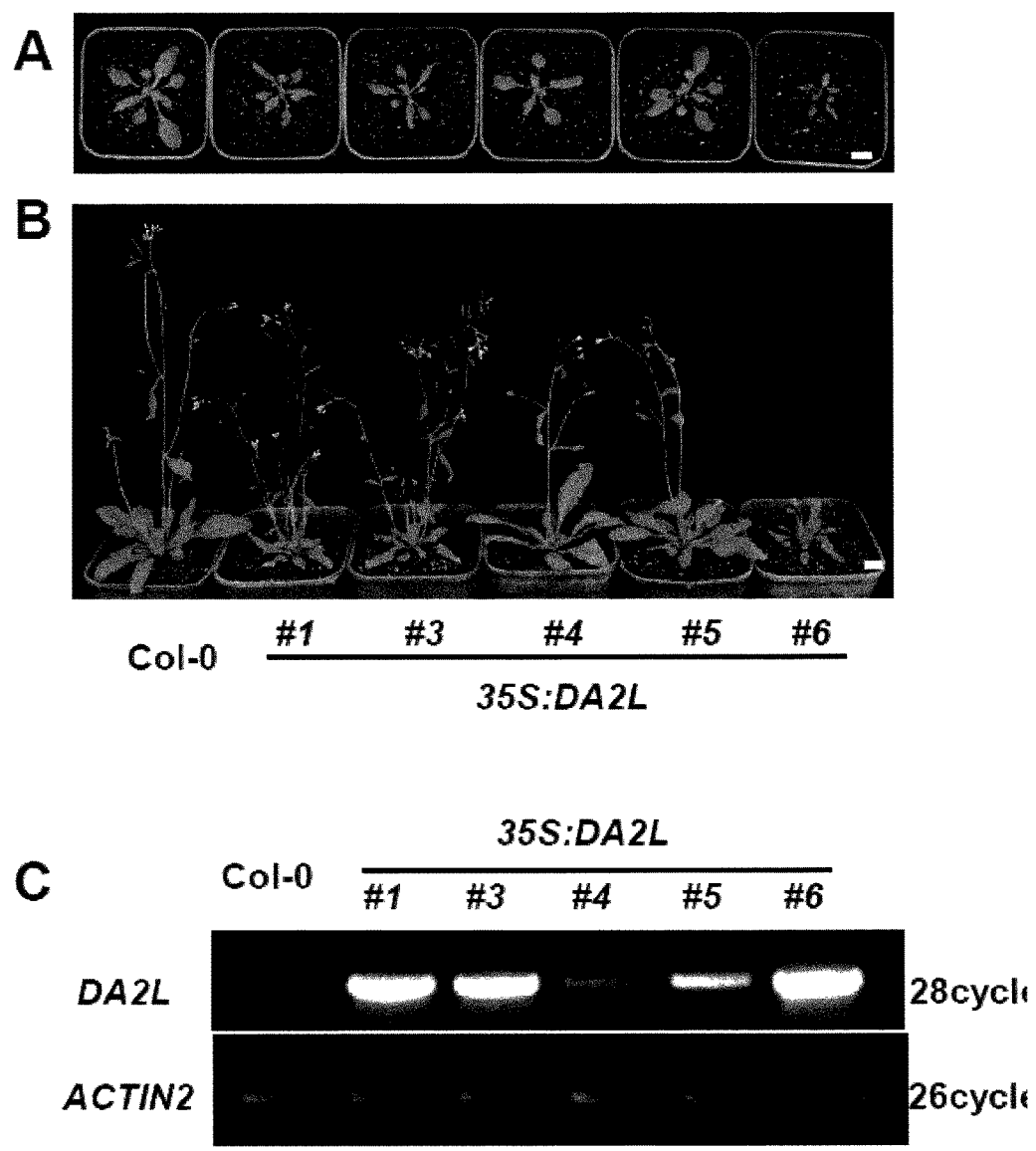
FIG. 18 shows that overexpression of DA2L restricts organ growth. 18A shows 20-day-old plants of Col-0, 35S:DA2L#1, 35S:DA2L#3, 35S:DA2L#4, 35S:DA2L#5, and 35S:DA2L#6. 18B shows 30-day-old plants of Col-0, 35S:DA2L#1, 35S:DA2L#3, 35S:DA2L#4, 35S:DA2L#5, and 35S:DA2L#6. 18C shows RT-PCR analysis of DA2L expression in Col-0, 35S:DA2L#1, 35S:DA2L#3, 35S:DA2L#4, 35S:DA2L#5 and 35S:DA2L#6 seedlings. RT-PCR was performed on first-strand cDNA prepared from 2-week-old seedlings. cDNA was standardized by reference to an ACTIN2 standard. Bars: A, 1 cm, B, 1 cm
Figure 19:
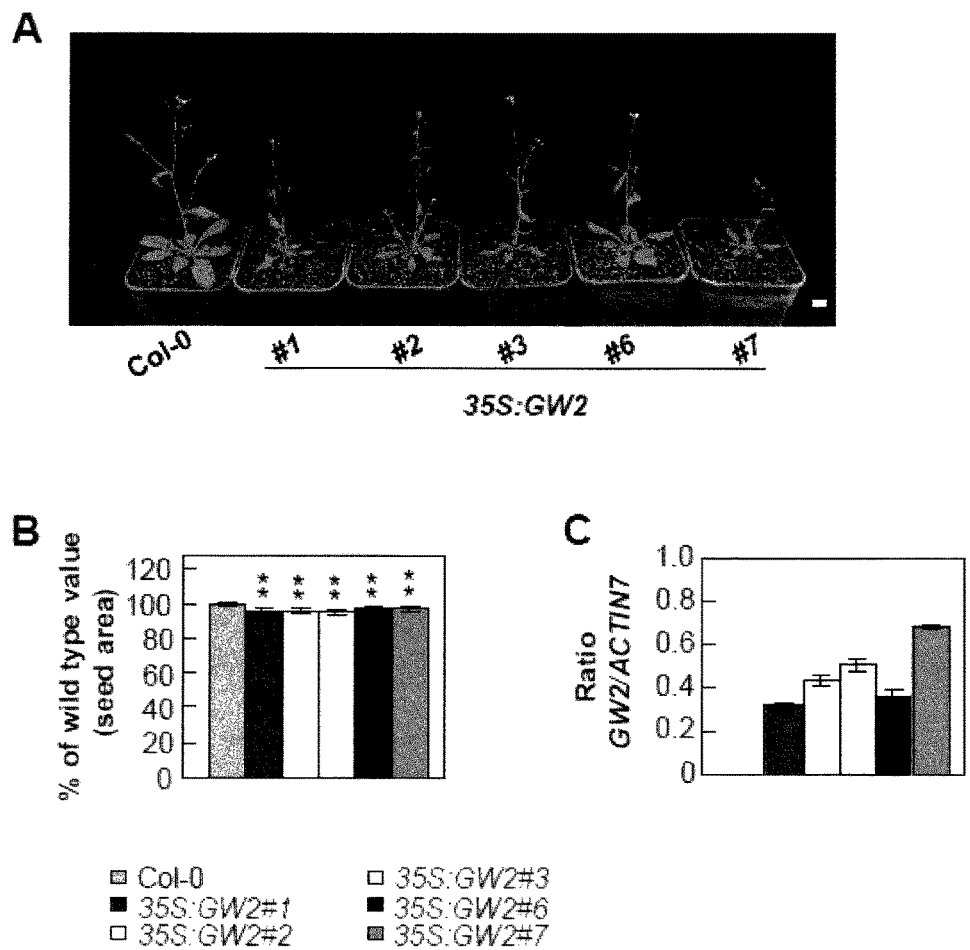
FIG. 19 shows that overexpression of GW2 restricts seed and organ growth. 19A shows 30-day-old plants of Col-0, 35S:GW2#1, 35S:GW2#2, 35S:GW2#3, 35S:GW2#6 and 35S:GW2L#7. 19B shows projective area of Col-0, 35S:GW2#1, 35S:GW2#2, 35S:GW2#3, 35S:GW2#6 and 35S:GW2L#7 seeds. 19C shows quantitative real-time RT-PCR analysis of the GW2 gene expression in Col-0, 35S:GW2#1, 35S:GW2#2, 35S:GW2#3, 35S:GW2#6 and 35S:GW2L#7 seedlings. Values (B) are given as mean±SE relative to Col-0 values, set at 100%. **, P<0.01 compared with the wild type (Student's t-test). Bar: A, 1 cm

Proteins that share significant homology with DA2 outside of the RING domain are found in *Arabidopsis* and crop plants including oilseed rape, soybean, rice, maize and barley (Table 2). One predicted protein in *Arabidopsis* shares extensive amino acid similarity with DA2 and is named DA2-like protein (DA2L; At1g17145). Like 35S: DA2 plants, DA2L-overexpressing lines exhibited small plants and organs (FIG. 18), providing indication that DA2 and DA2L have similar functions. The similar proteins in other plant species show a 39.2%-84.5% amino acid sequence identity with DA2 (Table 2). The homolog in *Brassica napus* had the highest amino acid sequence identity with DA2 (84.5%) (Table 2). Rice GW2 had 43.1% amino acid sequence identities with *Arabidopsis* DA2 (Table 2). As overexpression of GW2 reduced grain width in rice (Song et al., 2007), we asked whether DA2 and GW2 performs similar function in seed size control. We therefore overexpressed GW2 in wild-type plants. Like 35S:DA2 and 35S: DA2L transgenic lines, the *Arabidopsis* transgenic plants overexpressing GW2 produced smaller seeds and organs than wild-type plants, indicating conserved function for *Arabidopsis* DA2 and rice GW2 in seed and organ growth control.

2.7 DA2 and DA1 Show Similar Expression Patterns

Figure 11:
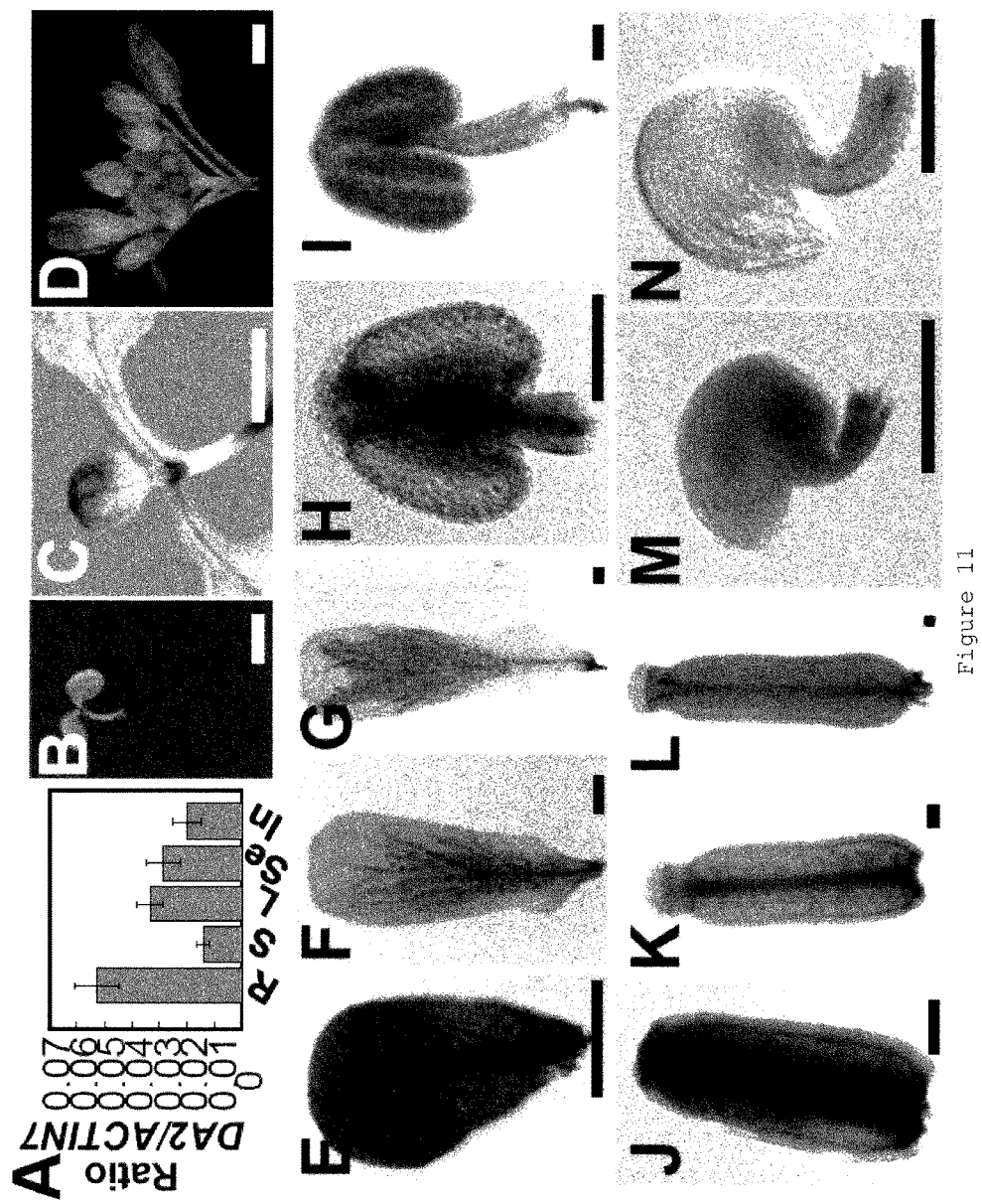
FIG. 11 shows expression patterns of DA2. 11A shows quantitative real-time RT-PCR analysis of the DA2 gene expression. Total RNA was isolated from roots (R), stems (S), leaves (L), seedlings (Se) and inflorescences (In). 11B-11N show DA2 expression activity monitored by pDA2: GUS transgene expression. Four GUS-expressing lines were observed, and all showed a similar pattern, although they differed slightly in the intensity of the staining. Histochemical analysis of GUS activity in a 4-d-old seedling (11B), a 10-d-old seedling (11C), a floral inflorescence (11D), the developing petals (11E-11G), the developing stamens (11H and 11I), the developing carpels (11J-11L), and the developing ovules (11M and 11N) Bars: B-D, 1 mm; E-N, 0.1 mm.

To determine the expression pattern of DA2, RNAs from roots, stems, leaves, seedlings and inflorescences were analyzed by quantitative real-time RT-PCR analysis. DA2 mRNA was detected in all plant organs tested (FIG. 11A). The tissue-specific expression patterns of DA2 were investigated using histochemical assay of GUS activity of transgenic plants containing a DA2 promoter:GUS fusion (pDA2:GUS). GUS activity was detected in roots, cotyledons, leaves and inflorescences (FIGS. 11B and 11C). Relatively high GUS activity was detected in leaf primordia and roots (FIGS. 11B and 11C). In flowers, relatively stronger expression of DA2 was observed in young floral organs than old floral organs (FIGS. 11D-11L). Similarly, higher GUS activity was detected in younger ovules than older ones (FIGS. 11M and 11N). This shows that DA2 expression is regulated temporally and spatially.

2.8 DA1 Interacts with DA2 In Vitro and In Vivo

Figure 12:
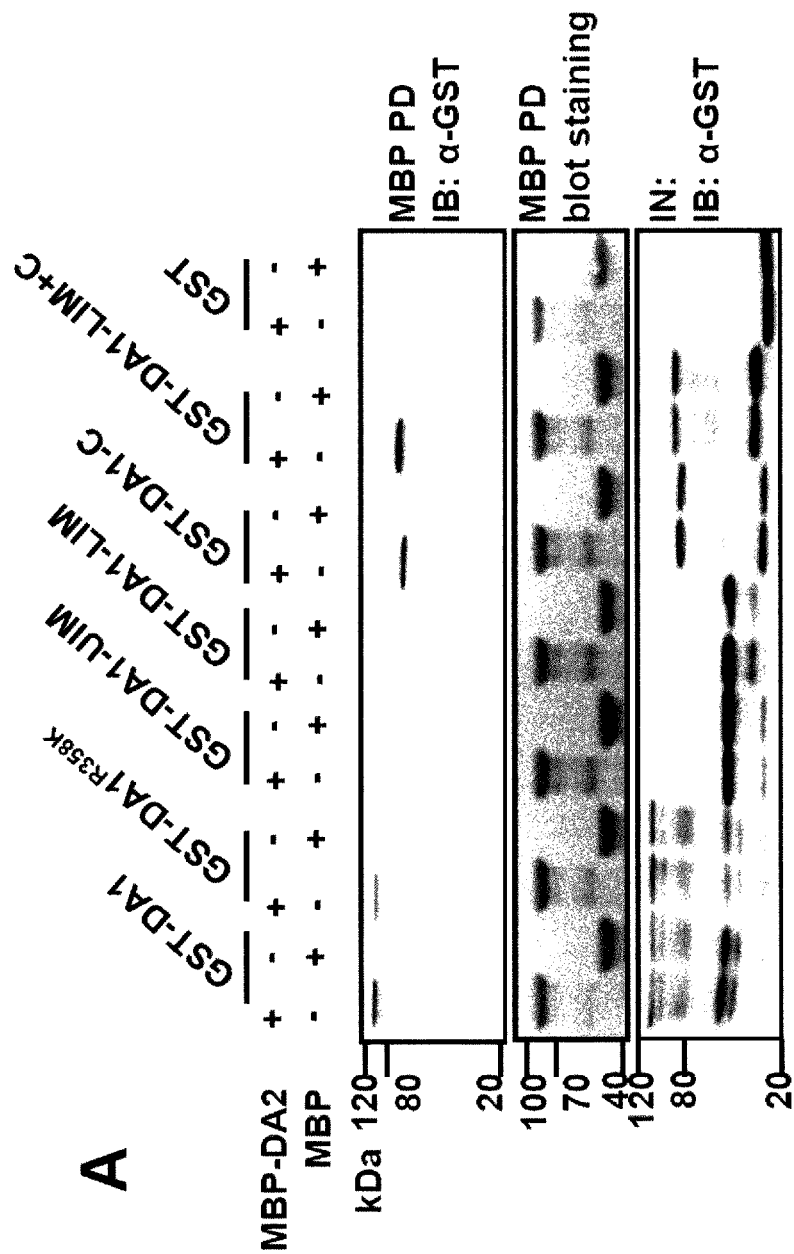
FIG. 12 shows that DA1 directly interacts with DA2 in vitro. GST-DA1, GST-DA1R358K, GST-DA1-UIM, GST-DA1-LIM, GST-DA1-LIM+C and GST-DA1-C were pulled down (PD) by MBP-DA2 immobilized on amylose resin and analyzed by immunoblotting (IB) using an anti-GST antibody.

Our genetic analyses show that DA1 acts synergistically with DA2 to restrict seed and organ growth. We therefore assessed whether DA1 interacts with the E3 ubiquitin ligase DA2 using an in vitro interaction/pull-down experiment. DA1 was expressed as a GST fusion protein, while DA2 was expressed as a MBP fusion protein. As shown in FIG. 12 (first and second lanes from left), GST-DA1 bound to MBP-DA2, while GST-DA1 did not bind to a negative control (MBP). This result indicates that DA1 physically interacts with DA2 in vitro.

Figure 13:
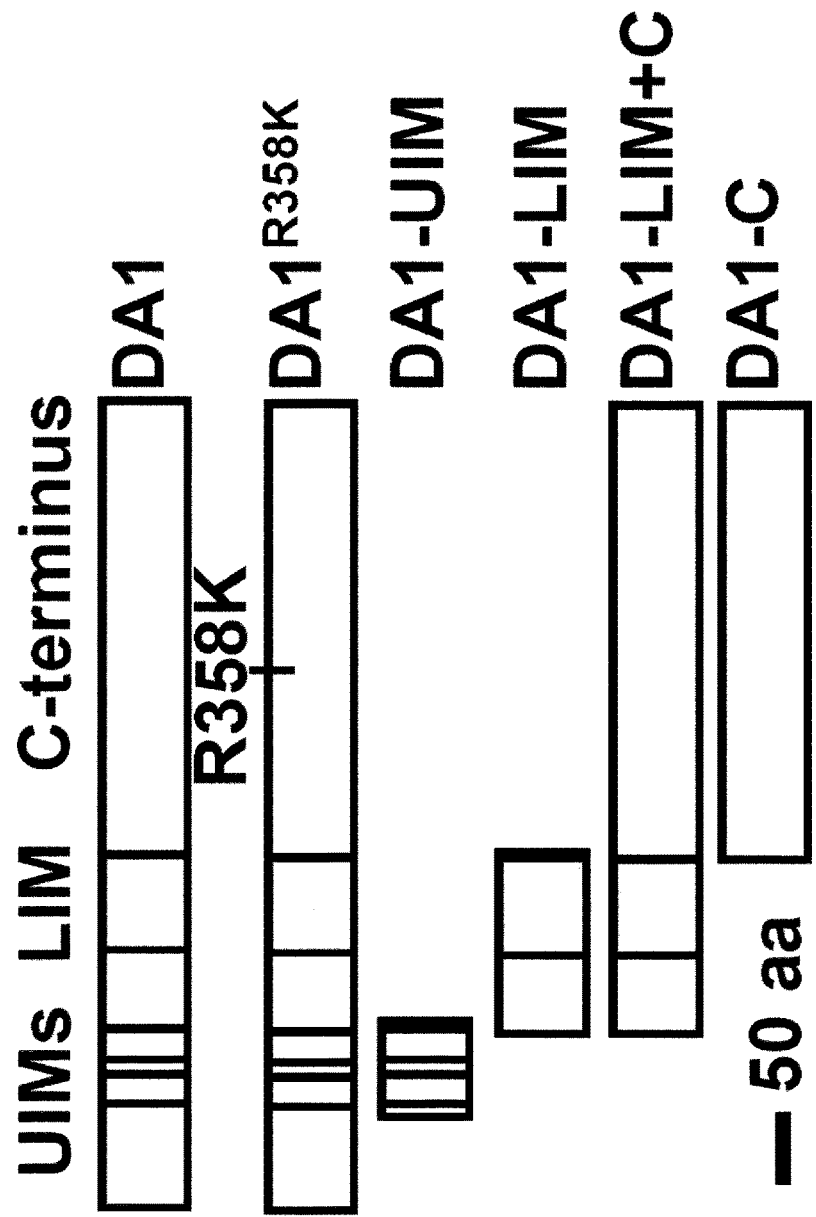
FIG. 13 shows a schematic diagram of DA1 and its derivatives containing specific protein domains. The predicted DA1 protein contains two UIM motifs, a single LIM domain and the C-terminal region.

DA1 contains two ubiquitin interaction motifs (UIM), a single LIM domain and the highly conserved C-terminal region (FIG. 13) (Li et al., 2008). We further asked which domain of DA1 is required for interaction between DA1 and DA2. A series of DA1 derivatives containing specific protein domains were expressed in *Escherichia coli*: DA1-UIM containing only the two UIM domains, DA1-LIM with only the LIM domain, DA1-LIM+C containing only the LIM domain and the C-terminal region, and DA1-C with only the C-terminal region, were expressed as GST fusion proteins (FIG. 13).

DA2 was expressed as an MBP fusion protein and used in pull-down experiments. As shown in FIG. 12, GST-DA1-LIM+C and GST-DA1-C interacted with MBP-DA2, but the GST-DA1-UIM and GST-DA1-LIM did not bind to MBP-DA2. This result indicates that the conserved C-terminal region of DA1 interacts with DA2.

Considering that the mutant protein encoded by the da1-1 allele (DA1R358K) has a mutation in the C-terminal region (FIG. 13) (Li et al., 2008), we asked whether the DA1R358K mutation affects interactions with DA2. Using a GST-DA1R358K fusion protein in pull-down experiments with MBP-DA2, we showed that the mutation in DA1R358K does not affect the interaction between DA1 and DA2 (FIG. 12, third lane from left).

Figure 14:
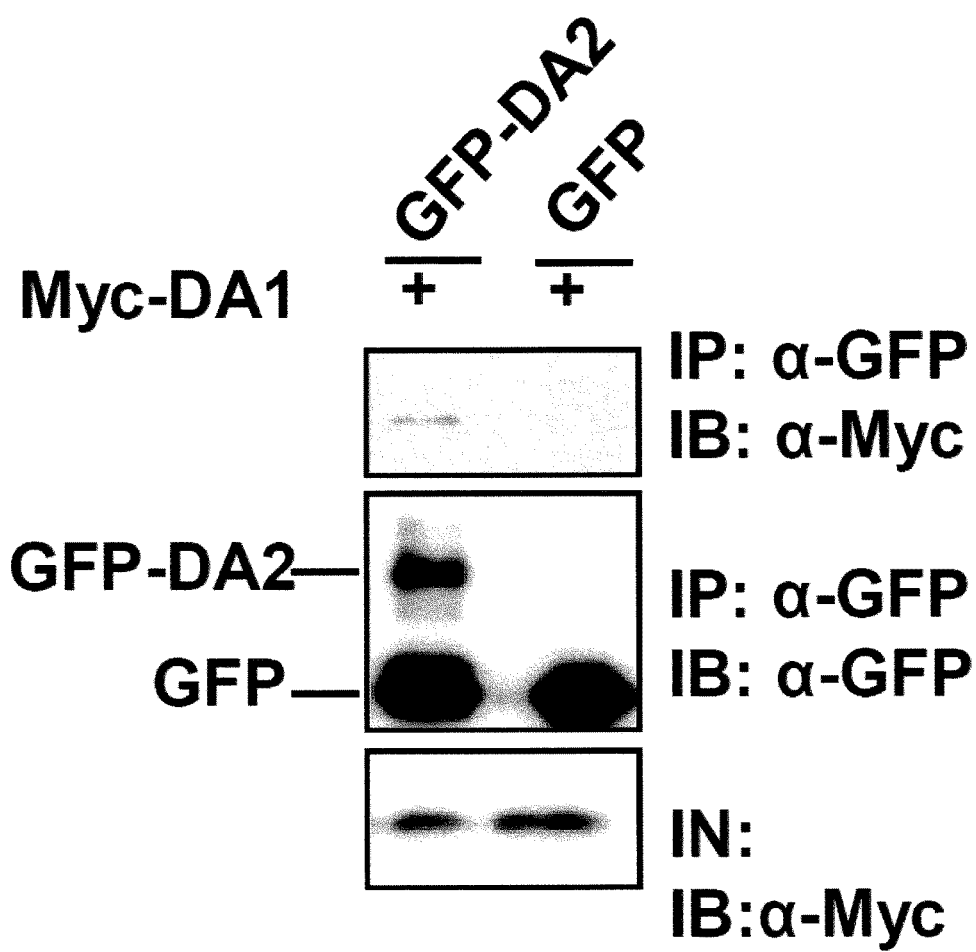
FIG. 14 shows that DA1 interacts with DA2 in vivo. *Nicotiana benthamiana* leaves were transformed by injection of *Agrobacterium tumefaciens* GV3101 cells harbouring 35S:Myc-DA1 and 35S:GFP-DA2 plasmids. Total proteins were immunoprecipitated with GFP-Trap-A, and the immunoblot was probed with anti-GFP and anti-Myc antibodies, respectively. Myc-DA1 was detected in the immunoprecipitated GFP-DA2 complex, indicating that there is a physical association between DA1 and DA2 in planta.

To further investigate possible association between DA1 and DA2 in planta, we used coimmunoprecipitation analysis to detect their interactions in vivo. We transiently coexpressed 35S:Myc-DA1 and 35S:GFP-DA2 in *Nicotiana benthamiana* leaves. Transient coexpression of 35S:GFP and 35S:Myc-DA1 in *Nicotiana benthamiana* leaves was used as a negative control. Total proteins were isolated and incubated with GFP-Trap-A agarose beads to immunoprecipitate GFP-DA2 or GFP. Precipitates were detected with anti-GFP and anti-Myc antibodies, respectively. As shown in FIG. 14, Myc-DA1 was detected in the immunoprecipitated GFP-DA2 complex but not in the negative control (GFP), indicating that there is a physical association between DA1 and DA2 in planta. As the C-terminal region of DA1 interacted with DA2 in the pull-down assay (FIG. 12), we further asked whether the C-terminus of DA1 interacts with DA2 in planta. The co-immunoprecipitation analysis showed that the C-terminal region of DA1 (Myc-DA1-C) was detected in the GFP-DA2 complex but not in the negative control (PEX10-GFP, a RING-type E3 ubiquitin ligase) (Platta et al., 2009; Kaur et al., 2013). Thus, these results indicate that the C-terminal region of DA1 is required for interaction with DA2 in vitro and in vivo.

Seed size in higher plants is a key determinant of evolutionary fitness, and is also an important agronomic trait in crop domestication (Gomez, 2004; Orsi and Tanksley, 2009). Several factors that act maternally to control seed size have been identified, such as ARF2/MNT, AP2, KLU/CYP78A5, EOD3/CYP78A6 and DA1. However, the genetic and molecular mechanisms of these factors in seed size control are nearly totally unknown. We previously demonstrated that the ubiquitin receptor DA1 acts synergistically with the E3 ubiquitin ligase EOD1/BB to control seed size (Li et al., 2008).

In this study, we identified *Arabidopsis* DA2 as another RING E3 ubiquitin ligase involved in controlling seed size. Genetic analyses show that DA2 functions synergistically with DA1 to control final seed size, but does so independently of the E3 ubiquitin ligase EOD1. We further revealed that DA1 interacts physically with DA2. Our results define a ubiquitin-based system involving DA1, DA2 and EOD1 that controls final seed size in *Arabidopsis*.

2.9 DA2 Acts Maternally to Control Seed Size

The da2-1 loss-of-function mutant formed large seeds and organs, whereas plants overexpressing DA2 produced small seeds and organs (FIG. 1A), indicating that DA2 is a negative factor of seed and organ size control. Surprisingly, *Arabidopsis* DA2 has been recently proposed as a positive regulator of organ growth, although nothing is known about how DA2 controls seed and organ growth (Van Daele et al., 2012). In this study, we have sufficient evidence to prove that DA2 acts as a negative factor of seed and organ growth control. The da2-1 loss-of-function mutant formed large seeds and organs (FIGS. 1 to 4). Supporting this, the da2-1 mutation synergistically enhanced the seed and organ size phenotypes of da1-1 and da1-ko1 (FIGS. 1 to 4). The da2-1 mutation also enhanced the seed and organ size phenotypes of eod1-2, further indicating that the da2-1 mutation promotes seed and organ growth. The da2-1 mutant formed large ovules with more cells in the integuments, and the da2-1 mutation synergistically enhanced the ovule size phenotype of da1-1 (FIG. 6).

In addition, most transgenic plants overexpressing DA2 and DA2L were smaller than wild-type plants (FIG. 2; Figure S9). The organ growth phenotypes of these transgenic plants were correlated with their respective expression levels (Figures S4 and S9). Therefore, our data clearly demonstrate that DA2 functions as a negative regulator of seed and organ size. Several *Arabidopsis* mutants with large organs also formed large seeds (Krizek, 1999; Mizukami and Fischer, 2000; Schruff et al., 2006; Li et al., 2008; Adamski et al., 2009), suggesting a possible link between organ size and seed growth. By contrast, several other mutants with large organs exhibited normal sized seeds (Hu et al., 2003; White, 2006; Xu and Li, 2011), indicating that organ and seed size is not invariably positively related.

These results suggest that seeds and organs have both common and distinct pathways to control their respective size.

Reciprocal cross experiments showed that DA2 acts maternally to influence seed growth, and the embryo and endosperm genotypes for DA2 do not affect seed size (FIG. 6). The integuments surrounding the ovule are maternal tissues and form the seed coat after fertilization. Alterations in maternal integument size, such as those seen in arf2, da1-1 and klu ovules, have been known to contribute to changes in seed size (Schruff et al., 2006; Li et al., 2008; Adamski et al., 2009). Mature da2-1 ovules were larger than mature wild-type ovules (FIGS. 5 and 7). The da2-1 mutation also synergistically enhanced the integument size of da1-1 ovules. Thus, a general theme emerging from these studies is that the control of maternal integument size is one of key mechanisms for determining final seed size. Consistent with this notion, plant maternal factors of seed size control (e.g. KLU, ARF2 and DA1) isolated to date influence integument size (Schruff et al., 2006; Li et al., 2008; Adamski et al., 2009).

The size of the integument or seed coat is determined by cell proliferation and cell expansion, two processes that are coordinated. Cell number in the integuments of the mature ovule sets the growth potential of the seed coat after fertilization. For example, arf2 mutants produced large ovules with more cells, leading to large seeds (Schruff et al. 2006), while klu mutants had small ovules with less cells, resulting in small seeds (Adamski et al., 2009). Our results show that the integuments of da1-1 and da2-1 seeds had more cells than those of wild-type seeds, and da1-1 and da2-1 acts synergistically to promote cell proliferation in the integuments. We also observed that cells in the outer integuments of da1-1, da2-1, and da1-1 da2-1 seeds were shorter than those in wild-type integuments, suggesting that a possible compensation mechanism between cell proliferation and cell elongation in the maternal integument. Thus, it is possible that the maternal integument or seed coat, which acts as a physical constraint on seed growth, can set an upper limit to final seed size.

2.10 A Genetic Framework for Ubiquitin-Mediated Control of Seed Size

DA2 encodes a protein with one predicted RING domain that is distinctive from any of the previously described plant RING domains. The RING domain of DA2 shared highest homology with that of rice GW2 (C5HC2), but it lacked one conserved metal ligand amino acid (a histidine residue) that was replaced by an asparagine residue (Song et al., 2007). It is still possible that the RING domain of DA2 might be a variant of that found in GW2. Many RING-type domains are found in E3 ubiquitin ligases that ubiquitinate substrates, often targeting them for subsequent proteasomal degradation (Smalle and Vierstra, 2004). We tested the E3 activity of recombinant DA2 in an in vitro ubiquitin-ligase assay and demonstrated that DA2 is a functional E3 ubiquitin ligase, suggesting that DA2 may target positive regulators of cell proliferation for ubiquitin-dependent degradation by the 26S proteasome. Proteins that share homology with DA2 outside the RING domain are found in *Arabidopsis* and other plant species. In *Arabidopsis*, the DA2-like protein (DA2L) shares extensive amino acid similarity with DA2. Like 35S:DA2 plants, DA2L-overexpressing lines showed small plants (FIG. 18), indicating that DA2 and DA2L may perform similar functions. The homolog of DA2 in rice is the RING-type (C5HC2) protein GW2 (Song et al., 2007), which has been known to act as a negative regulator of seed size. However, the genetic and molecular mechanisms of GW2 in seed size control are largely unknown in rice.

We previously identified DA1, a ubiquitin receptor with ubiquitin-binding activity, as a negative regulator of seed size (Li et al., 2008). A modifier screen identified an enhancer of da1-1 (EOD1) (Li et al., 2008), which is allelic to the E3 ubiquitin ligase BB (Disch et al., 2006). Analysis of double eod1-2 da1-1 mutants revealed synergistic genetic interactions between DA1 and EOD1 (Li et al., 2008), suggesting they may control seed growth by modulating the activity of a common target(s). Although genetic interactions between da1-1 and eod1-2 also synergistically enhanced seed and organ size, our genetic analyses show that DA2 acts independently of EOD1 to influence seed growth, suggesting DA2 and EOD1 may target distinct growth stimulators for degradation, with common regulation via DA1. Thus, our findings establish a framework for the control of seed and organ size by three ubiquitin-related proteins DA1, DA2 and EOD1. In addition, we observed that overexpression of GW2 restricts seed and organ growth in *Arabidopsis*, providing indication of a possible conserved function in *Arabidopsis* and rice. It could be interesting to investigate the effects of the combination of GW2 and rice homologs of DA1 and EOD1 on grain size in rice.

2.11 A Possible Molecular Mechanism of DA1 and DA2 in Seed Size Control

Our results demonstrate that the E3 ubiquitin ligase DA2 interacts with the ubiquitin receptor DA1 in vitro and in vivo (FIGS. 12-14). However, it is not likely that DA2 targets DA1 for proteasomal degradation because a T-DNA inserted mutant of the DA1 gene (da1-ko1) synergistically enhances the seed size phenotype of da1-1 (FIGS. 3 and 4). Nevertheless, many other types of ubiquitin modification regulate proteins in a proteasome independent manner (Schnell and Hicke, 2003). For example, monoubiquitination has been implicated in the activation of signaling proteins, endocytosis, and histone modification (Schnell and Hicke, 2003). In animals, monoubiquitination of the ubiquitin receptor eps15 depends on interaction between eps15 and the Nedd4 family of E3 ligases (Woelk et al., 2006). In contrast, an E3-independent monoubiquitination of ubiquitin receptors has also been reported (Hoeller et al., 2007). Considering that DA1 interacts with DA2, we tested whether DA2 can ubiquitinate or monoubiquitinate DA1. In the presence of E1, E2 and ubiquitin, DA2-His had an E3 ubiquitin ligase activity. However, in the presence of E1, E2, ubiquitin and DA2-His (E3), no ubiquitinated DA1-HA was detected under our reaction conditions. Ubiquitin receptors can interact with polyubiquitinated substrates of E3s via UIM domains and facilitate their degradation by the proteasome (Verma et al., 2004). We previously demonstrated that UIM domains of DA1 can bind ubiquitin (Li et al., 2008).

Taken together with its interaction with DA2 through its C-terminal region (FIGS. 12 and 14), DA1 may be involved in mediating the degradation of the ubiquitinated substrates of DA2 by the proteasome. One mechanism may involve DA1 interaction with DA2, which helps DA1 specifically recognize the ubiquitinated substrate(s) of DA2. DA1 may subsequently bind polyubiquitin chains of the ubiquitinated substrate(s) through its UIM domain and mediate the degradation of the ubiquitinated substrate(s). Improving seed yield is an important target for crop breeders worldwide, and the size of seeds is an important component of overall seed yields. We identified DA2 as an important regulator of seed size that functions synergistically with DA1 to influence seed size.

DA1 also acts synergistically with EOD1 to affect seed growth. Overexpression of a dominant negative da1-1 mutation (Zmda1-1) has been reported to increase seed mass of corn (Wang et al., 2012), indicating the promise of combining the effects of DA1, DA2 and EOD1 from different seed crops to engineer large seed size in these crops.

REFERENCES

Adamski, N. M. et al (2009) PNAS USA 106, 20115-20120.
Alexandru, G. et al (2008) Cell 134, 804-816.
Alonso-Blanco, C. et al (1999). PNAS USA 96, 4710-4717.
Bandau, S. et al (2012) BMC Biol 10, 36.
Bednarek, J. et a J. Exp. Bot. (2012) 63 16 5945-5955
Curtis, M. D. et al (2003) Plant physiology 133, 462-469.
Disch, S. et al (2006) Curr Biol 16, 272-279.
Fan, C. et al (2006) Theor Appl Genet 112, 1164-1171.
Fang, W. et al (2012) Plant J 70, 929-939.
Garcia, D. et al (2005) Plant Cell 17, 52-60.
Garcia, D. et al (2003) Plant Physiology 131, 1661-1670.
Gegas, V. C. et al (2010) Plant Cell 22, 1046-1056.
Gomez, J. M. (200) Int J Org Evol 58, 71-80.
Hoeller, D. et al (2007) Mol Cell 26, 891-898.
Hu, Y. et al (2003) Plant Cell 15, 1951-1961.
Jofuku, K. D. et al. (2005) PNAS USA 102, 3117-3122.
Kaur, N. et al (2013). J Int Plant Biol 55, 108-120.
Krizek, B. A. (1999. Dev Genet 25, 224-236.
Lanctot, A. A. et al (2013). Developmental cell 25, 241-255.
Li, Y., et al (2008) Genes Dev 22, 1331-1336.
Li, Y. et al (2006) Genome Res 16, 414-427.
Lopes, M. A. et al (1993) Plant Cell 5, 1383-1399.
Luo, M. et al (2005) PNAS USA 102, 17531-17536.
Mizukami, Y et al (2000) PNAS USA 97, 942-947.
Moles, A. T. et al (2005) Science 307, 576-580.
Ohto, M. A., et al (2005) PNAS USA 102, 3123-3128.
Ohto, M. A. et al (2009) Sex Plant Reprod 22, 277-289.
Orsi, C. H. et al (2009) PLoS Genet 5, e1000347.
Perez-Perez, J. M. et al (2009) Trends Genet 25, 368-376.
Platta, H. W. et al (2009) Mol Cell Biol 29, 5505-5516.
Schnell, J. D. et al (2003) J Biol Chem 278, 35857-35860.
Schruff, M. C. et al (2006) Development 133, 251-261.
Seo, H. S. et al (2003) Nature 423, 995-999.
Shomura, A., et al (2008) Nat Genet 40, 1023-1028.
Smalle, J. et al (2004) Annual review of plant biology 55, 555-590.
Song, X. J. et al (2007) Nat Genet 39, 623-630.
Stone, S. L. et al. (2005) Plant physiology 137, 13-30.
Van Daele, I. et al. (2012) Plant Biotech J 10, 488-500.
Verma, R. et al (2004) Cell 118, 99-110.
Voinnet, O. et al (2003) Plant J 33, 949-956.
Wang, A. et al (2010) Plant J.
Wang, et al (2012) Afrian Journal of Biotechnology 11, 13387-13395.
Weng, J. et al (2008) Cell Res 18, 1199-1209.
Westoby, M. et al (2002) Ann. Rev. Ecol. System. 33, 125-159.
White, D. W. (2006) PNAS USA 103, 13238-13243.
Woelk, T. et al (2006) Nat Cell Biol 8, 1246-1254.
Xie, Q. et al (2002) Nature 419, 167-170.
Xu, R. et al (2011) Development 138, 4545-4554.
Zhou, Y. et al (2009) Plant Cell 21, 106-117.

TABLE 1

Alignment of DA2 RING domains (SEQ ID NOS: 3-19).

| | | |
|---|---|---|
| Bd_Bradi3g09270 | C P I C F L Y P S L N K S K C C | S K G I C T E C F L Q M K P T H T A K P T Q C P F C |
| Hv_Yrg1 | C P I C F L Y P S L N K S K C C | S K G I C T E C F L Q M K P T H T A K P T Q C P F C |
| Zm_gi\|220961719 | C P I C F L Y P S L N K S K C C | S K G I C T E C F L Q M K P T H T A K P T Q C P F C |
| Sb_gi\|242064618 | C P I C F L Y P S L N K S K C C | S K G I C T E C F L Q M K P T H T A K P T Q C P F C |
| Os_GW2 | C P I C F L Y P S L N K S K C C | S K G I C T E C F L Q M K P T H T A Q P T Q C P F C |
| Pt_gi\|224061326 | C P I C F L Y P S L N K S K C C | M K G I C T E C F L Q M K N P N S T K P T Q C P F C |
| Cp_evm.model.supercontig_77 | C P I C F L Y P S L N K S K C C | M K G I C T E C F L Q M K N P N S T K P T Q C P F C |
| Rc_gi\|255578534 | C P I C F L Y P S L N K S K C C | M K G I C T E C F L Q M K N P N S T K P T Q C P F C |
| At_DA2 | C P I C F L Y P S L N K S K C C | M K S I C T E C F L Q M K N P N S A K P T Q C P F C |
| Bn_DA2 | C P I C F L Y P S L N K S K C C | M K S I C T E C F L K M K N P N S A K P T Q C P F C |
| At_DA2L | C P I C F L Y P S L N K S K C C | M K S I C T E C F L Q M K S P N S A Q P T Q C P F C |
| Gm_Glyma13g33260.1 | C P I C F L Y P S L N K S K C C | T K S I C T E C F L Q M K V P N S T K P T Q C P F C |
| Sb_Sb10g003820 | C P I C F L F Y P S L N K S K C C | A K G I C T E C F L Q M K S P T S C K P T Q C P Y C |
| Bd_Bradi1g49080 | C P I C F L F Y P S L N K S K C C | A K G I C T E C F L Q M K S P T S C K P T Q C P Y C |
| Zm_gi\|260935347 | C P I C F L F Y P S L N K S K C C | A K G I C T E C F L Q M K S P T S C K P T Q C P Y C |
| Os_gi\|218197613 | C P I C F L F Y P S L N K S K C C | A K G I C T E C F L Q M K T P T S C K P T Q C P Y C |
| Vv_DA2 | C P I C F L F Y P S L N K S K C C | T K G I C T E C F L Q M K N P N S T K P T Q C P Y C |

↑ ↑     ↑ ↑ ↑     ↑     ↑ ↑
C C     C C C     H/N/T     C C

TABLE 2

Alignment of DA2 polypeptides (SEQ ID NOS: 20-35)

```
Pt_GI-224061326.pro  MGNKLG---RRRQVVDERYTRPQGLYVHKDVDHKKLRKLILESKLAPCFPGDEDSCND--  55
Rc_GI-255578534.pro  MGNKLG---RRRQVVDERYTRPQGLYVEKDVDHKKLRKLILESKLAPCYPGDDEFGND--  55
Vv_GI-147817790.pro  MGNKLG---RRRQVVEDKYTRPQGLYQHKDVDHKKLRKLILDSKLAPCYPGDEEATND--  55
Gm_GI-356549538.pro  MGNKLG---RRRQVVDEKYTRPQGLYNHKDVDHKKLRKLILESKLAPCYPGDEETAYD--  55
At_GI-18411948.pro   MGNKLG---RKRQVVEERYTKPQGLYVNKDVDVKKLRKLIVESKLAPCYPGDDESCHD--  55
Ta_GI-408743661.pro  MGNRIGG--RRKAGVEERYTRPQGLYEHRDIDQKKLRKLILETKLAPCYPGADDAAGG--  56
Hv_GI-164371454.pro  MGNRIGG--RRKAGVEERYTRPQGLYEHRDIDQKKLRKLILETKLAPCYPGADDAAGA--  56
Bd_GI-357140854.pro  MGNRIGG--RRKAGVEERYTRPQGLYEHRDIDQKKLRKLILEAKLAPCYPGADDAAGG--  56
Os_GI-115445269.pro  MGNRIGG--RRKAGVEERYTRPQGLYEHRDIDQKKLRKLILEAELGPCYMGADDAAAAA-  57
Sb_GI-242064618.pro  MGNRKGG--RPKSGGEKRFTPPQGLYEHKDIDQKKLRKLILEAKLAPCYPGADDAAAAGG  58
Zm_GI-220961719.pro  MGNRKGG--RRKPGVEERFTRPQGLYEHKDIDQKKLRKLILEAKLAPCYPGADDAAAGGG  58
Ta_GI-408743658.pro  MGNRIGG--RRKAGVEERYTRPQGLYEHRDIDQKKLRKLILEAKLAPCYPGADDAAGG--  56
Bd_GI-357125256.pro  MGN------------------QGLYPHPDIDLKKLRRLIVEAKLAPCHPGSDDPRAD--  39
Os_GI-218197613.pro  MGNQVGGRRRRRPAVEERYTRPQGLYPHPDIDLKKLRRLIVEAKLAPCFPGSDDPRAD--  58
Zm_GI-260935347.pro  MGNQVGGRRRRRPPVDERYTRPQGLYPHPDIDLRKLRRLILEAKLAPCHPGADDARAD--  58
Sb_GI-242092026.pro  MGNQVGGRRRRRPAVDERYTQPQGLYPHPDIDLRKLRRLILEAKLAPCHPGADDARAD--  58
                    ***                 ****  : *:* :***:**::::*****. *  ::

Pt_GI-224061326.pro  ---HEECPICFLYYPSLNRSRCCMKGICTECFLQMKNPNSTRPTQCPFCKTSNYAVEYRG  112
Rc_GI-255578534.pro  ---HEECPICFLYYPSLNRSRCCMKGICTECFLQMKNPNSTRPTQCPFCKTTNYAVEYRG  112
Vv_GI-147817790.pro  ---FEECPICFLFYPSLNRSRCCTKGICTECFLQMKNPNSTRPTQCPYCKTANYAVEYRG  112
Gm_GI-356549538.pro  ---REECPICFLYYPSLNRSRCCTKSICTECFLQMKVPNSTRPTQCPFCKTANYAVEYRG  112
At_GI-18411948.pro   ---LEECPICFLYYPSLNRSRCCMKSICTECFLQMKNPNSARPTQCPFCKTPNYAVEYRG  112
Ta_GI-408743661.pro  --DLEECPICFLYYPSLNRSKCCSKGICTECFLQMKPTHTARPTQCPFCKTPNYAVEYRG  114
Hv_GI-164371454.pro  --DLEECPICFLYYPSLNRSKCCSKGICTECFLQMKPTHTARPTQCPFCKTPNYAVEYRG  114
Bd_GI-357140854.pro  --DLEECPICFLYYPSLNRSKCCSKGICTECFLQMKPTHTARPTQCPFCKTPNYAVEYRG  114
Os_GI-115445269.pro  --DLEECPICFLYYPSLNRSKCCSKGICTECFLQMKPTHAQPTQCPFCKTPSYAVEYRG  115
Sb_GI-242064618.pro  --DLEECPICFLYYPSLNRSKCCSKGICTECFLQMKPTHTARPTQCPFCCTPNYAVEYRG  116
Zm_GI-220961719.pro  DLDLEECPICFLYYPSLNRSKCCSKGICTECFLQMKPTHTARPTQCPFCKTANYAVEYRG  118
Ta_GI-408743658.pro  --DLEECPICFLYYPSLNRSKCCSKGICTECFLQMKPTHTARPTQCPFCKTPNYAVEYRG  114
Bd_GI-357125256.pro  ---LDECPICFLYYPSLNRSKCCAKGICTECFLQMKSPTSCRPTQCPYCKMLNYAVEYRG   96
Os_GI-218197613.pro  --LEECPICFLFYPSLNRSKCCAKGICTECFLQMRTPTSCRPTQCPYCKMASYAVEYRG  115
Zm_GI-260935347.pro  ---LDECPICFLYYPSLNRSKCCAKGICTECFLQMKSPTSCKPTQCPYCKTLNYAVEYRG  115
Sb_GI-242092026.pro  ---LDECPICFLFYPSLNRSKCCAKGICTECFLQMKSPTSCRPTQCPYCKTLNYAVEYRG  115
                       :******:****** ** *.*********:  :  :****:**  .*******

Pt_GI-224061326.pro  VKTKEEKGLEQIEEQRVIEAKIRMRQQELQDEEERMQKRLDVSSSSANIEPG-ELECGPT  171
Rc_GI-255578534.pro  VKTKEEKGMEQIEEQRVIEAKIRMRQQELQDEEERMQKRLELSSSSSSIAPG-EVECGSA  171
Vv_GI-147817790.pro  VKIKEEKGMEQIEEQRVIEAKIRMRQKEIQDEEERMQKRQEISSSSSILAQG-EVEYSTT  171
Gm_GI-356549538.pro  VKSKEEKGLEQIEEQRVIEAKIRMRQQELQDEEERMHKRLEMSSSNVNVAVA-DVEYSSN  171
At_GI-18411948.pro   VKSKEEKGIEQVEEQRVIEAKIRMRQKEMQDEEKMQKRLESCSSSTSAMTG-EMEYGST  171
Ta_GI-408743661.pro  VKTKEERSIEQFEEQKVIEAQMRMRQQALQDEEDKMKRKQSRCSSSRTIAPTTEVEYRDI  174
Hv_GI-164371454.pro  VKTKEERSIEQFEEQKVIEAQMRMRQQALQDEEDKMRRKQSRCSSSRTIAPTTEVEYRDI  174
Bd_GI-357140854.pro  VKTKEERSIEQLEEQKVIEAQMRMRQQALQDEEDKMKRKQSRCSSSRTIAPTTEVEYRDI  174
Os_GI-115445269.pro  VKTKEERSIEQFEEQKVIEAQMRMRQQALQDEEDKMKRKQNRCSSSRTITPTKEVEYRDI  175
Sb_GI-242064618.pro  VKTKEERSIEQFEEQKVIEAQLRMRQKELQDEEAKMKRKQSRCSSSRTVTPTTEVEYRDI  176
Zm_GI-220961719.pro  VKTKEERSIEQFEEQKVIEAQLRMRQKELQDEEAKMKRKQSRCSSSRIVTPTTEVEYRDI  178
Ta_GI-408743658.pro  VKTKEERSIEQFEEQKVIEAQMRVRQQALQDEEDKMKRKQSRCSSS-CKTPNYAVEYRGV  173
Bd_GI-357125256.pro  VKTKEEKGVEQLEEQRVIEAQIRMRHQEIKDDAERLKNKQ--TATLSDVITTPQVECCEA  154
Os_GI-218197613.pro  VKTKEEKGTEQIEEQRVIEAQIRMRQQELQDDAERMKKQ--AAALTDVVTTAQVEHCDT  173
Zm_GI-260935347.pro  VKTKEEKGIEQLEEQRVIEAQIRMRQQEVQDDAERMKNKR--TATLGDVVASAQVDSCNT  173
Sb_GI-242092026.pro  VKTKEEKGIEQLEEQRVIEAQIRMRQKELQDDAERMKNKQ--TATLGDIVASAQVDSCNT  173
                    **:***:. **.***:****::*.*:::  ::.:        ::            ::

Pt_GI-224061326.pro  TVPS-DTTPVE-------SGEIVSSQYS-----SRRPPHAGANRDDEFDLDLEDIMVEA218
Rc_GI-255578534.pro  AVQS-FRSPLE-------AEGSIPSQFS-----IRHPPHYRANRDDEFDLDLEDIMVEA218
Vv_GI-147817790.pro  AVPS-FRSPVE-------GDEIDSSQDPRAASMIIQTLPPRQNREDEFDLDLEDIMVEA223
Gm_GI-356549538.pro  AVSSSSVSVVE-------NDEIVSSQDSCATSVVRANATTRTNRDDEFDVDLEDIMVEA224
At_GI-18411948.pro   SAIS-YNSLMD-------DGEIAPSQNAS---VVRQHSRPRGNREDEVDVDLEELMVEA220
Ta_GI-408743661.pro  CSTS-YSVPSY--QCTEQETECCSSEPSCSAQANMRSFHSRHTRDDNIDMNIEDMMVMEA231
Hv_GI-164371454.pro  CSTS-YSAPPY--RCTEQETECCSSEPSCSAQANMRSFHSRHTRDGNIDMNIEDMMVMEA231
Bd_GI-357140854.pro  CSTS-YSVPSY--QCTEQEAECCSSEPSCSAQSNMRPVHSRHNRDDNIGMNIEEMMVMEA231
Os_GI-115445269.pro  CSTS-FSVPSY--RCAEQETECCSSEPSCSAQTSMRPFHSRENRDDNIDMNIEDMMVMEA232
Sb_GI-242064618.pro  CSTS-FSVPSY--QCTEQGNECCSSEPSCSSQANMRPFHSRHNRDDNVDVNLEDMMVMEA233
Zm_GI-220961719.pro  CSTS-FSVPSY--QRTEQGNECCSSEPSCSSQANMRPFHSRHNRDDNVDMNLEDMMVMET235
Ta_GI-408743658.pro  KTKEERSIEQFEEQKVIEAQMRVRQQALQDEEDKMKRKQSRCS--SSMDMNIEDMMVMEA231
Bd_GI-357125256.pro  GGTSTPAASSA------QGNDALLSQVHSELLLKNSERLKQMRENNFDVDLEEVMLMEA208
Os_GI-218197613.pro  GGASTTVKSSG------QGSDMLSSQVHAELLLKTSERLKQMRNNNFDMDPDEVMLVEA227
Zm_GI-260935347.pro  DGASTAVANSP------QGSNDVLSSEVQHSELISRNSEAFKQMRGNNFEVDLEEVMLMEA227
Sb_GI-242092026.pro  DGASTGAASSP------QGSDAISSEVQHSELILRNSEAFKQMRGNNFDVDLEEVMLMEA227
                                   .:                  ..  ::  :::*::*

Pt_GI-224061326.pro  IWLSIQ-ENGRQKNPLCGDAAP-----PAQYTMEARYVTP----AMAPPLAGSSSSPSGG268
Rc_GI-255578534.pro  IWLSIQ-ENGRQKNPIYTDAAS-----SENYAVQGHYALQ----AMPP-VTESSSSPSGG267
Vv_GI-147817790.pro  IWLSIQ-DNGRHRNPLYGDTTT-----AEQYVTEEHYVLP----AMAP-QVESSSSPSGG272
Gm_GI-356549538.pro  IWLSIQ-ENGRRENLSFVDATSGHYVADGRYVSSVSSVSS----VMGP-PTGSSSSPSGG278
At_GI-18411948.pro   IWLSVQ-ETGTQRNSASGEITS-----SRQYVTDNHSYVSSPPRVTPIVEPATPSSSSGG274
```

TABLE 2-continued

Alignment of DA2 polypeptides (SEQ ID NOS: 20-35)

```
Ta_GI-408743661.pro  IWRSIQ-EQGSIGNPACGSFMP--------FEQP-TCERQ----AFVAAPPLEIPHP-GG276
Hv_GI-164371454.pro  IWRSIQ-EQGSIGNPACGSFMP--------FEQP-TRERQ----AFVAASPLEIPHP-GG276
Bd_GI-357140854.pro  IWRSIQ-EQGSMGNPVCGNFMP--------VIEPPSRERQ----AFVPAP-LEIPHP-GG276
Os_GI-115445269.pro  IWRSIQ---GSIGNPVCGNFMP--------VTEPSPRERQ----PFVPAASLEIPHG-GG276
Sb_GI-242064618.pro  IWRSIQ-EQGHLVNPVCGSYFP--------VIEPPSRERQ----AFLPAAPLEMPHP-GG279
Zm_GI-220961719.pro  IWRSIQQEQGHLVNPVCGSYFP--------VIEPPSRERQ----AFVPAAPLEMPHP-GG282
Ta_GI-408743658.pro  IWRSIQ-EQGSIGNPSCGSFMP--------FEQP-TRERQ----AFVAAPPLEMPHP-GG276
Bd_GI-357125256.pro  IWLSVQ-D--ASGNPGITGAAP--------PTIPPRSYD------TSVTASAEAAPSG-G250
Os_GI-218197613.pro  LWLSLQ-DQEASGNPTCGNTVS--------SVHPPRSFE------GSMTIPAEAASSSSA272
Zm_GI-260935347.pro  IWLSIQ-DQEALGNPGCVSTTP--------SSIPSRPFDD-----GDMTTTAEAASSG-G272
Sb_GI-242092026.pro  IWLSIQ-DQEALGNSGCVSTTP--------SSIPSRPFD------GAMTTTPEAASSG-G271
                     :* *:*          *                  .           .        .

Pt_GI-224061326.pro  LACAIAALAERQQTGGES--IVHNSGNMPSFNMLPST-SSFYNRLEQDADNYSPAQSSSN325
Rc_GI-255578534.pro  LACAIAALAERQQTGGES--FAHNNENVAACNMLPGG-SSFYNRMDQDAENYSPAQGSNN324
Vv_GI-147817790.pro  LACAIAALAERQQMGGES--STNYNGNMPAFNMPPGS-SRFSNRVEQYPENYPPIESSMD329
Gm_GI-356549538.pro  LACAIAALAERQQMAGESS-MSLTNENMPSENTLPGS-RPFYNRLGRDMANYPPGDNLNE336
At_GI-18411948.pro   LSCAISALAERQMVGESSSHNHNHNVNVSSYSMLPGN-CDSYYDIEQEVDGIDNHHHHR-332
Ta_GI-408743661.pro  FSCAVAAMAEHQ-PSSMDFSYMTGSSAFPVEDMERRP-CNIAGGSMCAVE-SSPDSWSGI333
Hv_GI-164371454.pro  FSCAVAAMMEHQ-PSSMDFSYMTGSSAFPVEDMERRP-CNIAGGSLRAVE-SSLDSWSGI333
Bd_GI-357140854.pro  FSCAVASMAEHQ-PPSMDFSYMAGNSAFPVFDMERRQ-CNISGGSMCAVD-SSPDSWSGI333
Os_GI-115445269.pro  FSCAVAAMAEHQ-PPSMDFSYMAGSSAFPVEDMERRP-CNIAGGSMCNLE-SSPESNSGI333
Sb_GI-242064618.pro  YSCAVAALAEHQ-PASMDFSYMAGSSTYPVEDMIRRP-CNMSSGSLCGVENSSLDTWSGI337
Zm_GI-220961719.pro  YSCAVAALAEHQ-APSMDFSYMSGSSTYPVDMIRRP--CNMSSGSPCGAENSSLDTWSGI340
Ta_GI-408743658.pro  MDMNIEDMMVME-AIWRSIQEQ-GSIGNPSCGSFMPF-EQPTRERQAFVAAPPLEMPHPG333
Bd_GI-357125256.pro  FACAVAALAEQQHMLVGS--SIPATCQASKHDTLSRSDRSFTEDLSIAGSSSSGTRVDES308
Os_GI-218197613.pro  FACAVAALAEQQQMYGEA--SSTATCHTSRCDILSRSDRSFTEDLSINGSGSSGARSEEP330
Zm_GI-260935347.pro  FACAVAALAEQQHMHGES--SSASPCQTIREGTLSRPDRSTTQDLSVAGSSSSDSRVEEP330
Sb_GI-242092026.pro  FAFAVAALAEQQHMHGES--SSASACQTPREDILSRDRSSTEDLSVVGSSSSDSRVEEP329
                       :       :      :                                    .

Pt_GI-224061326.pro  VLPDCRMIVTRDDGEWGADRGSDAAEAGTSYASSETAEDAGGISSLLPPP--PPTDEIGG383
Rc_GI-255578534.pro  MLSDCRMA--RDDVQWVADRGSDAAEAGTSYASSETTEDSDGISVVLPPPPLPPPDEIVG382
Vv_GI-147817790.pro  ALPDGGLAVTKDDGEWGVDRGSEVAEALTSYASSDATDEAGGVAA------LPPTDEAEG383
Gm_GI-356549538.pro  EPLDEAVTMTRSHGEWDMEHGTQLTETATSYTNSVAAEDRGELSS------LPRSDDNDG390
At_GI-18411948.pro   -------------------HHYEMGETGSSNSYVSSYMTGEGFHN------FPPPP----363
Ta_GI-408743661.pro  ASSCSRREVVREEGECSTDHWSEGAEAGTSYAGSDIVVDAGTTPP------LPVTDN---384
Hv_GI-164371454.pro  APSGTRREMVREEGECSIDHWSEGAEAGTSYAGSDIMADAGTMPP------LPFADN---384
Bd_GI-357140854.pro  PPSCSR-EMIREEGECSTDHWSEGAEAGTSYAGSDIVADAGTMQQ------LPFAEN---383
Os_GI-115445269.pro  APSCSR-EVVREEGECSADHWSEGAEAGTSYAGSDIVADAGTMPQ------LPFAEN---383
Sb_GI-242064618.pro  APSCSR-EVVREEGECSTDHWSEGAEAGTSYAGSDIMADTGTMQP------LPFAEN---387
Zm_GI-220961719.pro  APSCSR-EVVRDEGECSADHWSEGAEAGTSYAGSDIMADAGAMQP------LPFAEN---390
Ta_GI-408743658.pro  GPSCSRREVVREEGECSTDHLSEGAEAGTSYAGSDIVVDAGTMLP------LPFADN---384
Bd_GI-357125256.pro  SINRTRQTREGAEHSNN-DRWSEVADASTSCAGSDITREAGAANL-------VASDG---357
Os_GI-218197613.pro  SSNKMHQTREGMEYSN--ERWSEMAEASSSFTGSDLTTEAGAAN----------SGG---375
Zm_GI-260935347.pro  PTSNTHRTIEAAEYSNSNVQWSEVAEAGTSIAESDGTVEAGVDNS-------STSAG---380
Sb_GI-242092025.pro  SSSSTHRTIEGSEYSNSNGRWSEVAEAGTSIAEDVIVEAGVGNS--------STSVG---379
                         :      : ::..:*  :                                   .

Pt_GI-224061326.pro  SFQNVSGPIP-ESFEEQMMLAMAVSLAEARAMTSG--PQSAWQ                423
Rc_GI-255578534.pro  S--DSGMIVP-ESFEEQMMLAMAVSLAEAQAMTGG--AGSAWQ                420
Vv_GI-147817790.pro  SFQNVGGPIVPESFEEQMMLAMAVSLAEARARTS---TQGVWQ                423
Gm_GI-355549538.pro  SLQSATEPIVPESFEEQMMLAMAVSLAEARAMSSG--QSASWQ                431
At_GI-18411948.pro   -----PLVIVPESFEEQMMMAMAVSMAEVRATTTCAPTEVTWQ                401
Ta_GI-408743661.pro  -YSMVASHFRPESIEEQMMYSMAVSLAEA-HGRTHT-QGLAWL                424
Hv_GI-164371454.pro  -YSMAASHFRPESIEEQMMYSMAVSLAEA-HGRTHT-QGLTWL                424
Bd_GI-357140854.pro  -YNMAPSHFRPESIEEQMMYSMTVSLAEA-HGRTHS-QGLAWL                423
Os_GI-115445269.pro  -FAMAPSHFRPESIEEQMMFSMALSLADG-HGRTHS-QGLAWL                423
Sb_GI-242064618.pro  -FTMAPSHFRPESIEEQMMESMAVSLAEARHGRTQA-QGLAWL                428
Zm_GI-220961719.pro  -FAMGPSHFRPESVEEQMMFSMAVSLAEAHHGRTQA-QGLAWL                431
Ta_GI-408743658.pro  -YSMVASHFRPESIEEQMMYSMAVSLAEA-HGRTHS-QGLAWL                424
Bd_GI-357125256.pro  --SSIGSGNIPDSFEDQMMLAISLSLVDARAMASSPGPGLTWQ                398
Os_GI-218197613.pro  --SDTGAGSIPDSFEEQMMLAMALSLADARAKASSPG--LTWR                414
Zm_GI-260935347.pro  --SNIDSVSVPDSFEEQMMLAMALSLVDARARAGSPG--LAWR                419
Sb_GI-242092026.pro  --SNIGSSSVPDSFEEQMMLAMALSLVDARSRAGSPG--LAWR                418
                       :*.*:***  ::::*:.:                 *
```

* indicates identical residues
: indicates conserved residues
. indicates semi-conserved residues
RING domain and first and second consensus domains are boxed.

TABLE 3

Alignment of DA1 proteins (SEQ ID NOS: 41-64)

```
Si_GI-514815267.pro    ------------------------------------------------------------
Bd_GI-357157184.pro    ------------------------------------------------------------
Br_DA1b.pro            ------------------------------------------------------------
Br_DA1a.pro            ------------------------------------------------------------
At_GI-15221983.pro     ------------------------------------------------------------
Tc_GI-508722773.pro    ------------------------------------------------------------
Gm_GI-356564241.pro    ------------------------------------------------------------
Gm_GI-356552145.pro    ------------------------------------------------------------
Vv_GI-302142429.pro    ------------------------------------------------------------
Vv_GI-359492104.pro    ------------------------------------------------------------
Sl_GI-460385048.pro    ------------------------------------------------------------
Os_GI-218197709.pro    ------------------------------------------------------------
Os_GI-115466772.pro    ------------------------------------------------------------
Bd_GI-357160893.pro    ------------------------------------------------------------
Bd_GI-357164660.pro    ------------------------------------------------------------
Sb_GI-242092232.pro    ------------------------------------------------------------
Zm_GI-212275448.pro    ------------------------------------------------------------
At_GI-240256211.pro    ------------------------------------------------------------
At_GI-145360806.pro    ------------------------------------------------------------
At_GI-22326876.pro     MEPPAARVTPSIKADCSHSVNIICEETVLHSLVSHLSAALRREGISVFVDACGLQETKFF      60
At_GI-30698242.pro     ------------------------------------------------------------
At_GI-30698240.pro     ------------------------------------------------------------
At_GI-15240018.pro     ------------------------------------------------------------
At_GI-334188680.pro    ------------------------------------------------------------

Si_GI-514815267.pro    ------------------------------------------------------------
Bd_GI-357157184.pro    ------------------------------------------------------------
Br_DA1b.pro            ------------------------------------------------------------
Br_DA1a.pro            ------------------------------------------------------------
At_GI-15221983.pro     ------------------------------------------------------------
Tc_GI-508722773.pro    ------------------------------------------------------------
Gm_GI-356564241.pro    ------------------------------------------------------------
Gm_GI-358552145.pro    ------------------------------------------------------------
Vv_GI-302142429.pro    ------------------------------------------------------------
Vv_GI-359492104.pro    ------------------------------------------------------------
Sl_GI-460385048.pro    ------------------------------------------------------------
Os_GI-218197709.pro    ------------------------------------------------------------
Os_GI-115466772.pro    ------------------------------------------------------------
Bd_GI-357160893.pro    ------------------------------------------------------------
Bd_GI-357164660.pro    ------------------------------------------------------------
Sb_GI-242092232.pro    ------------------------------------------------------------
Zm_GI-212275448.pro    ------------------------------------------------------------
At_GI-240256211.pro    ------------------------------------------------------------
At_GI-145360806.pro    ------------------------------------------------------------
At_GI-22326876.pro     SIKQNQPLTDGARVLVVVISDEVEFYDPWFPKFLKVIQGWQNNGHVVVPVFYGVDSLTRV    120
At_GI-30698242.pro     ------------------------------------------------------------
At_GI-30698240.pro     ------------------------------------------------------------
At_GI-15240018.pro     ------------------------------------------------------------
At_GI-334188680.pro    ------------------------------------------------------------

Si_GI-514815267.pro    ------------------------------------------------------------
Bd_GI-357157184.pro    ------------------------------------------------------------
Br_DA1b.pro            ------------------------------------------------------------
Br_DA1a.pro            ------------------------------------------------------------
At_GI-15221983.pro     ------------------------------------------------------------
Tc_GI-508722773.pro    ------------------------------------------------------------
Gm_GI-356564241.pro    ------------------------------------------------------------
Gm_GI-356552145.pro    ------------------------------------------------------------
Vv_GI-302142429.pro    ------------------------------------------------------------
Vv_GI-359492104.pro    ------------------------------------------------------------
Sl_GI-460385048.pro    ------------------------------------------------------------
Os_GI-218197709.pro    ------------------------------------------------------------
Os_GI-115466772.pro    ------------------------------------------------------------
Bd_GI-357160893.pro    ------------------------------------------------------------
Bd_GI-357164660.pro    ------------------------------------------------------------
Sb_GI-242092232.pro    ------------------------------------------------------------
Zm_GI-212275448.pro    ------------------------------------------------------------
At_GI-240255211.pro    ------------------------------------------------------------
At_GI-145360806.pro    ------------------------------------------------------------
At_GI-22326876.pro     YGWANSWLEAEKLTSHQSKILSNNVLTDSELNEEIVRDVYGKLYPAERVGIYARLLEIEK    180
At_GI-30698242.pro     ------------------------------------------------------------
At_GI-30698240.pro     ------------------------------------------------------------
At_GI-15240018.pro     ------------------------------------------------------------
At_GI-334188680.pro    ------------------------------------------------------------

Si_GI-514815267.pro    ------------------------------------------------------------
Bd_GI-357157184.pro    ------------------------------------------------------------
Br_DA1b.pro            ------------------------------------------------------------
```

TABLE 3-continued

Alignment of DA1 proteins (SEQ ID NOS: 41-64)

```
Br_DA1a.pro         ------------------------------------------------------------
At_GI-15221983.pro  ------------------------------------------------------------
Tc_GI-508722773.pro ------------------------------------------------------------
Gm_GI-356564241.pro ------------------------------------------------------------
Gm_GI-356552145.pro ------------------------------------------------------------
Vv_GI-302142429.pro ------------------------------------------------------------
Vv_GI-359492104.pro ------------------------------------------------------------
Sl_GI-460385048.pro ------------------------------------------------------------
Os_GI-218197709.pro ------------------------------------------------------------
Os_GI-115466772.pro ------------------------------------------------------------
Bd_GI-357160893.pro ------------------------------------------------------------
Bd_GI-357164660.pro ------------------------------------------------------------
Sb_GI-242092232.pro ------------------------------------------------------------
Zm_GI-212275448.pro ------------------------------------------------------------
At_GI-240256211.pro ------------------------------------------------------------
At_GI-145360806.pro ------------------------------------------------------------
At_GI-22326876.pro  LLYKQHRDIRSIGIWGMPGIGKTTLAKAVFNHMSTDYDASCFIENFDEAFHKEGLHRLLK  240
At_GI-30698242.pro  ------------------------------------------------------------
At_GI-30698240.pro  ------------------------------------------------------------
At_GI-15240018.pro  ------------------------------------------------------------
At_GI-334188680.pro ------------------------------------------------------------

Si_GI-514815267.pro ------------------------------------------------------------
Bd_GI-357157184.pro ------------------------------------------------------------
Br_DA1b.pro         ------------------------------------------------------------
Br_DA1a.pro         ------------------------------------------------------------
At_GI-15221983.pro  ------------------------------------------------------------
TC_GI-508722773.pro ------------------------------------------------------------
Gm_GI-356564241.pro ------------------------------------------------------------
Gm_GI-356552145.pro ------------------------------------------------------------
Vv_GI-302142429.pro ------------------------------------------------------------
Vv_GI-359492104.pro ------------------------------------------------------------
Sl_GI-460385048.pro ------------------------------------------------------------
Os_GI-218197709.pro ------------------------------------------------------------
Os_GI-115466772.pro ------------------------------------------------------------
Bd_GI-357160893.pro ------------------------------------------------------------
Bd_GI-357164660.pro ------------------------------------------------------------
Sb_GI-242092232.pro ------------------------------------------------------------
Zm_GI-212275448.pro ------------------------------------------------------------
At_GI-240256211.pro ------------------------------------------------------------
At_GI-145360806.pro ------------------------------------------------------------
At_GI-22326876.pro  ERIGKILKDEFDIESSYIMRPTLHRDKLYDKRILVVLDDVRDSDAABSFLKRLDWFGSGS  300
At_GI-30698242.pro  ------------------------------------------------------------
At_GI-30698240.pro  ------------------------------------------------------------
At_GI-15240018.pro  ------------------------------------------------------------
At_GI-334188680.pro ------------------------------------------------------------

Si_GI-514815267.pro ------------------------------------------------------------
Bd_GI-357157184.pro ------------------------------------------------------------
Br_DA1b.pro         ------------------------------------------------------------
Br_DA1a.pro         ------------------------------------------------------------
At_GI-15221983.pro  ------------------------------------------------------------
Tc_GI-508722773.pro ------------------------------------------------------------
Gm_GI-356564241.pro ------------------------------------------------------------
Gm_GI-356552145.pro ------------------------------------------------------------
Vv_GI-302142429.pro ------------------------------------------------------------
Vv_GI-359492104.pro ------------------------------------------------------------
Sl_GI-460385048.pro ------------------------------------------------------------
Os_GI-218197709.pro ------------------------------------------------------------
Os_GI-115466772.pro ------------------------------------------------------------
Bd_GI-357160893.pro ------------------------------------------------------------
Bd_GI-357164660.pro ------------------------------------------------------------
Sb_GI-242092232.pro ------------------------------------------------------------
Zm_GI-212275448.pro ------------------------------------------------------------
At_GI-240256211.pro ------------------------------------------------------------
At_GI-145360806.pro ------------------------------------------------------------
At_GI-22326876.pro  LIIITSVDKQVFAFCQINQIYTVQGLNVHEALQLFSQSVFGINEPEQNDRKLSMKVIDYV  360
At_GI-30698242.pro  ------------------------------------------------------------
At_GI-30698240.pro  ------------------------------------------------------------
At_GI-15240018.pro  ------------------------------------------------------------
At_GI-334188680.pro ------------------------------------------------------------

Si_GI-514815267.pro ------------------------------------------------------------
Bd_GI-357157184.pro ------------------------------------------------------------
Br_DA1b.pro         ------------------------------------------------------------
Br_DA1a.pro         ------------------------------------------------------------
At_GI-15221983.pro  ------------------------------------------------------------
Tc_GI-508722773.pro ------------------------------------------------------------
```

TABLE 3-continued

Alignment of DA1 proteins (SEQ ID NOS: 41-64)

```
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-460385048.pro      ------------------------------------------------------------
Os_GI-218197709.pro      ------------------------------------------------------------
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
Zm_GI-212275448.pro      ------------------------------------------------------------
At_GI-240256211.pro      ------------------------------------------------------------
At_GI-145360806.pro      ------------------------------------------------------------
At_GI-22326876.pro       NGNPLALSIYGRELMGKKSEMETAFFELKHCPPLKIQDVLKNAYSALSDNEKNIVLDIAF     420
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------

Si_GI-514815267.pro      ------------------------------------------------------------
Bd_GI-357157184.pro      ------------------------------------------------------------
Br_DA1b.pro              ------------------------------------------------------------
Er_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-460385048.pro      ------------------------------------------------------------
Os_GI-218197709.pro      ------------------------------------------------------------
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
Zm_Gi-212275448.pro      ------------------------------------------------------------
At_GI-240256211.pro      ------------------------------------------------------------
At_GI-145360806.pro      ------------------------------------------------------------
At_GI-22326876.pro       FFKGETVNYVMQLLEESHYFPRLAIDVLVDKCVLTISENTVQMNNLIQDTCQEIFNGEIE     480
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------

Si_GI-514815267.pro      ------------------------------------------------------------
Bd_GI-357157184.pro      ------------------------------------------------------------
Br_DA1b.pro              ------------------------------------------------------------
Br_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-460385048.pro      ------------------------------------------------------------
Os_GI-218197709.pro      ------------------------------------------------------------
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
ZM_GI-212275448.pro      ------------------------------------------------------------
At_GI-240256211.pro      ------------------------------------------------------------
At_GI-145360806.pro      ------------------------------------------------------------
At_GI-22326876.pro       TCTRMWEPSRIRYLLEYDELEGSGETKAMPKSGLVAEHIESIFLDTSNVKFDVKHDAFKN     540
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------

Si_GI-514815267.pro      ------------------------------------------------------------
Bd_GI-357157184.pro      ------------------------------------------------------------
Br_DA1b.pro              ------------------------------------------------------------
Br_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
```

TABLE 3-continued

Alignment of DA1 proteins (SEQ ID NOS: 41-64)

```
Vv_GI-359492104.pro      ------------------------------------------------------------
Sl_GI-460385048.pro      ------------------------------------------------------------
Os_GI-218197709.pro      ------------------------------------------------------------
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
Zm_GI-212275448.pro      ------------------------------------------------------------
At_GI-240256211.pro      ------------------------------------------------------------
At_GI-145360806.pro      ------------------------------------------------------------
At_GI-22326876.pro       MFNLKFLKIYNSCSKYISGLNFPKGLDSLPYELRLLHWENYPLQSLPQDFDFGHLVKLSM  600
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------

Si_GI-514815267.pro      ------------------------------------------------------------
Bd_GI-357157184.pro      ------------------------------------------------------------
Br_DA1b.pro              ------------------------------------------------------------
Br_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-460385048.pro      ------------------------------------------------------------
Os_GI-218197709.pro      ------------------------------------------------------------
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
Zm_GI-212275448.pro      ------------------------------------------------------------
At_GI-240256211.pro      ------------------------------------------------------------
At_GI-145360806.pro      ------------------------------------------------------------
At_GI-22326876.pro       PYSQLHKLGTRVKDLVMLKRLILSHSLQLVECDILIYAQNIELIDLQGCTGLQRFPDTSQ  660
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------

Si_GI-514815267.pro      ------------------------------------------------------------
Bd_GI-357157184.pro      ------------------------------------------------------------
Br_DA1b.pro              ------------------------------------------------------------
Br_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-460385048.pro      ------------------------------------------------------------
Os_GI-218197709.pro      -------------------------------------------------------MGDRP    5
Os_GI-115466772.pro      ------------------------------------------------------------
Bd_GI-357160893.pro      ------------------------------------------------------------
Bd_GI-357164660.pro      ------------------------------------------------------------
Sb_GI-242092232.pro      ------------------------------------------------------------
Zm_GI-212275448.pro      ------------------------------------------------------------
At_GI-240256211.pro      ------------------------------------------------------------
At_GI-145360806.pro      ------------------------------------------------------------
At_GI-22326876.pro       LQNLRVVNLSGCTEIKCFSGVPPNIEELHLQGTRIREIPIFNATHPPKVKLDRKKLWNLL  720
At_GI-30698242.pro       ------------------------------------------------------------
At_GI-30698240.pro       ------------------------------------------------------------
At_GI-15240018.pro       ------------------------------------------------------------
At_GI-334188680.pro      ------------------------------------------------------------

Si_GI-514815267.pro      ------------------------------------------------------------
Bd_GI-357157184.pro      ------------------------------------------------------------
Br_DA1b.pro              ------------------------------------------------------------
Br_DA1a.pro              ------------------------------------------------------------
At_GI-15221983.pro       ------------------------------------------------------------
Tc_GI-508722773.pro      ------------------------------------------------------------
Gm_GI-356564241.pro      ------------------------------------------------------------
Gm_GI-356552145.pro      ------------------------------------------------------------
Vv_GI-302142429.pro      ------------------------------------------------------------
Vv_GI-359492104.pro      ------------------------------------------------------------
Sl_GI-46038504B.pro      ------------------------------------------------------------
```

TABLE 3-continued

Alignment of DA1 proteins (SEQ ID NOS: 41-64)

```
Os_GI-218197708.pro  DMGAGVALRFSHNDWTLEEDSKALHFLQPDLVLFTGDYGNENVQLVKSISDLQLPKAAIL    65
Os_GI-115466772.pro  ------------------------------------------------------------
Bd_GI-357160893.pro  ------------------------------------------------------------
Bd_GI-357164660.pro  ------------------------------------------------------------
Sb_GI-242092232.pro  ------------------------------------------------------------
Zm_GI-212275448.pro  ------------------------------------------------------------
At_GI-240256211.pro  ------------------------------------------------------------
At_GI-145360806.pro  ------------------------------------------------------------
At_GI-22326876.pro   ENFSDVEHIDLECVTNLATVTSNNHVMGKLVCLNMKYCSNLRGLPDMVSLESLKVLYLSG   780
At_GI-30698242.pro   ------------------------------------------------------------
At_GI-30698240.pro   ------------------------------------------------------------
At_GI-15240018.pro   ------------------------------------------------------------
At_GI-334188680.pro  ------------------------------------------------------------

Si_GI-514815267.pro  ------------------------------------------------------------
Bd_GI-357157184.pro  ------------------------------------------------------------
Br_DA1b.pro          ------------------------------------------------------------
Br_DA1a.pro          ------------------------------------------------------------
At_GI-15221983.pro   ------------------------------------------------------------
Tc_GI-508722773.pro  ------------------------------------------------------------
Gm_GI-356564241.pro  ------------------------------------------------------------
Gm_GI-356552145.pro  ------------------------------------------------------------
Vv_GI-302142429.pro  ------------------------------------------------------------
Vv_GI-359492104.pro  ------------------------------------------------------------
Sl_GI-460385048.pro  ------------------------------------------------------------
Os_GI-218197709.pro  GNHDCWHTYQFSEKKVDRVQLQLESLGEQHVGYKCLDFPTIKLSVVGGRPFSCGGNRIFR   125
Os_GI-115466772.pro  ------------------------------------------------------------
Bd_GI-357160893.pro  ------------------------------------------------------------
Bd_GI-357164660.pro  ------------------------------------------------------------
Sb_GI-242092232.pro  ------------------------------------------------------------
Zm_GI-212275448.pro  ------------------------------------------------------------
At_GI-240256211.pro  ------------------------------------------------------------
At_GI-145360806.pro  ------------------------------------------------------------
At_GI-22326876.pro   CSELEKIMGFPRNLKKLYVGGTAIRELPQLPNSLEFLNAHGCKHLKSINLDFEQLPRHFI   840
At_GI-30698242.pro   ------------------------------------------------------------
At_GI-30698240.pro   ------------------------------------------------------------
At_GI-15240018.pro   ------------------------------------------------------------
At_GI-334188680.pro  ------------------------------------------------------------

Si_GI-514815267.pro  ------------------------------------------------------------
Bd_GI-357157184.pro  ------------------------------------------------------------
Br_dA1b.pro          ------------------------------------------------------------
Br_dA1a.pro          ------------------------------------------------------------
At_GI-15221983.pro   ------------------------------------------------------------
Tc_GI-508722773.pro  ------------------------------------------------------------
Gm_GI-356564241.pro  ------------------------------------------------------------
Gm_GI-356552145.pro  ------------------------------------------------------------
Vv_GI-302142429.pro  ------------------------------------------------------------
Vv_GI-359492104.pro  ------------------------------------------------------------
Sl_GI-460385048.pro  ------------------------------------------------------------
Os_GI-218197709.pro  PKLLSKWYGVNDMAESAKRIYDAATNAPKEHAVILLAHNGPTGLGSRMEDICGRDWVAGG   185
Os_GI-115466772.pro  ------------------------------------------------------------
Bd_GI-357160893.pro  ------------------------------------------------------------
Bd_GI-357164660.pro  ------------------------------------------------------------
Sb_GI-242092232.pro  ------------------------------------------------------------
Zm_GI-212275448.pro  ------------------------------------------------------------
At_GI-240256211.pro  ------------------------------------------------------------
At_GI-145360606.pro  ------------------------------------------------------------
At_GI-22326876.pro   FSNCYRFSSQVIAEFVEKGLVASLARAKQEELIKAPEVIICIPMDTRQRSSFRLQAGRNA   900
Ar_GI-30698242.pro   ------------------------------------------------------------
At_GI-30698240.pro   -----------------------------------------MPISDVASLVGGAALGAPLSE   21
At_GI-15240018.pro   -----------------------------------------MASDYYSSDDEGFGEKVGLIG   21
At_GI-334188680.pro  -----------------------------------------------MWCLSCFKPSTKHDP   15

Si_GI-514815267.pro  ------------------------------------------------------------
Bd_GI-357157184.pro  ------------------------------------------------------------
Br_DA1b.pro          ------------------------------------------------------------
Br_DA1a.pro          ------------------------------------------------------------
At_GI-15221983.pro   ------------------------------------------------------------
Tc_GI-508722773.pro  ------------------------------------------------------------
Gm_GI-356564241.pro  ------------------------------------------------------------
Gm_GI-356552145.pro  ------------------------------------------------------------
Vv_GI-302142429.pro  ------------------------------------------------------------
Vv_GI-359492104.pro  ------------------------------------------------------------
Sl_GI-460385048.pro  ------------------------------------------------------------
Os_GI-216197709.pro  GDHGDPDLEQAISDLQRETGVSIPLVVFGHMHKSLAYGRGLRKMIAFGANRTIYLNGAVV   245
Os_GI-115466772.pro  ------------------------------------------------------------
Bd_GI-357160893.pro  ------------------------------------------------------------
```

TABLE 3-continued

Alignment of DA1 proteins (SEQ ID NOS: 41-64)

```
Bd_GI-357164660.pro   ------------------------------------------------------------
Sb_GI-242092232.pro   ------------------------------------------------------------
Zm_GI-212275448.pro   ------------------------------------------------------------
At_GI-240256211.pro   ------------------------------------------------------------
At_GI-145360806.pro   ------------------------------------------------------------
At_GI-22326876.pro    MTDLVPWMQKPISGFSMSVVVSFQDDYHNDVGLRIRCVGTWKTWNNQPDRIVERFFQCWA   960
At_GI-30698242.pro    ------------------------------------------------------------
At_GI-30698240.pro    IFKLVIEEAKKVKDFKP-------------------------------------------L    39
Ar_GI-15240016.pro    EKDRFEAETIHVIEVSQ-------------------------------------------H    39
At_GI-334188680.pro   SEDRFEEETNIVTGIS--------------------------------------------     31

Si_GI-514815267.pro   ------------------------------------------------------------
Bd_GI-357157184.pro   ------------------------------------------------------------
Br_DA1b.pro           ------------------------------------------------------------
Br_DA1a.pro           ------------------------------------------------------------
At_GI-15221983.pro    ------------------------------------------------------------
Tc_GI-508722773.pro   ------------------------------------------------------------
Gm_GI-356564241.pro   ------------------------------------------------------------
Gm_GI-356552145.pro   ------------------------------------------------------------
Vv_GI-302142429.pro   ------------------------------------------------------------
Vv_GI-359492104.pro   ------------------------------------------------------------
Sl_GI-460385048.pro   ------------------------------------------------------------
Os_GI-218197709.pro   PRVNHAQSSRQPAISTSEKTGLEGLTGLMVPTSRAFTIVDLFEGAVEKISEVWVTVGDAR   305
Os_GI-115466772.pro   ------------------------------------------------------------
Bd_GI-357160893.pro   ------------------------------------------------------------
Bd_GI-357164660.pro   ------------------------------------------------------------
Sb_GI-242092232.pro   ------------------------------------------------------------
Zm_GI-212275448.pro   ------------------------------------------------------------
At_GI-240256211.pro   ------------------------------------------------------------
At_GI-145360806.pro   ------------------------------------MDSSSSSSSSPSSSYGVARVS      22
At_GI-22326876.pro    PTEAPKVVADHIFVLYDTKMHPSDSEENHISMWAHEVKFEFHTVSGENNPLGASCKVTEC  1020
At_GI-30698242.pro    ------------------------------------------------------------
At_GI-30698240.pro    SQDLASTMERLVPIFNEIDMMQQGSNRGTSELKVLTETMERAGEMVHKCSRIQWYSIAKK    99
At_GI-15240018.pro    EADIQKAKQRSLATHEAEKLDLATHEAEQLDLAIQEFSRQEEEEERRRTRELENDAQIAN    99
At_GI-334188680.pro   -------------LYEDVILRQRRSEADQIEWAIQDSFNPQE---TSRCRQREEDDQIAR    75

Si_GI-514815267.pro   ------------------------MGWLSKIFKGSVN-RVSRGHYNGNSHE----GYS    29
Bd_GI-357157184.pro   ------------------------MGWLNKIFKGSVN-RVSRGNYDGNWHD----GNS    29
Br_DA1b.pro           ------------------------MGWLNKIFKGSNQ-RHPLGNEHYHHNGGYYENYP   33
Br_DA1a.pro           ------------------------MGWFNKIFKGSTQ-RFRLGNDHDHN--GYYQSYP   31
At_GI-15221983.pro    ------------------------MGWFNKIFKGSNQ-RLRVGNNKHNHN-VYYDNYP   32
Tc_GI-508722773.pro   ------------------------MDWIKKIFKGCAE-KFSEG---HHHG-----NYV   25
Gm_GI-356564241.pro   ------------------------MGWLSRIFKGSDHNKLSEGHYYKEDA-----GYY   29
Gm_GI-356552145.pro   ------------------------MGWLSRIFKGSDENKLSEGHTYKEDA-----GYY   29
Vv_GI-302142429.pro   ------------------------MGWLNKIFKGSSH-KISEGNYHGRYQ-----GDT   28
Vv_GI-359492104.pro   ------------------------MGWLNKIFKGSSH-KISEGNYHGRYQ-----GDT   28
Sl_GI-460385048.pro   ------------------------MGWLNKIFRGSSH-KISEGQYDWRCE-----GHT   28
Os_GI-218197709.pro   TELEQELVLYKQPHKSVPSNIAIWSTMGWLTKFFRGSTH-KISEGQYHSKPAEETIWNGP  364
Os_GI-115466772.pro   ------------------------MGWLTKFFRGSTH-KISEGQYHSKPAEETIWNGP   33
Bd_GI-357160893.pro   ------------------------MGWLTKIFRGSTY-KISEGQRQSRPAEEAVWNEP   33
Bd_GI-357164660.pro   ------------------------MGWLTKFFRGSTH-NISEGQDQSKPAEETVWNEP   33
Sb_GI-242092232.pro   ------------------------MGWLTKFFRGSTH-NISEGQYHSRPAEDTANNEP   33
Zm_GI-212275448.pro   ------------------------MGWLTKFFRGSTH-NISEEQYHSRPAEDTAWNEP   33
At_GI-240256211.pro   ------------------------MGWLTKILKGSSH-KFSDGQCNGRYREDRNLEGP   33
At_GI-145360806.pro   HISNPCIFGEVGSSSSSTYRDKKWKLMKWVSKLFKSGSNGGGSGAHTNHHPPQFQEDENM   82
At_GI-22326876.pro    GVEVITAATGDTSVSGIIRESETITIIEKEDTIIDEEDTPLLSRKPEETNRSRSSSELQK 1080
At_GI-30698242.pro    ------------------------------------------------------------
At_GI-30698240.pro    ALYTREIKA--INQDFLKFCQIELQLIQHRNQLQYMRSMGMASVSTKADLLSDIGNEFSK  157
At_GI-15240018.pro    VLQHEERE---------RLINKKTALEDEEDELLARTLEESLKENNRRKMFEEQVNEDEQ  150
At_GI-334188680.pro   GLQYVEET-----------ELDKSVVDEED--------------------------QQ    96

Si_GI-514815267.pro   TQHTKSY-----------------------------------------------------    36
Bd_GI-357157184.pro   SENIR-------------------------------------------------------    34
Br_DA1b.pro           -HEHS------EPSAETDA------------------------------------DHT    48
Br_DA1a.pro           -HDEPSADTDPDPDPDE---------------------------------------THT    52
At_GI-15221983.pro    TASHDDEPSAADTDADNDEP-----------------------------------HHT   55
Tc_GI-508722773.pro   EDPHP--------------------------------------------------QF   32
Gm_GI-356564241.pro   LPSTS-------------------------------------------------------    34
Gm_GI-356552145.pro   LPSTS-------------------------------------------------------    34
Vv_GI-302142429.pro   VQNEP-------------------------------------------------------    33
Vv_GI-359492104.pro   VQNEP-------------------------------------------------------    33
Sl_GI-460385048.pro   EEDDP-------------------------------------------------------    33
Os_GI-218197709.pro   SNSAVVTMVYPLESTFGQLDLLLLATDLRQLVIDDVCCKLRQQAQPVLHLMYSQLQLLQ  424
Os_GI-115466772.pro   SNSAVVT-----------------------------------------------------    40
Hd_GI-357160893.pro   SSSTVVT-----------------------------------------------------    40
Bd_GI-357164650.pro   SSSTAVN-----------------------------------------------------    40
Sb_GI-242092232.pro   SSSPVVT-----------------------------------------------------    40
Zm_GI-212275448.pro   SSSPVVT-----------------------------------------------------    40
```

TABLE 3-continued

Alignment of DA1 proteins (SEQ ID NOS: 41-64)

```
At_GI-240256211.pro  RYSAEGSDFDKEEIECAIALSLS-------------------EQEHVIPQDDKGKKIIE    73
At_GI-145360806.pro  VFPLPPS---------------------------------------------------    89
At_GI-22326876.pro   LSSTSSKVRSKGNVFWKWLGCFP-----------------LQPKELRSRSHRTTALEEA  1122
At_GI-30698242.pro   ----------------------------------------------------------
At_GI-30698240.pro   LCLVAQPEVVTKFWLKRPLMELKKMLFEDGV----------VTVVVSAPYALGKTTLVTK   207
At_GI-15240018.pro   LALIVQESLNMEEYPIR-LEEYK-------------------SISRRAPLDVDEQ-FAKA   189
At_GI-334188680.pro  LSKIVEESLKE-----------------------------------------------   107

Si_GI-514815267.pro  --------GAHGNED-E----------DMDHAIALSLSEQDQRKGKAIDTEHELD--ED    74
Bd_GI-357157184.pro  --------GAYDESDNE----------DIDRAIALSLAEEDPNKGKAIIDPDYS-----    70
Br_DA1b.pro          QEPSTSEEETWNGKENE----------EVDRVIALSILEE-ENQRPETNTG--------    88
Br_DA1a.pro          QEPSTSEEDTS-GQENE----------DIDRAIALSLIENSQGQTNNTCAAN-------    93
At_GI-15221983.pro   QEPSTSEDNTSNDQENE----------DIDRAIALSLLEE--NQEQTSISG--------    94
Tc_GI-508722773.pro  NAPSVS-GDAWQELENE----------DVDRAIALSLLGE--SQKGRKVID--------    70
Gm_GI-356564241.pro  GVTN-------NQNENE----------DIDRAIALSLVEESRRANNNVNGER-------    69
Gm_GI-356552145.pro  GVTNDAWNQSQNQNENE----------DIDRAIALSLVEETQKANNNVN----------    73
Vv_GI-302142429.pro  ----SCSGDVWAETENE----------DIDRAIALSLSEE--EQKGKKVID--------    68
Vv_GI-359492104.pro  ----SCSGDVWAETENE----------DIDRAIALSLSEE--EQKGKKVIDE-------    69
Sl_GI-460385048.pro  ----STAEDSWSEIE------------EIDRAIALSLSEE--EQKGKIVID--------    66
Os_GI-218197709.pro  TSHAHQHGDVPSEFDNE----------DIARAISLSLLEEEQRKAKAIEKD--------   465
Os_GI-115466772.pro  --------DVPSEFDNE----------DIARAISLSLLEEEQRKAKAIEKD--------    73
Bd_GI-357160893.pro  --------DVLSEFDNE----------DIDRAIALSLSEE-QRKSKGTGKD--------    72
Bd_GI-357164660.pro  --------YALSEFDNE----------DIDRAIALSLSEERKSKGTGKD---------    73
Sb_GI-242092232.pro  --------DIFSEFNNE----------DIDRAIALSLSEEEQRKAKTIDKD--------    73
Zm_GI-212275448.pro  --------DILSEFNNE----------DIDRAIALSLSEEEQRKEKAIDKD--------    73
At_GI-240256211.pro  YKSETEEDDDDDEDEDEEYMRAQLEAAEEEERRVAQAQIEEEEKRRAEAQLEETEKLLAK   133
At_GI-145360806.pro  ----------SLDDRSRGARDKE----------TKRPHGYGWS--------------   125
At_GI-22326876.pro   LEEEALKEREKLEDTREL-----------QIALIESKKIKQADERDQIKHADER----  1167
At_GI-30698242.pro   ----MVRRKRQEEDEKI----------EIERVKEESLKLAKQAEEKRRLEESKEQ----    41
At_GI-30698240.pro   LCHDADVKEKFKQIFFI----------SVSKFPNVRLIGHKLLEHIGCKANEYEN----   252
At_GI-15240018.pro   VKESLKNKGKGKQFEDE----------QVKKDEQLALIVQESLNMVESPPRLEEN----   234
At_GI-334188680.pro  ------KGKSKQFEDD-----------QVENDEQQALMVQESLYMVELSAQLEED----   145

Si_GI-514815267.pro  EQLARALQENTSPTLDEDEQLAR------------------ALQESMNDEHP   108
Bd_GI-357157184.pro  -------------LEEDEQLAR------------------ALHESLNTGSP    90
Br_DA1b.pro          --------AWKHAM-MDDDEQLAR------------------AIQESMIARN-   113
Br_DA1a.pro          --------AGKYAM-VDEDEQLAR------------------AIQESMVGNT   119
At_GI-15221983.pro   ---------KYSMPVDEDEQLAR------------------ALQESMVVGNS   119
Tc_GI-508722773.pro  -----------DEYQLEEDEQLAR------------------ALQESLNFEPP    94
Gm_GI-356564241.pro  --------ILSLQTLLEEDEQLAR------------------AIEQSLNLESP    96
Gm_GI-356552145.pro  ---------DYRSQLEEDEQLAR------------------AIEQSLNLESP    98
Vv_GI-302142429.pro  ----------NEFQLEEDEQLAR------------------AIQESLNIESP    92
Vv_GI-359492104.pro  --------L-DNEFQLEEDEQLAR------------------AIQESLNIESP    95
Sl_GI-460385048.pro  ----------SESQLKEEDEQLAR------------------ALQESLNVESP    90
Os_GI-218197709.pro  ------------MHLEEDEQLAR------------------AIQESLNVESP   487
Os_GI-115466772.pro  ------------MHLEEDEQLAR------------------AIQESLNVESP    95
Bd_GI-357160893.pro  ------------LHLDEDEQLAR------------------AIHESLNVESP    94
Bd_GI-357164660.pro  ------------QHLDEDEQLAR------------------AIQESLNVESP    95
Sb_GI-242092232.pro  ------------MHLEEDEQLAR------------------AIQESLNVESP    95
Zm_GI-212275448.pro  ------------MHLEEDEQLAR------------------AIQESLNVESP    95
At_GI-240256211.pro  ARLEEEEMRRSKAQLEEDELLAK------------------ALQESMNVGSP   167
At_GI-145360806.pro  ---------------MDNNRDFPR------------------PHGGLNPSSF   145
At_GI-22326876.pro   ------EQRKHSKDHEEEEIESNEKEERRHSKDYVIEELVLKGKGKRKQLDDDKADEKEQ  1221
At_GI-30698242.pro   ------GKRIQVDDD-------------------------QLAKTTSKDKGQ    62
At_GI-30698240.pro   ------DLDAMLYIQQLLKQLGRNGSILLVLDDV-------------WAEEESLLQKFL   292
At_GI-15240018.pro   ------NNISTRAPVDEDEQLAK------------------AVEEESLKGKGQ   262
At_GI-334188680.pro  ------KNISTIPPLNEDAQLQK------------------VIWESAKGKGQ   173

Si_GI-514815267.pro  PR---------------------QHIPIEDVHSESAPASSLPPYVFPTNGSRVCA   142
Bd_GI-357157184.pro  PH---------------------QNVPVVDVPSERVPTREPPPPVFLSSGFRACA   124
Br_DA1b.pro          -----GTT------YDFGNAY------GNGHMHGGGNVYDNGDIYYPRPIAFSMDFRICA   156
Br_DA1a.pro          PRQKHGSS------YDIGNAYGAGDVYGNGHMHGGGNVYANGDIYYPRPTAFPMDFRICA   173
At_GI-15221983.pro   PRHKSGST------YDNGNAYGAGDLYGNGHMYGGGNVYANGDIYYPRPITFQMDFRICA   173
Tc_GI-508722773.pro  P----------------------QYENANMYQPMPVHFPMGYRICA   118
Gm_GI-356564241.pro  P----------------------RYGNENMYQPPIQYFPPLG--ICA   118
Gm_GI-356552145.pro  P----------------------RYGNENMYQPPIQYFPMGSRICA   122
Vv_GI-302142429.pro  PQ----------------------HGNGN--------GNGNIYQPIPFPYSTGFRICA   120
Vv_GI-359492104.pro  PQ----------------------HGNGN--------GNGNIYQPIPFPYSIGFRICA   123
Sl_GI-460385048.pro  PQ----------------------HVSRNDHGGGNVYGNGNFYHPVPFPYSASFRVCA   126
Os_GI-218197709.pro  --------------------------PRARENGNANGGNMYQPLPFMFSSGFRICA   517
Os_GI-115466772.pro  --------------------------PRARENGNANGGNMYQPLPFMFSSGFRTCA   125
Bd_GI-357160893.pro  PCARDNGSPPH---ARDNSSPPHARENSSHPRARENGIANGGNSIQHSPFMFSSGFRTCA   151
Bd_GI-357164660.pro  --------------------------PRAREKSSHPRARENGSANGGNSYQL-PLMFSSGFRTCA   133
Sb_GI-242092232.pro  P----------------------PSRENGSANGGNAYHPLPFMFSSGFRACA   125
Zm_GI-212275448.pro  PRRNGSAN-------GGTMYHPPRETGNAYQPPRENGSANGGNAYHPLPFMFSSGFRACA   148
At_GI-240256211.pro  P----------------------RYDPGNILQPYPFLIPSSHRICV   191
At_GI-145360806.pro  IP---------------------PYEPSYQYRRRQRICG   163
At_GI-22326876.pro   IKH---------------------SKDHVEE---------EVNPPLSKCK  1241
```

TABLE 3-continued

Alignment of DA1 proteins (SEQ ID NOS: 41-64)

```
At_GI-30698242.pro    INH-----------------------------SKDVVEE--------DVNPPPS--I    80
At_GI-30698240.pro    IQLPDYKILVTSRFEFTSFGPTFHLKPLIDDEVECRDEIEENEKLP----EVNPPLSMCG  348
At_GI-15240018.pro    IKQ-----------------------------SKDEVEGDGMLL----ELNPPPSLCG   287
At_GI-334188680.pro   IEH-----------------------------FKDPVEEDGNLPRVDLNVNHPHSICD   202

Si_GI-514815267.pro   GCKTPIGQGRFLSCMDSVWHPQCFRCYGCDIPISEYEFAVHE---DHAYHRSCYKERF-H  198
Bd_GI-357157184.pro   GCNNPIGNGRFLSCMDSVWHPQCFRCACNKPISEYEFAMHE---NQPYHKSCYKDFF-H  180
Br_DA1b.pro           GCNMEIGHGRYLNCLNALWHPQCFRCYGCSHPISEYEFSTSG---NYPFHKACYRERF-H  212
Br_DA1a.pro           GCNMEIGHGRYLNCLNALWHPECFRCYGCRHPISEYEFSTSG---NYPFHKACYRERY-H  229
At_GI-15221983.pro    GCNMEIGHGRFLNCLNSLWHPECFRCYGCSQPISEYEFSTSG---NYPFHKACYRERY-H  229
Tc_GI-508722773.pro   GCNTEIGHGRFLNCLNAFWHPECFRCHACNLPISDYEFSMSG---NYRFEKSCYKERY-H  174
Gm_GI-356564241.pro   GCYTEIGFGRYLNCLNAFWHPECFRCRACNLPISDYEFSTSG---NYPYHKSCYKESY-H  174
Gm_GI-356552145.pro   GCYTEIGYGRYLNCLNAFWHPECFRCRACNLPISDYEFSTSG---NYPYHKSCYKESY-H  178
Vv_GI-302142429.pro   GCNTEIGHGRFLSCMGAVWHPECFRCRCHCGYPISDYEYSMNG---NYPYHKSCYKEHY-H  176
Vv_GI-359492104.pro   GCNTEIGHGRFLSCMGAVWHPECFRCRCHCGYPISDYEYSMNG---NYPYBKSCYKEHY-H  179
Sl_GI-460385048.pro   GCSTEIGHGRFLSCMGAVWHPECFRCHACNQPISDYEFSMSG---NYPYHKTCYKEHY-H  182
Os_GI-218197709.pro   GCHSEIGHGRFLSCMGAVWHPECFRCHACNQPIYDYEFSMSG---NHPYHKTCYKERF-H  573
Os_GI-115466772.pro   GCHSEIGHGRFLSCMGAVWHPECFRCHACNQPIYDYEFSMSG---NHPYHKTCYKERF-H  181
Bd_GI-357160893.pro   GCHSEIGHGRFLSCMGAVWHPECFCHACSQPIYDYEFSMSG---NHPYHKTCYKERF-H  207
Bd_GI-357164660.pro   GCHSEIGHGRFLSCMGAVWEPECFCCHSCSQPIYDYEFSMSG---NHPYHKTCYKERF-H  189
Sb_GI-242092232.pro   GCHREIGHGRFLSCMGAVWHPECFRCHACSQPIYDYEFSMSG---NHPYHKTCYKEQF-H  181
Zm_GI-212275448.pro   GCHREIGHGRFLSCMGAVWHPECFRCHACSQPIYDYEFSMSG---NHPYHKTCYKEQF-H  204
At_GI-240256211.pro   GCQAEIGHGRFLSCMGGVWHPECFRCHACDKPIIDYEFSMSG---NRPYHKLCYKEQH-H  247
At_GI-145360806.pro   GCNSDIGSGNYLGCMGTFFHPECFRCHSCGYAITEHEFSLSG---TKPYHKLCFKELT-H  219
At_GI-22326876.pro    DCKSAIEDGISINAYGSVWHPQCFCCLRCREPIAMNEISDLR----GMYHKPCYKELR-H 1296
At_GI-30698242.pro    DGKSEIGDGTSVN-------PRCLCCFHCHRPFVMHEILKK-----GKFHIDCYKEYYRN  128
At_GI-30698240.pro    GCNSAVKHEESVNILGVLWHPCFCCCRDCKPIAIHELENHVSNSRGKFHKSCYER----   404
At_GI-15240018.pro    GCNFAVEHGGSVNILGVLWHPECFCCRACHKPIAIHDIENHVSNSRGKFHKSCYER----  343
At_GI-334188680.pro   GCKSAIEYGRSVHALGVNWHPECFCCRYCDKPIAMHEFS----NTKGRCHITCYERSH--  256
                       .     :       :     * *: * *  . :             *  *: .

Si_GI-514815267.pro   PKCDVCNSFIPTNKNGLIEYRAHPFWMQKYCPSHENDGTPRCCSCERMEPKHSQYITLDD  258
Bd_GI-357157184.pro   PKCDVCKDFIPTNKDGLIEYRAHPFWMQKYCPSHEDDGTPRCCSCERMEPTDIKYIRLDD  240
Br_DA1b.pro           PKCDVCSLFISTNHAGLIEYRAHPFWVQKYCPSHEHDATPRCCSCERMEPRNTGYFELND  272
Br_DA1a.pro           PKCDVCSLFIPTNHAGLIGYRAHPFWVQKYCPSHEHDATPRCCSCERMEPRNIGYVELND  289
At_GI-15221983.pro    PKCDVCSHFIPTNHAGLIEYRAHPFWVQKYCPSHEHDATPRCCSCERMEPRNTRYVELND  289
Tc_GI-508722773.pro   PKCDVCNDFIPTNPAGLIEYRAHPFWIQKYCPSHEHDSTPRCCSCERMEPQDTGYVALND  234
Gm_GI-356564241.pro   PKCDVCKHFIPTNPAGLIEYRAHPFWIQKYCPTHEHDGTPRCCSCERMESQEAGYIALKD  234
Gm_GI-356552145.pro   PKCDVCKHFIPTNPAGLIEYRAHPFWIQKYCPTHEHDGTTRCCSCERMESQEAGYIALKD  238
Vv_GI-302142429.pro   PKCDVCKHFIPTNPAGLIEYRAHPFWVQKYCPSHEHDRTPRCCSCERMEPRDTRYVALND  236
Vv_GI-359492104.pro   PKCDVCKHFIPTNPAGLIEYRAHPFWVQKYCPSHEHDRTPRCCSCERMEPRDTRYVALND  239
Sl_GI-460385048.pro   PKCDVCKHFIPTNAAGLIEYRAHPFWSQKYCPFHEHDGTPRCCSCERMEPRDTRYIALDD  242
Os_GI-218197709.pro   PKCDVCKQFIPTNMNGLIEYRAHPFWLQKYCPSHEVDGTPRCCSCERMEPRESRYVLLDD  633
Os_GI-115466772.pro   PKCDVCKQFIPTNMNGLIEYRAHPFWLQKYCPSHEVDGTPRCCSCERMEPRESRYVLLDD  241
Bd_GI-357160893.pro   PKCDVCKQFIPTNMNGLIEYRAHPFWLQKYCPSHEVDGTPRCCSCERMEPRESRYVLLDD  267
Bd_GI-357164660.pro   PKCDVCQQFIPTNTNGLIEYRAHPFWLQKYCPSHEVDGTPRCCSCERMEPRESRYVLLDD  249
Sb_GI-242092232.pro   PKCDVCKQFIPTNMNGLIEYRAHPFWLQKYCPSHEVDGTPRCCSCERMEPRESRYVLLDD  241
Zm_GI-212275448.pro   PKCDVCKQFIPTNMNGLIEYRAHPFWLQKYCPSHEVDGTPRCCSCERMEPRESKYVLLDD  264
At_GI-240256211.pro   PKCDVCHNFIPTNPAGLIEYRAHPFWMQKYCPSHERDGTPRCCSCERMEPKDTKYLILDD  307
At_GI-145360806.pro   PKCEVCHHFIPTNDAGLIEYRCHPFWNQKYCPSHEYDKTARCCSCERLESWDVRYYTLED  279
At_GI-22326876.pro    PNCYVCEKKIPRTAEGL-KYHEHPFWMETYCPSHDGDGTPKCCSCERLEHCGTQYVMLAD 1355
At_GI-30698242.pro    RNCYVCQQKIPVNAEGIRKFSEHPFWKEKYCPIHDEDGTAKCCCSCERLEPRGTNYVMLGD  188
At_GI-30698240.pro    -YCYVCKEKK------MKTYNIHPFWEERYCPVHEADGTPKCCSCERLEPRGTKYGKLSD  457
At_GI-15240018.pro    -YCYVCKEKK------MKTYNNHPFNEERYCPVHEADGTPKCCSCERLEPRESNYVMLAD  396
At_GI-334188680.pro   PNCHVCKKKFP-----GRKYKEHPFWKEKYCPFHEVDGTPKCCSCERLEPWGTKYVMLAD  311
                       * **                : ****  : *** *:  *  *.:*******.*     *  *  *

Si_GI-514815267.pro   GRRLCLECLHTAIMDTNECQPLYIDIQEFYEGMNMKVEQQVPLLLVERQALNEANEAEKI  318
Bd_GI-357157184.pro   GRKLCLECLTSATMDSPECQHLYMDIQEFFEGLNMKVEQQVPLLLVERQALNEALEAEKS  300
Br_DA1b.pro           GRKLCLECLDSSVMDTFQCQPLYLQIQEFYEGLNMTVEQEVPLLLVERQALNEAREGERN  332
Br_DA1a.pro           GRKLCLECLDSAVMDTFQCQPLYLQIQEFYEGLFMKVEQDVPLLLVERQALNEAREGEKN  349
At_GI-15221983.pro    GRKLCLECLDSAVMDTMQCQPLYLQIQNFYEGLNMKVEQEVPLLLVERQALNEAREGEKN  349
Tc_GI-508722773.pro   GRKLCLECLDSAVMDTKQCQPLYLDILEFYEGLNMKVEQQVPLLLVERQALNEAREGEKN  294
Gm_GI-356564241.pro   GRKLCLECLDSSIMDTNECQPLHADIQRFYDSLNMKLDQQIPLLLVERQALNEAREGEKN  294
Gm_GI-356552145.pro   GRKLCLECLDSAIMDTNECQPLHADIQRFYESLNMKLDQQIPLLLVERQALNEAREGEKN  298
Vv_GI-302142429.pro   GRKLCLECLDSAIMDTNECQPLYLDIQEFYEGLNMKVQQQVPLLLVERQALNEAMEGEKS  296
Vv_GI-359492104.pro   GRKLCLECLDSAIMDTNECQPLYLDIQEFYEGLNMKVQQQVPLLLVERQALNEAMEGEKS  299
Sl_GI-460385048.pro   GRKLCLECLDSAIMDTSQCQPLYYDIQEFYEGLNMKVEQKVPLLLVERQALNEAMDGERH  302
Os_GI-218197709.pro   GRKLCLECLDSAIMDTSECQPLYLEIQEFYEGLNMKVEQQVPLLLVERQALNEAMEGEKT  693
Os_GI-115466772.pro   GRKLCLECLDSAIMDTSECQPLYLEIQEFYEGLNMKVEQQVPLLLVERQALNEAMEGEKT  301
Bd_GI-357160893.pro   GRKLCLECLDSAVMDTTECQPLYLEIQEFYEGLNMKVEQQVPLLLVERQALNEAMEGEKT  327
Bd_GI-357164660.pro   GRKLCLECLDSAVMDTTECQPLYLEIQEFYEGLNMKVEQQVPLLLVERQALNEAMEGEKT  309
Sb_GI-242092232.pro   GRKLCLECLDSAIMDTNECQPLYLEIQEFYEGLNMKVEQQVPLLLVERQALNEAMEGEKA  301
Zm_GI-212275448.pro   GRKLCLECLDSAIMDTNDCQPLYLEIQEFYEGLNMKVEQQVPLLLVERQALNEAMEGEKA  324
At_GI-240256211.pro   GRKLCLECLDSAIMDTHECQPLYLEIREFYEGLHMKVEQQIPMLLVERSALNEAMEGEKH  367
At_GI-145360806.pro   GRSLCLECMETAITDTGECQPLYHAIRDYYEGMYMRLDQQIPMLLVQREALNDAIVGEKN  339
At_GI-22326876.pro    FRWLCRECMDSAIMDSDECQPLHFEIREFFEGLHMKIEEEFPVYLVEKNALNKAEKEEKI 1415
At_GI-30698242.pro    FRWLCIECMGSAVMDTNEVQPLHFEIREFFEGLELKVDKEFALLLVEKQALNKAEEEEKI  248
```

TABLE 3-continued

Alignment of DA1 proteins (SEQ ID NOS: 41-64)

```
At_GI-30698240.pro   GRWLCLECG-KSAMDSDECQPLYFDMRDFFESLNMKIEKEFPLILVRKELLNK--KEEKI    514
At_GI-15240018.pro   GRWLCLECMNSAVMDSDECQPLHFDMRDFFEGLNMKIEKEFPFLLVEKQALNKAEKEEKI    456
At_GI-334188680.pro  NRWLCVKCMECAVMDTYECQPLHFEIREFFGSLNMKVEKEFPLLLVEKEALKKAEAQEKI    371
                       * **  :*       :   *:  :  * *:     :     ::  .: :.:::..  **.:.  *:.       *:

↓

Si_GI-514815267.pro  G-HHLP---ETRGLCLSEEQIVRTILRRPII-GPGNRIIDMITGPYKLVRRCEVTAILIL    373
Bd_GI-357157184.pro  G-HHLP---ETRGLCLSEEQIVRTILRRPTI-GPGNRIIDMITGPYKLVRRCEVTAILIL    355
Br_DA1b.pro          GHYHMP---ETRGLCLSEEQTVRTVRKRSK----GNWSGNMITEQFKLTRRCEVTAILIL    385
Br_DA1a.pro          GHYHMP---ETRGLCLSEEQTVSTVRKRSH-GTGNWAGNMITEPYKLTRQCEVTAILIL    405
At_GI-15221983.pro   GHYHMP---ETRGLCLSEEQTVSTVRKRSH-GTGKWAGN-ITEPYKLTRQCEVTAILIL    404
Tc_GI-508722773.pro  GHYHMP---ETRGLCLSEEQTVSTILRQPRF-GTGNRAMDMITEPCKLTRRCEVTAILIL    350
Gm_GI-356564241.pro  GHYHMP---ETRGLCLSEE--LSTFSRRPRL-G---TAMDMRAQPYRPTTRCDVTAILVL    345
Gm_GI-356552145.pro  GHYHMP---ETRGLCLSEE--LSTFSRRPRL-G---TTMDMRAQPYRPTTRCDVTAILIL    349
Vv_GI-302142429.pro  GHHHMP---ETRGLCLSEEQTVSTILRRPKI-GTGNRVMNMITEPCKLTRRCDVTAVLIL    352
Vv_GI-359492104.pro  GHHHMP---ETRGLCLSEEQTVSTILRRPKI-GTGNRVMNMITEPCKLTRRCDVTAVLIL    355
Sl_GI-460385048.pro  GYHHMP---ETRGLCLSEEQTISTIQRRPRI-GAGNRVMDMRTEPYKLTRRCEVTAILIL    358
Os_GI-218197709.pro  GHHHLP---ETRGLCLSEEQTVSTILRRPRM-AGN-KVMEMITEPYRLTRRCEVTAILIL    748
Os_GI-115466772.pro  GHHHLP---ETRGLCLSEEQTVSTILRRPRM-AGN-KVMEMITEPYRLTRRCEVTAILIL    356
Bd_GI-357160893.pro  GHHHLP---ETRGLCLSEEQTVSTILRRPRM-TGN-KIMEMITEPYRLTRRCEVTAILIL    382
Bd_GI-357164660.pro  GHHHLP---ETRGLCLSEEQTVSTILRRPRM-AGN-KIMEMITEPYRLTRRCEVTAILIL    364
Sb_GI-242092232.pro  GHHHLP---ETRGLCLSEEQTVSTILRRPRM-AGN-KIMGMRTEPYRLTRRCEVTAILIL    356
Zm_GI-212275448.pro  GHHHLP---ETRGLCLSEEQTVSTILR-PRM-AGN-KIMGMITEPYRLTRRCEVTAILIL    378
At_GI-240256211.pro  GHHHLP---ETRGLCLSEEQTVTTVLRRPRI-GAGYKLIDMITEPCRLIRRCEVTAILIL    423
At_GI-145360806.pro  GYHHMP---ETRGLCLSEEQTVTSVLRRPRL-G-AHRLVGMRTQPQRLTRKCEVTAILVL    394
At_GI-22326876.pro   DKQGDQCLMVVRGICLSEEQIVTSVSQGVRR-MLNKQILDTVTESQRVVRKCEVTAILIL   1474
At_GI-30698242.pro   DYHR----AAVTRGLCMSEEQIVPSIIKGPRMGPDNQLITDIVTESQRVS-GFEVTGILII   304
At_GI-30698240.pro   DNEY----EVLIRAYCMSEQKIMTYVSEEPRT-GQNKQLIDMITEPQGVVHECKVTAILIL    570
At_GI-15240018.pro   DYQY----EVVTRGICLSEEQIVDSVSQRPVR-GPNNKLVGMATESQKVTRECEVTAILIL    512
At_GI-334188680.pro  DNQR----GVVTRGICLSEGQIVNSVFKKPTM-GPNGELVSLGTEPQKVVGGCEVTAILIL    427
                    *.  *:**    :    .            :         :              .**..:::

Si_GI-514815267.pro  YGLPRLLTGSILAHEMMHAYLRLK-------------------------GYRTLSPEV    406
Bd_GI-357157184.pro  YGLPRLQTGSILAREMMEAYLRLK-------------------------GYRSLSPQV    388
Br_DA1b.pro          FGLPRLLTGSILAHEMMHAWMRLK-------------------------GFRPLSQDV    418
Br_DA1a.pro          FGLPRLLTGSILAHEMMHAWMRLK-------------------------GFRTLSQDV    438
At_GI-15221983.pro   FGLPRLLTGSILAHEMMHAWMRLK-------------------------GFRTLSQDV    437
Tc_GI-508722773.pro  YGLPRLLTGSILAHEMMHAWMRLQ-------------------------GFRTLSQDV    383
Gm_GI-356564241.pro  YGLPRLLTGSILAHEMMHAWLRLK-------------------------GYRTLSQDV    378
Gm_GI-356552145.pro  YGLPRLLTGSILAHEMMHAWLRLK-------------------------GYRTLSQDV    382
Vv_GI-302142429.pro  YGLPRLLTGSILARHMMHAWLRLN-------------------------GYRTLAQDV    385
Vv_GI-359492104.pro  YGLPRLLTGSILAHEMMHAWLRLN-------------------------GYRTLAQDV    388
Sl_GI-460385048.pro  YGLPRLLTGSILAHEMMHAWLRLR-------------------------GYRTLSQDV    391
Os_GI-218197709.pro  YGLPRLLTGSILAHEMMHAWLRLK-------------------------GYRTLSPDV    781
Os_GI-115466772.pro  YGLPRLLTGSILAHEMMHAWLRLK-------------------------GYRTLSPDV    389
Bd_GI-357160893.pro  YGLPRLLTGSILAHEMMHAWLRLK-------------------------GYRTLSPEI    415
Bd_GI-357164660.pro  YGLPRLLTGSILAHEMMHAWLRLK-------------------------GYRTLSPDI    397
Sb_GI-242092232.pro  YGLPRLLTGSILAHEMMHAWLRLK-------------------------GYRTLSPDV    389
Zm_GI-212275448.pro  YGLPRLLTGSILAHEMMHAWLRLK-------------------------GYRTLSPDV    411
At_GI-240256211.pro  YGLPRLLTGSILAHEMMHAWLRLN-------------------------GYPNLRPEV    456
At_GI-145360806.pro  YGLPRLLTGAILAHELMHGWLRLN-------------------------GFRNLNPEV    427
At_GI-22326876.pro   YGLPRLLTGYILAHEMMHAYLRLN-------------------------GYRNLNMVL   1507
At_GI-30698242.pro   YGLPRLLTGYILAHEMMHAWLRLN-------------------------GYKNLKLEL    337
At_GI-30698240.pro   YGLPRLLTGYILAHEMMHAWLRLN-------------------------GHMNLNNIL    603
At_GI-15240018.pro   YGLPRLLTGYILAHEMMHAYLRLN-------------------------GHRNLNNIL    545
At_GI-334188680.pro  YGLPRLLTGYILAHEMMHAWLRLNGTTSTQFVFANQYGESSQLKVLFGLITGYRNLKLEL    487
                    :***** ** *****:**.::**.                          *. *   :

Si_GI-514815267.pro  EEGICQVLAHLWLESEITSGSGSMATTSAASSS-----SSTS--SSSKKGA-KTEFEKRL    458
Bd_GI-357157184.pro  EEGICQVLSHMWLESEIIAGASGETASTSVPSS-----SSAP--TSSKKGA-KTEFEKRL    440
Br_DA1b.pro          EEGICQVMAHKWLEAELAAGSRNSNAASSSSSS-----Y-----GGVKKGP-RSQYERKL    467
Br_DA1a.pro          EEGICQVMAHKWIEAELAAGSRNSNVASSSSS------------RGVKKGP-RSQYERKL    485
At_GI-15221983.pro   EEGICQVMAHKWLDAELAAGSTMSNAASSSSSS----------QGLKKGP-RSQYERKL    485
Tc_GI-508722773.pro  EEGICQVLAHMWLLTQLEYAS-SSNVASASSSA-----S-----SRLQKGK-RPQFEGKL    431
Gm_GI-356564241.pro  EEGICQVLAHMWLESELSSASGSNFVSASSSSA-----S-----HTSRKGK-RPQFERKL    427
Gm_GI-356552145.pro  EEGICQVLSHMNLESELSSASGSNFVSASSSSA-----S-----HTSRKGK-RPQFERKL    431
Vv_GI-302142429.pro  EEGICQVLAYMWLDAELTSGSGR-----------------------SQCEREL    415
Vv_GI-359492104.pro  EEGICQVLAYMWLDAELTSGSGSNV-PSTSSAS-----------TSSKKGA-GSQCERKL    435
Sl_GI-460385048.pro  EEGICQVLAHMWLETQIASISSSNGGASTSSGM-----------SSSKQGI-RSPFEREL    439
Os_GI-218197709.pro  EEGICQVLAHMWIESEIIAGSGSNGASTSSSSS-----AS----TSSKKGG-RSQFERKL    831
Os_GI-115466772.pro  EEGICQVLAHMWIESEIIAGSGSNGASTSSSSS-----AS----TSSKKGG-RSQFERKL    439
Bd_GI-357160893.pro  EEGICQVLAHMWIESEIMAGSSSNAASTSSSSS-----SS----ISSKKGG-RSQFERKL    465
Bd_GI-357164660.pro  EEGICQVLAHMWIESEITAGSSSNAASTSSSST-----S-------SKKGG-RSQFERKL    444
Sb_GI-242092232.pro  EEGICQVLAHLWIESEIMAGSGSGAASSSSGSS-----SS----MSSKKAG-RSQFEHKL    439
Zm_GI-212275448.pro  EEGICQVLAHMWIESEIMAGSGSSAASSSSSGSS-----SS----TSSKKGG-RSQFEHRL    461
```

TABLE 3-continued

Alignment of DA1 proteins (SEQ ID NOS: 41-64)

```
At_GI-240256211.pro  EEGICQVLAHMWLESETYAGSTLVDIASSSSSA-----VVS---ASSKKGE-RSDFEKKL   507
At_GI-145360806.pro  EEGICQVLSYMWLESEVLSDPSTRNLPSTSSVA-----TSSSSSFSNKKGG-KSNVEKKL   481
At_GI-22326876.pro   EEGLCQVLGYMWLECQTYVFD----TATIASSS--SSSRTPLSTTTSKKVD-PSDFEKRL  1560
At_GI-30698242.pro   EEGLCQALGLRWLESQTFASTDAAAAAVASSSSFSSSTAPPAAITSKKSDDWSIFEKKL   397
At_GI-30698240.pro   EEGICQVLGHLWLESQTYATADTTADAASASSS---SSRTPPAASASKKGE-WSDFDKKL   659
At_GI-15240018.pro   EEGICQVLGHLWLDSQTYATADATADASSSASS---SSRTPPAASASKKGE-WSDFDKKL   601
At_GI-334188680.pro  EEGICQVLGHMWLESQTYS----SSAAASSASS---SSRTP-AANASKKGA-QSDYEKKL   538
                     ***:**.:.  *: :                                        : :*

Si_GI-514815267.pro  GEFFKHQIETDPSVAYGDGFRAGMRAVERYG--LRSTLDHIKLTGSFP-----   504
Bd_GI-357157184.pro  GAFIKNQIETDSSVEYGDGFRAGNRAVERYG--LRSTLDHMKITGSFPY----   487
Br_DA1b.pro          GEFFKHQIESDASPVYGDGFRAGRLAVNKYG--LWRTLEHIQMTGRFPV----   514
Br_DA1a.pro          GEFFKHQIESDASPVYGDGFRAGRLAVNKYG--LPKTLEHIQMTGRFPV----   532
At_GI-15221983.pro   GEFFKHQIESDASPVYGDGFRAGRLAVHKYG--LRKTLEHIQMTGRFPV----   532
Tc_GI-508722773.pro  GEFFKHQIESDTSPVYGDGFRAGHQAVYKYG--LRRTLEHIRMTGRFPY----   478
Gm_GI-356564241.pro  GEFFKHQIESDISPVYGDGFRAGQKAVRKYG--LQRTLHHIRMTGTFPY----   474
Gm_GI-356552145.pro  GEFFKHQIESDISPVYGGGFRAGQKAVSKYG--LQRTLHHIRMTGTFPY----   478
Vv_GI-302142429.pro  GQFFKHQIESDTSLVYGAGFRAGHQAVLKYG--LPATLKHIHLTGNFTY----   462
Vv_GI-359492104.pro  GQFFKHQIESDTSLVYGAGFRAGHQAVLKYG--LPATLKHIHLTGNFPY----   482
Sl_GI-460385048.pro  GDFFKHQIESDTSPIYGNGFRAGNQAVLKYG--LERTLDHIRMTGTFPY----   486
Os_GI-218197709.pro  GDFFKHQIESDTSMAYGDGFRAGNRAVLQYG--LKRTLEHIRLTGTFPF----   878
Os_GI-115466772.pro  GDFFKHQIESDTSMAYGDGFRAGNRAVLQYG--LKRTLEHIRLTGTFPF----   486
Bd_GI-357160893.pro  GDFFKHQIESDTSVAYGNGFRSGNQAVLQYG--LKRTLEHIWLTGTWPF----   512
Bd_GI-357164660.pro  GDFFKHQIESDTSVAYGDGFRAGNQAVLQYG--LKRTLEHIRLTGTLPF----   491
Sb_GI-242092232.pro  GDFFKHQIETDTSMAYGEGFRAGNRAVLQYG--LKRTLEHIRLTGTFPF----   486
Zm_GI-212275448.pro  GDFFKHQIETATSMAYGDGFRTGNRAVLHYG--LKRTLEHIRLTGTFPF----   508
At_GI-240256211.pro  GEFFKHQIESDSSSAYGDGFRQGNQAVLKHG--LRRTLDHIRLTGTFP-----   553
At_GI-145360806.pro  GEFFKHQIAHDASPAYGGGFRAANAAACKYG--LRRTLDHIRLTGTFPL----   528
At_GI-22326876.pro   VNFCKHQIETDESPFFGDGFRKVNKMMASNNHSLKDTLKEIISISKTPQYSKL  1613
At_GI-30698242.pro   VEFCMNQIKEDDSPVYGLGFKQVYEMMVSNNYNIKDTLKDIVSASNATPDSTV   450
At_GI-30698240.pro   VEFCKNQIETDESPVYGLGFRTVNEMVTNS--SLQETLKEILRRR--------   702
At_GI-15240018.pro   VEFCKNQIETDDSPVYGLGFRTVNEMVTNS--SLQETLKEILRQR--------   644
At_GI-334188680.pro  VEFCEDQIETDDSPVYGVGFRKVNQMVSDS--SLHKILKSIQHWTKPDSNL--   587
                     *   .** *  *  :* **:           :    *. :
```

TABLE 4

Alignment of EOD1 proteins (SEQ ID NOS: 74-90)

```
Zm_GI-223973923.pro  ----------------------MNSS--RQMELHYINTGFPYTITESFMDFFEGLTYAHA   36
Sb_GI-242042045.pro  ----------------------MNSC--RQMELHYINTGFPYTITESFMDFFEGLTYAHA   36
Zm_GI-226496789.pro  ----------------------MTSS--RQMELHYINTGFPYTITESFMDFFEGLTYAHA   36
Os_GI-222624282.pro  MTESHERDTEVTRWQVHDPSEGMNGS--RQMELHYINTGFPYTITESFMDFFEGLTYAHA   58
Os_GI-115451045.pro  ----------------------MNGS--RQMELHYINTGFPYTITESMDFFEGLTYARA   36
Bd_GI-357113826.pro  ----------------------MNGS--RQMELHYINTGFPYTITESFMDFFEGLTYAHA   36
Sl_GI-460410949.pro  ----------------------MNWN--QQTEIYYTNGAMPYNSIGSFMDFFGGVTYDHV   36
Rc_GI-255582236.pro  ----------------------------MEVHYINTGFPYTVTESELDFFEGLSHVPV   30
Pt_GI-224059640.pro  ----------------------------MEVHYMNTDFPYTTTESEMDFFEGLTHAPV   30
Gm_GI-356548935.pro  ----------------------MNDG--RQMGVHYVDAGFPYAVNDNFVDFFQGFTHVPV   36
Gm_GI-356544176.pro  ----------------------MNDG--RQMGVNYVDAGFPYAVNENFVDFFQGFTPVPV   36
Vv_GI-359487286.pro  ----------------------MNGN--RQMEVRYINGFPYTITESEMDFFEGLGHVPV   36
Tc_GI-508704801.pro  ----------------------MNGN--RQMEVHYIDTGFPYTATESFMDFFEGLTHVPV   36
Pp_GI-462414664.pro  ----------------------MNGN--GQMDVEYIDTDFPYTPTESEMDFFGGVTHVPM   36
Cr_GI-482561003.pro  ---------------------MNGD-RPVEDAHYTEAEFPYAASGSYIDFYGGAPQGPL   37
At_GI-22331928.pro   ---------------------MNGDNRPVEDAHYTETGFPYAATGSYMDFYGGAAQGPL   38
Sl_GI-460370551.pro  ---------------------MSGD-QHMEAHYMNMGFPYNVPESFPGFLDGVSQAPI   37
                                          *  :   :**    .: .* *

Zm_GI-223973923.pro  DFALTDGFQDQ--GNPYWAMMHTNSYKYGYSGPG--NYYSYAHVYDIDDYMRRADGGRRI   92
Sb_GI-242042045.pro  DFALMDGFQDQ--GNPYWAMMHTNSYKYGYSGPG--NYYTYAHVYDIDDYMHRADGGRRV   92
Zm_GI-226496789.pro  DFALMDGFQDQ--GNPYWTMMHTNSYKYGYSGSG--NYYSYAHAYDIDDYMRTDGGRRT   92
Os_GI-222624282.pro  DFAIADAFHDQ--ANPYWAMMHTNSYKYGYSGAG--NYYSYGHVYDMNDYMHRADGGRRI  114
Os_GI-115451045.pro  DFAIADAFHDQ--ANPYWAMMHTNSYKYGYSGAG--NYYSYGHVYDMNDYMERADGGRRI   92
Bd_GI-357113826.pro  DFALADAFQDQ--ANPYWTMMQTNSYKYGYSGAS--NYYSYGHVYDMNDYMRADGGRRI   92
Sl_GI-460410949.pro  NYIFADPPYAQ--ES-LYPSISTNPYKFGYSEAGSFSYYDYDREYVVNDHVSGIEEHDRH   93
Rc_GI-255582236.pro  HYAHTGQVLDQ--VQENAYWSMNMNAYKYGFSGPGST-YYDP---YEVNDNLPRMDVSRST   85
Pt_GI-224059640.pro  NYAHNGPMHD---QDNAYWSMNMNAYKFGFSGLGSTSYYSP---YEVNDNLPRMDVSRMA   84
Gm_GI-356548935.pro  NYAFAGSIPDQ---ESVYWSMNMNPYKFGLSGPGSTSYYSS---YEVNGHLPRMEIDRAE   90
Gm_GI-356544176.pro  NYAFAGSIPDQ---ESVYWSMNMNPYKFGLSGPGSTSYYSS---YEVNGHLPRMEIDRAE   90
Vv_GI-359487286.pro  NYAQAEAMHNQSIQENFYWTMNMNSYKFGFSGPGS--YYSP---YDVNEHVPGIEVSRRP   92
Td_GI-508704801.pro  NYTHTVPMQDQ---ENIYWSMSMNAYKEGFSGPEST-FYSP---YEVSDHLPRMDVSRRT   89
Pp_GI-462414664.pro  NYCHAMPMHDQ---ETAYWSMNMHSYKFGSGPGSNSYYGNY---YEVNDHLPRMDVSRRT   91
Cr_GI-482561003.pro  NYAHAGTM------DNLYWTMNTNAYKFGFSGSDNPSFYNS---YDMTDHLSRMSIGRTN   88
At_GI-22331928.pro   NYDHAATMHPQ---DNLYWTMNTNAYKFGFSGSDNASFYGS---YDMNDHLSRMSIGRTN   92
Sl_GI-460370551.pro  IQYHNNPVQIQ--DQENAYWSMNMSYYKYEHSNLESTSYHSY---ETGNNHVSRPDFSERP   93
```

TABLE 4-continued

Alignment of EOD1 proteins (SEQ ID NOS: 74-90)

```
                           .   :     **:  *         ::          :   .
Zm_GI-223973923.pro  WDNTTPVNNVDSANVVLQGG-EAPHTTTNTINKECIQQ-VHQSPGSPQVVWQDNIEPDNM   150
Sb_GI-242042045.pro  WDNTTPANNVDSANVVLQGS-EAPRTTANTTTEECIQQ-VHQSPGSPHVVWQDNIDPDNM   150
Zm_GI-226496789.pro  WDNTTPVNNVDSANVVLQGG-EAPRTTANTTSEDCIQQ-VHQSPGSPQVVWQDNIDPDNM   150
Os_GI-222624282.pro  WDNATPVNNTESPNVVLQGG-ETPHANTSSTTEECIQQQVHQNSSSPQVIWQDNIDPDNM   173
Os_GI-115451045.pro  WDNATPVNNTESPNVVLQGG-ETPHANTSSTTEECIQQQVHQNSSSPQVIWQDNIDPDNM   151
Bd_GI-357113826.pro  WDNPTPASNTDSPNVVLQGAAEAPHPRASSTTEECIQQPVHQNSSSPQVVWQDNVDPDNM   152
Sl_GI-460410949.pro  LENPSTTTVNVAANVERE---EISGSNSLTNSVECPRG--QINTRDSEVVWQDNIDPDNM   148
Rc_GI-255582236.pro  WEYPSVVNMEEA-TTTDTQSEGDAVVGVHASPEECIPN-HT-SGDSPQGVWQDDVDPDNM   142
Pt_GI-224059640.pro  WEYPSVV------------------------------IKALWQDDVDPDTM           105
Gm_GI-356548935.pro  WEYPSTITTVEEPATTDSPPRRDGVTSMQTIPEECSPN-HHESNSSSQVIWQDNIYPDDM   149
Gm_GI-356544176.pro  WEYPSTITTVEEPATTDSPPRRDGVTNMQTIPEECSPN-HHESNSSSQVIWQDNIDPDNM   149
Vv_GI-359487286.pro  WEYPSSM-IVEEPTTIETQPTGNEVMNVHAIPEECSPN-HY-SATSSQAIWQDNVDPDNM   149
Tc_GI-508704801.pro  WDYPSTL-NSEEPATIDMQPGGEAVVGIHAIPEECITN-HQ-SNSNSQVVWQDNIDPDNM   146
Pp_GI-462414664.pro  WEHPSVM-NSEEPANIDSHPREEDAVA-EAAPEECIQN-QQ-NTNTSQVVWQEDIDPDNM   147
Cr_GI-482561003.pro  WEYHPMVNVDD-PDITLARSVQIGDSDEHSEAEDCIAN--EHDPDSPQVSWQDDIDPDTM   145
At_GI-22331928.pro   WDYHPMVNVADDPENTVARSVQIGDTDEHSEAEECIAN--EHDPDSPQVSWQDDIDPDTM   150
Sl_GI-460370551.pro  WEYAVPMNVHEG-VSTDVIYEENTVPVEDVGTEECVLS--NQDDSNHQDILEDEIDLDNM   150
                                                          .     ::::  * *

Zm_GI-223973923.pro  TYEELLDLGEAVGTQSRGLSQERISSLPVTKYKCG-FFSRKKTRRERCVI CQMEYRRGNL  209
Sb_GI-242042045.pro  TYEELLDLGEVVGTQSRGLSQERISSLPVTKYKCG-FFSRKKTRRERCVI CQMEYRRGNL  209
Zm_GI-226496789.pro  TYEELLDLGEAVGTQSRGLSQECISLLPITKYKCG-FFSRKKTRRERCVI CQMEYRRGNL  209
Os_GI-222624282.pro  TYEELLDLGEAVGTQSRGLSQERISSLPVTKYKCG-FFSRKKTRRERCVI CQMEYRRGNL  232
Os_GI-115451045.pro  TYEELLDLGEAVGTQSRGLSQERISLLPVTKYKCG-FFSRKKTRRERCVI CQMEYRRGNL  210
Bd_GI-357113826.pro  TYEELLDLGEAVGTQSRGLSQERISLLPVTKYRCG-FFSRKKTRRERCVI CQMEYRRGDL  211
Sl_GI-460410949.pro  TYEELLELGEAVGTQSRGLSQNQISLLPVTKFKCG-FFSRKKSRKERCVI CQMEYKRKDQ  207
Rc_GI-255582236.pro  TYEELLDLGETVGTQSRGLSQELISLLPTSKCKFRSFFLRKKAG-ERCVI CQMRYKRGDK  201
Pt_GI-224059640.pro  TYEELVDLGETVGTQSKGLSPELISLLPTSKCKFGSFFSRKRSG-ERCVI CQMKYKRGDK  164
Gm_GI-356548935.pro  TYEELLDLGEAVGTQSRGLSQELIDMLPTSKYFGSLFKRKNSG-KRCVI CQMTYRRGDQ   208
Gm_GI-356544176.pro  TYEELLDLGEAVGTQSRGLSQELIDMLPTSKYKFGNLFKRKNSG-KRCVI CQMTYRRGDQ   208
Vv_GI-359487286.pro  TYEELLDLGEAVGTQSRGLSQEHINLLPTCRYKSGRLFSRKRSA-ERCVI CQMGYKRGDR   208
Tc_GI-508704801.pro  TYEELLDLGETIGSQSRGLSQEISSLPTSKYKFGSFFSTKR---ERCVI CQMRYKRGEQ   203
Pp_GI-462414664.pro  TYEELLDLGEAVGTQSRGLSDELISLLPTSKYKCGSFFSRKKSG-ERCVI CQMRYKRGDR   206
Cr_GI-482561003.pro  TYEELVELGEAVGTESRGLSQELIETLPTRKFKFGSIFSRKRSG-ERCVI CQLKYKIGER   204
At_GI-22331928.pro   TYEELVELGEAVGTESRGLSQELIETLPTKKYKFGSIFSRKRAG-ERCVI CQLKYKIGER   209
Sl_GI-460370551.pro  TYEELLDLGETVGTESRGLAEELINLLPTTKYKSNGIFSRKKSE-ERCVI CQMRYKRGDR   209
                     *****::***.:*:.*:**:   *.  **     :  *    :*  *.  :******:  *:  :

Zm_GI-223973923.pro  QMTLPCKHVYHASCVTRWLGINKVCPVC FAEVPGEDPEAMSQQL  253
Sb_GI-242042045.pro  QMTLPCKHVYHASCVTRWLSINKVCPVC FAEVPGEDEPKRQ----  249
Zm_GI-226496789.pro  QITLPCKHVYHASCVTRWLSINKVCPVC FAEVPGEDSLRQ----  249
Os_GI-222624282.pro  QMTLPCKHVYHASCVTRWLSINKVCPVC FAEVPGEDEPKRQ----  272
Os_GI-115451045.pro  QMTLPCKHVYHASCVTRWLSINKVCPVC FAEVPGEDEPKRQ----  250
Bd_GI-357113826.pro  QMALPCKHVYHASCVTRWLSINKVCPVC FAEVPSEEPSRQ----  251
Sl_GI-460410949.pro  QVTLPCKHVYHAGCGSRWLSINKACPIC YTEVVINTSKR-----  246
Rc_GI-255582236.pro  QMKLPCKHVYHSECISKWLGINKVCPVC NNEVFGEDSRH-----  240
Pt_GI-224059640.pro  QIKLLCKHAYHSECITKWLGINKVCPVC NDEVFGEESRN-----  203
Gm_GI-356548935.pro  QMKLPCSHVYHGECITKWLSINKKCPVC NTEVFGEESTH-----  247
Gm_GI-356544176.pro  QMKLPCSHVYHGECITKWLSINKKCPVC NTEVFGEESTH-----  247
Vv_GI-359487286.pro  QIKLPCKHVYHTDCGTKWLTINKVCPVC NIEVFGEESRH-----  247
Tc_GI-508704801.pro  QMKLPCKHVYHSQCITKWLSINKICPVC NNEVFGEESRH-----  242
Pp_GI-462414664.pro  QINLPCKHVYHSECISKWLGINKVCPVC NLEVSGEESRH-----  245
Cr_GI-482561003.pro  QMNLPCKHVYHSECISKWLSINKVCPVC NTEVFGDPSIH-----  243
At_GI-22331928.pro   QMNLPCKHVYHSECISKWLSINKVCPVC NSEVFGEPSIH-----  248
Sl_GI-460370551.pro  QINFPCKHIYHTECGSKWLSINKRCSLM NEVVQW----------  243
                     *:  *.* ** *  :** ***  *.:       *
```

The invention claimed is:

1. A method of increasing the size of seeds and/or organs of a plant comprising;
reducing the expression or activity of a DA2 polypeptide within cells of said plant relative to a control or wild-type plant in which expression of the DA2 polypeptide has not been reduced,
wherein the DA2 polypeptide comprises a RING domain of SEQ ID NO: 1 and wherein the plant also has reduced DA1 and/or EOD1 expression or activity.

2. The method according to claim 1 wherein the expression or activity of the DA2 polypeptide is abolished in the cells of the plant.

3. The method of claim 1 wherein said reduced DA1 and/or EOD1 expression or activity results from
reducing the expression or activity of a DA1 polypeptide and/or a EOD1 polypeptide within cells of said plant.

4. The method according to claim 1, wherein the expression or activity of the DA2 polypeptide is reduced by introducing a mutation into the nucleotide sequence of the plant cell which encodes the DA2 polypeptide or which regulates its expression, and regenerating the plant from the mutated cell.

5. The method according to claim 1, wherein the expression or activity of the DA2 polypeptide is reduced by incorporating a heterologous nucleic acid, which expresses a suppressor nucleic acid which reduces expression of the DA2 polypeptide, into said plant cell.

6. The method according to claim 1 wherein the plant has increased plant size, seed size and/or organ size relative to wild type plants.

7. The method according to claim 1 comprising sexually or asexually propagating or growing off-spring or descendants of the plant having reduced DA2 expression or activity.

8. The method according to claim 1 wherein the DA2 polypeptide comprises a RING domain of SEQ ID NO:2.

9. The method according to claim 8 wherein the DA2 polypeptide comprises a first consensus domain of SEQ ID NO: 36.

10. The method according to claim 8 wherein the DA2 polypeptide comprises a second consensus domain of SEQ ID NO: 37.

11. The method according to claim 8 wherein the DA2 polypeptide comprises an amino acid sequence having at least 20% sequence identity to any one of SEQ ID NOS: 20 to 35.

12. The method according to claim 1 wherein the DA1 protein comprises a sequence having at least 20% sequence identity to any one of SEQ ID NOS: 41 to 64.

13. The method according to claim 1 wherein the DA1 comprises a dominant negative R to K substitution at the position in the amino acid sequence of the DA1 polypeptide that is equivalent to position 358 of the DA1 polypeptide of SEQ ID NO: 45.

14. The method according to claim 1 wherein the EOD1 polypeptide comprises a sequence having at least 20% sequence identity to any one of SEQ ID NOS: 74 to 90.

15. The method according to claim 1 wherein the plant is an agricultural plant selected from the group consisting of *Lithospermum erythrorhizon, Taxus* spp, tobacco, cucurbits, carrot, vegetable brassica, melons, capsicums, grape vines, lettuce, strawberry, oilseed brassica, sugar beet, wheat, barley, maize, rice, soyabeans, peas, sorghum, sunflower, tomato, potato, pepper, chrysanthemum, carnation, linseed, hemp and rye.

16. The method according to claim 1 wherein the plant is a higher plant.

17. A method of producing a plant with an increased seed size and/or organ size relative to a control or wild-type plant comprising:
   providing a plant cell that is deficient in the expression or activity of DA1, EOD1 or both DA1and EOD1,
   incorporating a heterologous nucleic acid which reduces the expression or activity of a DA2 polypeptide comprising a RING domain of SEQ ID NO: 1; or introducing a mutation which reduces the expression or activity of a DA2 polypeptide comprising a RING domain of SEQ ID NO: 1 into the plant cell, and;
   regenerating the plant from one or more transformed cells.

18. The method according to claim 17 wherein the heterologous nucleic acid expresses a suppressor nucleic acid which reduces expression of the DA2 polypeptide into said plant cell.

19. The method according to claim 17 wherein the heterologous nucleic acid abolishes the expression or activity of a DA2 polypeptide in the cell of the plant.

20. A plant having reduced expression or activity relative to a control or wild-type plant of a DA2 polypeptide comprising a RING domain of SEQ ID NO: 1and reduced expression or activity of a DA1 polypeptide and/or a EOD1 polypeptide,
   wherein the expression or activity of one or more of said DA2, DA1 and EOD1polypeptides is reduced by the incorporation of heterologous nucleic acids which reduce the expression or activity of said DA2, DA1 and/or EOD1, into one or more cells of the plant.

* * * * *

SEQUENCE LISTING

<160> NUMBER OF SEQ IDS: 91

<210> SEQ ID NO 1
<211> LENGTH: 43
<212> TYPE: PRT
<213> ORGANISM: Artificial sequence
<220> FEATURE:
<223> OTHER INFORMATION: Synthetic sequence: RING domain
<220> FEATURE:
<221> NAME/KEY: VARIANT
<222> LOCATION: (2)..(3)
<223> OTHER INFORMATION: Xaa is any amino acid
<220> FEATURE:

```
<221> NAME/KEY: VARIANT
<222> LOCATION: (5)..(15)
<223> OTHER INFORMATION: Xaa is any amino acid
<220> FEATURE:
<221> NAME/KEY: VARIANT
<222> LOCATION: (18)..(21)
<223> OTHER INFORMATION: Xaa is any amino acid
<220> FEATURE:
<221> NAME/KEY: VARIANT
<222> LOCATION: (23)..(24)
<223> OTHER INFORMATION: Xaa is any amino acid
<220> FEATURE:
<221> NAME/KEY: VARIANT
<222> LOCATION: (26)..(32)
<223> OTHER INFORMATION: Xaa is any amino acid
<220> FEATURE:
<221> NAME/KEY: VARIANT
<222> LOCATION: (33)..(33)
<223> OTHER INFORMATION: Xaa is His, Asn or Thr
<220> FEATURE:
<221> NAME/KEY: VARIANT
<222> LOCATION: (34)..(39)
<223> OTHER INFORMATION: Xaa is any amino acid
<220> FEATURE:
<221> NAME/KEY: VARIANT
<222> LOCATION: (41)..(42)
<223> OTHER INFORMATION: Xaa is any amino acid

<400> SEQUENCE: 1

Cys Xaa Xaa Cys Xaa Xaa Xaa Xaa Xaa Xaa Xaa Xaa Xaa Xaa Xaa Cys
1               5                   10                  15

Cys Xaa Xaa Xaa Xaa Cys Xaa Xaa Cys Xaa Xaa Xaa Xaa Xaa Xaa Xaa
                20                  25                  30

Xaa Xaa Xaa Xaa Xaa Xaa Xaa Cys Xaa Xaa Cys
            35                  40

<210> SEQ ID NO 2
<211> LENGTH: 43
<212> TYPE: PRT
<213> ORGANISM: Artificial sequence
<220> FEATURE:
<223> OTHER INFORMATION: Synthetic sequence RING domain
<220> FEATURE:
<221> NAME/KEY: VARIANT
<222> LOCATION: (7)..(7)
<223> OTHER INFORMATION: Xaa is Tyr or Phe
<220> FEATURE:
<221> NAME/KEY: VARIANT
<222> LOCATION: (15)..(15)
<223> OTHER INFORMATION: Xaa is Lys or Arg
<220> FEATURE:
<221> NAME/KEY: VARIANT
<222> LOCATION: (18)..(18)
<223> OTHER INFORMATION: Xaa is Ser, Met, Thr or Ala
<220> FEATURE:
<221> NAME/KEY: VARIANT
<222> LOCATION: (20)..(20)
<223> OTHER INFORMATION: Xaa is Gly or Ser
<220> FEATURE:
<221> NAME/KEY: VARIANT
<222> LOCATION: (28)..(28)
<223> OTHER INFORMATION: Xaa is Gln or Arg
<220> FEATURE:
<221> NAME/KEY: VARIANT
<222> LOCATION: (31)..(31)
<223> OTHER INFORMATION: Xaa is Pro, Asn, Ser, Val, Thr or Asn
<220> FEATURE:
<221> NAME/KEY: VARIANT
<222> LOCATION: (32)..(32)
<223> OTHER INFORMATION: Xaa is Thr or Pro
<220> FEATURE:
<221> NAME/KEY: VARIANT
<222> LOCATION: (33)..(33)
<223> OTHER INFORMATION: Xaa is His, Asn or Thr
<220> FEATURE:
```

```
<221> NAME/KEY: VARIANT
<222> LOCATION: (34)..(34)
<223> OTHER INFORMATION: Xaa is Thr or Ser
<220> FEATURE:
<221> NAME/KEY: VARIANT
<222> LOCATION: (35)..(35)
<223> OTHER INFORMATION: Xaa is Ala, Thr or Cys
<220> FEATURE:
<221> NAME/KEY: VARIANT
<222> LOCATION: (36)..(36)
<223> OTHER INFORMATION: Xaa is Arg, Gln or Lys
<220> FEATURE:
<221> NAME/KEY: VARIANT
<222> LOCATION: (42)..(42)
<223> OTHER INFORMATION: Xaa is Phe or Tyr

<400> SEQUENCE: 2

Cys Pro Ile Cys Phe Leu Xaa Tyr Pro Ser Leu Asn Arg Ser Xaa Cys
1               5                   10                  15

Cys Xaa Lys Xaa Ile Cys Thr Glu Cys Phe Leu Xaa Met Lys Xaa Xaa
            20                  25                  30

Xaa Xaa Xaa Xaa Pro Thr Gln Cys Pro Xaa Cys
            35                  40

<210> SEQ ID NO 3
<211> LENGTH: 43
<212> TYPE: PRT
<213> ORGANISM: Brachypodium distachyon

<400> SEQUENCE: 3

Cys Pro Ile Cys Phe Leu Tyr Tyr Pro Ser Leu Asn Arg Ser Lys Cys
1               5                   10                  15

Cys Ser Lys Gly Ile Cys Thr Glu Cys Phe Leu Gln Met Lys Pro Thr
            20                  25                  30

His Thr Ala Arg Pro Thr Gln Cys Pro Phe Cys
            35                  40

<210> SEQ ID NO 4
<211> LENGTH: 43
<212> TYPE: PRT
<213> ORGANISM: Hordeum vulgare

<400> SEQUENCE: 4

Cys Pro Ile Cys Phe Leu Tyr Tyr Pro Ser Leu Asn Arg Ser Lys Cys
1               5                   10                  15

Cys Ser Lys Gly Ile Cys Thr Glu Cys Phe Leu Gln Met Lys Pro Thr
            20                  25                  30

His Thr Ala Arg Pro Thr Gln Cys Pro Phe Cys
            35                  40

<210> SEQ ID NO 5
<211> LENGTH: 43
<212> TYPE: PRT
<213> ORGANISM: Zea mays

<400> SEQUENCE: 5

Cys Pro Ile Cys Phe Leu Tyr Tyr Pro Ser Leu Asn Arg Ser Lys Cys
1               5                   10                  15

Cys Ser Lys Gly Ile Cys Thr Glu Cys Phe Leu Gln Met Lys Pro Thr
            20                  25                  30

His Thr Ala Arg Pro Thr Gln Cys Pro Phe Cys
            35                  40
```

```
<210> SEQ ID NO 6
<211> LENGTH: 43
<212> TYPE: PRT
<213> ORGANISM: Sorghum bicolor

<400> SEQUENCE: 6

Cys Pro Ile Cys Phe Leu Tyr Tyr Pro Ser Leu Asn Arg Ser Lys Cys
1               5                   10                  15

Cys Ser Lys Gly Ile Cys Thr Glu Cys Phe Leu Gln Met Lys Pro Thr
            20                  25                  30

His Thr Ala Arg Pro Thr Gln Cys Pro Phe Cys
        35                  40

<210> SEQ ID NO 7
<211> LENGTH: 43
<212> TYPE: PRT
<213> ORGANISM: Oryza sativa

<400> SEQUENCE: 7

Cys Pro Ile Cys Phe Leu Tyr Tyr Pro Ser Leu Asn Arg Ser Lys Cys
1               5                   10                  15

Cys Ser Lys Gly Ile Cys Thr Glu Cys Phe Leu Gln Met Lys Pro Thr
            20                  25                  30

His Thr Ala Gln Pro Thr Gln Cys Pro Phe Cys
        35                  40

<210> SEQ ID NO 8
<211> LENGTH: 43
<212> TYPE: PRT
<213> ORGANISM: Populus trichocarpa

<400> SEQUENCE: 8

Cys Pro Ile Cys Phe Leu Tyr Tyr Pro Ser Leu Asn Arg Ser Arg Cys
1               5                   10                  15

Cys Met Lys Gly Ile Cys Thr Glu Cys Phe Leu Gln Met Lys Asn Pro
            20                  25                  30

Asn Ser Thr Arg Pro Thr Gln Cys Pro Phe Cys
        35                  40

<210> SEQ ID NO 9
<211> LENGTH: 43
<212> TYPE: PRT
<213> ORGANISM: Carica papaya

<400> SEQUENCE: 9

Cys Pro Ile Cys Phe Leu Tyr Tyr Pro Ser Leu Asn Arg Ser Arg Cys
1               5                   10                  15

Cys Met Lys Gly Ile Cys Thr Glu Cys Phe Leu Gln Met Lys Asn Pro
            20                  25                  30

Asn Ser Thr Arg Pro Thr Gln Cys Pro Phe Cys
        35                  40

<210> SEQ ID NO 10
<211> LENGTH: 43
<212> TYPE: PRT
<213> ORGANISM: Ricinus communis

<400> SEQUENCE: 10

Cys Pro Ile Cys Phe Leu Tyr Tyr Pro Ser Leu Asn Arg Ser Arg Cys
1               5                   10                  15

Cys Met Lys Gly Ile Cys Thr Glu Cys Phe Leu Gln Met Lys Asn Pro
```

```
                  20                  25                  30

Asn Ser Thr Arg Pro Thr Gln Cys Pro Phe Cys
        35                  40

<210> SEQ ID NO 11
<211> LENGTH: 43
<212> TYPE: PRT
<213> ORGANISM: Arabidopsis thaliana

<400> SEQUENCE: 11

Cys Pro Ile Cys Phe Leu Tyr Tyr Pro Ser Leu Asn Arg Ser Arg Cys
1               5                   10                  15

Cys Met Lys Ser Ile Cys Thr Glu Cys Phe Leu Gln Met Lys Asn Pro
                20                  25                  30

Asn Ser Ala Arg Pro Thr Gln Cys Pro Phe Cys
        35                  40

<210> SEQ ID NO 12
<211> LENGTH: 43
<212> TYPE: PRT
<213> ORGANISM: Brassica napus

<400> SEQUENCE: 12

Cys Pro Ile Cys Phe Leu Tyr Tyr Pro Ser Leu Asn Arg Ser Arg Cys
1               5                   10                  15

Cys Met Lys Ser Ile Cys Thr Glu Cys Phe Leu Gln Met Lys Asn Pro
                20                  25                  30

Asn Ser Ala Arg Pro Thr Gln Cys Pro Phe Cys
        35                  40

<210> SEQ ID NO 13
<211> LENGTH: 43
<212> TYPE: PRT
<213> ORGANISM: Arabidopsis thaliana

<400> SEQUENCE: 13

Cys Pro Ile Cys Phe Leu Tyr Tyr Pro Ser Leu Asn Arg Ser Arg Cys
1               5                   10                  15

Cys Met Lys Ser Ile Cys Thr Glu Cys Phe Leu Arg Met Lys Ser Pro
                20                  25                  30

Asn Ser Ala Gln Pro Thr Gln Cys Pro Phe Cys
        35                  40

<210> SEQ ID NO 14
<211> LENGTH: 43
<212> TYPE: PRT
<213> ORGANISM: Glycine max

<400> SEQUENCE: 14

Cys Pro Ile Cys Phe Leu Tyr Tyr Pro Ser Leu Asn Arg Ser Arg Cys
1               5                   10                  15

Cys Thr Lys Ser Ile Cys Thr Glu Cys Phe Leu Gln Met Lys Val Pro
                20                  25                  30

Asn Ser Thr Arg Pro Thr Gln Cys Pro Phe Cys
        35                  40

<210> SEQ ID NO 15
<211> LENGTH: 43
<212> TYPE: PRT
<213> ORGANISM: Sorghum bicolor
```

```
<400> SEQUENCE: 15

Cys Pro Ile Cys Phe Leu Phe Tyr Pro Ser Leu Asn Arg Ser Lys Cys
1               5                   10                  15

Cys Ala Lys Gly Ile Cys Thr Glu Cys Phe Leu Gln Met Lys Ser Pro
            20                  25                  30

Thr Ser Cys Arg Pro Thr Gln Cys Pro Tyr Cys
            35                  40

<210> SEQ ID NO 16
<211> LENGTH: 43
<212> TYPE: PRT
<213> ORGANISM: Brachypodium distachyon

<400> SEQUENCE: 16

Cys Pro Ile Cys Phe Leu Phe Tyr Pro Ser Leu Asn Arg Ser Lys Cys
1               5                   10                  15

Cys Ala Lys Gly Ile Cys Thr Glu Cys Phe Leu Gln Met Lys Ser Pro
            20                  25                  30

Thr Ser Cys Arg Pro Thr Gln Cys Pro Tyr Cys
            35                  40

<210> SEQ ID NO 17
<211> LENGTH: 43
<212> TYPE: PRT
<213> ORGANISM: Zea mays

<400> SEQUENCE: 17

Cys Pro Ile Cys Phe Leu Phe Tyr Pro Ser Leu Asn Arg Ser Lys Cys
1               5                   10                  15

Cys Ala Lys Gly Ile Cys Thr Glu Cys Phe Leu Gln Met Lys Ser Pro
            20                  25                  30

Thr Ser Cys Lys Pro Thr Gln Cys Pro Tyr Cys
            35                  40

<210> SEQ ID NO 18
<211> LENGTH: 43
<212> TYPE: PRT
<213> ORGANISM: Oryza sativa

<400> SEQUENCE: 18

Cys Pro Ile Cys Phe Leu Phe Tyr Pro Ser Leu Asn Arg Ser Lys Cys
1               5                   10                  15

Cys Ala Lys Gly Ile Cys Thr Glu Cys Phe Leu Gln Met Arg Thr Pro
            20                  25                  30

Thr Ser Cys Arg Pro Thr Gln Cys Pro Tyr Cys
            35                  40

<210> SEQ ID NO 19
<211> LENGTH: 43
<212> TYPE: PRT
<213> ORGANISM: Vitis vinifera

<400> SEQUENCE: 19

Cys Pro Ile Cys Phe Leu Phe Tyr Pro Ser Leu Asn Arg Ser Arg Cys
1               5                   10                  15

Cys Thr Lys Gly Ile Cys Thr Glu Cys Phe Leu Gln Met Lys Asn Pro
            20                  25                  30

Asn Ser Thr Arg Pro Thr Gln Cys Pro Tyr Cys
            35                  40
```

<210> SEQ ID NO 20
<211> LENGTH: 423
<212> TYPE: PRT
<213> ORGANISM: Populus trichocarpa

<400> SEQUENCE: 20

Met Gly Asn Lys Leu Gly Arg Arg Gln Val Val Asp Glu Arg Tyr
1               5                   10                  15

Thr Arg Pro Gln Gly Leu Tyr Val His Lys Asp Val Asp His Lys Lys
            20                  25                  30

Leu Arg Lys Leu Ile Leu Glu Ser Lys Leu Ala Pro Cys Phe Pro Gly
                35                  40                  45

Asp Glu Asp Ser Cys Asn Asp His Glu Glu Cys Pro Ile Cys Phe Leu
            50                  55                  60

Tyr Tyr Pro Ser Leu Asn Arg Ser Arg Cys Cys Met Lys Gly Ile Cys
65              70                  75                  80

Thr Glu Cys Phe Leu Gln Met Lys Asn Pro Asn Ser Thr Arg Pro Thr
                85                  90                  95

Gln Cys Pro Phe Cys Lys Thr Ser Asn Tyr Ala Val Glu Tyr Arg Gly
            100                 105                 110

Val Lys Thr Lys Glu Glu Lys Gly Leu Glu Gln Ile Glu Glu Gln Arg
                115                 120                 125

Val Ile Glu Ala Lys Ile Arg Met Arg Gln Gln Glu Leu Gln Asp Glu
            130                 135                 140

Glu Glu Arg Met Gln Lys Arg Leu Asp Val Ser Ser Ser Ser Ala Asn
145                 150                 155                 160

Ile Glu Pro Gly Glu Leu Glu Cys Gly Pro Thr Thr Val Pro Ser Asp
                165                 170                 175

Thr Thr Pro Val Glu Ser Gly Glu Ile Val Ser Ser Gln Tyr Ser Ser
            180                 185                 190

Arg Arg Pro Pro His Ala Gly Ala Asn Arg Asp Asp Glu Phe Asp Leu
                195                 200                 205

Asp Leu Glu Asp Ile Met Val Met Glu Ala Ile Trp Leu Ser Ile Gln
            210                 215                 220

Glu Asn Gly Arg Gln Lys Asn Pro Leu Cys Gly Asp Ala Ala Pro Pro
225                 230                 235                 240

Ala Gln Tyr Thr Met Glu Ala Arg Tyr Val Thr Pro Ala Met Ala Pro
                245                 250                 255

Pro Leu Ala Gly Ser Ser Ser Pro Ser Gly Gly Leu Ala Cys Ala
            260                 265                 270

Ile Ala Ala Leu Ala Glu Arg Gln Gln Thr Gly Gly Glu Ser Ile Val
                275                 280                 285

His Asn Ser Gly Asn Met Pro Ser Phe Asn Met Leu Pro Ser Thr Ser
290                 295                 300

Ser Phe Tyr Asn Arg Leu Glu Gln Asp Ala Asp Asn Tyr Ser Pro Ala
305                 310                 315                 320

Gln Ser Ser Ser Asn Val Leu Pro Asp Cys Arg Met Ile Val Thr Arg
                325                 330                 335

Asp Asp Gly Glu Trp Gly Ala Asp Arg Gly Ser Asp Ala Ala Glu Ala
            340                 345                 350

Gly Thr Ser Tyr Ala Ser Ser Glu Thr Ala Glu Asp Ala Gly Gly Ile
                355                 360                 365

Ser Ser Leu Leu Pro Pro Pro Pro Thr Asp Glu Ile Gly Gly Ser
            370                 375                 380

Phe Gln Asn Val Ser Gly Pro Ile Pro Glu Ser Phe Glu Glu Gln Met
385                 390                 395                 400

Met Leu Ala Met Ala Val Ser Leu Ala Glu Ala Arg Ala Met Thr Ser
            405                 410                 415

Gly Pro Gln Ser Ala Trp Gln
            420

<210> SEQ ID NO 21
<211> LENGTH: 420
<212> TYPE: PRT
<213> ORGANISM: Ricinus communis

<400> SEQUENCE: 21

Met Gly Asn Lys Leu Gly Arg Arg Gln Val Val Asp Glu Arg Tyr
1               5                   10                  15

Thr Arg Pro Gln Gly Leu Tyr Val His Lys Asp Val Asp His Lys Lys
            20                  25                  30

Leu Arg Lys Leu Ile Leu Glu Ser Lys Leu Ala Pro Cys Tyr Pro Gly
        35                  40                  45

Asp Asp Glu Phe Gly Asn Asp His Glu Glu Cys Pro Ile Cys Phe Leu
50                  55                  60

Tyr Tyr Pro Ser Leu Asn Arg Ser Arg Cys Cys Met Lys Gly Ile Cys
65                  70                  75                  80

Thr Glu Cys Phe Leu Gln Met Lys Asn Pro Asn Ser Thr Arg Pro Thr
                85                  90                  95

Gln Cys Pro Phe Cys Lys Thr Thr Asn Tyr Ala Val Glu Tyr Arg Gly
            100                 105                 110

Val Lys Thr Lys Glu Glu Lys Gly Met Glu Gln Ile Glu Glu Gln Arg
        115                 120                 125

Val Ile Glu Ala Lys Ile Arg Met Arg Gln Gln Glu Leu Gln Asp Glu
130                 135                 140

Glu Glu Arg Met Gln Lys Arg Leu Glu Leu Ser Ser Ser Ser Ser Ser
145                 150                 155                 160

Ile Ala Pro Gly Glu Val Glu Cys Gly Ser Ala Ala Val Gln Ser Phe
                165                 170                 175

Arg Ser Pro Leu Glu Ala Glu Gly Ser Ile Pro Ser Gln Phe Ser Ile
            180                 185                 190

Arg His Pro Pro His Tyr Arg Ala Asn Arg Asp Asp Glu Phe Asp Leu
        195                 200                 205

Asp Leu Glu Asp Ile Met Val Met Glu Ala Ile Trp Leu Ser Ile Gln
210                 215                 220

Glu Asn Gly Arg Gln Lys Asn Pro Ile Tyr Thr Asp Ala Ala Ser Ser
225                 230                 235                 240

Glu Asn Tyr Ala Val Gln Gly His Tyr Ala Leu Gln Ala Met Pro Pro
                245                 250                 255

Val Thr Glu Ser Ser Ser Ser Pro Ser Gly Gly Leu Ala Cys Ala Ile
            260                 265                 270

Ala Ala Leu Ala Glu Arg Gln Gln Thr Gly Gly Glu Ser Phe Ala His
        275                 280                 285

Asn Asn Glu Asn Val Ala Ala Cys Asn Met Leu Pro Gly Gly Ser Ser
290                 295                 300

Phe Tyr Asn Arg Met Asp Gln Asp Ala Glu Asn Tyr Ser Pro Ala Gln
305                 310                 315                 320

Gly Ser Asn Asn Met Leu Ser Asp Cys Arg Met Ala Arg Asp Asp Val

```
                    325                 330                 335
Gln Trp Val Ala Asp Arg Gly Ser Asp Ala Ala Glu Ala Gly Thr Ser
                340                 345                 350

Tyr Ala Ser Ser Glu Thr Thr Glu Asp Ser Asp Gly Ile Ser Val Val
            355                 360                 365

Leu Pro Pro Pro Leu Pro Pro Asp Glu Ile Val Gly Ser Asp
        370                 375                 380

Ser Gly Met Ile Val Pro Glu Ser Phe Glu Glu Gln Met Met Leu Ala
385                 390                 395                 400

Met Ala Val Ser Leu Ala Glu Ala Gln Ala Met Thr Gly Gly Ala Gly
                405                 410                 415

Ser Ala Trp Gln
            420

<210> SEQ ID NO 22
<211> LENGTH: 423
<212> TYPE: PRT
<213> ORGANISM: Vitis vinifera

<400> SEQUENCE: 22

Met Gly Asn Lys Leu Gly Arg Arg Gln Val Val Glu Asp Lys Tyr
1               5                   10                  15

Thr Arg Pro Gln Gly Leu Tyr Gln His Lys Asp Val Asp His Lys Lys
                20                  25                  30

Leu Arg Lys Leu Ile Leu Asp Ser Lys Leu Ala Pro Cys Tyr Pro Gly
            35                  40                  45

Asp Glu Glu Ala Thr Asn Asp Phe Glu Glu Cys Pro Ile Cys Phe Leu
        50                  55                  60

Phe Tyr Pro Ser Leu Asn Arg Ser Arg Cys Cys Thr Lys Gly Ile Cys
65                  70                  75                  80

Thr Glu Cys Phe Leu Gln Met Lys Asn Pro Asn Ser Thr Arg Pro Thr
                85                  90                  95

Gln Cys Pro Tyr Cys Lys Thr Ala Asn Tyr Ala Val Glu Tyr Arg Gly
            100                 105                 110

Val Lys Thr Lys Glu Glu Lys Gly Met Glu Gln Ile Glu Glu Gln Arg
        115                 120                 125

Val Ile Glu Ala Lys Ile Arg Met Arg Gln Lys Glu Ile Gln Asp Glu
130                 135                 140

Glu Glu Arg Met Gln Lys Arg Gln Glu Ile Ser Ser Ser Ser Ser Ile
145                 150                 155                 160

Leu Ala Gln Gly Glu Val Glu Tyr Ser Thr Thr Ala Val Pro Ser Phe
                165                 170                 175

Arg Ser Pro Val Glu Gly Asp Glu Ile Asp Ser Ser Gln Asp Pro Arg
            180                 185                 190

Ala Ala Ser Met Ile Ile Gln Thr Leu Pro Pro Arg Gln Asn Arg Asp
        195                 200                 205

Glu Glu Phe Asp Leu Asp Leu Glu Asp Ile Met Val Met Glu Ala Ile
    210                 215                 220

Trp Leu Ser Ile Gln Asp Asn Gly Arg His Arg Asn Pro Leu Tyr Gly
225                 230                 235                 240

Asp Thr Thr Thr Ala Glu Gln Tyr Val Thr Glu His Tyr Val Leu
                245                 250                 255

Pro Ala Met Ala Pro Gln Val Glu Ser Ser Ser Pro Ser Gly Gly
            260                 265                 270
```

```
Leu Ala Cys Ala Ile Ala Ala Leu Ala Glu Arg Gln Gln Met Gly Gly
            275                 280                 285

Glu Ser Ser Thr Asn Tyr Asn Gly Asn Met Pro Ala Phe Asn Met Pro
        290                 295                 300

Pro Gly Ser Ser Arg Phe Ser Asn Arg Val Glu Gln Tyr Pro Glu Asn
305                 310                 315                 320

Tyr Pro Pro Ile Glu Ser Ser Met Asp Ala Leu Pro Asp Gly Gly Leu
                325                 330                 335

Ala Val Thr Lys Asp Asp Gly Glu Trp Gly Val Asp Arg Gly Ser Glu
            340                 345                 350

Val Ala Glu Ala Gly Thr Ser Tyr Ala Ser Ser Asp Ala Thr Asp Glu
        355                 360                 365

Ala Gly Gly Val Ala Ala Leu Pro Pro Thr Asp Glu Ala Glu Gly Ser
    370                 375                 380

Phe Gln Asn Val Gly Gly Pro Ile Val Pro Glu Ser Phe Glu Glu Gln
385                 390                 395                 400

Met Met Leu Ala Met Ala Val Ser Leu Ala Glu Ala Arg Ala Arg Thr
                405                 410                 415

Ser Thr Gln Gly Val Trp Gln
            420

<210> SEQ ID NO 23
<211> LENGTH: 431
<212> TYPE: PRT
<213> ORGANISM: Glycine max

<400> SEQUENCE: 23

Met Gly Asn Lys Leu Gly Arg Arg Gln Val Val Asp Glu Lys Tyr
1               5                   10                  15

Thr Arg Pro Gln Gly Leu Tyr Asn His Lys Asp Val Asp His Lys Lys
            20                  25                  30

Leu Arg Lys Leu Ile Leu Glu Ser Lys Leu Ala Pro Cys Tyr Pro Gly
        35                  40                  45

Asp Glu Glu Thr Ala Tyr Asp Arg Glu Glu Cys Pro Ile Cys Phe Leu
50                  55                  60

Tyr Tyr Pro Ser Leu Asn Arg Ser Arg Cys Cys Thr Lys Ser Ile Cys
65                  70                  75                  80

Thr Glu Cys Phe Leu Gln Met Lys Val Pro Asn Ser Thr Arg Pro Thr
                85                  90                  95

Gln Cys Pro Phe Cys Lys Thr Ala Asn Tyr Ala Val Glu Tyr Arg Gly
            100                 105                 110

Val Lys Ser Lys Glu Glu Lys Gly Leu Glu Gln Ile Glu Glu Gln Arg
        115                 120                 125

Val Ile Glu Ala Lys Ile Arg Met Arg Gln Gln Leu Gln Asp Glu
130                 135                 140

Glu Glu Arg Met His Lys Arg Leu Glu Met Ser Ser Ser Asn Val Asn
145                 150                 155                 160

Val Ala Val Ala Asp Val Glu Tyr Ser Ser Asn Ala Val Ser Ser Ser
                165                 170                 175

Ser Val Ser Val Val Glu Asn Asp Glu Ile Val Ser Ser Gln Asp Ser
            180                 185                 190

Cys Ala Thr Ser Val Val Arg Ala Asn Ala Thr Thr Arg Thr Asn Arg
        195                 200                 205

Asp Asp Glu Phe Asp Val Asp Leu Glu Asp Ile Met Val Met Glu Ala
210                 215                 220
```

Ile Trp Leu Ser Ile Gln Glu Asn Gly Arg Arg Asn Leu Ser Phe
225                 230                 235                 240

Val Asp Ala Thr Ser Gly His Tyr Val Ala Asp Gly Arg Tyr Val Ser
            245                 250                 255

Ser Val Ser Ser Val Ser Ser Val Met Gly Pro Pro Thr Gly Ser Ser
        260                 265                 270

Ser Ser Pro Ser Gly Gly Leu Ala Cys Ala Ile Ala Ala Leu Ala Glu
    275                 280                 285

Arg Gln Gln Met Ala Gly Glu Ser Ser Met Ser Leu Thr Asn Glu Asn
290                 295                 300

Met Pro Ser Phe Asn Thr Leu Pro Gly Ser Arg Arg Phe Tyr Asn Arg
305                 310                 315                 320

Leu Gly Arg Asp Met Ala Asn Tyr Pro Pro Gly Asp Asn Leu Asn Glu
                325                 330                 335

Glu Pro Leu Asp Glu Ala Val Thr Met Thr Arg Ser His Gly Glu Trp
            340                 345                 350

Asp Met Asp His Gly Thr Gln Leu Thr Glu Thr Ala Thr Ser Tyr Thr
        355                 360                 365

Asn Ser Val Ala Ala Glu Asp Arg Gly Glu Leu Ser Ser Leu Pro Arg
    370                 375                 380

Ser Asp Asp Asn Asp Gly Ser Leu Gln Ser Ala Thr Glu Pro Ile Val
385                 390                 395                 400

Pro Glu Ser Phe Glu Glu Gln Met Met Leu Ala Met Ala Val Ser Leu
                405                 410                 415

Ala Glu Ala Arg Ala Met Ser Ser Gly Gln Ser Ala Ser Trp Gln
            420                 425                 430

<210> SEQ ID NO 24
<211> LENGTH: 401
<212> TYPE: PRT
<213> ORGANISM: Arabidopsis thaliana

<400> SEQUENCE: 24

Met Gly Asn Lys Leu Gly Arg Lys Arg Gln Val Val Glu Glu Arg Tyr
1               5                   10                  15

Thr Lys Pro Gln Gly Leu Tyr Val Asn Lys Asp Val Asp Val Lys Lys
            20                  25                  30

Leu Arg Lys Leu Ile Val Glu Ser Lys Leu Ala Pro Cys Tyr Pro Gly
        35                  40                  45

Asp Asp Glu Ser Cys His Asp Leu Glu Glu Cys Pro Ile Cys Phe Leu
    50                  55                  60

Tyr Tyr Pro Ser Leu Asn Arg Ser Arg Cys Cys Met Lys Ser Ile Cys
65                  70                  75                  80

Thr Glu Cys Phe Leu Gln Met Lys Asn Pro Asn Ser Ala Arg Pro Thr
                85                  90                  95

Gln Cys Pro Phe Cys Lys Thr Pro Asn Tyr Ala Val Glu Tyr Arg Gly
            100                 105                 110

Val Lys Ser Lys Glu Glu Lys Gly Ile Glu Gln Val Glu Glu Gln Arg
        115                 120                 125

Val Ile Glu Ala Lys Ile Arg Met Arg Gln Lys Glu Met Gln Asp Asp
    130                 135                 140

Glu Glu Lys Met Gln Lys Arg Leu Glu Ser Cys Ser Ser Ser Thr Ser
145                 150                 155                 160

Ala Met Thr Gly Glu Met Glu Tyr Gly Ser Thr Ser Ala Ile Ser Tyr

```
                    165                 170                 175
Asn Ser Leu Met Asp Asp Gly Glu Ile Ala Pro Ser Gln Asn Ala Ser
                180                 185                 190

Val Val Arg Gln His Ser Arg Pro Arg Gly Asn Arg Glu Asp Glu Val
                195                 200                 205

Asp Val Asp Leu Glu Glu Leu Met Val Met Glu Ala Ile Trp Leu Ser
            210                 215                 220

Val Gln Glu Thr Gly Thr Gln Arg Asn Ser Ala Ser Gly Glu Ile Thr
225                 230                 235                 240

Ser Ser Arg Gln Tyr Val Thr Asp Asn His Ser Tyr Val Ser Ser Pro
                245                 250                 255

Pro Arg Val Thr Pro Ile Val Glu Pro Ala Thr Pro Ser Ser Ser Ser
                260                 265                 270

Gly Gly Leu Ser Cys Ala Ile Ser Ala Leu Ala Glu Arg Gln Met Val
                275                 280                 285

Gly Glu Ser Ser Ser His Asn His Asn His Asn Val Asn Val Ser Ser
            290                 295                 300

Tyr Ser Met Leu Pro Gly Asn Cys Asp Ser Tyr Tyr Asp Ile Glu Gln
305                 310                 315                 320

Glu Val Asp Gly Ile Asp Asn His His His Arg His His Tyr Glu
                325                 330                 335

Met Gly Glu Thr Gly Ser Ser Asn Ser Tyr Val Ser Ser Tyr Met Thr
                340                 345                 350

Gly Glu Gly Phe His Asn Phe Pro Pro Pro Pro Leu Val Ile Val
                355                 360                 365

Pro Glu Ser Phe Glu Glu Gln Met Met Met Ala Met Ala Val Ser Met
            370                 375                 380

Ala Glu Val His Ala Thr Thr Thr Cys Ala Pro Thr Glu Val Thr Trp
385                 390                 395                 400

Gln

<210> SEQ ID NO 25
<211> LENGTH: 424
<212> TYPE: PRT
<213> ORGANISM: Triticum aestivum

<400> SEQUENCE: 25

Met Gly Asn Arg Ile Gly Gly Arg Arg Lys Ala Gly Val Glu Glu Arg
1               5                   10                  15

Tyr Thr Arg Pro Gln Gly Leu Tyr Glu His Arg Asp Ile Asp Gln Lys
                20                  25                  30

Lys Leu Arg Lys Leu Ile Leu Glu Ala Lys Leu Ala Pro Cys Tyr Pro
            35                  40                  45

Gly Ala Asp Asp Ala Ala Gly Gly Asp Leu Glu Glu Cys Pro Ile Cys
        50                  55                  60

Phe Leu Tyr Tyr Pro Ser Leu Asn Arg Ser Lys Cys Cys Ser Lys Gly
65                  70                  75                  80

Ile Cys Thr Glu Cys Phe Leu Gln Met Lys Pro Thr His Thr Ala Arg
                85                  90                  95

Pro Thr Gln Cys Pro Phe Cys Lys Thr Pro Asn Tyr Ala Val Glu Tyr
                100                 105                 110

Arg Gly Val Lys Thr Lys Glu Glu Arg Ser Ile Glu Gln Phe Glu Glu
            115                 120                 125

Gln Lys Val Ile Glu Ala Gln Met Arg Met Arg Gln Gln Ala Leu Gln
```

```
            130                 135                 140
Asp Glu Glu Asp Lys Met Lys Arg Lys Gln Ser Arg Cys Ser Ser Ser
145                 150                 155                 160

Arg Thr Ile Ala Pro Thr Thr Glu Val Glu Tyr Arg Asp Ile Cys Ser
                165                 170                 175

Thr Ser Tyr Ser Val Pro Ser Tyr Gln Cys Thr Glu Gln Glu Thr Glu
            180                 185                 190

Cys Cys Ser Ser Glu Pro Ser Cys Ser Ala Gln Ala Asn Met Arg Ser
            195                 200                 205

Phe His Ser Arg His Thr Arg Asp Asp Asn Ile Asp Met Asn Ile Glu
            210                 215                 220

Asp Met Met Val Met Glu Ala Ile Trp Arg Ser Ile Gln Glu Gln Gly
225                 230                 235                 240

Ser Ile Gly Asn Pro Ala Cys Gly Ser Phe Met Pro Phe Glu Gln Pro
                245                 250                 255

Thr Cys Glu Arg Gln Ala Phe Val Ala Ala Pro Pro Leu Glu Ile Pro
                260                 265                 270

His Pro Gly Gly Phe Ser Cys Ala Val Ala Ala Met Ala Glu His Gln
            275                 280                 285

Pro Ser Ser Met Asp Phe Ser Tyr Met Thr Gly Ser Ser Ala Phe Pro
            290                 295                 300

Val Phe Asp Met Phe Arg Arg Pro Cys Asn Ile Ala Gly Gly Ser Met
305                 310                 315                 320

Cys Ala Val Glu Ser Ser Pro Asp Ser Trp Ser Gly Ile Ala Ser Ser
                325                 330                 335

Cys Ser Arg Arg Glu Val Val Arg Glu Glu Gly Glu Cys Ser Thr Asp
            340                 345                 350

His Trp Ser Glu Gly Ala Glu Ala Gly Thr Ser Tyr Ala Gly Ser Asp
            355                 360                 365

Ile Val Val Asp Ala Gly Thr Thr Pro Pro Leu Pro Val Thr Asp Asn
370                 375                 380

Tyr Ser Met Val Ala Ser His Phe Arg Pro Glu Ser Ile Glu Glu Gln
385                 390                 395                 400

Met Met Tyr Ser Met Ala Val Ser Leu Ala Glu Ala His Gly Arg Thr
                405                 410                 415

His Thr Gln Gly Leu Ala Trp Leu
            420

<210> SEQ ID NO 26
<211> LENGTH: 424
<212> TYPE: PRT
<213> ORGANISM: Hordeum vulgare

<400> SEQUENCE: 26

Met Gly Asn Arg Ile Gly Gly Arg Arg Lys Ala Gly Val Glu Glu Arg
1               5                   10                  15

Tyr Thr Arg Pro Gln Gly Leu Tyr Glu His Arg Asp Ile Asp Gln Lys
                20                  25                  30

Lys Leu Arg Lys Leu Ile Leu Glu Thr Lys Leu Ala Pro Cys Tyr Pro
            35                  40                  45

Gly Ala Asp Asp Ala Ala Gly Ala Asp Leu Glu Glu Cys Pro Ile Cys
        50                  55                  60

Phe Leu Tyr Tyr Pro Ser Leu Asn Arg Ser Lys Cys Cys Ser Lys Gly
65                  70                  75                  80
```

Ile Cys Thr Glu Cys Phe Leu Gln Met Lys Pro Thr His Thr Ala Arg
            85                  90                  95

Pro Thr Gln Cys Pro Phe Cys Lys Thr Pro Asn Tyr Ala Val Glu Tyr
        100                 105                 110

Arg Gly Val Lys Thr Lys Glu Arg Ser Ile Glu Gln Phe Glu Glu
        115                 120                 125

Gln Lys Val Ile Glu Ala Gln Met Arg Met Arg Gln Gln Ala Leu Gln
130                 135                 140

Asp Glu Glu Asp Lys Met Arg Arg Lys Gln Ser Arg Cys Ser Ser Ser
145                 150                 155                 160

Arg Thr Ile Ala Pro Thr Thr Glu Val Glu Tyr Arg Asp Ile Cys Ser
                165                 170                 175

Thr Ser Tyr Ser Ala Pro Pro Tyr Arg Cys Thr Glu Gln Glu Thr Glu
            180                 185                 190

Cys Cys Ser Ser Glu Pro Ser Cys Ser Ala Gln Ala Asn Met Arg Ser
        195                 200                 205

Phe His Ser Arg His Thr Arg Asp Gly Asn Ile Asp Met Asn Ile Glu
    210                 215                 220

Asp Met Met Val Met Glu Ala Ile Trp Arg Ser Ile Gln Glu Gln Gly
225                 230                 235                 240

Ser Ile Gly Asn Pro Ala Cys Gly Ser Phe Met Pro Phe Glu Gln Pro
                245                 250                 255

Thr Arg Glu Arg Gln Ala Phe Val Ala Ala Ser Pro Leu Glu Ile Pro
            260                 265                 270

His Pro Gly Gly Phe Ser Cys Ala Val Ala Ala Met Thr Glu His Gln
        275                 280                 285

Pro Ser Ser Met Asp Phe Ser Tyr Met Thr Gly Ser Ser Ala Phe Pro
    290                 295                 300

Val Phe Asp Met Phe Arg Arg Pro Cys Asn Ile Ala Gly Gly Ser Leu
305                 310                 315                 320

Arg Ala Val Glu Ser Ser Leu Asp Ser Trp Ser Gly Ile Ala Pro Ser
                325                 330                 335

Gly Thr Arg Arg Glu Met Val Arg Glu Glu Gly Glu Cys Ser Ile Asp
            340                 345                 350

His Trp Ser Glu Gly Ala Glu Ala Gly Thr Ser Tyr Ala Gly Ser Asp
        355                 360                 365

Ile Met Ala Asp Ala Gly Thr Met Pro Pro Leu Pro Phe Ala Asp Asn
    370                 375                 380

Tyr Ser Met Ala Ala Ser His Phe Arg Pro Glu Ser Ile Glu Glu Gln
385                 390                 395                 400

Met Met Tyr Ser Met Ala Val Ser Leu Ala Glu Ala His Gly Arg Thr
                405                 410                 415

His Thr Gln Gly Leu Thr Trp Leu
            420

<210> SEQ ID NO 27
<211> LENGTH: 423
<212> TYPE: PRT
<213> ORGANISM: Brachypodium distachyon

<400> SEQUENCE: 27

Met Gly Asn Arg Ile Gly Gly Arg Arg Lys Ala Gly Val Glu Arg
1               5                   10                  15

Tyr Thr Arg Pro Gln Gly Leu Tyr Glu His Arg Asp Ile Asp Gln Lys
            20                  25                  30

```
Lys Leu Arg Lys Leu Ile Leu Glu Ala Lys Leu Ala Pro Cys Tyr Pro
            35                  40                  45
Gly Ala Asp Asp Ala Ala Gly Gly Asp Leu Glu Glu Cys Pro Ile Cys
 50                  55                  60
Phe Leu Tyr Tyr Pro Ser Leu Asn Arg Ser Lys Cys Cys Ser Lys Gly
 65                  70                  75                  80
Ile Cys Thr Glu Cys Phe Leu Gln Met Lys Pro Thr His Thr Ala Arg
                85                  90                  95
Pro Thr Gln Cys Pro Phe Cys Lys Thr Pro Asn Tyr Ala Val Glu Tyr
               100                 105                 110
Arg Gly Val Lys Thr Lys Glu Arg Ser Ile Glu Gln Leu Glu Glu
               115                 120                 125
Gln Lys Val Ile Glu Ala Gln Met Arg Met Arg Gln Gln Ala Leu Gln
130                 135                 140
Asp Glu Glu Asp Lys Met Lys Arg Lys Gln Ser Arg Cys Ser Ser Ser
145                 150                 155                 160
Arg Thr Ile Ala Pro Thr Thr Glu Val Glu Tyr Arg Asp Ile Cys Ser
               165                 170                 175
Thr Ser Tyr Ser Val Pro Ser Tyr Gln Cys Thr Glu Gln Glu Ala Glu
               180                 185                 190
Cys Cys Ser Ser Glu Pro Ser Cys Ser Ala Gln Ser Asn Met Arg Pro
               195                 200                 205
Val His Ser Arg His Asn Arg Asp Asp Asn Ile Gly Met Asn Ile Glu
               210                 215                 220
Glu Met Met Val Met Glu Ala Ile Trp Arg Ser Ile Gln Glu Gln Gly
225                 230                 235                 240
Ser Met Gly Asn Pro Val Cys Gly Asn Phe Met Pro Val Ile Glu Pro
               245                 250                 255
Pro Ser Arg Glu Arg Gln Ala Phe Val Pro Ala Pro Leu Glu Ile Pro
               260                 265                 270
His Pro Gly Gly Phe Ser Cys Ala Val Ala Ser Met Ala Glu His Gln
               275                 280                 285
Pro Pro Ser Met Asp Phe Ser Tyr Met Ala Gly Asn Ser Ala Phe Pro
               290                 295                 300
Val Phe Asp Met Phe Arg Arg Gln Cys Asn Ile Ser Gly Gly Ser Met
305                 310                 315                 320
Cys Ala Val Asp Ser Ser Pro Asp Ser Trp Ser Gly Ile Pro Pro Ser
               325                 330                 335
Cys Ser Arg Glu Met Ile Arg Glu Glu Gly Glu Cys Ser Thr Asp His
               340                 345                 350
Trp Ser Glu Gly Ala Glu Ala Gly Thr Ser Tyr Ala Gly Ser Asp Ile
               355                 360                 365
Val Ala Asp Ala Gly Thr Met Gln Gln Leu Pro Phe Ala Glu Asn Tyr
370                 375                 380
Asn Met Ala Pro Ser His Phe Arg Pro Glu Ser Ile Glu Glu Gln Met
385                 390                 395                 400
Met Tyr Ser Met Thr Val Ser Leu Ala Glu Ala His Gly Arg Thr His
               405                 410                 415
Ser Gln Gly Leu Ala Trp Leu
               420
```

<210> SEQ ID NO 28
<211> LENGTH: 423

<212> TYPE: PRT
<213> ORGANISM: Oryza sativa

<400> SEQUENCE: 28

```
Met Gly Asn Arg Ile Gly Gly Arg Arg Lys Ala Gly Val Glu Glu Arg
1               5                   10                  15

Tyr Thr Arg Pro Gln Gly Leu Tyr Glu His Arg Asp Ile Asp Gln Lys
            20                  25                  30

Lys Leu Arg Lys Leu Ile Leu Glu Ala Lys Leu Ala Pro Cys Tyr Met
        35                  40                  45

Gly Ala Asp Asp Ala Ala Ala Ala Asp Leu Glu Glu Cys Pro Ile
    50                  55                  60

Cys Phe Leu Tyr Tyr Pro Ser Leu Asn Arg Ser Lys Cys Cys Ser Lys
65                  70                  75                  80

Gly Ile Cys Thr Glu Cys Phe Leu Gln Met Lys Pro Thr His Thr Ala
                85                  90                  95

Gln Pro Thr Gln Cys Pro Phe Cys Lys Thr Pro Ser Tyr Ala Val Glu
            100                 105                 110

Tyr Arg Gly Val Lys Thr Lys Glu Glu Arg Ser Ile Glu Gln Phe Glu
        115                 120                 125

Glu Gln Lys Val Ile Glu Ala Gln Met Arg Met Arg Gln Gln Ala Leu
130                 135                 140

Gln Asp Glu Glu Asp Lys Met Lys Arg Lys Gln Asn Arg Cys Ser Ser
145                 150                 155                 160

Ser Arg Thr Ile Thr Pro Thr Lys Glu Val Glu Tyr Arg Asp Ile Cys
                165                 170                 175

Ser Thr Ser Phe Ser Val Pro Ser Tyr Arg Cys Ala Glu Gln Glu Thr
            180                 185                 190

Glu Cys Cys Ser Ser Glu Pro Ser Cys Ser Ala Gln Thr Ser Met Arg
        195                 200                 205

Pro Phe His Ser Arg His Asn Arg Asp Asp Asn Ile Asp Met Asn Ile
    210                 215                 220

Glu Asp Met Met Val Met Glu Ala Ile Trp Arg Ser Ile Gln Gly Ser
225                 230                 235                 240

Ile Gly Asn Pro Val Cys Gly Asn Phe Met Pro Val Thr Glu Pro Ser
                245                 250                 255

Pro Arg Glu Arg Gln Pro Phe Val Pro Ala Ala Ser Leu Glu Ile Pro
            260                 265                 270

His Gly Gly Gly Phe Ser Cys Ala Val Ala Ala Met Ala Glu His Gln
        275                 280                 285

Pro Pro Ser Met Asp Phe Ser Tyr Met Ala Gly Ser Ser Ala Phe Pro
290                 295                 300

Val Phe Asp Met Phe Arg Arg Pro Cys Asn Ile Ala Gly Gly Ser Met
305                 310                 315                 320

Cys Asn Leu Glu Ser Ser Pro Glu Ser Trp Ser Gly Ile Ala Pro Ser
                325                 330                 335

Cys Ser Arg Glu Val Val Arg Glu Glu Gly Glu Cys Ser Ala Asp His
            340                 345                 350

Trp Ser Glu Gly Ala Glu Ala Gly Thr Ser Tyr Ala Gly Ser Asp Ile
        355                 360                 365

Val Ala Asp Ala Gly Thr Met Pro Gln Leu Pro Phe Ala Glu Asn Phe
370                 375                 380

Ala Met Ala Pro Ser His Phe Arg Pro Glu Ser Ile Glu Glu Gln Met
385                 390                 395                 400
```

```
Met Phe Ser Met Ala Leu Ser Leu Ala Asp Gly His Gly Arg Thr His
                405                 410                 415
Ser Gln Gly Leu Ala Trp Leu
            420

<210> SEQ ID NO 29
<211> LENGTH: 428
<212> TYPE: PRT
<213> ORGANISM: Sorghum bicolor

<400> SEQUENCE: 29

Met Gly Asn Arg Lys Gly Arg Pro Lys Ser Gly Gly Glu Lys Arg
1               5                   10                  15
Phe Thr Pro Pro Gln Gly Leu Tyr Glu His Lys Asp Ile Asp Gln Lys
                20                  25                  30
Lys Leu Arg Lys Leu Ile Leu Glu Ala Lys Leu Ala Pro Cys Tyr Pro
                35                  40                  45
Gly Ala Asp Asp Ala Ala Ala Gly Gly Asp Leu Glu Glu Cys Pro
            50                  55                  60
Ile Cys Phe Leu Tyr Tyr Pro Ser Leu Asn Arg Ser Lys Cys Cys Ser
65                  70                  75                  80
Lys Gly Ile Cys Thr Glu Cys Phe Leu Gln Met Lys Pro Thr His Thr
                85                  90                  95
Ala Arg Pro Thr Gln Cys Pro Phe Cys Lys Thr Pro Asn Tyr Ala Val
                100                 105                 110
Glu Tyr Arg Gly Val Lys Thr Lys Glu Glu Arg Ser Ile Glu Gln Phe
            115                 120                 125
Glu Glu Gln Lys Val Ile Glu Ala Gln Leu Arg Met Arg Gln Lys Glu
            130                 135                 140
Leu Gln Asp Glu Glu Ala Lys Met Lys Arg Lys Gln Ser Arg Cys Ser
145                 150                 155                 160
Ser Ser Arg Thr Val Thr Pro Thr Thr Glu Val Glu Tyr Arg Asp Ile
                165                 170                 175
Cys Ser Thr Ser Phe Ser Val Pro Ser Tyr Gln Cys Thr Glu Gln Gly
                180                 185                 190
Asn Glu Cys Cys Ser Ser Glu Pro Ser Cys Ser Ser Gln Ala Asn Met
            195                 200                 205
Arg Pro Phe His Ser Arg His Asn Arg Asp Asp Asn Val Asp Val Asn
            210                 215                 220
Leu Glu Asp Met Met Val Met Glu Ala Ile Trp Arg Ser Ile Gln Glu
225                 230                 235                 240
Gln Gly His Leu Val Asn Pro Val Cys Gly Ser Tyr Phe Pro Val Ile
                245                 250                 255
Glu Pro Pro Ser Arg Glu Arg Gln Ala Phe Leu Pro Ala Ala Pro Leu
                260                 265                 270
Glu Met Pro His Pro Gly Gly Tyr Ser Cys Ala Val Ala Ala Leu Ala
            275                 280                 285
Glu His Gln Pro Ala Ser Met Asp Phe Ser Tyr Met Ala Gly Ser Ser
        290                 295                 300
Thr Tyr Pro Val Phe Asp Met Ile Arg Arg Pro Cys Asn Met Ser Ser
305                 310                 315                 320
Gly Ser Leu Cys Gly Val Glu Asn Ser Ser Leu Asp Thr Trp Ser Gly
                325                 330                 335
Ile Ala Pro Ser Cys Ser Arg Glu Val Val Arg Glu Glu Gly Glu Cys
```

```
                    340                 345                 350
Ser Thr Asp His Trp Ser Glu Gly Ala Glu Ala Gly Thr Ser Tyr Ala
                355                 360                 365

Gly Ser Asp Ile Met Ala Asp Thr Gly Thr Met Gln Pro Leu Pro Phe
            370                 375                 380

Ala Glu Asn Phe Thr Met Ala Pro Ser His Phe Arg Pro Glu Ser Ile
385                 390                 395                 400

Glu Glu Gln Met Met Phe Ser Met Ala Val Ser Leu Ala Glu Ala His
                405                 410                 415

His Gly Arg Thr Gln Ala Gln Gly Leu Ala Trp Leu
                420                 425
```

<210> SEQ ID NO 30
<211> LENGTH: 431
<212> TYPE: PRT
<213> ORGANISM: Zea mays

<400> SEQUENCE: 30

```
Met Gly Asn Arg Ile Gly Gly Arg Arg Lys Pro Gly Val Glu Glu Arg
1               5                   10                  15

Phe Thr Arg Pro Gln Gly Leu Tyr Glu His Lys Asp Ile Asp Gln Lys
                20                  25                  30

Lys Leu Arg Lys Leu Ile Leu Glu Ala Lys Leu Ala Pro Cys Tyr Pro
            35                  40                  45

Gly Ala Asp Asp Ala Ala Gly Gly Asp Leu Asp Leu Glu Glu
        50                  55                  60

Cys Pro Ile Cys Phe Leu Tyr Tyr Pro Ser Leu Asn Arg Ser Lys Cys
65                  70                  75                  80

Cys Ser Lys Gly Ile Cys Thr Glu Cys Phe Leu Gln Met Lys Pro Thr
                85                  90                  95

His Thr Ala Arg Pro Thr Gln Cys Pro Phe Cys Lys Thr Ala Asn Tyr
            100                 105                 110

Ala Val Glu Tyr Arg Gly Val Lys Thr Lys Glu Glu Arg Ser Ile Glu
        115                 120                 125

Gln Phe Glu Glu Gln Lys Val Ile Glu Ala Gln Leu Arg Met Arg Gln
    130                 135                 140

Lys Glu Leu Gln Asp Glu Glu Ala Lys Met Lys Arg Lys Gln Ser Arg
145                 150                 155                 160

Cys Ser Ser Ser Arg Thr Val Thr Pro Thr Thr Glu Val Glu Tyr Arg
                165                 170                 175

Asp Ile Cys Ser Thr Ser Phe Ser Val Pro Ser Tyr Gln Arg Thr Glu
            180                 185                 190

Gln Gly Asn Glu Cys Cys Ser Ser Glu Pro Ser Cys Ser Ser Gln Ala
        195                 200                 205

Asn Met Arg Pro Phe His Ser Arg His Asn Arg Asp Asp Asn Val Asp
    210                 215                 220

Met Asn Leu Glu Asp Met Met Val Met Glu Thr Ile Trp Arg Ser Ile
225                 230                 235                 240

Gln Gln Glu Gln Gly His Leu Val Asn Pro Val Cys Gly Ser Tyr Phe
                245                 250                 255

Pro Val Ile Glu Pro Pro Ser Arg Glu Arg Gln Ala Phe Val Pro Ala
            260                 265                 270

Ala Pro Leu Glu Met Pro His Pro Gly Gly Tyr Ser Cys Ala Val Ala
        275                 280                 285
```

```
Ala Leu Ala Glu His Gln Ala Pro Ser Met Asp Phe Ser Tyr Met Ser
    290                 295                 300
Gly Ser Ser Thr Tyr Pro Val Phe Asp Met Ile Arg Arg Pro Cys Asn
305                 310                 315                 320
Met Ser Ser Gly Ser Pro Cys Gly Ala Glu Asn Ser Ser Leu Asp Thr
                325                 330                 335
Trp Ser Gly Ile Ala Pro Ser Cys Ser Arg Glu Val Val Arg Asp Glu
            340                 345                 350
Gly Glu Cys Ser Ala Asp His Trp Ser Glu Gly Ala Glu Ala Gly Thr
        355                 360                 365
Ser Tyr Ala Gly Ser Asp Ile Met Ala Asp Ala Gly Ala Met Gln Pro
    370                 375                 380
Leu Pro Phe Ala Glu Asn Phe Ala Met Gly Pro Ser His Phe Arg Pro
385                 390                 395                 400
Glu Ser Val Glu Glu Gln Met Met Phe Ser Met Ala Val Ser Leu Ala
                405                 410                 415
Glu Ala His His Gly Arg Thr Gln Ala Gln Gly Leu Ala Trp Leu
            420                 425                 430

<210> SEQ ID NO 31
<211> LENGTH: 424
<212> TYPE: PRT
<213> ORGANISM: Triticum aestivum

<400> SEQUENCE: 31

Met Gly Asn Arg Ile Gly Gly Arg Arg Lys Ala Gly Val Glu Glu Arg
1               5                   10                  15
Tyr Thr Arg Pro Gln Gly Leu Tyr Glu His Arg Asp Ile Asp Gln Lys
            20                  25                  30
Lys Leu Arg Lys Leu Ile Leu Glu Ala Lys Leu Ala Pro Cys Tyr Pro
        35                  40                  45
Gly Ala Asp Asp Ala Ala Gly Gly Asp Leu Glu Glu Cys Pro Ile Cys
    50                  55                  60
Phe Leu Tyr Tyr Pro Ser Leu Asn Arg Ser Lys Cys Cys Ser Lys Gly
65                  70                  75                  80
Ile Cys Thr Glu Cys Phe Leu Gln Met Lys Pro Thr His Thr Ala Arg
                85                  90                  95
Pro Thr Gln Cys Pro Phe Cys Lys Thr Pro Asn Tyr Ala Val Glu Tyr
            100                 105                 110
Arg Gly Val Lys Thr Lys Glu Glu Arg Ser Ile Glu Gln Phe Glu Glu
        115                 120                 125
Gln Lys Val Ile Glu Ala Gln Met Arg Val Arg Gln Gln Ala Leu Gln
    130                 135                 140
Asp Glu Glu Asp Lys Met Lys Arg Lys Gln Ser Arg Cys Ser Ser Ser
145                 150                 155                 160
Cys Lys Thr Pro Asn Tyr Ala Val Glu Tyr Arg Gly Val Lys Thr Lys
                165                 170                 175
Glu Glu Arg Ser Ile Glu Gln Phe Glu Glu Gln Lys Val Ile Glu Ala
            180                 185                 190
Gln Met Arg Val Arg Gln Ala Leu Gln Asp Glu Glu Asp Lys Met
        195                 200                 205
Lys Arg Lys Gln Ser Arg Cys Ser Ser Ser Met Asp Met Asn Ile Glu
    210                 215                 220
Asp Met Met Val Met Glu Ala Ile Trp Arg Ser Ile Gln Glu Gln Gly
225                 230                 235                 240
```

```
Ser Ile Gly Asn Pro Ser Cys Gly Ser Phe Met Pro Phe Glu Gln Pro
                245                 250                 255

Thr Arg Glu Arg Gln Ala Phe Val Ala Ala Pro Pro Leu Glu Met Pro
            260                 265                 270

His Pro Gly Gly Met Asp Met Asn Ile Glu Asp Met Met Val Met Glu
        275                 280                 285

Ala Ile Trp Arg Ser Ile Gln Glu Gln Gly Ser Ile Gly Asn Pro Ser
290                 295                 300

Cys Gly Ser Phe Met Pro Phe Glu Gln Pro Thr Arg Glu Arg Gln Ala
305                 310                 315                 320

Phe Val Ala Ala Pro Pro Leu Glu Met Pro His Pro Gly Gly Pro Ser
                325                 330                 335

Cys Ser Arg Arg Glu Val Val Arg Glu Glu Gly Glu Cys Ser Thr Asp
            340                 345                 350

His Leu Ser Glu Gly Ala Glu Ala Gly Thr Ser Tyr Ala Gly Ser Asp
        355                 360                 365

Ile Val Val Asp Ala Gly Thr Met Leu Pro Leu Pro Phe Ala Asp Asn
370                 375                 380

Tyr Ser Met Val Ala Ser His Phe Arg Pro Glu Ser Ile Glu Glu Gln
385                 390                 395                 400

Met Met Tyr Ser Met Ala Val Ser Leu Ala Glu Ala His Gly Arg Thr
                405                 410                 415

His Ser Gln Gly Leu Ala Trp Leu
            420
```

<210> SEQ ID NO 32
<211> LENGTH: 398
<212> TYPE: PRT
<213> ORGANISM: Brachypodium distachyon

<400> SEQUENCE: 32

```
Met Gly Asn Gln Gly Leu Tyr Pro His Pro Asp Ile Asp Leu Lys Lys
1               5                   10                  15

Leu Arg Arg Leu Ile Val Glu Ala Lys Leu Ala Pro Cys His Pro Gly
            20                  25                  30

Ser Asp Asp Pro Arg Ala Asp Leu Asp Glu Cys Pro Ile Cys Phe Leu
        35                  40                  45

Phe Tyr Pro Ser Leu Asn Arg Ser Lys Cys Cys Ala Lys Gly Ile Cys
    50                  55                  60

Thr Glu Cys Phe Leu Gln Met Lys Ser Pro Thr Ser Cys Arg Pro Thr
65                  70                  75                  80

Gln Cys Pro Tyr Cys Lys Met Leu Asn Tyr Ala Val Glu Tyr Arg Gly
                85                  90                  95

Val Lys Thr Lys Glu Glu Lys Gly Val Glu Gln Leu Glu Glu Gln Arg
            100                 105                 110

Val Ile Glu Ala Gln Ile Arg Met Arg His Gln Glu Ile Lys Asp Asp
        115                 120                 125

Ala Glu Arg Leu Lys Asn Lys Gln Thr Ala Thr Leu Ser Asp Val Ile
    130                 135                 140

Thr Thr Pro Gln Val Glu Cys Cys Glu Ala Gly Gly Thr Ser Thr Pro
145                 150                 155                 160

Ala Ala Ser Ser Ala Gln Gly Asn Asp Ala Leu Leu Ser Gln Val Gln
                165                 170                 175

His Ser Glu Leu Leu Leu Lys Asn Ser Glu Arg Leu Lys Gln Met Arg
```

```
            180                 185                 190
Glu Asn Asn Phe Asp Val Asp Leu Glu Glu Val Met Leu Met Glu Ala
        195                 200                 205

Ile Trp Leu Ser Val Gln Asp Ala Ser Gly Asn Pro Gly Ile Thr Gly
    210                 215                 220

Ala Ala Pro Pro Thr Ile Pro Pro Arg Ser Tyr Asp Thr Ser Val Thr
225                 230                 235                 240

Ala Ser Ala Glu Ala Pro Ser Gly Gly Phe Ala Cys Ala Val Ala
        245                 250                 255

Ala Leu Ala Glu Gln Gln His Met Leu Val Gly Ser Ser Ile Pro Ala
        260                 265                 270

Thr Cys Gln Ala Ser Lys His Asp Thr Leu Ser Arg Ser Asp Arg Ser
        275                 280                 285

Phe Thr Glu Asp Leu Ser Ile Ala Gly Ser Ser Ser Gly Thr Arg
        290                 295                 300

Val Asp Glu Ser Ser Ile Asn Arg Thr Arg Gln Thr Arg Glu Gly Ala
305                 310                 315                 320

Glu His Ser Asn Asn Asp Arg Trp Ser Glu Val Ala Asp Ala Ser Thr
                325                 330                 335

Ser Cys Ala Gly Ser Asp Ile Thr Arg Glu Ala Gly Ala Ala Asn Leu
                340                 345                 350

Val Ala Ser Asp Gly Ser Ser Ile Gly Ser Gly Asn Ile Pro Asp Ser
                355                 360                 365

Phe Glu Asp Gln Met Met Leu Ala Ile Ser Leu Ser Leu Val Asp Ala
        370                 375                 380

Arg Ala Met Ala Ser Ser Pro Gly Pro Gly Leu Thr Trp Gln
385                 390                 395

<210> SEQ ID NO 33
<211> LENGTH: 414
<212> TYPE: PRT
<213> ORGANISM: Oryza sativa

<400> SEQUENCE: 33

Met Gly Asn Gln Val Gly Gly Arg Arg Arg Arg Pro Ala Val Glu
1               5                   10                  15

Glu Arg Tyr Thr Arg Pro Gln Gly Leu Tyr Pro His Pro Asp Ile Asp
            20                  25                  30

Leu Lys Lys Leu Arg Arg Leu Ile Val Glu Ala Lys Leu Ala Pro Cys
        35                  40                  45

Phe Pro Gly Ser Asp Asp Pro Arg Ala Asp Leu Glu Glu Cys Pro Ile
    50                  55                  60

Cys Phe Leu Phe Tyr Pro Ser Leu Asn Arg Ser Lys Cys Cys Ala Lys
65                  70                  75                  80

Gly Ile Cys Thr Glu Cys Phe Leu Gln Met Arg Thr Pro Thr Ser Cys
                85                  90                  95

Arg Pro Thr Gln Cys Pro Tyr Cys Lys Met Ala Ser Tyr Ala Val Glu
            100                 105                 110

Tyr Arg Gly Val Lys Thr Lys Glu Glu Lys Gly Thr Glu Gln Ile Glu
        115                 120                 125

Glu Gln Arg Val Ile Glu Ala Gln Ile Arg Met Arg Gln Gln Glu Leu
    130                 135                 140

Gln Asp Asp Ala Glu Arg Met Lys Lys Lys Gln Ala Ala Ala Leu Thr
145                 150                 155                 160
```

Asp Val Val Thr Thr Ala Gln Val Glu His Cys Asp Thr Gly Gly Ala
            165                 170                 175

Ser Thr Thr Val Lys Ser Ser Gly Gln Gly Ser Asp Met Leu Ser Ser
            180                 185                 190

Gln Val Gln His Ala Glu Leu Leu Lys Thr Ser Glu Arg Leu Lys
        195                 200                 205

Gln Met Arg Asn Asn Asn Phe Asp Met Asp Pro Asp Glu Val Met Leu
        210                 215                 220

Val Glu Ala Leu Trp Leu Ser Leu Gln Asp Gln Glu Ala Ser Gly Asn
225                 230                 235                 240

Pro Thr Cys Gly Asn Thr Val Ser Ser Val His Pro Pro Arg Ser Phe
                245                 250                 255

Glu Gly Ser Met Thr Ile Pro Ala Glu Ala Ser Ser Ser Ser Ala
            260                 265                 270

Phe Ala Cys Ala Val Ala Ala Leu Ala Glu Gln Gln Gln Met Tyr Gly
        275                 280                 285

Glu Ala Ser Ser Thr Ala Thr Cys His Thr Ser Arg Cys Asp Ile Leu
        290                 295                 300

Ser Arg Ser Asp Arg Ser Phe Thr Glu Asp Leu Ser Ile Asn Gly Ser
305                 310                 315                 320

Gly Ser Ser Gly Ala Arg Ser Glu Glu Pro Ser Ser Asn Lys Met His
                325                 330                 335

Gln Thr Arg Glu Gly Met Glu Tyr Ser Asn Glu Arg Trp Ser Glu Met
            340                 345                 350

Ala Glu Ala Ser Ser Ser Phe Thr Gly Ser Asp Leu Thr Thr Glu Ala
        355                 360                 365

Gly Ala Ala Asn Ser Gly Gly Ser Asp Thr Gly Ala Gly Ser Ile Pro
    370                 375                 380

Asp Ser Phe Glu Glu Gln Met Met Leu Ala Met Ala Leu Ser Leu Ala
385                 390                 395                 400

Asp Ala Arg Ala Lys Ala Ser Ser Pro Gly Leu Thr Trp Arg
                405                 410

<210> SEQ ID NO 34
<211> LENGTH: 419
<212> TYPE: PRT
<213> ORGANISM: Zea mays

<400> SEQUENCE: 34

Met Gly Asn Gln Val Gly Gly Arg Arg Arg Arg Pro Val Asp
1               5                   10                  15

Glu Arg Tyr Thr Arg Pro Gln Gly Leu Tyr Pro His Pro Asp Ile Asp
            20                  25                  30

Leu Arg Lys Leu Arg Arg Leu Ile Leu Glu Ala Lys Leu Ala Pro Cys
        35                  40                  45

His Pro Gly Ala Asp Asp Ala Arg Ala Asp Leu Asp Glu Cys Pro Ile
    50                  55                  60

Cys Phe Leu Phe Tyr Pro Ser Leu Asn Arg Ser Lys Cys Cys Ala Lys
65                  70                  75                  80

Gly Ile Cys Thr Glu Cys Phe Leu Gln Met Lys Ser Pro Thr Ser Cys
                85                  90                  95

Lys Pro Thr Gln Cys Pro Tyr Cys Lys Thr Leu Asn Tyr Ala Val Glu
            100                 105                 110

Tyr Arg Gly Val Lys Thr Lys Glu Glu Lys Gly Ile Glu Gln Leu Glu
        115                 120                 125

-continued

Glu Gln Arg Val Ile Glu Ala Gln Ile Arg Met Arg Gln Gln Glu Val
         130                 135                 140

Gln Asp Asp Ala Glu Arg Met Lys Asn Lys Arg Thr Ala Thr Leu Gly
145                 150                 155                 160

Asp Val Val Ala Ser Ala Gln Val Asp Ser Cys Asn Thr Asp Gly Ala
                165                 170                 175

Ser Thr Ala Val Ala Asn Ser Pro Arg Gly Asn Asp Val Leu Ser Ser
            180                 185                 190

Glu Val Gln His Ser Glu Leu Ile Ser Arg Asn Ser Glu Ala Phe Lys
        195                 200                 205

Gln Met Arg Gly Asn Asn Phe Glu Val Asp Leu Glu Glu Val Met Leu
    210                 215                 220

Met Glu Ala Ile Trp Leu Ser Ile Gln Asp Gln Glu Ala Leu Gly Asn
225                 230                 235                 240

Pro Gly Cys Val Ser Thr Thr Pro Ser Ser Ile Pro Ser Arg Pro Phe
                245                 250                 255

Asp Asp Gly Asp Met Thr Thr Thr Ala Glu Ala Ala Ser Ser Gly Gly
            260                 265                 270

Phe Ala Cys Ala Val Ala Ala Leu Ala Glu Gln Gln His Met His Gly
        275                 280                 285

Glu Ser Ser Ser Ala Ser Pro Cys Gln Thr Ile Arg Phe Gly Thr Leu
    290                 295                 300

Ser Arg Pro Asp Arg Ser Thr Thr Gln Asp Leu Ser Val Ala Gly Ser
305                 310                 315                 320

Ser Ser Ser Asp Ser Arg Val Glu Glu Pro Pro Thr Ser Asn Thr His
                325                 330                 335

Arg Thr Ile Glu Ala Ala Glu Tyr Ser Asn Ser Asn Val Gln Trp Ser
            340                 345                 350

Glu Val Ala Glu Ala Gly Thr Ser Ile Ala Glu Ser Asp Gly Thr Val
        355                 360                 365

Glu Ala Gly Val Asp Asn Ser Ser Thr Ser Ala Gly Ser Asn Ile Asp
    370                 375                 380

Ser Val Ser Val Pro Asp Ser Phe Glu Glu Gln Met Met Leu Ala Met
385                 390                 395                 400

Ala Leu Ser Leu Val Asp Ala Arg Ala Arg Ala Gly Ser Pro Gly Leu
                405                 410                 415

Ala Trp Arg

<210> SEQ ID NO 35
<211> LENGTH: 418
<212> TYPE: PRT
<213> ORGANISM: Sorghum bicolor

<400> SEQUENCE: 35

Met Gly Asn Gln Val Gly Gly Arg Arg Arg Arg Pro Ala Val Asp
1               5                   10                  15

Glu Arg Tyr Thr Gln Pro Gln Gly Leu Tyr Pro His Pro Asp Ile Asp
            20                  25                  30

Leu Arg Lys Leu Arg Arg Leu Ile Leu Glu Ala Lys Leu Ala Pro Cys
        35                  40                  45

His Pro Gly Ala Asp Asp Ala Arg Ala Asp Leu Asp Glu Cys Pro Ile
    50                  55                  60

Cys Phe Leu Phe Tyr Pro Ser Leu Asn Arg Ser Lys Cys Cys Ala Lys
65                  70                  75                  80

```
Gly Ile Cys Thr Glu Cys Phe Leu Gln Met Lys Ser Pro Thr Ser Cys
                85                  90                  95

Arg Pro Thr Gln Cys Pro Tyr Cys Lys Thr Leu Asn Tyr Ala Val Glu
            100                 105                 110

Tyr Arg Gly Val Lys Thr Lys Glu Glu Lys Gly Ile Glu Gln Leu Glu
        115                 120                 125

Glu Gln Arg Val Ile Glu Ala Gln Ile Arg Met Arg Gln Lys Glu Leu
    130                 135                 140

Gln Asp Asp Ala Glu Arg Met Lys Asn Lys Gln Thr Ala Thr Leu Gly
145                 150                 155                 160

Asp Ile Val Ala Ser Ala Gln Val Asp Ser Cys Asn Thr Asp Gly Ala
                165                 170                 175

Ser Thr Gly Ala Ala Ser Ser Pro Gln Gly Ser Asp Ala Ile Ser Ser
            180                 185                 190

Glu Val Gln His Ser Glu Leu Ile Leu Arg Asn Ser Glu Ala Phe Lys
        195                 200                 205

Gln Met Arg Gly Asn Asn Phe Asp Val Asp Leu Glu Glu Val Met Leu
    210                 215                 220

Met Glu Ala Ile Trp Leu Ser Ile Gln Asp Gln Glu Ala Leu Gly Asn
225                 230                 235                 240

Ser Gly Cys Val Ser Thr Thr Pro Ser Ser Ile Pro Ser Arg Pro Phe
                245                 250                 255

Asp Gly Ala Met Thr Thr Thr Pro Glu Ala Ala Ser Ser Gly Gly Phe
            260                 265                 270

Ala Phe Ala Val Ala Ala Leu Ala Glu Gln Gln His Met His Gly Glu
        275                 280                 285

Ser Ser Ser Ala Ser Ala Cys Gln Thr Pro Arg Phe Asp Ile Leu Ser
    290                 295                 300

Arg Ser Asp Arg Ser Ser Thr Glu Asp Leu Ser Val Val Gly Ser Ser
305                 310                 315                 320

Ser Ser Asp Ser Arg Val Glu Glu Pro Ser Ser Ser Thr His Arg
                325                 330                 335

Thr Ile Glu Gly Ser Glu Tyr Ser Asn Ser Asn Gly Arg Trp Ser Glu
            340                 345                 350

Val Ala Glu Ala Gly Thr Ser Ile Ala Glu Ala Asp Val Ile Val Glu
        355                 360                 365

Ala Gly Val Gly Asn Ser Ser Thr Ser Val Gly Ser Asn Ile Gly Ser
    370                 375                 380

Ser Ser Val Pro Asp Ser Phe Glu Glu Gln Met Met Leu Ala Met Ala
385                 390                 395                 400

Leu Ser Leu Val Asp Ala Arg Ser Arg Ala Gly Ser Pro Gly Leu Ala
                405                 410                 415

Trp Arg

<210> SEQ ID NO 36
<211> LENGTH: 27
<212> TYPE: PRT
<213> ORGANISM: Artificial sequence
<220> FEATURE:
<223> OTHER INFORMATION: Synthetic sequence: DA2 polypeptide first
      consensus domain
<220> FEATURE:
<221> NAME/KEY: VARIANT
<222> LOCATION: (2)..(2)
<223> OTHER INFORMATION: May be present or absent; if present, Xaa is
      Gln
```

```
<220> FEATURE:
<221> NAME/KEY: VARIANT
<222> LOCATION: (6)..(6)
<223> OTHER INFORMATION: Xaa is Pro, Met, Asn, Val, Gln, Leu, Val or Glu
<220> FEATURE:
<221> NAME/KEY: VARIANT
<222> LOCATION: (7)..(7)
<223> OTHER INFORMATION: Xaa is His, Ser or Asn
<220> FEATURE:
<221> NAME/KEY: VARIANT
<222> LOCATION: (8)..(8)
<223> OTHER INFORMATION: Xaa is Pro, Lys or Arg
<220> FEATURE:
<221> NAME/KEY: VARIANT
<222> LOCATION: (10)..(10)
<223> OTHER INFORMATION: Xaa is Ile or Val
<220> FEATURE:
<221> NAME/KEY: VARIANT
<222> LOCATION: (12)..(12)
<223> OTHER INFORMATION: Xaa is Leu, Ile, His, Val or Gln
<220> FEATURE:
<221> NAME/KEY: VARIANT
<222> LOCATION: (13)..(13)
<223> OTHER INFORMATION: Xaa is Lys or Arg
<220> FEATURE:
<221> NAME/KEY: VARIANT
<222> LOCATION: (16)..(16)
<223> OTHER INFORMATION: Xaa is Arg or Lys
<220> FEATURE:
<221> NAME/KEY: VARIANT
<222> LOCATION: (17)..(17)
<223> OTHER INFORMATION: Xaa is Arg or Lys
<220> FEATURE:
<221> NAME/KEY: VARIANT
<222> LOCATION: (20)..(20)
<223> OTHER INFORMATION: Xaa is Val or Leu
<220> FEATURE:
<221> NAME/KEY: VARIANT
<222> LOCATION: (21)..(21)
<223> OTHER INFORMATION: Xaa is Glu or Asp
<220> FEATURE:
<221> NAME/KEY: VARIANT
<222> LOCATION: (22)..(22)
<223> OTHER INFORMATION: Xaa is Ala, Ser or Thr

<400> SEQUENCE: 36

Gln Xaa Gly Leu Tyr Xaa Xaa Xaa Asp Xaa Asp Xaa Xaa Lys Leu Xaa
1               5                   10                  15

Xaa Leu Ile Xaa Xaa Xaa Lys Leu Ala Pro Cys
            20                  25

<210> SEQ ID NO 37
<211> LENGTH: 36
<212> TYPE: PRT
<213> ORGANISM: Artificial sequence
<220> FEATURE:
<223> OTHER INFORMATION: Synthetic sequence: DA2 polypeptide second
      consensus domain
<220> FEATURE:
<221> NAME/KEY: VARIANT
<222> LOCATION: (1)..(1)
<223> OTHER INFORMATION: Xaa is Asn or Ser
<220> FEATURE:
<221> NAME/KEY: VARIANT
<222> LOCATION: (9)..(9)
<223> OTHER INFORMATION: Xaa is Val or Gly
<220> FEATURE:
<221> NAME/KEY: VARIANT
<222> LOCATION: (11)..(11)
<223> OTHER INFORMATION: Xaa is Thr or Ser
<220> FEATURE:
<221> NAME/KEY: VARIANT
<222> LOCATION: (15)..(15)
<223> OTHER INFORMATION: Xaa is Lys or Arg
<220> FEATURE:
<221> NAME/KEY: VARIANT
```

```
<222> LOCATION: (16)..(16)
<223> OTHER INFORMATION: Xaa is Gly or Ser
<220> FEATURE:
<221> NAME/KEY: VARIANT
<222> LOCATION: (17)..(17)
<223> OTHER INFORMATION: Xaa is Val, Thr, Ile, Phe, Leu or Met
<220> FEATURE:
<221> NAME/KEY: VARIANT
<222> LOCATION: (20)..(20)
<223> OTHER INFORMATION: Xaa is Leu, Ile, Val or Phe
<220> FEATURE:
<221> NAME/KEY: VARIANT
<222> LOCATION: (24)..(24)
<223> OTHER INFORMATION: Xaa is Arg, Leu or Lys
<220> FEATURE:
<221> NAME/KEY: VARIANT
<222> LOCATION: (29)..(29)
<223> OTHER INFORMATION: Xaa is Gln or Lys
<220> FEATURE:
<221> NAME/KEY: VARIANT
<222> LOCATION: (30)..(30)
<223> OTHER INFORMATION: Xaa is Ile or Met
<220> FEATURE:
<221> NAME/KEY: VARIANT
<222> LOCATION: (34)..(34)
<223> OTHER INFORMATION: Xaa is His or Gln
<220> FEATURE:
<221> NAME/KEY: VARIANT
<222> LOCATION: (35)..(35)
<223> OTHER INFORMATION: Xaa is Lys or Gln
<220> FEATURE:
<221> NAME/KEY: VARIANT
<222> LOCATION: (36)..(36)
<223> OTHER INFORMATION: Xaa is Glu or Ala

<400> SEQUENCE: 37

Xaa Tyr Ala Val Glu Tyr Arg Gly Xaa Lys Xaa Lys Glu Glu Xaa Xaa
1               5                   10                  15

Xaa Glu Gln Xaa Glu Glu Gln Xaa Val Ile Glu Ala Xaa Xaa Arg Met
            20                  25                  30

Arg Xaa Xaa Xaa
        35

<210> SEQ ID NO 38
<211> LENGTH: 66
<212> TYPE: PRT
<213> ORGANISM: Artificial sequence
<220> FEATURE:
<223> OTHER INFORMATION: Synthetic sequence: LIM domain
<220> FEATURE:
<221> NAME/KEY: VARIANT
<222> LOCATION: (2)..(3)
<223> OTHER INFORMATION: Xaa is any amino acid
<220> FEATURE:
<221> NAME/KEY: VARIANT
<222> LOCATION: (5)..(27)
<223> OTHER INFORMATION: Xaa at positions 5 to 27 is any amino acid
      and up to seven of them may be absent; represents a range of 16 -
      23 amino acids.
<220> FEATURE:
<221> NAME/KEY: VARIANT
<222> LOCATION: (28)..(28)
<223> OTHER INFORMATION: Xaa is His or Cys
<220> FEATURE:
<221> NAME/KEY: VARIANT
<222> LOCATION: (29)..(32)
<223> OTHER INFORMATION: Xaa at positions 29 to 32 is any amino acid
      and any two of them may be absent; represents a string of 2 or 4
      amino acids.
<220> FEATURE:
<221> NAME/KEY: VARIANT
<222> LOCATION: (33)..(33)
<223> OTHER INFORMATION: Xaa is Cys, His or Glu
<220> FEATURE:
<221> NAME/KEY: VARIANT
```

```
<222> LOCATION: (34)..(35)
<223> OTHER INFORMATION: Xaa is any amino acid
<220> FEATURE:
<221> NAME/KEY: VARIANT
<222> LOCATION: (37)..(38)
<223> OTHER INFORMATION: Xaa is any amino acid
<220> FEATURE:
<221> NAME/KEY: VARIANT
<222> LOCATION: (40)..(60)
<223> OTHER INFORMATION: Xaa at positions 40 to 60 is any amino acid
      and up to seven of them may be absent; represents a range of 14 -
      21 amino acids.
<220> FEATURE:
<221> NAME/KEY: VARIANT
<222> LOCATION: (61)..(61)
<223> OTHER INFORMATION: Xaa is Cys or His
<220> FEATURE:
<221> NAME/KEY: VARIANT
<222> LOCATION: (62)..(64)
<223> OTHER INFORMATION: Xaa at positions 62 - 64 is any amino acid and
      any one or two of them may be absent; represents a string of 2 or
      1 or 3 amino acids.
<220> FEATURE:
<221> NAME/KEY: VARIANT
<222> LOCATION: (65)..(65)
<223> OTHER INFORMATION: Xaa is Cys, His, Asp or Glu
<220> FEATURE:
<221> NAME/KEY: VARIANT
<222> LOCATION: (66)..(66)
<223> OTHER INFORMATION: Xaa is any amino acid

<400> SEQUENCE: 38

Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Cys Xaa Xaa Cys Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa
65

<210> SEQ ID NO 39
<211> LENGTH: 63
<212> TYPE: PRT
<213> ORGANISM: Artificial sequence
<220> FEATURE:
<223> OTHER INFORMATION: Synthetic sequence: LIM domain
<220> FEATURE:
<221> NAME/KEY: VARIANT
<222> LOCATION: (2)..(3)
<223> OTHER INFORMATION: Xaa is any amino acid
<220> FEATURE:
<221> NAME/KEY: VARIANT
<222> LOCATION: (5)..(27)
<223> OTHER INFORMATION: Xaa at positions 5 - 27 is any amino acid and
      up to seven of them may be absent; represents a range of 16 - 23
      amino acids.
<220> FEATURE:
<221> NAME/KEY: VARIANT
<222> LOCATION: (29)..(30)
<223> OTHER INFORMATION: Xaa is any amino acid
<220> FEATURE:
<221> NAME/KEY: VARIANT
<222> LOCATION: (32)..(33)
<223> OTHER INFORMATION: Xaa is any amino acid
<220> FEATURE:
<221> NAME/KEY: VARIANT
<222> LOCATION: (35)..(36)
<223> OTHER INFORMATION: Xaa is any amino acid
<220> FEATURE:
<221> NAME/KEY: VARIANT
```

```
<222> LOCATION: (38)..(58)
<223> OTHER INFORMATION: Xaa at positions 38 to 58 is any amino acid and
      up to seven of them may be absent; represents a range of 14 - 21
      amino acids.
<220> FEATURE:
<221> NAME/KEY: VARIANT
<222> LOCATION: (60)..(61)
<223> OTHER INFORMATION: Xaa is any amino acid
<220> FEATURE:
<221> NAME/KEY: VARIANT
<222> LOCATION: (63)..(63)
<223> OTHER INFORMATION: Xaa is any amino acid

<400> SEQUENCE: 39

Cys Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa His Xaa Xaa Cys Xaa
            20                  25                  30

Xaa Cys Xaa Xaa Cys Xaa Xaa Xaa Xaa Xaa Xaa Xaa Xaa Xaa
        35                  40                  45

Xaa Xaa Xaa Xaa Xaa Xaa Xaa Xaa Xaa Xaa His Xaa Xaa Cys Xaa
    50                  55                  60

<210> SEQ ID NO 40
<211> LENGTH: 53
<212> TYPE: PRT
<213> ORGANISM: Arabidopsis thaliana

<400> SEQUENCE: 40

Cys Ala Gly Cys Asn Met Glu Ile Gly His Gly Arg Phe Leu Asn Cys
1               5                   10                  15

Leu Asn Ser Leu Trp His Pro Glu Cys Phe Arg Cys Tyr Gly Cys Ser
            20                  25                  30

Gln Pro Ile Ser Glu Tyr Glu Phe Ser Thr Ser Gly Asn Tyr Pro Phe
        35                  40                  45

His Lys Ala Cys Tyr
    50

<210> SEQ ID NO 41
<211> LENGTH: 504
<212> TYPE: PRT
<213> ORGANISM: Setaria italica

<400> SEQUENCE: 41

Met Gly Trp Leu Ser Lys Ile Phe Lys Gly Ser Val Asn Arg Val Ser
1               5                   10                  15

Arg Gly His Tyr Asn Gly Asn Ser His Glu Gly Tyr Ser Thr Gln His
            20                  25                  30

Thr Lys Ser Tyr Gly Ala His Gly Asn Glu Asp Glu Met Asp His
        35                  40                  45

Ala Ile Ala Leu Ser Leu Ser Glu Gln Asp Gln Arg Lys Gly Lys Ala
    50                  55                  60

Ile Asp Thr Glu His His Leu Asp Glu Asp Glu Gln Leu Ala Arg Ala
65                  70                  75                  80

Leu Gln Glu Asn Thr Ser Pro Thr Leu Asp Gly Asp Glu Gln Leu Ala
                85                  90                  95

Arg Ala Leu Gln Glu Ser Met Asn Asp Glu His Pro Arg Gln His
            100                 105                 110

Ile Pro Ile Glu Asp Val His Ser Glu Ser Ala Pro Ala Ser Ser Leu
        115                 120                 125
```

```
Pro Pro Tyr Val Phe Pro Thr Asn Gly Ser Arg Val Cys Ala Gly Cys
    130                 135                 140

Lys Thr Pro Ile Gly Gln Gly Arg Phe Leu Ser Cys Met Asp Ser Val
145                 150                 155                 160

Trp His Pro Gln Cys Phe Arg Cys Tyr Gly Cys Asp Ile Pro Ile Ser
                165                 170                 175

Glu Tyr Glu Phe Ala Val His Glu Asp His Ala Tyr His Arg Ser Cys
                180                 185                 190

Tyr Lys Glu Arg Phe His Pro Lys Cys Asp Val Cys Asn Ser Phe Ile
            195                 200                 205

Pro Thr Asn Lys Asn Gly Leu Ile Glu Tyr Arg Ala His Pro Phe Trp
    210                 215                 220

Met Gln Lys Tyr Cys Pro Ser His Glu Asn Asp Gly Thr Pro Arg Cys
225                 230                 235                 240

Cys Ser Cys Glu Arg Met Glu Pro Lys His Ser Gln Tyr Ile Thr Leu
                245                 250                 255

Asp Asp Gly Arg Arg Leu Cys Leu Glu Cys Leu His Thr Ala Ile Met
                260                 265                 270

Asp Thr Asn Glu Cys Gln Pro Leu Tyr Ile Asp Ile Gln Glu Phe Tyr
    275                 280                 285

Glu Gly Met Asn Met Lys Val Glu Gln Gln Val Pro Leu Leu Leu Val
    290                 295                 300

Glu Arg Gln Ala Leu Asn Glu Ala Met Glu Ala Lys Ile Gly His
305                 310                 315                 320

His Leu Pro Glu Thr Arg Gly Leu Cys Leu Ser Glu Glu Gln Ile Val
                325                 330                 335

Arg Thr Ile Leu Arg Arg Pro Ile Ile Gly Pro Gly Asn Arg Ile Ile
                340                 345                 350

Asp Met Ile Thr Gly Pro Tyr Lys Leu Val Arg Arg Cys Glu Val Thr
    355                 360                 365

Ala Ile Leu Ile Leu Tyr Gly Leu Pro Arg Leu Leu Thr Gly Ser Ile
    370                 375                 380

Leu Ala His Glu Met Met His Ala Tyr Leu Arg Leu Lys Gly Tyr Arg
385                 390                 395                 400

Thr Leu Ser Pro Glu Val Glu Glu Gly Ile Cys Gln Val Leu Ala His
                405                 410                 415

Leu Trp Leu Glu Ser Glu Ile Thr Ser Gly Ser Gly Ser Met Ala Thr
                420                 425                 430

Thr Ser Ala Ala Ser Ser Ser Ser Thr Ser Ser Ser Lys Lys
    435                 440                 445

Gly Ala Lys Thr Glu Phe Glu Lys Arg Leu Gly Glu Phe Phe Lys His
    450                 455                 460

Gln Ile Glu Thr Asp Pro Ser Val Ala Tyr Gly Asp Gly Phe Arg Ala
465                 470                 475                 480

Gly Met Arg Ala Val Glu Arg Tyr Gly Leu Arg Ser Thr Leu Asp His
                485                 490                 495

Ile Lys Leu Thr Gly Ser Phe Pro
                500

<210> SEQ ID NO 42
<211> LENGTH: 487
<212> TYPE: PRT
<213> ORGANISM: Brachypodium distachyon

<400> SEQUENCE: 42
```

-continued

```
Met Gly Trp Leu Asn Lys Ile Phe Lys Gly Ser Val Asn Arg Val Ser
1               5                   10                  15

Arg Gly Asn Tyr Asp Gly Asn Trp His Asp Gly Asn Ser Ser Glu Asn
                20                  25                  30

Ile Arg Gly Ala Tyr Asp Glu Ser Asp Asn Glu Asp Ile Asp Arg Ala
                35                  40                  45

Ile Ala Leu Ser Leu Ala Glu Glu Asp Pro Asn Lys Gly Lys Ala Ile
50                  55                  60

Ile Asp Pro Asp Tyr Ser Leu Glu Glu Asp Glu Gln Leu Ala Arg Ala
65                  70                  75                  80

Leu His Glu Ser Leu Asn Thr Gly Ser Pro Pro His Gln Asn Val Pro
                85                  90                  95

Val Val Asp Val Pro Ser Glu Arg Val Pro Thr Arg Glu Pro Pro Pro
                100                 105                 110

Pro Val Phe Leu Ser Ser Gly Phe Arg Ala Cys Ala Gly Cys Asn Asn
                115                 120                 125

Pro Ile Gly Asn Gly Arg Phe Leu Ser Cys Met Asp Ser Val Trp His
130                 135                 140

Pro Gln Cys Phe Arg Cys Phe Ala Cys Asn Lys Pro Ile Ser Glu Tyr
145                 150                 155                 160

Glu Phe Ala Met His Glu Asn Gln Pro Tyr His Lys Ser Cys Tyr Lys
                165                 170                 175

Asp Phe Phe His Pro Lys Cys Asp Val Cys Lys Asp Phe Ile Pro Thr
                180                 185                 190

Asn Lys Asp Gly Leu Ile Glu Tyr Arg Ala His Pro Phe Trp Met Gln
                195                 200                 205

Lys Tyr Cys Pro Ser His Glu Asp Asp Gly Thr Pro Arg Cys Cys Ser
210                 215                 220

Cys Glu Arg Met Glu Pro Thr Asp Ile Lys Tyr Ile Arg Leu Asp Asp
225                 230                 235                 240

Gly Arg Lys Leu Cys Leu Glu Cys Leu Thr Ser Ala Thr Met Asp Ser
                245                 250                 255

Pro Glu Cys Gln His Leu Tyr Met Asp Ile Gln Glu Phe Phe Glu Gly
                260                 265                 270

Leu Asn Met Lys Val Glu Gln Gln Val Pro Leu Leu Leu Val Glu Arg
                275                 280                 285

Gln Ala Leu Asn Glu Ala Leu Glu Ala Glu Lys Ser Gly His His Leu
290                 295                 300

Pro Glu Thr Arg Gly Leu Cys Leu Ser Glu Glu Gln Ile Val Arg Thr
305                 310                 315                 320

Ile Leu Arg Arg Pro Thr Ile Gly Pro Gly Asn Arg Ile Ile Asp Met
                325                 330                 335

Ile Thr Gly Pro Tyr Lys Leu Val Arg Arg Cys Glu Val Thr Ala Ile
                340                 345                 350

Leu Ile Leu Tyr Gly Leu Pro Arg Leu Gln Thr Gly Ser Ile Leu Ala
                355                 360                 365

His Glu Met Met His Ala Tyr Leu Arg Leu Lys Gly Tyr Arg Ser Leu
370                 375                 380

Ser Pro Gln Val Glu Glu Gly Ile Cys Gln Val Leu Ser His Met Trp
385                 390                 395                 400

Leu Glu Ser Glu Ile Ile Ala Gly Ala Ser Gly Asn Thr Ala Ser Thr
                405                 410                 415
```

```
Ser Val Pro Ser Ser Ser Ala Pro Thr Ser Ser Lys Lys Gly Ala
            420             425                 430

Lys Thr Glu Phe Glu Lys Arg Leu Gly Ala Phe Ile Lys Asn Gln Ile
            435             440                 445

Glu Thr Asp Ser Ser Val Glu Tyr Gly Asp Gly Phe Arg Ala Gly Asn
    450                 455                 460

Arg Ala Val Glu Arg Tyr Gly Leu Arg Ser Thr Leu Asp His Met Lys
465                 470                 475                 480

Ile Thr Gly Ser Phe Pro Tyr
                485

<210> SEQ ID NO 43
<211> LENGTH: 514
<212> TYPE: PRT
<213> ORGANISM: Brassica rapa

<400> SEQUENCE: 43

Met Gly Trp Leu Asn Lys Ile Phe Lys Gly Ser Asn Gln Arg His Pro
1               5                   10                  15

Leu Gly Asn Glu His Tyr His His Asn Gly Tyr Tyr Glu Asn Tyr
            20                  25                  30

Pro His Glu His Ser Glu Pro Ser Ala Glu Thr Asp Ala Asp His Thr
            35                  40                  45

Gln Glu Pro Ser Thr Ser Glu Glu Thr Trp Asn Gly Lys Glu Asn
    50                  55                  60

Glu Glu Val Asp Arg Val Ile Ala Leu Ser Ile Leu Glu Glu Asn
65                  70                  75                  80

Gln Arg Pro Glu Thr Asn Thr Gly Ala Trp Lys His Ala Met Met Asp
                85                  90                  95

Asp Asp Glu Gln Leu Ala Arg Ala Ile Gln Glu Ser Met Ile Ala Arg
            100                 105                 110

Asn Gly Thr Thr Tyr Asp Phe Gly Asn Ala Tyr Gly Asn Gly His Met
            115                 120                 125

His Gly Gly Gly Asn Val Tyr Asp Asn Gly Asp Ile Tyr Tyr Pro Arg
    130                 135                 140

Pro Ile Ala Phe Ser Met Asp Phe Arg Ile Cys Ala Gly Cys Asn Met
145                 150                 155                 160

Glu Ile Gly His Gly Arg Tyr Leu Asn Cys Leu Asn Ala Leu Trp His
                165                 170                 175

Pro Gln Cys Phe Arg Cys Tyr Gly Cys Ser His Pro Ile Ser Glu Tyr
            180                 185                 190

Glu Phe Ser Thr Ser Gly Asn Tyr Pro Phe His Lys Ala Cys Tyr Arg
            195                 200                 205

Glu Arg Phe His Pro Lys Cys Asp Val Cys Ser Leu Phe Ile Ser Thr
    210                 215                 220

Asn His Ala Gly Leu Ile Glu Tyr Arg Ala His Pro Phe Trp Val Gln
225                 230                 235                 240

Lys Tyr Cys Pro Ser His Glu His Asp Ala Thr Pro Arg Cys Cys Ser
                245                 250                 255

Cys Glu Arg Met Glu Pro Arg Asn Thr Gly Tyr Phe Glu Leu Asn Asp
            260                 265                 270

Gly Arg Lys Leu Cys Leu Glu Cys Leu Asp Ser Ser Val Met Asp Thr
            275                 280                 285

Phe Gln Cys Gln Pro Leu Tyr Leu Gln Ile Gln Glu Phe Tyr Glu Gly
    290                 295                 300
```

-continued

```
Leu Asn Met Thr Val Glu Gln Glu Val Pro Leu Leu Val Glu Arg
305                 310                 315                 320

Gln Ala Leu Asn Glu Ala Arg Glu Gly Glu Arg Asn Gly His Tyr His
            325                 330                 335

Met Pro Glu Thr Arg Gly Leu Cys Leu Ser Glu Glu Gln Thr Val Arg
        340                 345                 350

Thr Val Arg Lys Arg Ser Lys Gly Asn Trp Ser Gly Asn Met Ile Thr
    355                 360                 365

Glu Gln Phe Lys Leu Thr Arg Arg Cys Glu Val Thr Ala Ile Leu Ile
370                 375                 380

Leu Phe Gly Leu Pro Arg Leu Leu Thr Gly Ser Ile Leu Ala His Glu
385                 390                 395                 400

Met Met His Ala Trp Met Arg Leu Lys Gly Phe Arg Pro Leu Ser Gln
            405                 410                 415

Asp Val Glu Glu Gly Ile Cys Gln Val Met Ala His Lys Trp Leu Glu
        420                 425                 430

Ala Glu Leu Ala Ala Gly Ser Arg Asn Ser Asn Ala Ala Ser Ser Ser
    435                 440                 445

Ser Ser Ser Tyr Gly Gly Val Lys Lys Gly Pro Arg Ser Gln Tyr Glu
450                 455                 460

Arg Lys Leu Gly Glu Phe Phe Lys His Gln Ile Glu Ser Asp Ala Ser
465                 470                 475                 480

Pro Val Tyr Gly Asp Gly Phe Arg Ala Gly Arg Leu Ala Val Asn Lys
            485                 490                 495

Tyr Gly Leu Trp Arg Thr Leu Glu His Ile Gln Met Thr Gly Arg Phe
        500                 505                 510

Pro Val

<210> SEQ ID NO 44
<211> LENGTH: 532
<212> TYPE: PRT
<213> ORGANISM: Brassica rapa

<400> SEQUENCE: 44

Met Gly Trp Phe Asn Lys Ile Phe Lys Gly Ser Thr Gln Arg Phe Arg
1                   5                   10                  15

Leu Gly Asn Asp His Asp His Asn Gly Tyr Tyr Gln Ser Tyr Pro His
            20                  25                  30

Asp Glu Pro Ser Ala Asp Thr Asp Pro Asp Pro Asp Pro Asp Pro Asp
        35                  40                  45

Glu Thr His Thr Gln Glu Pro Ser Thr Ser Glu Glu Asp Thr Ser Gly
    50                  55                  60

Gln Glu Asn Glu Asp Ile Asp Arg Ala Ile Ala Leu Ser Leu Ile Glu
65                  70                  75                  80

Asn Ser Gln Gly Gln Thr Asn Asn Thr Cys Ala Ala Asn Ala Gly Lys
            85                  90                  95

Tyr Ala Met Val Asp Glu Asp Glu Gln Leu Ala Arg Ala Ile Gln Glu
        100                 105                 110

Ser Met Val Val Gly Asn Thr Pro Arg Gln Lys His Gly Ser Ser Tyr
    115                 120                 125

Asp Ile Gly Asn Ala Tyr Gly Ala Gly Asp Val Tyr Gly Asn Gly His
130                 135                 140

Met His Gly Gly Gly Asn Val Tyr Ala Asn Gly Asp Ile Tyr Tyr Pro
145                 150                 155                 160
```

-continued

Arg Pro Thr Ala Phe Pro Met Asp Phe Arg Ile Cys Ala Gly Cys Asn
                165                 170                 175

Met Glu Ile Gly His Gly Arg Tyr Leu Asn Cys Leu Asn Ala Leu Trp
            180                 185                 190

His Pro Glu Cys Phe Arg Cys Tyr Gly Cys Arg His Pro Ile Ser Glu
        195                 200                 205

Tyr Glu Phe Ser Thr Ser Gly Asn Tyr Pro Phe His Lys Ala Cys Tyr
    210                 215                 220

Arg Glu Arg Tyr His Pro Lys Cys Asp Val Cys Ser Leu Phe Ile Pro
225                 230                 235                 240

Thr Asn His Ala Gly Leu Ile Gly Tyr Arg Ala His Pro Phe Trp Val
                245                 250                 255

Gln Lys Tyr Cys Pro Ser His Glu His Asp Ala Thr Pro Arg Cys Cys
            260                 265                 270

Ser Cys Glu Arg Met Glu Pro Arg Asn Thr Gly Tyr Val Glu Leu Asn
        275                 280                 285

Asp Gly Arg Lys Leu Cys Leu Glu Cys Leu Asp Ser Ala Val Met Asp
    290                 295                 300

Thr Phe Gln Cys Gln Pro Leu Tyr Leu Gln Ile Gln Glu Phe Tyr Glu
305                 310                 315                 320

Gly Leu Phe Met Lys Val Glu Gln Asp Val Pro Leu Leu Val Glu
                325                 330                 335

Arg Gln Ala Leu Asn Glu Ala Arg Glu Gly Glu Lys Asn Gly His Tyr
            340                 345                 350

His Met Pro Glu Thr Arg Gly Leu Cys Leu Ser Glu Gln Thr Val
        355                 360                 365

Ser Thr Val Arg Lys Arg Ser Lys His Gly Thr Gly Asn Trp Ala Gly
    370                 375                 380

Asn Met Ile Thr Glu Pro Tyr Lys Leu Thr Arg Gln Cys Glu Val Thr
385                 390                 395                 400

Ala Ile Leu Ile Leu Phe Gly Leu Pro Arg Leu Leu Thr Gly Ser Ile
                405                 410                 415

Leu Ala His Glu Met Met His Ala Trp Met Arg Leu Lys Gly Phe Arg
            420                 425                 430

Thr Leu Ser Gln Asp Val Glu Glu Gly Ile Cys Gln Val Met Ala His
    435                 440                 445

Lys Trp Leu Glu Ala Glu Leu Ala Ala Gly Ser Arg Asn Ser Asn Val
450                 455                 460

Ala Ser Ser Ser Ser Arg Gly Val Lys Lys Gly Pro Arg Ser Gln
465                 470                 475                 480

Tyr Glu Arg Lys Leu Gly Glu Phe Phe Lys His Gln Ile Glu Ser Asp
                485                 490                 495

Ala Ser Pro Val Tyr Gly Asp Gly Phe Arg Ala Gly Arg Leu Ala Val
            500                 505                 510

Asn Lys Tyr Gly Leu Pro Lys Thr Leu Glu His Ile Gln Met Thr Gly
        515                 520                 525

Arg Phe Pro Val
    530

<210> SEQ ID NO 45
<211> LENGTH: 532
<212> TYPE: PRT
<213> ORGANISM: Arabidopsis thaliana

```
<400> SEQUENCE: 45

Met Gly Trp Phe Asn Lys Ile Phe Lys Gly Ser Asn Gln Arg Leu Arg
1               5                   10                  15

Val Gly Asn Asn Lys His Asn His Asn Val Tyr Tyr Asp Asn Tyr Pro
            20                  25                  30

Thr Ala Ser His Asp Asp Glu Pro Ser Ala Ala Asp Thr Asp Ala Asp
        35                  40                  45

Asn Asp Glu Pro His His Thr Gln Glu Pro Ser Thr Ser Glu Asp Asn
    50                  55                  60

Thr Ser Asn Asp Gln Glu Asn Glu Asp Ile Asp Arg Ala Ile Ala Leu
65                  70                  75                  80

Ser Leu Leu Glu Glu Asn Gln Glu Gln Thr Ser Ile Ser Gly Lys Tyr
                85                  90                  95

Ser Met Pro Val Asp Glu Asp Glu Gln Leu Ala Arg Ala Leu Gln Glu
            100                 105                 110

Ser Met Val Val Gly Asn Ser Pro Arg His Lys Ser Gly Ser Thr Tyr
            115                 120                 125

Asp Asn Gly Asn Ala Tyr Gly Ala Gly Asp Leu Tyr Gly Asn Gly His
    130                 135                 140

Met Tyr Gly Gly Asn Val Tyr Ala Asn Gly Asp Ile Tyr Tyr Pro
145                 150                 155                 160

Arg Pro Ile Thr Phe Gln Met Asp Phe Arg Ile Cys Ala Gly Cys Asn
                165                 170                 175

Met Glu Ile Gly His Gly Arg Phe Leu Asn Cys Leu Asn Ser Leu Trp
            180                 185                 190

His Pro Glu Cys Phe Arg Cys Tyr Gly Cys Ser Gln Pro Ile Ser Glu
        195                 200                 205

Tyr Glu Phe Ser Thr Ser Gly Asn Tyr Pro Phe His Lys Ala Cys Tyr
    210                 215                 220

Arg Glu Arg Tyr His Pro Lys Cys Asp Val Cys Ser His Phe Ile Pro
225                 230                 235                 240

Thr Asn His Ala Gly Leu Ile Glu Tyr Arg Ala His Pro Phe Trp Val
                245                 250                 255

Gln Lys Tyr Cys Pro Ser His Glu His Asp Ala Thr Pro Arg Cys Cys
            260                 265                 270

Ser Cys Glu Arg Met Glu Pro Arg Asn Thr Arg Tyr Val Glu Leu Asn
            275                 280                 285

Asp Gly Arg Lys Leu Cys Leu Glu Cys Leu Asp Ser Ala Val Met Asp
    290                 295                 300

Thr Met Gln Cys Gln Pro Leu Tyr Leu Gln Ile Gln Asn Phe Tyr Glu
305                 310                 315                 320

Gly Leu Asn Met Lys Val Glu Gln Glu Val Pro Leu Leu Leu Val Glu
                325                 330                 335

Arg Gln Ala Leu Asn Glu Ala Arg Glu Gly Glu Lys Asn Gly His Tyr
            340                 345                 350

His Met Pro Glu Thr Arg Gly Leu Cys Leu Ser Glu Glu Gln Thr Val
        355                 360                 365

Ser Thr Val Arg Lys Arg Ser Lys His Gly Thr Gly Lys Trp Ala Gly
    370                 375                 380

Asn Ile Thr Glu Pro Tyr Lys Leu Thr Arg Gln Cys Glu Val Thr Ala
385                 390                 395                 400

Ile Leu Ile Leu Phe Gly Leu Pro Arg Leu Leu Thr Gly Ser Ile Leu
                405                 410                 415
```

Ala His Glu Met Met His Ala Trp Met Arg Leu Lys Gly Phe Arg Thr
            420                 425                 430

Leu Ser Gln Asp Val Glu Gly Ile Cys Gln Val Met Ala His Lys
        435                 440                 445

Trp Leu Asp Ala Glu Leu Ala Ala Gly Ser Thr Asn Ser Asn Ala Ala
    450                 455                 460

Ser Ser Ser Ser Ser Ser Gln Gly Leu Lys Lys Gly Pro Arg Ser Gln
465                 470                 475                 480

Tyr Glu Arg Lys Leu Gly Glu Phe Phe Lys His Gln Ile Glu Ser Asp
                485                 490                 495

Ala Ser Pro Val Tyr Gly Asp Gly Phe Arg Ala Gly Arg Leu Ala Val
            500                 505                 510

His Lys Tyr Gly Leu Arg Lys Thr Leu Glu His Ile Gln Met Thr Gly
        515                 520                 525

Arg Phe Pro Val
    530

<210> SEQ ID NO 46
<211> LENGTH: 478
<212> TYPE: PRT
<213> ORGANISM: Theobroma cacao

<400> SEQUENCE: 46

Met Asp Trp Ile Lys Lys Ile Phe Lys Gly Cys Ala His Lys Phe Ser
1               5                   10                  15

Glu Gly His His His Gly Asn Tyr Val Glu Asp Pro His Pro Gln Phe
            20                  25                  30

Asn Ala Pro Ser Val Ser Gly Asp Ala Trp Gln Glu Leu Glu Asn Glu
        35                  40                  45

Asp Val Asp Arg Ala Ile Ala Leu Ser Leu Leu Gly Glu Ser Gln Lys
    50                  55                  60

Gly Arg Lys Val Ile Asp Asp Glu Tyr Gln Leu Glu Glu Asp Glu Gln
65                  70                  75                  80

Leu Ala Arg Ala Leu Gln Glu Ser Leu Asn Phe Glu Pro Pro Gln
                85                  90                  95

Tyr Glu Asn Ala Asn Met Tyr Gln Pro Met Pro Val His Phe Pro Met
            100                 105                 110

Gly Tyr Arg Ile Cys Ala Gly Cys Asn Thr Glu Ile Gly His Gly Arg
        115                 120                 125

Phe Leu Asn Cys Leu Asn Ala Phe Trp His Pro Glu Cys Phe Arg Cys
    130                 135                 140

His Ala Cys Asn Leu Pro Ile Ser Asp Tyr Glu Phe Ser Met Ser Gly
145                 150                 155                 160

Asn Tyr Arg Phe His Lys Ser Cys Tyr Lys Glu Arg Tyr His Pro Lys
                165                 170                 175

Cys Asp Val Cys Asn Asp Phe Ile Pro Thr Asn Pro Ala Gly Leu Ile
            180                 185                 190

Glu Tyr Arg Ala His Pro Phe Trp Ile Gln Lys Tyr Cys Pro Ser His
        195                 200                 205

Glu His Asp Ser Thr Pro Arg Cys Cys Ser Cys Glu Arg Met Glu Pro
    210                 215                 220

Gln Asp Thr Gly Tyr Val Ala Leu Asn Asp Gly Arg Lys Leu Cys Leu
225                 230                 235                 240

Glu Cys Leu Asp Ser Ala Val Met Asp Thr Lys Gln Cys Gln Pro Leu 245                 250                 255
Tyr Leu Asp Ile Leu Glu Phe Tyr Glu Gly Leu Asn Met Lys Val Glu
            260                 265                 270

Gln Gln Val Pro Leu Leu Val Glu Arg Gln Ala Leu Asn Glu Ala
        275                 280                 285

Arg Glu Gly Glu Lys Asn Gly His Tyr His Met Pro Glu Thr Arg Gly
290                 295                 300

Leu Cys Leu Ser Glu Gln Thr Val Ser Thr Ile Leu Arg Gln Pro
305                 310                 315                 320

Arg Phe Gly Thr Gly Asn Arg Ala Met Asp Met Ile Thr Glu Pro Cys
                325                 330                 335

Lys Leu Thr Arg Arg Cys Glu Val Thr Ala Ile Leu Ile Leu Tyr Gly
            340                 345                 350

Leu Pro Arg Leu Leu Thr Gly Ser Ile Leu Ala His Glu Met Met His
        355                 360                 365

Ala Trp Met Arg Leu Gln Gly Phe Arg Thr Leu Ser Gln Asp Val Glu
    370                 375                 380

Glu Gly Ile Cys Gln Val Leu Ala His Met Trp Leu Leu Thr Gln Leu
385                 390                 395                 400

Glu Tyr Ala Ser Ser Ser Asn Val Ala Ser Ala Ser Ser Ser Ala Ser
                405                 410                 415

Ser Arg Leu Gln Lys Gly Lys Arg Pro Gln Phe Glu Gly Lys Leu Gly
            420                 425                 430

Glu Phe Phe Lys His Gln Ile Glu Ser Asp Thr Ser Pro Val Tyr Gly
        435                 440                 445

Asp Gly Phe Arg Ala Gly His Gln Ala Val Tyr Lys Tyr Gly Leu Arg
    450                 455                 460

Arg Thr Leu Glu His Ile Arg Met Thr Gly Arg Phe Pro Tyr
465                 470                 475

<210> SEQ ID NO 47
<211> LENGTH: 474
<212> TYPE: PRT
<213> ORGANISM: Glycine max

<400> SEQUENCE: 47

Met Gly Trp Leu Ser Arg Ile Phe Lys Gly Ser Asp His Asn Lys Leu
1               5                   10                  15

Ser Glu Gly His Tyr Tyr Lys Glu Asp Ala Gly Tyr Tyr Leu Pro Ser
            20                  25                  30

Thr Ser Gly Val Thr Asn Asn Gln Asn Glu Asn Glu Asp Ile Asp Arg
        35                  40                  45

Ala Ile Ala Leu Ser Leu Val Glu Glu Ser Arg Arg Ala Asn Asn Asn
    50                  55                  60

Val Asn Gly Glu Arg Ile Leu Ser Leu Gln Thr Leu Leu Glu Glu Asp
65                  70                  75                  80

Glu Gln Leu Ala Arg Ala Ile Glu Gln Ser Leu Asn Leu Glu Ser Pro
                85                  90                  95

Pro Arg Tyr Gly Asn Glu Asn Met Tyr Gln Pro Pro Ile Gln Tyr Phe
            100                 105                 110

Pro Leu Gly Ile Cys Ala Gly Cys Tyr Thr Glu Ile Gly Phe Gly Arg
        115                 120                 125

Tyr Leu Asn Cys Leu Asn Ala Phe Trp His Pro Glu Cys Phe Arg Cys
    130                 135                 140

```
Arg Ala Cys Asn Leu Pro Ile Ser Asp Tyr Glu Phe Ser Thr Ser Gly
145                 150                 155                 160

Asn Tyr Pro Tyr His Lys Ser Cys Tyr Lys Glu Ser Tyr His Pro Lys
                165                 170                 175

Cys Asp Val Cys Lys His Phe Ile Pro Thr Asn Pro Ala Gly Leu Ile
            180                 185                 190

Glu Tyr Arg Ala His Pro Phe Trp Ile Gln Lys Tyr Cys Pro Thr His
        195                 200                 205

Glu His Asp Gly Thr Pro Arg Cys Cys Ser Cys Arg Met Glu Ser
    210                 215                 220

Gln Glu Ala Gly Tyr Ile Ala Leu Lys Asp Gly Arg Lys Leu Cys Leu
225                 230                 235                 240

Glu Cys Leu Asp Ser Ser Ile Met Asp Thr Asn Glu Cys Gln Pro Leu
                245                 250                 255

His Ala Asp Ile Gln Arg Phe Tyr Asp Ser Leu Asn Met Lys Leu Asp
            260                 265                 270

Gln Gln Ile Pro Leu Leu Leu Val Glu Arg Gln Ala Leu Asn Glu Ala
        275                 280                 285

Arg Glu Gly Glu Lys Asn Gly His Tyr His Met Pro Glu Thr Arg Gly
290                 295                 300

Leu Cys Leu Ser Glu Glu Leu Ser Thr Phe Ser Arg Arg Pro Arg Leu
305                 310                 315                 320

Gly Thr Ala Met Asp Met Arg Ala Gln Pro Tyr Arg Pro Thr Thr Arg
                325                 330                 335

Cys Asp Val Thr Ala Ile Leu Val Leu Tyr Gly Leu Pro Arg Leu Leu
            340                 345                 350

Thr Gly Ser Ile Leu Ala His Glu Met Met His Ala Trp Leu Arg Leu
        355                 360                 365

Lys Gly Tyr Arg Thr Leu Ser Gln Asp Val Glu Glu Gly Ile Cys Gln
370                 375                 380

Val Leu Ala His Met Trp Leu Glu Ser Glu Leu Ser Ser Ala Ser Gly
385                 390                 395                 400

Ser Asn Phe Val Ser Ala Ser Ser Ser Ala Ser His Thr Ser Arg
                405                 410                 415

Lys Gly Lys Arg Pro Gln Phe Glu Arg Lys Leu Gly Glu Phe Phe Lys
                420                 425                 430

His Gln Ile Glu Ser Asp Ile Ser Pro Val Tyr Gly Asp Gly Phe Arg
            435                 440                 445

Ala Gly Gln Lys Ala Val Arg Lys Tyr Gly Leu Gln Arg Thr Leu His
        450                 455                 460

His Ile Arg Met Thr Gly Thr Phe Pro Tyr
465                 470

<210> SEQ ID NO 48
<211> LENGTH: 478
<212> TYPE: PRT
<213> ORGANISM: Glycine max

<400> SEQUENCE: 48

Met Gly Trp Leu Ser Arg Ile Phe Lys Gly Ser Asp His Asn Lys Leu
1               5                   10                  15

Ser Glu Gly His Tyr Tyr Lys Glu Asp Ala Gly Tyr Tyr Leu Pro Ser
                20                  25                  30

Thr Ser Gly Val Thr Asn Asp Ala Trp Asn Gln Ser Gln Asn Gln Asn
            35                  40                  45
```

Glu Asn Glu Asp Ile Asp Arg Ala Ile Ala Leu Ser Leu Val Glu Glu
        50                  55                  60

Thr Gln Lys Ala Asn Asn Asn Val Asn Asp Tyr Arg Ser Gln Leu Glu
65                  70                  75                  80

Glu Asp Glu Gln Leu Ala Arg Ala Ile Glu Gln Ser Leu Asn Leu Glu
                85                  90                  95

Ser Pro Pro Arg Tyr Gly Asn Glu Asn Met Tyr Gln Pro Pro Ile Gln
            100                 105                 110

Tyr Phe Pro Met Gly Ser Arg Ile Cys Ala Gly Cys Tyr Thr Glu Ile
        115                 120                 125

Gly Tyr Gly Arg Tyr Leu Asn Cys Leu Asn Ala Phe Trp His Pro Glu
    130                 135                 140

Cys Phe Arg Cys Arg Ala Cys Asn Leu Pro Ile Ser Asp Tyr Glu Phe
145                 150                 155                 160

Ser Thr Ser Gly Asn Tyr Pro Tyr His Lys Ser Cys Tyr Lys Glu Ser
                165                 170                 175

Tyr His Pro Lys Cys Asp Val Cys Lys His Phe Ile Pro Thr Asn Pro
            180                 185                 190

Ala Gly Leu Ile Glu Tyr Arg Ala His Pro Phe Trp Ile Gln Lys Tyr
        195                 200                 205

Cys Pro Thr His Glu His Asp Gly Thr Thr Arg Cys Cys Ser Cys Glu
    210                 215                 220

Arg Met Glu Ser Gln Glu Ala Gly Tyr Ile Ala Leu Lys Asp Gly Arg
225                 230                 235                 240

Lys Leu Cys Leu Glu Cys Leu Asp Ser Ala Ile Met Asp Thr Asn Glu
                245                 250                 255

Cys Gln Pro Leu His Ala Asp Ile Gln Arg Phe Tyr Glu Ser Leu Asn
            260                 265                 270

Met Lys Leu Asp Gln Gln Ile Pro Leu Leu Leu Val Glu Arg Gln Ala
        275                 280                 285

Leu Asn Glu Ala Arg Glu Gly Glu Lys Asn Gly His Tyr His Met Pro
    290                 295                 300

Glu Thr Arg Gly Leu Cys Leu Ser Glu Glu Leu Ser Thr Phe Ser Arg
305                 310                 315                 320

Arg Pro Arg Leu Gly Thr Thr Met Asp Met Arg Ala Gln Pro Tyr Arg
                325                 330                 335

Pro Thr Thr Arg Cys Asp Val Thr Ala Ile Leu Ile Leu Tyr Gly Leu
            340                 345                 350

Pro Arg Leu Leu Thr Gly Ser Ile Leu Ala His Glu Met Met His Ala
        355                 360                 365

Trp Leu Arg Leu Lys Gly Tyr Arg Thr Leu Ser Gln Asp Val Glu Glu
    370                 375                 380

Gly Ile Cys Gln Val Leu Ser His Met Trp Leu Glu Ser Glu Leu Ser
385                 390                 395                 400

Ser Ala Ser Gly Ser Asn Phe Val Ser Ala Ser Ser Ser Ala Ser
                405                 410                 415

His Thr Ser Arg Lys Gly Lys Arg Pro Gln Phe Glu Arg Lys Leu Gly
            420                 425                 430

Glu Phe Phe Lys His Gln Ile Glu Ser Asp Ile Ser Pro Val Tyr Gly
        435                 440                 445

Gly Gly Phe Arg Ala Gly Gln Lys Ala Val Ser Lys Tyr Gly Leu Gln
    450                 455                 460

Arg Thr Leu His His Ile Arg Met Thr Gly Thr Phe Pro Tyr
465                 470                 475

<210> SEQ ID NO 49
<211> LENGTH: 462
<212> TYPE: PRT
<213> ORGANISM: Vitis vinifera

<400> SEQUENCE: 49

Met Gly Trp Leu Asn Lys Ile Phe Lys Gly Ser His Lys Ile Ser
1               5                   10                  15

Glu Gly Asn Tyr His Gly Arg Tyr Gln Gly Asp Thr Val Gln Asn Glu
                20                  25                  30

Pro Ser Cys Ser Gly Asp Val Trp Ala Glu Thr Glu Asn Glu Asp Ile
            35                  40                  45

Asp Arg Ala Ile Ala Leu Ser Leu Ser Glu Glu Glu Gln Lys Gly Lys
        50                  55                  60

Lys Val Ile Asp Asn Glu Phe Gln Leu Glu Glu Asp Glu Gln Leu Ala
65                  70                  75                  80

Arg Ala Ile Gln Glu Ser Leu Asn Ile Glu Ser Pro Pro Gln His Gly
                85                  90                  95

Asn Gly Asn Gly Asn Gly Asn Ile Tyr Gln Pro Ile Pro Phe Pro Tyr
                100                 105                 110

Ser Thr Gly Phe Arg Ile Cys Ala Gly Cys Asn Thr Glu Ile Gly His
                115                 120                 125

Gly Arg Phe Leu Ser Cys Met Gly Ala Val Trp His Pro Glu Cys Phe
                130                 135                 140

Arg Cys His Gly Cys Gly Tyr Pro Ile Ser Asp Tyr Glu Tyr Ser Met
145                 150                 155                 160

Asn Gly Asn Tyr Pro Tyr His Lys Ser Cys Tyr Lys Glu His Tyr His
                165                 170                 175

Pro Lys Cys Asp Val Cys Lys His Phe Ile Pro Thr Asn Pro Ala Gly
                180                 185                 190

Leu Ile Glu Tyr Arg Ala His Pro Phe Trp Val Gln Lys Tyr Cys Pro
                195                 200                 205

Ser His Glu His Asp Arg Thr Pro Arg Cys Cys Ser Cys Glu Arg Met
                210                 215                 220

Glu Pro Arg Asp Thr Arg Tyr Val Ala Leu Asn Asp Gly Arg Lys Leu
225                 230                 235                 240

Cys Leu Glu Cys Leu Asp Ser Ala Ile Met Asp Thr Asn Glu Cys Gln
                245                 250                 255

Pro Leu Tyr Leu Asp Ile Gln Glu Phe Tyr Glu Gly Leu Asn Met Lys
                260                 265                 270

Val Gln Gln Gln Val Pro Leu Leu Val Glu Arg Gln Ala Leu Asn
                275                 280                 285

Glu Ala Met Glu Gly Glu Lys Ser Gly His His Met Pro Glu Thr
                290                 295                 300

Arg Gly Leu Cys Leu Ser Glu Glu Gln Thr Val Ser Thr Ile Leu Arg
305                 310                 315                 320

Arg Pro Lys Ile Gly Thr Gly Asn Arg Val Met Asn Met Ile Thr Glu
                325                 330                 335

Pro Cys Lys Leu Thr Arg Arg Cys Asp Val Thr Ala Val Leu Ile Leu
                340                 345                 350

Tyr Gly Leu Pro Arg Leu Leu Thr Gly Ser Ile Leu Ala His Glu Met
                355                 360                 365

```
Met His Ala Trp Leu Arg Leu Asn Gly Tyr Arg Thr Leu Ala Gln Asp
    370                 375                 380

Val Glu Glu Gly Ile Cys Gln Val Leu Ala Tyr Met Trp Leu Asp Ala
385                 390                 395                 400

Glu Leu Thr Ser Gly Ser Gly Arg Ser Gln Cys Glu Arg Lys Leu Gly
            405                 410                 415

Gln Phe Phe Lys His Gln Ile Glu Ser Asp Thr Ser Leu Val Tyr Gly
            420                 425                 430

Ala Gly Phe Arg Ala Gly His Gln Ala Val Leu Lys Tyr Gly Leu Pro
        435                 440                 445

Ala Thr Leu Lys His Ile His Leu Thr Gly Asn Phe Pro Tyr
    450                 455                 460

<210> SEQ ID NO 50
<211> LENGTH: 482
<212> TYPE: PRT
<213> ORGANISM: Vitis vinifera

<400> SEQUENCE: 50

Met Gly Trp Leu Asn Lys Ile Phe Lys Gly Ser Ser His Lys Ile Ser
1               5                   10                  15

Glu Gly Asn Tyr His Gly Arg Tyr Gln Gly Asp Thr Val Gln Asn Glu
            20                  25                  30

Pro Ser Cys Ser Gly Asp Val Trp Ala Glu Thr Glu Asn Glu Asp Ile
        35                  40                  45

Asp Arg Ala Ile Ala Leu Ser Leu Ser Glu Glu Glu Lys Gly Lys
50                  55                  60

Lys Val Ile Asp Glu Leu Asp Asn Glu Phe Gln Leu Glu Glu Asp Glu
65                  70                  75                  80

Gln Leu Ala Arg Ala Ile Gln Glu Ser Leu Asn Ile Glu Ser Pro Pro
            85                  90                  95

Gln His Gly Asn Gly Asn Gly Asn Ile Tyr Gln Pro Ile Pro
        100                 105                 110

Phe Pro Tyr Ser Thr Gly Phe Arg Ile Cys Ala Gly Cys Asn Thr Glu
        115                 120                 125

Ile Gly His Gly Arg Phe Leu Ser Cys Met Gly Ala Val Trp His Pro
    130                 135                 140

Glu Cys Phe Arg Cys His Gly Cys Gly Tyr Pro Ile Ser Asp Tyr Glu
145                 150                 155                 160

Tyr Ser Met Asn Gly Asn Tyr Pro Tyr His Lys Ser Cys Tyr Lys Glu
            165                 170                 175

His Tyr His Pro Lys Cys Asp Val Cys Lys His Phe Ile Pro Thr Asn
        180                 185                 190

Pro Ala Gly Leu Ile Glu Tyr Arg Ala His Pro Phe Trp Val Gln Lys
    195                 200                 205

Tyr Cys Pro Ser His Glu His Asp Arg Thr Pro Arg Cys Cys Ser Cys
    210                 215                 220

Glu Arg Met Glu Pro Arg Asp Thr Arg Tyr Val Ala Leu Asn Asp Gly
225                 230                 235                 240

Arg Lys Leu Cys Leu Glu Cys Leu Asp Ser Ala Ile Met Asp Thr Asn
            245                 250                 255

Glu Cys Gln Pro Leu Tyr Leu Asp Ile Gln Glu Phe Tyr Glu Gly Leu
        260                 265                 270

Asn Met Lys Val Gln Gln Gln Val Pro Leu Leu Leu Val Glu Arg Gln
```

Ala Leu Asn Glu Ala Met Glu Gly Glu Lys Ser Gly His His His Met
            275                 280                 285
Pro Glu Thr Arg Gly Leu Cys Leu Ser Glu Glu Gln Thr Val Ser Thr
290                 295                 300
Ile Leu Arg Arg Pro Lys Ile Gly Thr Gly Asn Arg Val Met Asn Met
305                 310                 315                 320
Ile Thr Glu Pro Cys Lys Leu Thr Arg Arg Cys Asp Val Thr Ala Val
            325                 330                 335
Leu Ile Leu Tyr Gly Leu Pro Arg Leu Leu Thr Gly Ser Ile Leu Ala
            340                 345                 350
His Glu Met Met His Ala Trp Leu Arg Leu Asn Gly Tyr Arg Thr Leu
355                 360                 365
Ala Gln Asp Val Glu Gly Ile Cys Gln Val Leu Ala Tyr Met Trp
370                 375                 380
Leu Asp Ala Glu Leu Thr Ser Gly Ser Gly Ser Asn Val Pro Ser Thr
385                 390                 395                 400
Ser Ser Ala Ser Thr Ser Ser Lys Lys Gly Ala Gly Ser Gln Cys Glu
            405                 410                 415
Arg Lys Leu Gly Gln Phe Phe Lys His Gln Ile Glu Ser Asp Thr Ser
            420                 425                 430
Leu Val Tyr Gly Ala Gly Phe Arg Ala Gly His Gln Ala Val Leu Lys
            435                 440                 445
Tyr Gly Leu Pro Ala Thr Leu Lys His Ile His Leu Thr Gly Asn Phe
450                 455                 460
Pro Tyr
465                 470                 475                 480

<210> SEQ ID NO 51
<211> LENGTH: 486
<212> TYPE: PRT
<213> ORGANISM: Solanum lycopersicum

<400> SEQUENCE: 51

Met Gly Trp Leu Asn Lys Ile Phe Arg Gly Ser Ser His Lys Ile Ser
1               5                   10                  15
Glu Gly Gln Tyr Asp Trp Arg Cys Glu Gly His Thr Glu Glu Asp Asp
            20                  25                  30
Pro Ser Thr Ala Glu Asp Ser Trp Ser Glu Ile Glu Glu Ile Asp Arg
        35                  40                  45
Ala Ile Ala Ile Ser Leu Ser Glu Glu Gln Lys Gly Lys Ile Val
    50                  55                  60
Ile Asp Ser Glu Ser Gln Leu Lys Glu Asp Glu Gln Leu Ala Arg Ala
65                  70                  75                  80
Leu Gln Glu Ser Leu Asn Val Glu Ser Pro Gln His Val Ser Arg
                85                  90                  95
Asn Asp His Gly Gly Gly Asn Val Tyr Gly Asn Gly Asn Phe Tyr His
                100                 105                 110
Pro Val Pro Phe Pro Tyr Ser Ala Ser Phe Arg Val Cys Ala Gly Cys
            115                 120                 125
Ser Thr Glu Ile Gly His Gly Arg Phe Leu Ser Cys Met Gly Ala Val
            130                 135                 140
Trp His Pro Glu Cys Phe Arg Cys His Ala Cys Asn Gln Pro Ile Ser
145                 150                 155                 160
Asp Tyr Glu Phe Ser Met Ser Gly Asn Tyr Pro Tyr His Lys Thr Cys

```
                    165                 170                 175
Tyr Lys Glu His Tyr His Pro Lys Cys Asp Val Cys Lys His Phe Ile
                180                 185                 190

Pro Thr Asn Ala Ala Gly Leu Ile Glu Tyr Arg Ala His Pro Phe Trp
            195                 200                 205

Ser Gln Lys Tyr Cys Pro Phe His Glu His Asp Gly Thr Pro Arg Cys
        210                 215                 220

Cys Ser Cys Glu Arg Met Glu Pro Arg Asp Thr Arg Tyr Ile Ala Leu
225                 230                 235                 240

Asp Asp Gly Arg Lys Leu Cys Leu Glu Cys Leu Asp Ser Ala Ile Met
                245                 250                 255

Asp Thr Ser Gln Cys Gln Pro Leu Tyr Tyr Asp Ile Gln Glu Phe Tyr
            260                 265                 270

Glu Gly Leu Asn Met Lys Val Glu Gln Lys Val Pro Leu Leu Leu Val
        275                 280                 285

Glu Arg Gln Ala Leu Asn Glu Ala Met Asp Gly Glu Arg His Gly Tyr
    290                 295                 300

His His Met Pro Glu Thr Arg Gly Leu Cys Leu Ser Glu Glu Gln Thr
305                 310                 315                 320

Ile Ser Thr Ile Gln Arg Arg Pro Arg Ile Gly Ala Gly Asn Arg Val
                325                 330                 335

Met Asp Met Arg Thr Glu Pro Tyr Lys Leu Thr Arg Arg Cys Glu Val
            340                 345                 350

Thr Ala Ile Leu Ile Leu Tyr Gly Leu Pro Arg Leu Leu Thr Gly Ser
        355                 360                 365

Ile Leu Ala His Glu Met Met His Ala Trp Leu Arg Leu Arg Gly Tyr
    370                 375                 380

Arg Thr Leu Ser Gln Asp Val Glu Glu Gly Ile Cys Gln Val Leu Ala
385                 390                 395                 400

His Met Trp Leu Glu Thr Gln Ile Ala Ser Ile Ser Ser Ser Asn Gly
                405                 410                 415

Gly Ala Ser Thr Ser Ser Gly Met Ser Ser Ser Lys Gln Gly Ile Arg
            420                 425                 430

Ser Pro Phe Glu Arg Lys Leu Gly Asp Phe Phe Lys His Gln Ile Glu
        435                 440                 445

Ser Asp Thr Ser Pro Ile Tyr Gly Asn Gly Phe Arg Ala Gly Asn Gln
    450                 455                 460

Ala Val Leu Lys Tyr Gly Leu Glu Arg Thr Leu Asp His Ile Arg Met
465                 470                 475                 480

Thr Gly Thr Phe Pro Tyr
                485

<210> SEQ ID NO 52
<211> LENGTH: 878
<212> TYPE: PRT
<213> ORGANISM: Oryza sativa

<400> SEQUENCE: 52

Met Gly Asp Arg Pro Asp Met Gly Ala Gly Val Ala Leu Arg Phe Ser
1               5                   10                  15

His Asn Asp Trp Thr Leu Glu Glu Asp Ser Lys Ala Leu His Phe Leu
            20                  25                  30

Gln Pro Asp Leu Val Leu Phe Thr Gly Asp Tyr Gly Asn Glu Asn Val
        35                  40                  45
```

Gln Leu Val Lys Ser Ile Ser Asp Leu Gln Leu Pro Lys Ala Ala Ile
    50              55              60

Leu Gly Asn His Asp Cys Trp His Thr Tyr Gln Phe Ser Glu Lys Lys
65              70              75              80

Val Asp Arg Val Gln Leu Gln Leu Glu Ser Leu Gly Glu Gln His Val
                85              90              95

Gly Tyr Lys Cys Leu Asp Phe Pro Thr Ile Lys Leu Ser Val Val Gly
            100             105             110

Gly Arg Pro Phe Ser Cys Gly Gly Asn Arg Ile Phe Arg Pro Lys Leu
            115             120             125

Leu Ser Lys Trp Tyr Gly Val Asn Asp Met Ala Glu Ser Ala Lys Arg
130             135             140

Ile Tyr Asp Ala Ala Thr Asn Ala Pro Lys Glu His Ala Val Ile Leu
145             150             155             160

Leu Ala His Asn Gly Pro Thr Gly Leu Gly Ser Arg Met Glu Asp Ile
                165             170             175

Cys Gly Arg Asp Trp Val Ala Gly Gly Asp His Gly Asp Pro Asp
            180             185             190

Leu Glu Gln Ala Ile Ser Asp Leu Gln Arg Glu Thr Gly Val Ser Ile
        195             200             205

Pro Leu Val Val Phe Gly His Met His Lys Ser Leu Ala Tyr Gly Arg
210             215             220

Gly Leu Arg Lys Met Ile Ala Phe Gly Ala Asn Arg Thr Ile Tyr Leu
225             230             235             240

Asn Gly Ala Val Val Pro Arg Val Asn His Ala Gln Ser Ser Arg Gln
                245             250             255

Pro Ala Ile Ser Thr Ser Glu Lys Thr Gly Leu Glu Gly Leu Thr Gly
            260             265             270

Leu Met Val Pro Thr Ser Arg Ala Phe Thr Ile Val Asp Leu Phe Glu
        275             280             285

Gly Ala Val Glu Lys Ile Ser Glu Val Trp Val Thr Val Gly Asp Ala
290             295             300

Arg Thr Glu Leu Glu Gln Glu Leu Val Leu Tyr Lys Gln Pro His Lys
305             310             315             320

Ser Val Pro Ser Asn Ile Ala Ile Trp Ser Thr Met Gly Trp Leu Thr
                325             330             335

Lys Phe Phe Arg Gly Ser Thr His Lys Ile Ser Glu Gly Gln Tyr His
            340             345             350

Ser Lys Pro Ala Glu Glu Thr Ile Trp Asn Gly Pro Ser Asn Ser Ala
        355             360             365

Val Val Thr Met Val Tyr Pro Leu Glu Ser Thr Phe Gly Gln Leu Asp
        370             375             380

Leu Leu Leu Leu Ala Thr Asp Leu Arg Gln Leu Val Ile Asp Asp Val
385             390             395             400

Asp Cys Cys Lys Leu Arg Gln Gln Ala Gln Pro Val Leu His Leu Met
            405             410             415

Tyr Ser Gln Leu Gln Leu Leu Gln Thr Ser His Ala His Gln His Gly
        420             425             430

Asp Val Pro Ser Glu Phe Asp Asn Glu Asp Ile Ala Arg Ala Ile Ser
            435             440             445

Leu Ser Leu Leu Glu Glu Glu Gln Arg Lys Ala Lys Ala Ile Glu Lys
450             455             460

Asp Met His Leu Glu Glu Asp Glu Gln Leu Ala Arg Ala Ile Gln Glu

```
                465                 470                 475                 480
        Ser Leu Asn Val Glu Ser Pro Pro Arg Ala Arg Glu Asn Gly Asn Ala
                        485                 490                 495

Asn Gly Gly Asn Met Tyr Gln Pro Leu Pro Phe Met Phe Ser Ser Gly
                        500                 505                 510

Phe Arg Thr Cys Ala Gly Cys His Ser Glu Ile Gly His Gly Arg Phe
                        515                 520                 525

Leu Ser Cys Met Gly Ala Val Trp His Pro Glu Cys Phe Arg Cys His
                        530                 535                 540

Ala Cys Asn Gln Pro Ile Tyr Asp Tyr Glu Phe Ser Met Ser Gly Asn
        545                 550                 555                 560

His Pro Tyr His Lys Thr Cys Tyr Lys Glu Arg Phe His Pro Lys Cys
                        565                 570                 575

Asp Val Cys Lys Gln Phe Ile Pro Thr Asn Met Asn Gly Leu Ile Glu
                        580                 585                 590

Tyr Arg Ala His Pro Phe Trp Leu Gln Lys Tyr Cys Pro Ser His Glu
                        595                 600                 605

Val Asp Gly Thr Pro Arg Cys Cys Ser Cys Glu Arg Met Glu Pro Arg
                        610                 615                 620

Glu Ser Arg Tyr Val Leu Leu Asp Asp Gly Arg Lys Leu Cys Leu Glu
        625                 630                 635                 640

Cys Leu Asp Ser Ala Val Met Asp Thr Ser Glu Cys Gln Pro Leu Tyr
                        645                 650                 655

Leu Glu Ile Gln Glu Phe Tyr Glu Gly Leu Asn Met Lys Val Glu Gln
                        660                 665                 670

Gln Val Pro Leu Leu Leu Val Glu Arg Gln Ala Leu Asn Glu Ala Met
                        675                 680                 685

Glu Gly Glu Lys Thr Gly His His His Leu Pro Glu Thr Arg Gly Leu
                        690                 695                 700

Cys Leu Ser Glu Glu Gln Thr Val Ser Thr Ile Leu Arg Arg Pro Arg
        705                 710                 715                 720

Met Ala Gly Asn Lys Val Met Glu Met Ile Thr Glu Pro Tyr Arg Leu
                        725                 730                 735

Thr Arg Arg Cys Glu Val Thr Ala Ile Leu Ile Leu Tyr Gly Leu Pro
                        740                 745                 750

Arg Leu Leu Thr Gly Ser Ile Leu Ala His Glu Met Met His Ala Trp
                        755                 760                 765

Leu Arg Leu Lys Gly Tyr Arg Thr Leu Ser Pro Asp Val Glu Glu Gly
                        770                 775                 780

Ile Cys Gln Val Leu Ala His Met Trp Ile Glu Ser Glu Ile Ile Ala
        785                 790                 795                 800

Gly Ser Gly Ser Asn Gly Ala Ser Thr Ser Ser Ser Ser Ala Ser
                        805                 810                 815

Thr Ser Ser Lys Lys Gly Arg Ser Gln Phe Glu Arg Lys Leu Gly
                        820                 825                 830

Asp Phe Phe Lys His Gln Ile Glu Ser Asp Thr Ser Met Ala Tyr Gly
                        835                 840                 845

Asp Gly Phe Arg Ala Gly Asn Arg Ala Val Leu Gln Tyr Gly Leu Lys
                        850                 855                 860

Arg Thr Leu Glu His Ile Arg Leu Thr Gly Thr Phe Pro Phe
        865                 870                 875

<210> SEQ ID NO 53
```

```
<211> LENGTH: 486
<212> TYPE: PRT
<213> ORGANISM: Oryza sativa

<400> SEQUENCE: 53
```

| | | | | | | | | | | | | | | |
|---|---|---|---|---|---|---|---|---|---|---|---|---|---|---|
| Met | Gly | Trp | Leu | Thr | Lys | Phe | Phe | Arg | Gly | Ser | Thr | His | Lys | Ile | Ser |
| 1 | | | | 5 | | | | | 10 | | | | | 15 | |

| Glu | Gly | Gln | Tyr | His | Ser | Lys | Pro | Ala | Glu | Thr | Ile | Trp | Asn | Gly |
|---|---|---|---|---|---|---|---|---|---|---|---|---|---|---|
| | | | 20 | | | | 25 | | | | 30 | | | |

| Pro | Ser | Asn | Ser | Ala | Val | Val | Thr | Asp | Val | Pro | Ser | Glu | Phe | Asp | Asn |
|---|---|---|---|---|---|---|---|---|---|---|---|---|---|---|---|
| | | | 35 | | | | 40 | | | | 45 | | | | |

| Glu | Asp | Ile | Ala | Arg | Ala | Ile | Ser | Leu | Ser | Leu | Leu | Glu | Glu | Glu | Gln |
|---|---|---|---|---|---|---|---|---|---|---|---|---|---|---|---|
| | 50 | | | | | 55 | | | | 60 | | | | | |

| Arg | Lys | Ala | Lys | Ala | Ile | Glu | Lys | Asp | Met | His | Leu | Glu | Glu | Asp | Glu |
|---|---|---|---|---|---|---|---|---|---|---|---|---|---|---|---|
| 65 | | | | 70 | | | | | 75 | | | | | 80 | |

| Gln | Leu | Ala | Arg | Ala | Ile | Gln | Glu | Ser | Leu | Asn | Val | Glu | Ser | Pro | Pro |
|---|---|---|---|---|---|---|---|---|---|---|---|---|---|---|---|
| | | | | 85 | | | | | 90 | | | | | 95 | |

| Arg | Ala | Arg | Glu | Asn | Gly | Asn | Ala | Asn | Gly | Gly | Asn | Met | Tyr | Gln | Pro |
|---|---|---|---|---|---|---|---|---|---|---|---|---|---|---|---|
| | | | 100 | | | | | 105 | | | | | 110 | | |

| Leu | Pro | Phe | Met | Phe | Ser | Ser | Gly | Phe | Arg | Thr | Cys | Ala | Gly | Cys | His |
|---|---|---|---|---|---|---|---|---|---|---|---|---|---|---|---|
| | | | 115 | | | | | 120 | | | | | 125 | | |

| Ser | Glu | Ile | Gly | His | Gly | Arg | Phe | Leu | Ser | Cys | Met | Gly | Ala | Val | Trp |
|---|---|---|---|---|---|---|---|---|---|---|---|---|---|---|---|
| | 130 | | | | | 135 | | | | | 140 | | | | |

| His | Pro | Glu | Cys | Phe | Arg | Cys | His | Ala | Cys | Asn | Gln | Pro | Ile | Tyr | Asp |
|---|---|---|---|---|---|---|---|---|---|---|---|---|---|---|---|
| 145 | | | | | 150 | | | | | 155 | | | | | 160 |

| Tyr | Glu | Phe | Ser | Met | Ser | Gly | Asn | His | Pro | Tyr | His | Lys | Thr | Cys | Tyr |
|---|---|---|---|---|---|---|---|---|---|---|---|---|---|---|---|
| | | | | 165 | | | | | 170 | | | | | 175 | |

| Lys | Glu | Arg | Phe | His | Pro | Lys | Cys | Asp | Val | Cys | Lys | Gln | Phe | Ile | Pro |
|---|---|---|---|---|---|---|---|---|---|---|---|---|---|---|---|
| | | | 180 | | | | | 185 | | | | | 190 | | |

| Thr | Asn | Met | Asn | Gly | Leu | Ile | Glu | Tyr | Arg | Ala | His | Pro | Phe | Trp | Leu |
|---|---|---|---|---|---|---|---|---|---|---|---|---|---|---|---|
| | | | 195 | | | | | 200 | | | | | 205 | | |

| Gln | Lys | Tyr | Cys | Pro | Ser | His | Glu | Val | Asp | Gly | Thr | Pro | Arg | Cys | Cys |
|---|---|---|---|---|---|---|---|---|---|---|---|---|---|---|---|
| | 210 | | | | | 215 | | | | | 220 | | | | |

| Ser | Cys | Glu | Arg | Met | Glu | Pro | Arg | Glu | Ser | Arg | Tyr | Val | Leu | Leu | Asp |
|---|---|---|---|---|---|---|---|---|---|---|---|---|---|---|---|
| 225 | | | | | 230 | | | | | 235 | | | | | 240 |

| Asp | Gly | Arg | Lys | Leu | Cys | Leu | Glu | Cys | Leu | Asp | Ser | Ala | Val | Met | Asp |
|---|---|---|---|---|---|---|---|---|---|---|---|---|---|---|---|
| | | | | 245 | | | | | 250 | | | | | 255 | |

| Thr | Ser | Glu | Cys | Gln | Pro | Leu | Tyr | Leu | Glu | Ile | Gln | Glu | Phe | Tyr | Glu |
|---|---|---|---|---|---|---|---|---|---|---|---|---|---|---|---|
| | | | 260 | | | | | 265 | | | | | 270 | | |

| Gly | Leu | Asn | Met | Lys | Val | Glu | Gln | Gln | Val | Pro | Leu | Leu | Leu | Val | Glu |
|---|---|---|---|---|---|---|---|---|---|---|---|---|---|---|---|
| | | | 275 | | | | | 280 | | | | | 285 | | |

| Arg | Gln | Ala | Leu | Asn | Glu | Ala | Met | Glu | Gly | Glu | Lys | Thr | Gly | His | His |
|---|---|---|---|---|---|---|---|---|---|---|---|---|---|---|---|
| | 290 | | | | | 295 | | | | | 300 | | | | |

| His | Leu | Pro | Glu | Thr | Arg | Gly | Leu | Cys | Leu | Ser | Glu | Glu | Gln | Thr | Val |
|---|---|---|---|---|---|---|---|---|---|---|---|---|---|---|---|
| 305 | | | | | 310 | | | | | 315 | | | | | 320 |

| Ser | Thr | Ile | Leu | Arg | Arg | Pro | Arg | Met | Ala | Gly | Asn | Lys | Val | Met | Glu |
|---|---|---|---|---|---|---|---|---|---|---|---|---|---|---|---|
| | | | | 325 | | | | | 330 | | | | | 335 | |

| Met | Ile | Thr | Glu | Pro | Tyr | Arg | Leu | Thr | Arg | Arg | Cys | Glu | Val | Thr | Ala |
|---|---|---|---|---|---|---|---|---|---|---|---|---|---|---|---|
| | | | 340 | | | | | 345 | | | | | 350 | | |

| Ile | Leu | Ile | Leu | Tyr | Gly | Leu | Pro | Arg | Leu | Leu | Thr | Gly | Ser | Ile | Leu |
|---|---|---|---|---|---|---|---|---|---|---|---|---|---|---|---|
| | | | 355 | | | | | 360 | | | | | 365 | | |

| Ala | His | Glu | Met | Met | His | Ala | Trp | Leu | Arg | Leu | Lys | Gly | Tyr | Arg | Thr |
|---|---|---|---|---|---|---|---|---|---|---|---|---|---|---|---|
| | 370 | | | | | 375 | | | | | 380 | | | | |

| Leu | Ser | Pro | Asp | Val | Glu | Glu | Gly | Ile | Cys | Gln | Val | Leu | Ala | His | Met |

```
              385                 390                 395                 400
Trp Ile Glu Ser Glu Ile Ile Ala Gly Ser Gly Ser Asn Gly Ala Ser
                405                 410                 415

Thr Ser Ser Ser Ser Ala Ser Thr Ser Ser Lys Lys Gly Gly Arg
            420                 425                 430

Ser Gln Phe Glu Arg Lys Leu Gly Asp Phe Lys His Gln Ile Glu
            435                 440                 445

Ser Asp Thr Ser Met Ala Tyr Gly Asp Gly Phe Arg Ala Gly Asn Arg
450                 455                 460

Ala Val Leu Gln Tyr Gly Leu Lys Arg Thr Leu Glu His Ile Arg Leu
465                 470                 475                 480

Thr Gly Thr Phe Pro Phe
                485

<210> SEQ ID NO 54
<211> LENGTH: 512
<212> TYPE: PRT
<213> ORGANISM: Brachypodium distachyon

<400> SEQUENCE: 54

Met Gly Trp Leu Thr Lys Ile Phe Arg Gly Ser Thr Tyr Lys Ile Ser
1               5                   10                  15

Glu Gly Gln Arg Gln Ser Arg Pro Ala Glu Ala Val Trp Asn Glu
            20                  25                  30

Pro Ser Ser Ser Thr Val Val Thr Asp Val Leu Ser Glu Phe Asp Asn
            35                  40                  45

Glu Asp Ile Asp Arg Ala Ile Ala Leu Ser Leu Ser Glu Glu Gln Arg
        50                  55                  60

Lys Ser Lys Gly Thr Gly Lys Asp Leu His Leu Asp Glu Asp Glu Gln
65                  70                  75                  80

Leu Ala Arg Ala Ile His Glu Ser Leu Asn Val Glu Ser Pro Pro Cys
                85                  90                  95

Ala Arg Asp Asn Gly Ser Pro His Ala Arg Asp Asn Ser Ser Pro
            100                 105                 110

Pro His Ala Arg Glu Asn Ser Ser His Pro Arg Ala Arg Glu Asn Gly
        115                 120                 125

Ile Ala Asn Gly Gly Asn Ser Ile Gln His Ser Pro Phe Met Phe Ser
130                 135                 140

Ser Gly Phe Arg Thr Cys Ala Gly Cys His Ser Glu Ile Gly His Gly
145                 150                 155                 160

Arg Phe Leu Ser Cys Met Gly Ala Val Trp His Pro Glu Cys Phe Cys
                165                 170                 175

Cys His Ala Cys Ser Gln Pro Ile Tyr Asp Tyr Glu Phe Ser Met Ser
            180                 185                 190

Gly Asn His Pro Tyr His Lys Thr Cys Tyr Lys Glu Arg Phe His Pro
        195                 200                 205

Lys Cys Asp Val Cys Lys Gln Phe Ile Pro Thr Asn Met Asn Gly Leu
        210                 215                 220

Ile Glu Tyr Arg Ala His Pro Phe Trp Leu Gln Lys Tyr Cys Pro Ser
225                 230                 235                 240

His Glu Val Asp Gly Thr Pro Arg Cys Cys Ser Cys Glu Arg Met Glu
                245                 250                 255

Pro Arg Glu Ser Arg Tyr Val Leu Leu Asp Asp Gly Arg Lys Leu Cys
            260                 265                 270
```

Leu Glu Cys Leu Asp Ser Ala Val Met Asp Thr Thr Glu Cys Gln Pro
            275                 280                 285

Leu Tyr Leu Glu Ile Gln Glu Phe Tyr Glu Gly Leu Asn Met Lys Val
        290                 295                 300

Glu Gln Gln Val Pro Leu Leu Val Glu Arg Gln Ala Leu Asn Glu
305                 310                 315                 320

Ala Met Glu Gly Glu Lys Thr Gly His His His Leu Pro Glu Thr Arg
                325                 330                 335

Gly Leu Cys Leu Ser Glu Glu Gln Thr Val Ser Thr Ile Leu Arg Arg
            340                 345                 350

Pro Arg Met Thr Gly Asn Lys Ile Met Glu Met Ile Thr Glu Pro Tyr
        355                 360                 365

Arg Leu Thr Arg Arg Cys Glu Val Thr Ala Ile Leu Ile Leu Tyr Gly
    370                 375                 380

Leu Pro Arg Leu Leu Thr Gly Ser Ile Leu Ala His Glu Met Met His
385                 390                 395                 400

Ala Trp Leu Arg Leu Lys Gly Tyr Arg Thr Leu Ser Pro Glu Ile Glu
                405                 410                 415

Glu Gly Ile Cys Gln Val Leu Ala His Met Trp Ile Glu Ser Glu Ile
            420                 425                 430

Met Ala Gly Ser Ser Asn Ala Ala Ser Thr Ser Ser Ser Ser Ser
        435                 440                 445

Ser Ser Ile Ser Ser Lys Lys Gly Gly Arg Ser Gln Phe Glu Arg Lys
    450                 455                 460

Leu Gly Asp Phe Phe Lys His Gln Ile Glu Ser Asp Thr Ser Val Ala
465                 470                 475                 480

Tyr Gly Asn Gly Phe Arg Ser Gly Asn Gln Ala Val Leu Gln Tyr Gly
                485                 490                 495

Leu Lys Arg Thr Leu Glu His Ile Trp Leu Thr Gly Thr Trp Pro Phe
            500                 505                 510

<210> SEQ ID NO 55
<211> LENGTH: 491
<212> TYPE: PRT
<213> ORGANISM: Brachypodium distachyon

<400> SEQUENCE: 55

Met Gly Trp Leu Thr Lys Phe Phe Arg Gly Ser Thr His Asn Ile Ser
1               5                   10                  15

Glu Gly Gln Asp Gln Ser Lys Pro Ala Glu Glu Thr Val Trp Asn Glu
            20                  25                  30

Pro Ser Ser Ser Thr Ala Val Asn Tyr Ala Leu Ser Glu Phe Asp Asn
        35                  40                  45

Glu Asp Ile Asp Arg Ala Ile Ala Leu Ser Leu Ser Glu Glu Glu Gln
    50                  55                  60

Arg Lys Ser Lys Gly Thr Gly Lys Asp Gln His Leu Asp Glu Asp Glu
65                  70                  75                  80

Gln Leu Ala Arg Ala Ile Gln Glu Ser Leu Asn Val Glu Ser Pro Pro
                85                  90                  95

Arg Ala Arg Glu Lys Ser Ser His Pro Arg Ala Arg Glu Asn Gly Ser
            100                 105                 110

Ala Asn Gly Gly Asn Ser Tyr Gln Leu Pro Leu Met Phe Ser Ser Gly
        115                 120                 125

Phe Arg Thr Cys Ala Gly Cys His Ser Glu Ile Gly His Gly Arg Phe
    130                 135                 140

Leu Ser Cys Met Gly Ala Val Trp His Pro Glu Cys Phe Cys Cys His
145                 150                 155                 160

Gly Cys Ser Gln Pro Ile Tyr Asp Tyr Glu Phe Ser Met Ser Gly Asn
            165                 170                 175

His Pro Tyr His Lys Thr Cys Tyr Lys Glu Arg Phe His Pro Lys Cys
        180                 185                 190

Asp Val Cys Gln Gln Phe Ile Pro Thr Asn Thr Asn Gly Leu Ile Glu
    195                 200                 205

Tyr Arg Ala His Pro Phe Trp Leu Gln Lys Tyr Cys Pro Ser His Glu
210                 215                 220

Val Asp Gly Thr Pro Arg Cys Cys Ser Cys Glu Arg Met Glu Pro Arg
225                 230                 235                 240

Glu Ser Arg Tyr Val Leu Leu Asp Asp Gly Arg Lys Leu Cys Leu Glu
            245                 250                 255

Cys Leu Asp Ser Ala Val Met Asp Thr Thr Glu Cys Gln Pro Leu Tyr
        260                 265                 270

Leu Glu Ile Gln Glu Phe Tyr Glu Gly Leu Asn Met Lys Val Glu Gln
    275                 280                 285

Gln Val Pro Leu Leu Val Glu Arg Gln Ala Leu Asn Glu Ala Met
290                 295                 300

Glu Gly Glu Lys Thr Gly His His Leu Pro Glu Thr Arg Gly Leu
305                 310                 315                 320

Cys Leu Ser Glu Glu Gln Thr Val Ser Thr Ile Leu Arg Arg Pro Arg
            325                 330                 335

Met Ala Gly Asn Lys Ile Met Glu Met Arg Thr Glu Pro Tyr Arg Leu
        340                 345                 350

Thr Arg Arg Cys Glu Val Thr Ala Ile Leu Ile Leu Tyr Gly Leu Pro
    355                 360                 365

Arg Leu Leu Thr Gly Ser Ile Leu Ala His Glu Met Met His Ala Trp
370                 375                 380

Leu Arg Leu Lys Gly Tyr Arg Thr Leu Ser Pro Asp Ile Glu Glu Gly
385                 390                 395                 400

Ile Cys Gln Val Leu Ala His Met Trp Ile Glu Ser Glu Ile Thr Ala
            405                 410                 415

Gly Ser Gly Ser Asn Ala Ala Ser Thr Ser Ser Ser Thr Ser Ser
        420                 425                 430

Lys Lys Gly Gly Arg Ser Gln Phe Glu Arg Lys Leu Gly Asp Phe Phe
    435                 440                 445

Lys His Gln Ile Glu Ser Asp Thr Ser Val Ala Tyr Gly Asp Gly Phe
450                 455                 460

Arg Ala Gly Asn Gln Ala Val Leu Gln Tyr Gly Leu Lys Arg Thr Leu
465                 470                 475                 480

Glu His Ile Arg Leu Thr Gly Thr Leu Pro Phe
            485                 490

<210> SEQ ID NO 56
<211> LENGTH: 486
<212> TYPE: PRT
<213> ORGANISM: Sorghum bicolor

<400> SEQUENCE: 56

Met Gly Trp Leu Thr Lys Phe Phe Arg Gly Ser Thr His Asn Ile Ser
1               5                   10                  15

Glu Gly Gln Tyr His Ser Arg Pro Ala Glu Asp Thr Ala Trp Asn Glu

```
                20                  25                  30
Pro Ser Ser Ser Pro Val Val Thr Asp Ile Phe Ser Glu Phe Asn Asn
            35                  40                  45
Glu Asp Ile Asp Arg Ala Ile Ala Leu Ser Leu Ser Glu Glu Glu Gln
        50                  55                  60
Arg Lys Ala Lys Thr Ile Asp Lys Asp Met His Leu Glu Glu Asp Glu
65                  70                  75                  80
Gln Leu Ala Arg Ala Ile Gln Glu Ser Leu Asn Val Glu Ser Pro Pro
                85                  90                  95
Pro Ser Arg Glu Asn Gly Ser Ala Asn Gly Gly Asn Ala Tyr His Pro
            100                 105                 110
Leu Pro Phe Met Phe Ser Ser Gly Phe Arg Ala Cys Ala Gly Cys His
        115                 120                 125
Arg Glu Ile Gly His Gly Arg Phe Leu Ser Cys Met Gly Ala Val Trp
    130                 135                 140
His Pro Glu Cys Phe Arg Cys His Ala Cys Ser Gln Pro Ile Tyr Asp
145                 150                 155                 160
Tyr Glu Phe Ser Met Ser Gly Asn His Pro Tyr His Lys Thr Cys Tyr
                165                 170                 175
Lys Glu Gln Phe His Pro Lys Cys Asp Val Cys Lys Gln Phe Ile Pro
            180                 185                 190
Thr Asn Met Asn Gly Leu Ile Glu Tyr Arg Ala His Pro Phe Trp Leu
        195                 200                 205
Gln Lys Tyr Cys Pro Ser His Glu Val Asp Gly Thr Pro Arg Cys Cys
    210                 215                 220
Ser Cys Glu Arg Met Glu Pro Arg Glu Ser Arg Tyr Val Leu Leu Asp
225                 230                 235                 240
Asp Gly Arg Lys Leu Cys Leu Glu Cys Leu Asp Ser Ala Val Met Asp
                245                 250                 255
Thr Asn Glu Cys Gln Pro Leu Tyr Leu Glu Ile Gln Glu Phe Tyr Glu
            260                 265                 270
Gly Leu Asn Met Lys Val Glu Gln Gln Val Pro Leu Leu Leu Val Glu
        275                 280                 285
Arg Gln Ala Leu Asn Glu Ala Met Glu Gly Glu Lys Ala Gly His His
    290                 295                 300
His Leu Pro Glu Thr Arg Gly Leu Cys Leu Ser Glu Glu Gln Thr Val
305                 310                 315                 320
Ser Thr Ile Leu Arg Arg Pro Arg Met Ala Gly Asn Lys Ile Met Gly
                325                 330                 335
Met Ile Thr Glu Pro Tyr Arg Leu Thr Arg Arg Cys Glu Val Thr Ala
            340                 345                 350
Ile Leu Ile Leu Tyr Gly Leu Pro Arg Leu Leu Thr Gly Ser Ile Leu
        355                 360                 365
Ala His Glu Met Met His Ala Trp Leu Arg Leu Lys Gly Tyr Arg Thr
    370                 375                 380
Leu Ser Pro Asp Val Glu Glu Gly Ile Cys Gln Val Leu Ala His Leu
385                 390                 395                 400
Trp Ile Glu Ser Glu Ile Met Ala Gly Ser Gly Ser Gly Ala Ala Ser
                405                 410                 415
Ser Ser Ser Gly Ser Ser Ser Met Ser Ser Lys Lys Ala Gly Arg
            420                 425                 430
Ser Gln Phe Glu His Lys Leu Gly Asp Phe Phe Lys His Gln Ile Glu
        435                 440                 445
```

```
Thr Asp Thr Ser Met Ala Tyr Gly Glu Gly Phe Arg Ala Gly Asn Arg
    450                 455                 460

Ala Val Leu Gln Tyr Gly Leu Lys Arg Thr Leu Glu His Ile Arg Leu
465                 470                 475                 480

Thr Gly Thr Phe Pro Phe
                485

<210> SEQ ID NO 57
<211> LENGTH: 508
<212> TYPE: PRT
<213> ORGANISM: Zea mays

<400> SEQUENCE: 57

Met Gly Trp Leu Thr Lys Phe Phe Arg Gly Ser Thr His Asn Ile Ser
1               5                   10                  15

Glu Glu Gln Tyr His Ser Arg Pro Ala Glu Asp Thr Ala Trp Asn Glu
            20                  25                  30

Pro Ser Ser Ser Pro Val Val Thr Asp Ile Leu Ser Glu Phe Asn Asn
        35                  40                  45

Glu Asp Ile Asp Arg Ala Ile Ala Leu Ser Leu Ser Glu Glu Glu Gln
50                  55                  60

Arg Lys Glu Lys Ala Ile Asp Lys Asp Met His Leu Glu Glu Asp Glu
65                  70                  75                  80

Gln Leu Ala Arg Ala Ile Gln Glu Ser Leu Asn Val Glu Ser Pro Pro
                85                  90                  95

Arg Arg Asn Gly Ser Ala Asn Gly Gly Thr Met Tyr His Pro Pro Arg
            100                 105                 110

Glu Thr Gly Asn Ala Tyr Gln Pro Pro Arg Glu Asn Gly Ser Ala Asn
        115                 120                 125

Gly Gly Asn Ala Tyr His Pro Leu Pro Phe Met Phe Ser Ser Gly Phe
130                 135                 140

Arg Ala Cys Ala Gly Cys His Arg Glu Ile Gly His Gly Arg Phe Leu
145                 150                 155                 160

Ser Cys Met Gly Ala Val Trp His Pro Glu Cys Phe Arg Cys His Ala
                165                 170                 175

Cys Ser Gln Pro Ile Tyr Asp Tyr Glu Phe Ser Met Ser Gly Asn His
            180                 185                 190

Pro Tyr His Lys Thr Cys Tyr Lys Glu Gln Phe His Pro Lys Cys Asp
        195                 200                 205

Val Cys Lys Gln Phe Ile Pro Thr Asn Met Asn Gly Leu Ile Glu Tyr
210                 215                 220

Arg Ala His Pro Phe Trp Val Gln Lys Tyr Cys Pro Ser His Glu Met
225                 230                 235                 240

Asp Gly Thr Pro Arg Cys Cys Ser Cys Glu Arg Met Glu Pro Arg Glu
                245                 250                 255

Ser Lys Tyr Val Leu Leu Asp Asp Gly Arg Lys Leu Cys Leu Glu Cys
            260                 265                 270

Leu Asp Ser Ala Val Met Asp Thr Asn Asp Cys Gln Pro Leu Tyr Leu
        275                 280                 285

Glu Ile Gln Glu Phe Tyr Glu Gly Leu Asn Met Lys Val Glu Gln Gln
290                 295                 300

Val Pro Leu Leu Leu Val Glu Arg Gln Ala Leu Asn Glu Ala Met Glu
305                 310                 315                 320

Gly Glu Lys Ala Gly His His His Leu Pro Glu Thr Arg Gly Leu Cys
```

```
                    325                 330                 335
Leu Ser Glu Glu Gln Thr Val Ser Thr Ile Leu Arg Pro Arg Met Ala
            340                 345                 350
Gly Asn Lys Ile Met Gly Met Ile Thr Glu Pro Tyr Arg Leu Thr Arg
            355                 360                 365
Arg Cys Glu Val Thr Ala Ile Leu Ile Leu Tyr Gly Leu Pro Arg Leu
            370                 375                 380
Leu Thr Gly Ser Ile Leu Ala His Glu Met Met His Ala Trp Leu Arg
385                 390                 395                 400
Leu Lys Gly Tyr Arg Thr Leu Ser Pro Asp Val Glu Glu Gly Ile Cys
                405                 410                 415
Gln Val Leu Ala His Met Trp Ile Glu Ser Glu Ile Met Ala Gly Ser
            420                 425                 430
Gly Ser Ser Ala Ala Ser Ser Ser Gly Ser Ser Ser Ser Thr Ser
            435                 440                 445
Ser Lys Lys Gly Gly Arg Ser Gln Phe Glu His Arg Leu Gly Asp Phe
    450                 455                 460
Phe Lys His Gln Ile Glu Thr Asp Thr Ser Met Ala Tyr Gly Asp Gly
465                 470                 475                 480
Phe Arg Thr Gly Asn Arg Ala Val Leu His Tyr Gly Leu Lys Arg Thr
                485                 490                 495
Leu Glu His Ile Arg Leu Thr Gly Thr Phe Pro Phe
                500                 505

<210> SEQ ID NO 58
<211> LENGTH: 553
<212> TYPE: PRT
<213> ORGANISM: Arabidopsis thaliana

<400> SEQUENCE: 58

Met Gly Trp Leu Thr Lys Ile Leu Lys Gly Ser Ser His Lys Phe Ser
1               5                   10                  15
Asp Gly Gln Cys Asn Gly Arg Tyr Arg Glu Asp Arg Asn Leu Glu Gly
            20                  25                  30
Pro Arg Tyr Ser Ala Glu Gly Ser Asp Phe Asp Lys Glu Glu Ile Glu
        35                  40                  45
Cys Ala Ile Ala Leu Ser Leu Ser Glu Gln Glu His Val Ile Pro Gln
    50                  55                  60
Asp Asp Lys Gly Lys Lys Ile Ile Glu Tyr Lys Ser Glu Thr Glu Glu
65                  70                  75                  80
Asp Asp Asp Asp Glu Asp Glu Asp Glu Tyr Met Arg Ala Gln
                85                  90                  95
Leu Glu Ala Ala Glu Glu Glu Arg Arg Val Ala Gln Ala Gln Ile
            100                 105                 110
Glu Glu Glu Glu Lys Arg Arg Ala Glu Ala Gln Leu Glu Glu Thr Glu
        115                 120                 125
Lys Leu Leu Ala Lys Ala Arg Leu Glu Glu Glu Met Arg Arg Ser
    130                 135                 140
Lys Ala Gln Leu Glu Glu Asp Glu Leu Leu Ala Lys Ala Leu Gln Glu
145                 150                 155                 160
Ser Met Asn Val Gly Ser Pro Pro Arg Tyr Asp Pro Gly Asn Ile Leu
                165                 170                 175
Gln Pro Tyr Pro Phe Leu Ile Pro Ser Ser His Arg Ile Cys Val Gly
            180                 185                 190
```

```
Cys Gln Ala Glu Ile Gly His Gly Arg Phe Leu Ser Cys Met Gly Gly
            195                 200                 205

Val Trp His Pro Glu Cys Phe Cys Cys Asn Ala Cys Asp Lys Pro Ile
    210                 215                 220

Ile Asp Tyr Glu Phe Ser Met Ser Gly Asn Arg Pro Tyr His Lys Leu
225                 230                 235                 240

Cys Tyr Lys Glu Gln His His Pro Lys Cys Asp Val Cys His Asn Phe
                245                 250                 255

Ile Pro Thr Asn Pro Ala Gly Leu Ile Glu Tyr Arg Ala His Pro Phe
                260                 265                 270

Trp Met Gln Lys Tyr Cys Pro Ser His Glu Arg Asp Gly Thr Pro Arg
            275                 280                 285

Cys Cys Ser Cys Glu Arg Met Glu Pro Lys Asp Thr Lys Tyr Leu Ile
    290                 295                 300

Leu Asp Asp Gly Arg Lys Leu Cys Leu Glu Cys Leu Asp Ser Ala Ile
305                 310                 315                 320

Met Asp Thr His Glu Cys Gln Pro Leu Tyr Leu Glu Ile Arg Glu Phe
                325                 330                 335

Tyr Glu Gly Leu His Met Lys Val Glu Gln Gln Ile Pro Met Leu Leu
                340                 345                 350

Val Glu Arg Ser Ala Leu Asn Glu Ala Met Glu Gly Glu Lys His Gly
            355                 360                 365

His His His Leu Pro Glu Thr Arg Gly Leu Cys Leu Ser Glu Glu Gln
    370                 375                 380

Thr Val Thr Thr Val Leu Arg Arg Pro Arg Ile Gly Ala Gly Tyr Lys
385                 390                 395                 400

Leu Ile Asp Met Ile Thr Glu Pro Cys Arg Leu Ile Arg Arg Cys Glu
                405                 410                 415

Val Thr Ala Ile Leu Ile Leu Tyr Gly Leu Pro Arg Leu Leu Thr Gly
                420                 425                 430

Ser Ile Leu Ala His Glu Met Met His Ala Trp Leu Arg Leu Asn Gly
            435                 440                 445

Tyr Pro Asn Leu Arg Pro Glu Val Glu Glu Gly Ile Cys Gln Val Leu
    450                 455                 460

Ala His Met Trp Leu Glu Ser Glu Thr Tyr Ala Gly Ser Thr Leu Val
465                 470                 475                 480

Asp Ile Ala Ser Ser Ser Ser Ala Val Ser Ala Ser Ser Lys
                485                 490                 495

Lys Gly Glu Arg Ser Asp Phe Glu Lys Lys Leu Gly Glu Phe Phe Lys
            500                 505                 510

His Gln Ile Glu Ser Asp Ser Ser Ala Tyr Gly Asp Gly Phe Arg
    515                 520                 525

Gln Gly Asn Gln Ala Val Leu Lys His Gly Leu Arg Arg Thr Leu Asp
530                 535                 540

His Ile Arg Leu Thr Gly Thr Phe Pro
545                 550

<210> SEQ ID NO 59
<211> LENGTH: 528
<212> TYPE: PRT
<213> ORGANISM: Arabidopsis thaliana

<400> SEQUENCE: 59

Met Asp Ser Ser Ser Ser Ser Ser Ser Pro Ser Ser Tyr
1               5                   10                  15
```

Gly Val Ala Arg Val Ser His Ile Ser Asn Pro Cys Ile Phe Gly Glu
            20                  25                  30
Val Gly Ser Ser Ser Ser Thr Tyr Arg Asp Lys Lys Trp Lys Leu
        35                  40                  45
Met Lys Trp Val Ser Lys Leu Phe Lys Ser Gly Ser Asn Gly Gly Gly
50                  55                  60
Ser Gly Ala His Thr Asn His His Pro Pro Gln Phe Gln Glu Asp Glu
65                  70                  75                  80
Asn Met Val Phe Pro Leu Pro Pro Ser Ser Leu Asp Asp Arg Ser Arg
                85                  90                  95
Gly Ala Arg Asp Lys Glu Glu Leu Asp Arg Ser Ile Ser Leu Ser Leu
            100                 105                 110
Ala Asp Asn Thr Lys Arg Pro His Gly Tyr Gly Trp Ser Met Asp Asn
            115                 120                 125
Asn Arg Asp Phe Pro Arg Pro Phe His Gly Leu Asn Pro Ser Ser
130                 135                 140
Phe Ile Pro Pro Tyr Glu Pro Ser Tyr Gln Tyr Arg Arg Arg Gln Arg
145                 150                 155                 160
Ile Cys Gly Gly Cys Asn Ser Asp Ile Gly Ser Gly Asn Tyr Leu Gly
                165                 170                 175
Cys Met Gly Thr Phe Phe His Pro Glu Cys Phe Arg Cys His Ser Cys
            180                 185                 190
Gly Tyr Ala Ile Thr Glu His Glu Phe Ser Leu Ser Gly Thr Lys Pro
            195                 200                 205
Tyr His Lys Leu Cys Phe Lys Glu Leu Thr His Pro Lys Cys Glu Val
            210                 215                 220
Cys His His Phe Ile Pro Thr Asn Asp Ala Gly Leu Ile Glu Tyr Arg
225                 230                 235                 240
Cys His Pro Phe Trp Asn Gln Lys Tyr Cys Pro Ser His Glu Tyr Asp
                245                 250                 255
Lys Thr Ala Arg Cys Cys Ser Cys Glu Arg Leu Glu Ser Trp Asp Val
            260                 265                 270
Arg Tyr Tyr Thr Leu Glu Asp Gly Arg Ser Leu Cys Leu Glu Cys Met
            275                 280                 285
Glu Thr Ala Ile Thr Asp Thr Gly Glu Cys Gln Pro Leu Tyr His Ala
            290                 295                 300
Ile Arg Asp Tyr Tyr Glu Gly Met Tyr Met Lys Leu Asp Gln Gln Ile
305                 310                 315                 320
Pro Met Leu Leu Val Gln Arg Glu Ala Leu Asn Asp Ala Ile Val Gly
                325                 330                 335
Glu Lys Asn Gly Tyr His His Met Pro Glu Thr Arg Gly Leu Cys Leu
            340                 345                 350
Ser Glu Glu Gln Thr Val Thr Ser Val Leu Arg Arg Pro Arg Leu Gly
            355                 360                 365
Ala His Arg Leu Val Gly Met Arg Thr Gln Pro Gln Arg Leu Thr Arg
            370                 375                 380
Lys Cys Glu Val Thr Ala Ile Leu Val Leu Tyr Gly Leu Pro Arg Leu
385                 390                 395                 400
Leu Thr Gly Ala Ile Leu Ala His Glu Leu Met His Gly Trp Leu Arg
                405                 410                 415
Leu Asn Gly Phe Arg Asn Leu Asn Pro Glu Val Glu Glu Gly Ile Cys
            420                 425                 430

Gln Val Leu Ser Tyr Met Trp Leu Glu Ser Glu Val Leu Ser Asp Pro
            435                 440                 445

Ser Thr Arg Asn Leu Pro Ser Thr Ser Ser Val Ala Thr Ser Ser Ser
450                 455                 460

Ser Ser Phe Ser Asn Lys Lys Gly Gly Lys Ser Asn Val Glu Lys Lys
465                 470                 475                 480

Leu Gly Glu Phe Phe Lys His Gln Ile Ala His Asp Ala Ser Pro Ala
                485                 490                 495

Tyr Gly Gly Gly Phe Arg Ala Ala Asn Ala Ala Ala Cys Lys Tyr Gly
            500                 505                 510

Leu Arg Arg Thr Leu Asp His Ile Arg Leu Thr Gly Thr Phe Pro Leu
            515                 520                 525

<210> SEQ ID NO 60
<211> LENGTH: 1613
<212> TYPE: PRT
<213> ORGANISM: Arabidopsis thaliana

<400> SEQUENCE: 60

Met Glu Pro Pro Ala Ala Arg Val Thr Pro Ser Ile Lys Ala Asp Cys
1               5                   10                  15

Ser His Ser Val Asn Ile Ile Cys Glu Glu Thr Val Leu His Ser Leu
                20                  25                  30

Val Ser His Leu Ser Ala Ala Leu Arg Arg Glu Gly Ile Ser Val Phe
            35                  40                  45

Val Asp Ala Cys Gly Leu Gln Glu Thr Lys Phe Phe Ser Ile Lys Gln
        50                  55                  60

Asn Gln Pro Leu Thr Asp Gly Ala Arg Val Leu Val Val Ile Ser
65                  70                  75                  80

Asp Glu Val Glu Phe Tyr Asp Pro Trp Phe Pro Lys Phe Leu Lys Val
                85                  90                  95

Ile Gln Gly Trp Gln Asn Asn Gly His Val Val Val Pro Val Phe Tyr
            100                 105                 110

Gly Val Asp Ser Leu Thr Arg Val Tyr Gly Trp Ala Asn Ser Trp Leu
        115                 120                 125

Glu Ala Glu Lys Leu Thr Ser His Gln Ser Lys Ile Leu Ser Asn Asn
130                 135                 140

Val Leu Thr Asp Ser Glu Leu Val Glu Ile Val Arg Asp Val Tyr
145                 150                 155                 160

Gly Lys Leu Tyr Pro Ala Glu Arg Val Gly Ile Tyr Ala Arg Leu Leu
                165                 170                 175

Glu Ile Glu Lys Leu Leu Tyr Lys Gln His Arg Asp Ile Arg Ser Ile
            180                 185                 190

Gly Ile Trp Gly Met Pro Gly Ile Gly Lys Thr Thr Leu Ala Lys Ala
        195                 200                 205

Val Phe Asn His Met Ser Thr Asp Tyr Asp Ala Ser Cys Phe Ile Glu
210                 215                 220

Asn Phe Asp Glu Ala Phe His Lys Glu Gly Leu His Arg Leu Leu Lys
225                 230                 235                 240

Glu Arg Ile Gly Lys Ile Leu Lys Asp Glu Phe Asp Ile Glu Ser Ser
                245                 250                 255

Tyr Ile Met Arg Pro Thr Leu His Arg Asp Lys Leu Tyr Asp Lys Arg
            260                 265                 270

Ile Leu Val Val Leu Asp Asp Val Arg Asp Ser Leu Ala Ala Glu Ser
        275                 280                 285

```
Phe Leu Lys Arg Leu Asp Trp Phe Gly Ser Gly Ser Leu Ile Ile Ile
    290                 295                 300

Thr Ser Val Asp Lys Gln Val Phe Ala Phe Cys Gln Ile Asn Gln Ile
305                 310                 315                 320

Tyr Thr Val Gln Gly Leu Asn Val His Glu Ala Leu Gln Leu Phe Ser
                325                 330                 335

Gln Ser Val Phe Gly Ile Asn Glu Pro Glu Gln Asn Asp Arg Lys Leu
                340                 345                 350

Ser Met Lys Val Ile Asp Tyr Val Asn Gly Asn Pro Leu Ala Leu Ser
            355                 360                 365

Ile Tyr Gly Arg Glu Leu Met Gly Lys Lys Ser Glu Met Glu Thr Ala
    370                 375                 380

Phe Phe Glu Leu Lys His Cys Pro Pro Leu Lys Ile Gln Asp Val Leu
385                 390                 395                 400

Lys Asn Ala Tyr Ser Ala Leu Ser Asp Asn Glu Lys Asn Ile Val Leu
                405                 410                 415

Asp Ile Ala Phe Phe Lys Gly Glu Thr Val Asn Tyr Val Met Gln
                420                 425                 430

Leu Leu Glu Glu Ser His Tyr Phe Pro Arg Leu Ala Ile Asp Val Leu
            435                 440                 445

Val Asp Lys Cys Val Leu Thr Ile Ser Glu Asn Thr Val Gln Met Asn
    450                 455                 460

Asn Leu Ile Gln Asp Thr Cys Gln Glu Ile Phe Asn Gly Glu Ile Glu
465                 470                 475                 480

Thr Cys Thr Arg Met Trp Glu Pro Ser Arg Ile Arg Tyr Leu Leu Glu
                485                 490                 495

Tyr Asp Glu Leu Glu Gly Ser Gly Glu Thr Lys Ala Met Pro Lys Ser
            500                 505                 510

Gly Leu Val Ala Glu His Ile Glu Ser Ile Phe Leu Asp Thr Ser Asn
            515                 520                 525

Val Lys Phe Asp Val Lys His Asp Ala Phe Lys Asn Met Phe Asn Leu
    530                 535                 540

Lys Phe Leu Lys Ile Tyr Asn Ser Cys Ser Lys Tyr Ile Ser Gly Leu
545                 550                 555                 560

Asn Phe Pro Lys Gly Leu Asp Ser Leu Pro Tyr Glu Leu Arg Leu Leu
                565                 570                 575

His Trp Glu Asn Tyr Pro Leu Gln Ser Leu Pro Gln Asp Phe Asp Phe
            580                 585                 590

Gly His Leu Val Lys Leu Ser Met Pro Tyr Ser Gln Leu His Lys Leu
    595                 600                 605

Gly Thr Arg Val Lys Asp Leu Val Met Leu Lys Arg Leu Ile Leu Ser
    610                 615                 620

His Ser Leu Gln Leu Val Glu Cys Asp Ile Leu Ile Tyr Ala Gln Asn
625                 630                 635                 640

Ile Glu Leu Ile Asp Leu Gln Gly Cys Thr Gly Leu Gln Arg Phe Pro
                645                 650                 655

Asp Thr Ser Gln Leu Gln Asn Leu Arg Val Val Asn Leu Ser Gly Cys
                660                 665                 670

Thr Glu Ile Lys Cys Phe Ser Gly Val Pro Pro Asn Ile Glu Glu Leu
            675                 680                 685

His Leu Gln Gly Thr Arg Ile Arg Glu Ile Pro Ile Phe Asn Ala Thr
    690                 695                 700
```

```
His Pro Pro Lys Val Lys Leu Asp Arg Lys Lys Leu Trp Asn Leu Leu
705                 710                 715                 720

Glu Asn Phe Ser Asp Val Glu His Ile Asp Leu Glu Cys Val Thr Asn
            725                 730                 735

Leu Ala Thr Val Thr Ser Asn Asn His Val Met Gly Lys Leu Val Cys
        740                 745                 750

Leu Asn Met Lys Tyr Cys Ser Asn Leu Arg Gly Leu Pro Asp Met Val
            755                 760                 765

Ser Leu Glu Ser Leu Lys Val Leu Tyr Leu Ser Gly Cys Ser Glu Leu
    770                 775                 780

Glu Lys Ile Met Gly Phe Pro Arg Asn Leu Lys Lys Leu Tyr Val Gly
785                 790                 795                 800

Gly Thr Ala Ile Arg Glu Leu Pro Gln Leu Pro Asn Ser Leu Glu Phe
                805                 810                 815

Leu Asn Ala His Gly Cys Lys His Leu Lys Ser Ile Asn Leu Asp Phe
            820                 825                 830

Glu Gln Leu Pro Arg His Phe Ile Phe Ser Asn Cys Tyr Arg Phe Ser
    835                 840                 845

Ser Gln Val Ile Ala Glu Phe Val Lys Gly Leu Val Ala Ser Leu
850                 855                 860

Ala Arg Ala Lys Gln Glu Glu Leu Ile Lys Ala Pro Glu Val Ile Ile
865                 870                 875                 880

Cys Ile Pro Met Asp Thr Arg Gln Arg Ser Phe Arg Leu Gln Ala
                885                 890                 895

Gly Arg Asn Ala Met Thr Asp Leu Val Pro Trp Met Gln Lys Pro Ile
                900                 905                 910

Ser Gly Phe Ser Met Ser Val Val Ser Phe Gln Asp Asp Tyr His
            915                 920                 925

Asn Asp Val Gly Leu Arg Ile Arg Cys Val Gly Thr Trp Lys Thr Trp
        930                 935                 940

Asn Asn Gln Pro Asp Arg Ile Val Glu Arg Phe Phe Gln Cys Trp Ala
945                 950                 955                 960

Pro Thr Glu Ala Pro Lys Val Val Ala Asp His Ile Phe Val Leu Tyr
                965                 970                 975

Asp Thr Lys Met His Pro Ser Asp Ser Glu Glu Asn His Ile Ser Met
            980                 985                 990

Trp Ala His Glu Val Lys Phe Glu Phe His Thr Val Ser Gly Glu Asn
                995                 1000                1005

Asn Pro Leu Gly Ala Ser Cys Lys Val Thr Glu Cys Gly Val Glu
    1010                1015                1020

Val Ile Thr Ala Ala Thr Gly Asp Thr Ser Val Ser Gly Ile Ile
    1025                1030                1035

Arg Glu Ser Glu Thr Ile Thr Ile Glu Lys Glu Asp Thr Ile
    1040                1045                1050

Ile Asp Glu Glu Asp Thr Pro Leu Leu Ser Arg Lys Pro Glu Glu
    1055                1060                1065

Thr Asn Arg Ser Arg Ser Ser Glu Leu Gln Lys Leu Ser Ser
    1070                1075                1080

Thr Ser Ser Lys Val Arg Ser Lys Gly Asn Val Phe Trp Lys Trp
    1085                1090                1095

Leu Gly Cys Phe Pro Leu Gln Pro Lys Asn Leu Arg Ser Arg Ser
    1100                1105                1110

Arg Arg Thr Thr Ala Leu Glu Glu Ala Leu Glu Glu Ala Leu Lys
```

```
                  1115                1120                1125
Glu Arg Glu Lys Leu Glu Asp Thr Arg Glu Leu Gln Ile Ala Leu
            1130                1135                1140
Ile Glu Ser Lys Lys Ile Lys Lys Ile Lys Gln Ala Asp Glu Arg
            1145                1150                1155
Asp Gln Ile Lys His Ala Asp Glu Arg Glu Gln Arg Lys His Ser
            1160                1165                1170
Lys Asp His Glu Glu Glu Ile Glu Ser Asn Glu Lys Glu Glu
            1175                1180                1185
Arg Arg His Ser Lys Asp Tyr Val Ile Glu Glu Leu Val Leu Lys
            1190                1195                1200
Gly Lys Gly Lys Arg Lys Gln Leu Asp Asp Lys Ala Asp Glu
            1205                1210                1215
Lys Glu Gln Ile Lys His Ser Lys Asp His Val Glu Glu Val
            1220                1225                1230
Asn Pro Pro Leu Ser Lys Cys Lys Asp Cys Lys Ser Ala Ile Glu
            1235                1240                1245
Asp Gly Ile Ser Ile Asn Ala Tyr Gly Ser Val Trp His Pro Gln
            1250                1255                1260
Cys Phe Cys Cys Leu Arg Cys Arg Glu Pro Ile Ala Met Asn Glu
            1265                1270                1275
Ile Ser Asp Leu Arg Gly Met Tyr His Lys Pro Cys Tyr Lys Glu
            1280                1285                1290
Leu Arg His Pro Asn Cys Tyr Val Cys Glu Lys Lys Ile Pro Arg
            1295                1300                1305
Thr Ala Glu Gly Leu Lys Tyr His Glu His Pro Phe Trp Met Glu
            1310                1315                1320
Thr Tyr Cys Pro Ser His Asp Gly Asp Gly Thr Pro Lys Cys Cys
            1325                1330                1335
Ser Cys Glu Arg Leu Glu His Cys Gly Thr Gln Tyr Val Met Leu
            1340                1345                1350
Ala Asp Phe Arg Trp Leu Cys Arg Glu Cys Met Asp Ser Ala Ile
            1355                1360                1365
Met Asp Ser Asp Glu Cys Gln Pro Leu His Phe Glu Ile Arg Glu
            1370                1375                1380
Phe Phe Glu Gly Leu His Met Lys Ile Glu Glu Phe Pro Val
            1385                1390                1395
Tyr Leu Val Glu Lys Asn Ala Leu Asn Lys Ala Glu Lys Glu Glu
            1400                1405                1410
Lys Ile Asp Lys Gln Gly Asp Gln Cys Leu Met Val Val Arg Gly
            1415                1420                1425
Ile Cys Leu Ser Glu Glu Gln Ile Val Thr Ser Val Ser Gln Gly
            1430                1435                1440
Val Arg Arg Met Leu Asn Lys Gln Ile Leu Asp Thr Val Thr Glu
            1445                1450                1455
Ser Gln Arg Val Val Arg Lys Cys Glu Val Thr Ala Ile Leu Ile
            1460                1465                1470
Leu Tyr Gly Leu Pro Arg Leu Leu Thr Gly Tyr Ile Leu Ala His
            1475                1480                1485
Glu Met Met His Ala Tyr Leu Arg Leu Asn Gly Tyr Arg Asn Leu
            1490                1495                1500
Asn Met Val Leu Glu Glu Gly Leu Cys Gln Val Leu Gly Tyr Met
            1505                1510                1515
```

Trp Leu Glu Cys Gln Thr Tyr Val Phe Asp Thr Ala Thr Ile Ala
1520                1525                1530

Ser Ser Ser Ser Ser Arg Thr Pro Leu Ser Thr Thr Thr Ser
1535                1540                1545

Lys Lys Val Asp Pro Ser Asp Phe Glu Lys Arg Leu Val Asn Phe
1550                1555                1560

Cys Lys His Gln Ile Glu Thr Asp Glu Ser Pro Phe Phe Gly Asp
1565                1570                1575

Gly Phe Arg Lys Val Asn Lys Met Met Ala Ser Asn Asn His Ser
1580                1585                1590

Leu Lys Asp Thr Leu Lys Glu Ile Ile Ser Ile Ser Lys Thr Pro
1595                1600                1605

Gln Tyr Ser Lys Leu
1610

<210> SEQ ID NO 61
<211> LENGTH: 450
<212> TYPE: PRT
<213> ORGANISM: Arabidopsis thaliana

<400> SEQUENCE: 61

Met Val Arg Arg Lys Arg Gln Glu Glu Asp Glu Lys Ile Glu Ile Glu
1               5                   10                  15

Arg Val Lys Glu Glu Ser Leu Lys Leu Ala Lys Gln Ala Glu Glu Lys
                20                  25                  30

Arg Arg Leu Glu Glu Ser Lys Glu Gln Gly Lys Arg Ile Gln Val Asp
            35                  40                  45

Asp Asp Gln Leu Ala Lys Thr Thr Ser Lys Asp Lys Gly Gln Ile Asn
        50                  55                  60

His Ser Lys Asp Val Val Glu Glu Asp Val Asn Pro Pro Pro Ser Ile
65                  70                  75                  80

Asp Gly Lys Ser Glu Ile Gly Asp Gly Thr Ser Val Asn Pro Arg Cys
                85                  90                  95

Leu Cys Cys Phe His Cys His Arg Pro Phe Val Met His Glu Ile Leu
            100                 105                 110

Lys Lys Gly Lys Phe His Ile Asp Cys Tyr Lys Glu Tyr Tyr Arg Asn
        115                 120                 125

Arg Asn Cys Tyr Val Cys Gln Gln Lys Ile Pro Val Asn Ala Glu Gly
    130                 135                 140

Ile Arg Lys Phe Ser Glu His Pro Phe Trp Lys Glu Lys Tyr Cys Pro
145                 150                 155                 160

Ile His Asp Glu Asp Gly Thr Ala Lys Cys Cys Ser Cys Glu Arg Leu
                165                 170                 175

Glu Pro Arg Gly Thr Asn Tyr Val Met Leu Gly Asp Phe Arg Trp Leu
            180                 185                 190

Cys Ile Glu Cys Met Gly Ser Ala Val Met Asp Thr Asn Glu Val Gln
        195                 200                 205

Pro Leu His Phe Glu Ile Arg Glu Phe Phe Glu Gly Leu Phe Leu Lys
    210                 215                 220

Val Asp Lys Glu Phe Ala Leu Leu Leu Val Glu Lys Gln Ala Leu Asn
225                 230                 235                 240

Lys Ala Glu Glu Glu Glu Lys Ile Asp Tyr His Arg Ala Ala Val Thr
                245                 250                 255

Arg Gly Leu Cys Met Ser Glu Glu Gln Ile Val Pro Ser Ile Ile Lys

```
                260                 265                 270
Gly Pro Arg Met Gly Pro Asp Asn Gln Leu Ile Thr Asp Ile Val Thr
                275                 280                 285

Glu Ser Gln Arg Val Ser Gly Phe Glu Val Thr Gly Ile Leu Ile Ile
                290                 295                 300

Tyr Gly Leu Pro Arg Leu Leu Thr Gly Tyr Ile Leu Ala His Glu Met
305                 310                 315                 320

Met His Ala Trp Leu Arg Leu Asn Gly Tyr Lys Asn Leu Lys Leu Glu
                325                 330                 335

Leu Glu Glu Gly Leu Cys Gln Ala Leu Gly Leu Arg Trp Leu Glu Ser
                340                 345                 350

Gln Thr Phe Ala Ser Thr Asp Ala Ala Ala Ala Ala Val Ala Ser
                355                 360                 365

Ser Ser Ser Phe Ser Ser Thr Ala Pro Ala Ala Ile Thr Ser
                370                 375                 380

Lys Lys Ser Asp Asp Trp Ser Ile Phe Glu Lys Lys Leu Val Glu Phe
385                 390                 395                 400

Cys Met Asn Gln Ile Lys Glu Asp Asp Ser Pro Val Tyr Gly Leu Gly
                405                 410                 415

Phe Lys Gln Val Tyr Glu Met Met Val Ser Asn Asn Tyr Asn Ile Lys
                420                 425                 430

Asp Thr Leu Lys Asp Ile Val Ser Ala Ser Asn Ala Thr Pro Asp Ser
                435                 440                 445

Thr Val
    450

<210> SEQ ID NO 62
<211> LENGTH: 702
<212> TYPE: PRT
<213> ORGANISM: Arabidopsis thaliana

<400> SEQUENCE: 62

Met Pro Ile Ser Asp Val Ala Ser Leu Val Gly Gly Ala Ala Leu Gly
1               5                   10                  15

Ala Pro Leu Ser Glu Ile Phe Lys Leu Val Ile Glu Glu Ala Lys Lys
                20                  25                  30

Val Lys Asp Phe Lys Pro Leu Ser Gln Asp Leu Ala Ser Thr Met Glu
            35                  40                  45

Arg Leu Val Pro Ile Phe Asn Glu Ile Asp Met Met Gln Gln Gly Ser
    50                  55                  60

Asn Arg Gly Thr Ser Glu Leu Lys Val Leu Thr Glu Thr Met Glu Arg
65                  70                  75                  80

Ala Gly Glu Met Val His Lys Cys Ser Arg Ile Gln Trp Tyr Ser Ile
                85                  90                  95

Ala Lys Lys Ala Leu Tyr Thr Arg Glu Ile Lys Ala Ile Asn Gln Asp
                100                 105                 110

Phe Leu Lys Phe Cys Gln Ile Glu Leu Gln Leu Ile Gln His Arg Asn
            115                 120                 125

Gln Leu Gln Tyr Met Arg Ser Met Gly Met Ala Ser Val Ser Thr Lys
    130                 135                 140

Ala Asp Leu Leu Ser Asp Ile Gly Asn Glu Phe Ser Lys Leu Cys Leu
145                 150                 155                 160

Val Ala Gln Pro Glu Val Val Thr Lys Phe Trp Leu Lys Arg Pro Leu
                165                 170                 175
```

```
Met Glu Leu Lys Lys Met Leu Phe Glu Asp Gly Val Val Val
            180                 185                 190

Val Ser Ala Pro Tyr Ala Leu Gly Lys Thr Thr Leu Val Thr Lys Leu
            195                 200                 205

Cys His Asp Ala Asp Val Lys Glu Lys Phe Lys Gln Ile Phe Phe Ile
            210                 215                 220

Ser Val Ser Lys Phe Pro Asn Val Arg Leu Ile Gly His Lys Leu Leu
225                 230                 235                 240

Glu His Ile Gly Cys Lys Ala Asn Glu Tyr Glu Asn Asp Leu Asp Ala
                245                 250                 255

Met Leu Tyr Ile Gln Gln Leu Leu Lys Gln Leu Gly Arg Asn Gly Ser
            260                 265                 270

Ile Leu Leu Val Leu Asp Asp Val Trp Ala Glu Glu Ser Leu Leu
            275                 280                 285

Gln Lys Phe Leu Ile Gln Leu Pro Asp Tyr Lys Ile Leu Val Thr Ser
            290                 295                 300

Arg Phe Glu Phe Thr Ser Phe Gly Pro Thr Phe His Leu Lys Pro Leu
305                 310                 315                 320

Ile Asp Asp Glu Val Glu Cys Arg Asp Glu Ile Glu Glu Asn Glu Lys
                325                 330                 335

Leu Pro Glu Val Asn Pro Leu Ser Met Cys Gly Gly Cys Asn Ser
            340                 345                 350

Ala Val Lys His Glu Glu Ser Val Asn Ile Leu Gly Val Leu Trp His
            355                 360                 365

Pro Gly Cys Phe Cys Arg Ser Cys Asp Lys Pro Ile Ala Ile His
            370                 375                 380

Glu Leu Glu Asn His Val Ser Asn Ser Arg Gly Lys Phe His Lys Ser
385                 390                 395                 400

Cys Tyr Glu Arg Tyr Cys Tyr Val Cys Lys Glu Lys Met Lys Thr
                405                 410                 415

Tyr Asn Ile His Pro Phe Trp Glu Glu Arg Tyr Cys Pro Val His Glu
            420                 425                 430

Ala Asp Gly Thr Pro Lys Cys Cys Ser Cys Glu Arg Leu Glu Pro Arg
            435                 440                 445

Gly Thr Lys Tyr Gly Lys Leu Ser Asp Gly Arg Trp Leu Cys Leu Glu
450                 455                 460

Cys Gly Lys Ser Ala Met Asp Ser Asp Glu Cys Gln Pro Leu Tyr Phe
465                 470                 475                 480

Asp Met Arg Asp Phe Phe Glu Ser Leu Asn Met Lys Ile Glu Lys Glu
                485                 490                 495

Phe Pro Leu Ile Leu Val Arg Lys Glu Leu Leu Asn Lys Lys Glu Glu
            500                 505                 510

Lys Ile Asp Asn His Tyr Glu Val Leu Ile Arg Ala Tyr Cys Met Ser
            515                 520                 525

Glu Gln Lys Ile Met Thr Tyr Val Ser Glu Pro Arg Thr Gly Gln
            530                 535                 540

Asn Lys Gln Leu Ile Asp Met Asp Thr Glu Pro Gln Gly Val Val His
545                 550                 555                 560

Glu Cys Lys Val Thr Ala Ile Leu Ile Leu Tyr Gly Leu Pro Arg Leu
                565                 570                 575

Leu Thr Gly Tyr Ile Leu Ala His Glu Met Met His Ala Trp Leu Arg
            580                 585                 590

Leu Asn Gly His Met Asn Leu Asn Asn Ile Leu Glu Glu Gly Ile Cys
```

```
                  595                 600                 605
Gln Val Leu Gly His Leu Trp Leu Glu Ser Gln Thr Tyr Ala Thr Ala
    610                 615                 620

Asp Thr Thr Ala Asp Ala Ala Ser Ala Ser Ser Ser Ser Arg Thr
625                 630                 635                 640

Pro Pro Ala Ala Ser Ala Ser Lys Lys Gly Glu Trp Ser Asp Phe Asp
                645                 650                 655

Lys Lys Leu Val Glu Phe Cys Lys Asn Gln Ile Glu Thr Asp Glu Ser
                660                 665                 670

Pro Val Tyr Gly Leu Gly Phe Arg Thr Val Asn Glu Met Val Thr Asn
                675                 680                 685

Ser Ser Leu Gln Glu Thr Leu Lys Glu Ile Leu Arg Arg Arg
                690                 695                 700

<210> SEQ ID NO 63
<211> LENGTH: 644
<212> TYPE: PRT
<213> ORGANISM: Arabidopsis thaliana

<400> SEQUENCE: 63

Met Ala Ser Asp Tyr Tyr Ser Ser Asp Asp Glu Gly Phe Gly Glu Lys
1               5                   10                  15

Val Gly Leu Ile Gly Glu Lys Asp Arg Phe Glu Ala Glu Thr Ile His
                20                  25                  30

Val Ile Glu Val Ser Gln His Glu Ala Asp Ile Gln Lys Ala Lys Gln
            35                  40                  45

Arg Ser Leu Ala Thr His Glu Ala Glu Lys Leu Asp Leu Ala Thr His
    50                  55                  60

Glu Ala Glu Gln Leu Asp Leu Ala Ile Gln Glu Phe Ser Arg Gln Glu
65                  70                  75                  80

Glu Glu Glu Glu Arg Arg Arg Thr Arg Glu Leu Glu Asn Asp Ala Gln
                85                  90                  95

Ile Ala Asn Val Leu Gln His Glu Glu Arg Glu Arg Leu Ile Asn Lys
                100                 105                 110

Lys Thr Ala Leu Glu Asp Glu Glu Asp Glu Leu Leu Ala Arg Thr Leu
            115                 120                 125

Glu Glu Ser Leu Lys Glu Asn Asn Arg Arg Lys Met Phe Glu Glu Gln
    130                 135                 140

Val Asn Lys Asp Glu Gln Leu Ala Leu Ile Val Gln Glu Ser Leu Asn
145                 150                 155                 160

Met Glu Glu Tyr Pro Ile Arg Leu Glu Glu Tyr Lys Ser Ile Ser Arg
                165                 170                 175

Arg Ala Pro Leu Asp Val Asp Glu Gln Phe Ala Lys Ala Val Lys Glu
                180                 185                 190

Ser Leu Lys Asn Lys Gly Lys Gly Lys Gln Phe Glu Asp Glu Gln Val
            195                 200                 205

Lys Lys Asp Glu Gln Leu Ala Leu Ile Val Gln Glu Ser Leu Asn Met
    210                 215                 220

Val Glu Ser Pro Pro Arg Leu Glu Glu Asn Asn Ile Ser Thr Arg
225                 230                 235                 240

Ala Pro Val Asp Glu Asp Glu Gln Leu Ala Lys Ala Val Glu Glu Ser
                245                 250                 255

Leu Lys Gly Lys Gly Gln Ile Lys Gln Ser Lys Asp Glu Val Glu Gly
                260                 265                 270
```

```
Asp Gly Met Leu Leu Glu Leu Asn Pro Pro Ser Leu Cys Gly Gly
            275                 280                 285

Cys Asn Phe Ala Val Glu His Gly Gly Ser Val Asn Ile Leu Gly Val
    290                 295                 300

Leu Trp His Pro Gly Cys Phe Cys Cys Arg Ala Cys His Lys Pro Ile
305                 310                 315                 320

Ala Ile His Asp Ile Glu Asn His Val Ser Asn Ser Arg Gly Lys Phe
                325                 330                 335

His Lys Ser Cys Tyr Glu Arg Tyr Cys Tyr Val Cys Lys Glu Lys Lys
            340                 345                 350

Met Lys Thr Tyr Asn Asn His Pro Phe Trp Glu Glu Arg Tyr Cys Pro
            355                 360                 365

Val His Glu Ala Asp Gly Thr Pro Lys Cys Cys Ser Cys Glu Arg Leu
    370                 375                 380

Glu Pro Arg Glu Ser Asn Tyr Val Met Leu Ala Asp Gly Arg Trp Leu
385                 390                 395                 400

Cys Leu Glu Cys Met Asn Ser Ala Val Met Asp Ser Asp Glu Cys Gln
                405                 410                 415

Pro Leu His Phe Asp Met Arg Asp Phe Phe Glu Gly Leu Asn Met Lys
            420                 425                 430

Ile Glu Lys Glu Phe Pro Phe Leu Val Glu Lys Gln Ala Leu Asn
            435                 440                 445

Lys Ala Glu Lys Glu Lys Ile Asp Tyr Gln Tyr Glu Val Val Thr
            450                 455                 460

Arg Gly Ile Cys Leu Ser Glu Glu Gln Ile Val Asp Ser Val Ser Gln
465                 470                 475                 480

Arg Pro Val Arg Gly Pro Asn Asn Lys Leu Val Gly Met Ala Thr Glu
                485                 490                 495

Ser Gln Lys Val Thr Arg Glu Cys Glu Val Thr Ala Ile Leu Ile Leu
            500                 505                 510

Tyr Gly Leu Pro Arg Leu Leu Thr Gly Tyr Ile Leu Ala His Glu Met
            515                 520                 525

Met His Ala Tyr Leu Arg Leu Asn Gly His Arg Asn Leu Asn Asn Ile
    530                 535                 540

Leu Glu Glu Gly Ile Cys Gln Val Leu Gly His Leu Trp Leu Asp Ser
545                 550                 555                 560

Gln Thr Tyr Ala Thr Ala Asp Ala Thr Ala Asp Ala Ser Ser Ser Ala
                565                 570                 575

Ser Ser Ser Arg Thr Pro Pro Ala Ala Ser Ala Ser Lys Lys Gly
            580                 585                 590

Glu Trp Ser Asp Phe Asp Lys Lys Leu Val Glu Phe Cys Lys Asn Gln
            595                 600                 605

Ile Glu Thr Asp Asp Ser Pro Val Tyr Gly Leu Gly Phe Arg Thr Val
            610                 615                 620

Asn Glu Met Val Thr Asn Ser Ser Leu Gln Glu Thr Leu Lys Glu Ile
625                 630                 635                 640

Leu Arg Gln Arg

<210> SEQ ID NO 64
<211> LENGTH: 587
<212> TYPE: PRT
<213> ORGANISM: Arabidopsis thaliana

<400> SEQUENCE: 64
```

```
Met Trp Cys Leu Ser Cys Phe Lys Pro Ser Thr Lys His Asp Pro Ser
1               5                   10                  15

Glu Asp Arg Phe Glu Glu Glu Thr Asn Ile Val Thr Gly Ile Ser Leu
            20                  25                  30

Tyr Glu Asp Val Ile Leu Arg Gln Arg Arg Ser Glu Ala Asp Gln Ile
                35                  40                  45

Glu Trp Ala Ile Gln Asp Ser Phe Asn Pro Gln Glu Thr Ser Arg Cys
    50                  55                  60

Arg Gln Arg Glu Glu Asp Asp Gln Ile Ala Arg Gly Leu Gln Tyr Val
65                  70                  75                  80

Glu Glu Thr Glu Leu Asp Lys Ser Val Val Asp Glu Glu Asp Gln Gln
                85                  90                  95

Leu Ser Lys Ile Val Glu Glu Ser Leu Lys Glu Lys Gly Lys Ser Lys
                100                 105                 110

Gln Phe Glu Asp Asp Gln Val Glu Asn Asp Glu Gln Gln Ala Leu Met
            115                 120                 125

Val Gln Glu Ser Leu Tyr Met Val Glu Leu Ser Ala Gln Leu Glu Glu
    130                 135                 140

Asp Lys Asn Ile Ser Thr Ile Pro Pro Leu Asn Glu Asp Ala Gln Leu
145                 150                 155                 160

Gln Lys Val Ile Trp Glu Ser Ala Lys Gly Lys Gly Gln Ile Glu His
                165                 170                 175

Phe Lys Asp Pro Val Glu Asp Gly Asn Leu Pro Arg Val Asp Leu
            180                 185                 190

Asn Val Asn His Pro His Ser Ile Cys Asp Gly Cys Lys Ser Ala Ile
                195                 200                 205

Glu Tyr Gly Arg Ser Val His Ala Leu Gly Val Asn Trp His Pro Glu
    210                 215                 220

Cys Phe Cys Cys Arg Tyr Cys Asp Lys Pro Ile Ala Met His Glu Phe
225                 230                 235                 240

Ser Asn Thr Lys Gly Arg Cys His Ile Thr Cys Tyr Glu Arg Ser His
                245                 250                 255

Pro Asn Cys His Val Cys Lys Lys Lys Phe Pro Gly Arg Lys Tyr Lys
                260                 265                 270

Glu His Pro Phe Trp Lys Glu Lys Tyr Cys Pro Phe His Glu Val Asp
    275                 280                 285

Gly Thr Pro Lys Cys Cys Ser Cys Glu Arg Leu Glu Pro Trp Gly Thr
    290                 295                 300

Lys Tyr Val Met Leu Ala Asp Asn Arg Trp Leu Cys Val Lys Cys Met
305                 310                 315                 320

Glu Cys Ala Val Met Asp Thr Tyr Glu Cys Gln Pro Leu His Phe Glu
                325                 330                 335

Ile Arg Glu Phe Phe Gly Ser Leu Asn Met Lys Val Glu Lys Glu Phe
            340                 345                 350

Pro Leu Leu Leu Val Glu Lys Glu Ala Leu Lys Ala Glu Ala Gln
                355                 360                 365

Glu Lys Ile Asp Asn Gln His Gly Val Val Thr Arg Gly Ile Cys Leu
    370                 375                 380

Ser Glu Gly Gln Ile Val Asn Ser Val Phe Lys Lys Pro Thr Met Gly
385                 390                 395                 400

Pro Asn Gly Glu Leu Val Ser Leu Gly Thr Glu Pro Gln Lys Val Val
            405                 410                 415

Gly Gly Cys Glu Val Thr Ala Ile Leu Ile Leu Tyr Gly Leu Pro Arg
```

```
                    420                 425                 430
Leu Leu Thr Gly Tyr Ile Leu Ala His Glu Met Met His Ala Trp Leu
            435                 440                 445

Arg Leu Asn Gly Thr Thr Ser Thr Gln Phe Val Phe Ala Asn Gln Tyr
    450                 455                 460

Gly Glu Ser Ser Gln Leu Lys Val Leu Phe Gly Leu Ile Thr Gly Tyr
465                 470                 475                 480

Arg Asn Leu Lys Leu Glu Leu Glu Gly Ile Cys Gln Val Leu Gly
                485                 490                 495

His Met Trp Leu Glu Ser Gln Thr Tyr Ser Ser Ser Ala Ala Ala Ser
            500                 505                 510

Ser Ala Ser Ser Ser Arg Thr Pro Ala Ala Asn Ala Ser Lys Lys
        515                 520                 525

Gly Ala Gln Ser Asp Tyr Glu Lys Lys Leu Val Glu Phe Cys Lys Asp
    530                 535                 540

Gln Ile Glu Thr Asp Asp Ser Pro Val Tyr Gly Val Gly Phe Arg Lys
545                 550                 555                 560

Val Asn Gln Met Val Ser Asp Ser Ser Leu His Lys Ile Leu Lys Ser
                565                 570                 575

Ile Gln His Trp Thr Lys Pro Asp Ser Asn Leu
            580                 585
```

```
<210> SEQ ID NO 65
<211> LENGTH: 5
<212> TYPE: PRT
<213> ORGANISM: Artificial sequence
<220> FEATURE:
<223> OTHER INFORMATION: Synthetic sequence: Metallopetidase motif

<400> SEQUENCE: 65

His Glu Met Met His
1               5

<210> SEQ ID NO 66
<211> LENGTH: 19
<212> TYPE: PRT
<213> ORGANISM: Artificial sequence
<220> FEATURE:
<223> OTHER INFORMATION: Synthetic sequence: Carboxyl terminal region
      motif
<220> FEATURE:
<221> NAME/KEY: VARIANT
<222> LOCATION: (3)..(10)
<223> OTHER INFORMATION: Xaa is any amino acid
<220> FEATURE:
<221> NAME/KEY: VARIANT
<222> LOCATION: (12)..(15)
<223> OTHER INFORMATION: Xaa is any amino acid

<400> SEQUENCE: 66

Glu Lys Xaa Xaa Xaa Xaa Xaa Xaa Xaa Arg Xaa Xaa Xaa Xaa Ser
1               5                   10                  15

Glu Glu Gln

<210> SEQ ID NO 67
<211> LENGTH: 18
<212> TYPE: PRT
<213> ORGANISM: Artificial sequence
<220> FEATURE:
<223> OTHER INFORMATION: Synthetic sequence: Carboxyl terminal region
      motif
<220> FEATURE:
<221> NAME/KEY: VARIANT
```

<222> LOCATION: (3)..(10)
<223> OTHER INFORMATION: Xaa is any amino acid
<220> FEATURE:
<221> NAME/KEY: VARIANT
<222> LOCATION: (12)..(15)
<223> OTHER INFORMATION: Xaa is any amino acid

<400> SEQUENCE: 67

Glu Lys Xaa Xaa Xaa Xaa Xaa Xaa Xaa Xaa Arg Xaa Xaa Xaa Xaa Ser
1               5                   10                  15

Glu Gln

<210> SEQ ID NO 68
<211> LENGTH: 21
<212> TYPE: PRT
<213> ORGANISM: Artificial sequence
<220> FEATURE:
<223> OTHER INFORMATION: Synthetic sequence: UIM1 domain
<220> FEATURE:
<221> NAME/KEY: VARIANT
<222> LOCATION: (1)..(1)
<223> OTHER INFORMATION: Xaa is a polar amino acid residue, for example
      Cys, Asp, Glu, His, Lys, Asn, Gln, Arg, Ser or Thr
<220> FEATURE:
<221> NAME/KEY: VARIANT
<222> LOCATION: (2)..(4)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is a polar amino acid residue, for example
      Cys, Asp, Glu, His, Lys, Asn, Gln, Arg, Ser or Thr
<220> FEATURE:
<221> NAME/KEY: VARIANT
<222> LOCATION: (7)..(7)
<223> OTHER INFORMATION: Xaa is a polar amino acid residue, for example
      Cys, Asp, Glu, His, Lys, Asn, Gln, Arg, Ser or Thr
<220> FEATURE:
<221> NAME/KEY: VARIANT
<222> LOCATION: (8)..(8)
<223> OTHER INFORMATION: Xaa is a big amino acid residue, for example
      Glu, Phe, His, Ile, Lys, Met, Gln, Arg, Trp or Tyr
<220> FEATURE:
<221> NAME/KEY: VARIANT
<222> LOCATION: (10)..(10)
<223> OTHER INFORMATION: Xaa is an aliphatic amino acid residue, for
      example Ile, Leu or Val
<220> FEATURE:
<221> NAME/KEY: VARIANT
<222> LOCATION: (11)..(11)
<223> OTHER INFORMATION: Xaa is a polar amino acid residue, for example
      Cys, Asp, Glu, His, Lys, Asn, Gln, Arg, Ser or Thr
<220> FEATURE:
<221> NAME/KEY: VARIANT
<222> LOCATION: (12)..(12)
<223> OTHER INFORMATION: Xaa is a big amino acid residue, for example
      Glu, Phe, His, Ile, Lys, Met, Gln, Arg, Trp or Tyr
<220> FEATURE:
<221> NAME/KEY: VARIANT
<222> LOCATION: (13)..(13)
<223> OTHER INFORMATION: May be present or absent. If present, Xaa is
      any amino acid.
<220> FEATURE:
<221> NAME/KEY: VARIANT
<222> LOCATION: (15)..(15)
<223> OTHER INFORMATION: Xaa is a big amino acid residue, for example
      Glu, Phe, His, Ile, Lys, Met, Gln, Arg, Trp or Tyr
<220> FEATURE:
<221> NAME/KEY: VARIANT
<222> LOCATION: (16)..(16)
<223> OTHER INFORMATION: Xaa is a polar amino acid residue, for example
      Cys, Asp, Glu, His, Lys, Asn, Gln, Arg, Ser or Thr
<220> FEATURE:
<221> NAME/KEY: VARIANT
<222> LOCATION: (17)..(17)
<223> OTHER INFORMATION: Xaa is any amino acid -continued

```
<220> FEATURE:
<221> NAME/KEY: VARIANT
<222> LOCATION: (18)..(18)
<223> OTHER INFORMATION: May be present or absent. If present, Xaa is
      any amino acid.
<220> FEATURE:
<221> NAME/KEY: VARIANT
<222> LOCATION: (19)..(21)
<223> OTHER INFORMATION: Xaa is a polar amino acid residue, for example
      Cys, Asp, Glu, His, Lys, Asn, Gln, Arg, Ser or Thr

<400> SEQUENCE: 68

Xaa Xaa Xaa Xaa Xaa Leu Xaa Xaa Ala Xaa Xaa Xaa Xaa Ser Xaa Xaa
1               5                   10                  15

Xaa Xaa Xaa Xaa Xaa
            20

<210> SEQ ID NO 69
<211> LENGTH: 21
<212> TYPE: PRT
<213> ORGANISM: Artificial sequence
<220> FEATURE:
<223> OTHER INFORMATION: Synthetic sequence: UIM2 domain
<220> FEATURE:
<221> NAME/KEY: VARIANT
<222> LOCATION: (1)..(1)
<223> OTHER INFORMATION: Xaa is a polar amino acid residue, for example
      Cys, Asp, Glu, His, Lys, Asn, Gln, Arg, Ser or Thr
<220> FEATURE:
<221> NAME/KEY: VARIANT
<222> LOCATION: (2)..(4)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is a polar amino acid residue, for example
      Cys, Asp, Glu, His, Lys, Asn, Gln, Arg, Ser or Thr
<220> FEATURE:
<221> NAME/KEY: VARIANT
<222> LOCATION: (7)..(7)
<223> OTHER INFORMATION: Xaa is a polar amino acid residue, for example
      Cys, Asp, Glu, His, Lys, Asn, Gln, Arg, Ser or Thr
<220> FEATURE:
<221> NAME/KEY: VARIANT
<222> LOCATION: (8)..(8)
<223> OTHER INFORMATION: Xaa is a big amino acid residue, for example
      Glu, Phe, His, Ile, Lys, Met, Gln, Arg, Trp or Tyr
<220> FEATURE:
<221> NAME/KEY: VARIANT
<222> LOCATION: (10)..(10)
<223> OTHER INFORMATION: Xaa is an aliphatic amino acid residue, for
      example Ile, Leu or Val
<220> FEATURE:
<221> NAME/KEY: VARIANT
<222> LOCATION: (11)..(11)
<223> OTHER INFORMATION: Xaa is a polar amino acid residue, for example
      Cys, Asp, Glu, His, Lys, Asn, Gln, Arg, Ser or Thr
<220> FEATURE:
<221> NAME/KEY: VARIANT
<222> LOCATION: (12)..(12)
<223> OTHER INFORMATION: Xaa is a big amino acid residue, for example
      Glu, Phe, His, Ile, Lys, Met, Gln, Arg, Trp or Tyr
<220> FEATURE:
<221> NAME/KEY: VARIANT
<222> LOCATION: (13)..(13)
<223> OTHER INFORMATION: May be present or absent. If present, Xaa is
      any amino acid.
<220> FEATURE:
<221> NAME/KEY: VARIANT
<222> LOCATION: (15)..(15)
<223> OTHER INFORMATION: Xaa is a big amino acid residue, for example
      Glu, Phe, His, Ile, Lys, Met, Gln, Arg, Trp or Tyr
<220> FEATURE:
<221> NAME/KEY: VARIANT
<222> LOCATION: (16)..(16)
<223> OTHER INFORMATION: Xaa is a polar amino acid residue, for example
```

```
        Cys, Asp, Glu, His, Lys, Asn, Gln, Arg, Ser or Thr
<220> FEATURE:
<221> NAME/KEY: VARIANT
<222> LOCATION: (17)..(17)
<223> OTHER INFORMATION: Xaa is any amino acid
<220> FEATURE:
<221> NAME/KEY: VARIANT
<222> LOCATION: (18)..(18)
<223> OTHER INFORMATION: Xaa is a small amino acid residue, for example
        Ala, Cys, Asp, Gly, Asn, Pro, Ser, Thr or Val
<220> FEATURE:
<221> NAME/KEY: VARIANT
<222> LOCATION: (19)..(21)
<223> OTHER INFORMATION: Xaa is a polar amino acid residue, for example
        Cys, Asp, Glu, His, Lys, Asn, Gln, Arg, Ser or Thr

<400> SEQUENCE: 69

Xaa Xaa Xaa Xaa Xaa Leu Xaa Xaa Ala Xaa Xaa Xaa Xaa Ser Xaa Xaa
1               5                   10                  15

Xaa Xaa Xaa Xaa Xaa
            20

<210> SEQ ID NO 70
<211> LENGTH: 20
<212> TYPE: PRT
<213> ORGANISM: Artificial sequence
<220> FEATURE:
<223> OTHER INFORMATION: Synthetic sequence: UIM1 domain

<400> SEQUENCE: 70

Gln Glu Asn Glu Asp Ile Asp Arg Ala Ile Ala Leu Ser Leu Leu Glu
1               5                   10                  15

Glu Asn Gln Glu
            20

<210> SEQ ID NO 71
<211> LENGTH: 20
<212> TYPE: PRT
<213> ORGANISM: Artificial sequence
<220> FEATURE:
<223> OTHER INFORMATION: Synthetic sequence: UIM2 domain

<400> SEQUENCE: 71

Asp Glu Asp Glu Gln Ile Ala Arg Ala Leu Gln Glu Ser Met Val Val
1               5                   10                  15

Gly Asn Ser Pro
            20

<210> SEQ ID NO 72
<211> LENGTH: 53
<212> TYPE: PRT
<213> ORGANISM: Artificial sequence
<220> FEATURE:
<223> OTHER INFORMATION: Synthetic sequence: LIM domain

<400> SEQUENCE: 72

Ile Cys Ala Gly Cys Asn Met Glu Ile Gly His Gly Arg Phe Leu Asn
1               5                   10                  15

Cys Leu Asn Ser Leu Trp His Pro Glu Cys Phe Arg Cys Tyr Gly Cys
            20                  25                  30

Ser Gln Pro Ile Ser Glu Tyr Glu Phe Ser Thr Ser Gly Asn Tyr Pro
        35                  40                  45

Phe His Lys Ala Cys
    50
```

```
<210> SEQ ID NO 73
<211> LENGTH: 43
<212> TYPE: PRT
<213> ORGANISM: Artificial sequence
<220> FEATURE:
<223> OTHER INFORMATION: Synthetic sequence: EOD domain
<220> FEATURE:
<221> NAME/KEY: VARIANT
<222> LOCATION: (1)..(1)
<223> OTHER INFORMATION: Xaa is Glu or Lys
<220> FEATURE:
<221> NAME/KEY: VARIANT
<222> LOCATION: (8)..(8)
<223> OTHER INFORMATION: Xaa is Leu or Met
<220> FEATURE:
<221> NAME/KEY: VARIANT
<222> LOCATION: (9)..(9)
<223> OTHER INFORMATION: Xaa is Lys, Arg, Gly, Thr or Glu
<220> FEATURE:
<221> NAME/KEY: VARIANT
<222> LOCATION: (11)..(11)
<223> OTHER INFORMATION: Xaa is Lys or Arg
<220> FEATURE:
<221> NAME/KEY: VARIANT
<222> LOCATION: (12)..(12)
<223> OTHER INFORMATION: Xaa is Arg or Ile
<220> FEATURE:
<221> NAME/KEY: VARIANT
<222> LOCATION: (13)..(13)
<223> OTHER INFORMATION: Xaa is Gly or Lys
<220> FEATURE:
<221> NAME/KEY: VARIANT
<222> LOCATION: (14)..(14)
<223> OTHER INFORMATION: Xaa is Asp, Asn or Glu
<220> FEATURE:
<221> NAME/KEY: VARIANT
<222> LOCATION: (15)..(15)
<223> OTHER INFORMATION: Xaa is Arg, Gln, Lys or Leu
<220> FEATURE:
<221> NAME/KEY: VARIANT
<222> LOCATION: (17)..(17)
<223> OTHER INFORMATION: Xaa is Ile, Met or Val
<220> FEATURE:
<221> NAME/KEY: VARIANT
<222> LOCATION: (18)..(18)
<223> OTHER INFORMATION: Xaa is Lys, Asn, Thr or Ala
<220> FEATURE:
<221> NAME/KEY: VARIANT
<222> LOCATION: (20)..(20)
<223> OTHER INFORMATION: Xaa is Leu or Pro
<220> FEATURE:
<221> NAME/KEY: VARIANT
<222> LOCATION: (22)..(22)
<223> OTHER INFORMATION: Xaa is Lys or Ser
<220> FEATURE:
<221> NAME/KEY: VARIANT
<222> LOCATION: (24)..(24)
<223> OTHER INFORMATION: Xaa is Val or Ala
<220> FEATURE:
<221> NAME/KEY: VARIANT
<222> LOCATION: (27)..(27)
<223> OTHER INFORMATION: Xaa is Ser, Thr, Gly or Ala
<220> FEATURE:
<221> NAME/KEY: VARIANT
<222> LOCATION: (28)..(28)
<223> OTHER INFORMATION: Xaa is Glu, Gln, Asp, Ser or Gly
<220> FEATURE:
<221> NAME/KEY: VARIANT
<222> LOCATION: (30)..(30)
<223> OTHER INFORMATION: Xaa is Ile, Gly, Thr or Val
<220> FEATURE:
<221> NAME/KEY: VARIANT
<222> LOCATION: (31)..(31)
<223> OTHER INFORMATION: Xaa is Ser or Thr
<220> FEATURE:
<221> NAME/KEY: VARIANT
<222> LOCATION: (32)..(32)
<223> OTHER INFORMATION: Xaa is Lys or Arg
<220> FEATURE:
```

```
<221> NAME/KEY: VARIANT
<222> LOCATION: (35)..(35)
<223> OTHER INFORMATION: Xaa is Gly, Thr or Ser
<220> FEATURE:
<221> NAME/KEY: VARIANT
<222> LOCATION: (39)..(39)
<223> OTHER INFORMATION: Xaa is Val, Ile, Ala or Lys
<220> FEATURE:
<221> NAME/KEY: VARIANT
<222> LOCATION: (42)..(42)
<223> OTHER INFORMATION: Xaa is Val or Ile

<400> SEQUENCE: 73

Xaa Arg Cys Val Ile Cys Gln Xaa Xaa Tyr Xaa Xaa Xaa Xaa Gln
1               5                   10                  15

Xaa Xaa Leu Xaa Cys Xaa His Xaa Tyr His Xaa Xaa Cys Xaa Xaa Xaa
            20                  25                  30

Trp Leu Xaa Ile Asn Lys Xaa Cys Pro Xaa Cys
            35                  40

<210> SEQ ID NO 74
<211> LENGTH: 253
<212> TYPE: PRT
<213> ORGANISM: Zea mays

<400> SEQUENCE: 74

Met Asn Ser Ser Arg Gln Met Glu Leu His Tyr Ile Asn Thr Gly Phe
1               5                   10                  15

Pro Tyr Thr Ile Thr Glu Ser Phe Met Asp Phe Phe Glu Gly Leu Thr
            20                  25                  30

Tyr Ala His Ala Asp Phe Ala Leu Thr Asp Gly Phe Gln Asp Gln Gly
        35                  40                  45

Asn Pro Tyr Trp Ala Met Met His Thr Asn Ser Tyr Lys Tyr Gly Tyr
    50                  55                  60

Ser Gly Pro Gly Asn Tyr Tyr Ser Tyr Ala His Val Tyr Asp Ile Asp
65                  70                  75                  80

Asp Tyr Met Arg Arg Ala Asp Gly Gly Arg Ile Trp Asp Asn Thr
                85                  90                  95

Thr Pro Val Asn Asn Val Asp Ser Ala Asn Val Val Leu Gln Gly Gly
            100                 105                 110

Glu Ala Pro His Thr Thr Thr Asn Thr Ile Asn Lys Glu Cys Ile Gln
        115                 120                 125

Gln Val His Gln Ser Pro Gly Ser Pro Gln Val Val Trp Gln Asp Asn
    130                 135                 140

Ile Glu Pro Asp Asn Met Thr Tyr Glu Glu Leu Leu Asp Leu Gly Glu
145                 150                 155                 160

Ala Val Gly Thr Gln Ser Arg Gly Leu Ser Gln Glu Arg Ile Ser Ser
                165                 170                 175

Leu Pro Val Thr Lys Tyr Lys Cys Gly Phe Phe Ser Arg Lys Lys Thr
            180                 185                 190

Arg Arg Glu Arg Cys Val Ile Cys Gln Met Glu Tyr Arg Arg Gly Asn
        195                 200                 205

Leu Gln Met Thr Leu Pro Cys Lys His Val Tyr His Ala Ser Cys Val
    210                 215                 220

Thr Arg Trp Leu Gly Ile Asn Lys Val Cys Pro Val Cys Phe Ala Glu
225                 230                 235                 240

Val Pro Gly Glu Asp Pro Glu Ala Met Ser Gln Gln Leu
                245                 250
```

<210> SEQ ID NO 75
<211> LENGTH: 249
<212> TYPE: PRT
<213> ORGANISM: Sorghum bicolor

<400> SEQUENCE: 75

Met Asn Ser Cys Arg Gln Met Glu Leu His Tyr Ile Asn Thr Gly Phe
1               5                   10                  15

Pro Tyr Thr Ile Thr Glu Ser Phe Met Asp Phe Phe Glu Gly Leu Thr
            20                  25                  30

Tyr Ala His Ala Asp Phe Ala Leu Met Asp Gly Phe Gln Asp Gln Gly
        35                  40                  45

Asn Pro Tyr Trp Ala Met Met His Thr Asn Ser Tyr Lys Tyr Gly Tyr
    50                  55                  60

Ser Gly Pro Gly Asn Tyr Tyr Tyr Ala His Val Tyr Asp Ile Asp
65                  70                  75                  80

Asp Tyr Met His Arg Ala Asp Gly Gly Arg Arg Val Trp Asp Asn Thr
                85                  90                  95

Thr Pro Ala Asn Asn Val Asp Ser Ala Asn Val Val Leu Gln Gly Ser
            100                 105                 110

Glu Ala Pro Arg Thr Thr Ala Asn Thr Thr Thr Glu Glu Cys Ile Gln
        115                 120                 125

Gln Val His Gln Ser Pro Gly Ser Pro His Val Val Trp Gln Asp Asn
    130                 135                 140

Ile Asp Pro Asp Asn Met Thr Tyr Glu Glu Leu Leu Asp Leu Gly Glu
145                 150                 155                 160

Val Val Gly Thr Gln Ser Arg Gly Leu Ser Gln Glu Arg Ile Ser Ser
                165                 170                 175

Leu Pro Val Thr Lys Tyr Lys Cys Gly Phe Phe Ser Arg Lys Lys Thr
            180                 185                 190

Arg Arg Glu Arg Cys Val Ile Cys Gln Met Glu Tyr Arg Arg Gly Asn
        195                 200                 205

Leu Gln Met Thr Leu Pro Cys Lys His Val Tyr His Ala Ser Cys Val
    210                 215                 220

Thr Arg Trp Leu Ser Ile Asn Lys Val Cys Pro Val Cys Phe Ala Glu
225                 230                 235                 240

Val Pro Gly Asp Glu Pro Lys Arg Gln
                245

<210> SEQ ID NO 76
<211> LENGTH: 249
<212> TYPE: PRT
<213> ORGANISM: Zea mays

<400> SEQUENCE: 76

Met Thr Ser Ser Arg Gln Met Glu Leu His Tyr Ile Asn Thr Gly Phe
1               5                   10                  15

Pro Tyr Thr Ile Thr Glu Ser Phe Met Asp Phe Phe Glu Gly Leu Thr
            20                  25                  30

Tyr Ala His Ala Asp Phe Ala Leu Met Asp Gly Phe Gln Asp Gln Gly
        35                  40                  45

Asn Pro Tyr Trp Thr Met Met His Thr Asn Ser Tyr Lys Tyr Gly Tyr
    50                  55                  60

Ser Gly Ser Gly Asn Tyr Tyr Ser Tyr Ala His Ala Tyr Asp Ile Asp
65                  70                  75                  80

```
Asp Tyr Met His Arg Thr Asp Gly Gly Arg Arg Thr Trp Asp Asn Thr
                85                  90                  95

Thr Pro Val Asn Asn Val Asp Ser Ala Asn Val Val Leu Gln Gly Gly
            100                 105                 110

Glu Ala Pro Arg Thr Thr Ala Asn Thr Thr Ser Glu Asp Cys Ile Gln
        115                 120                 125

Gln Val His Gln Ser Pro Gly Ser Pro Gln Val Val Trp Gln Asp Asn
130                 135                 140

Ile Asp Pro Asp Asn Met Thr Tyr Glu Glu Leu Leu Asp Leu Gly Glu
145                 150                 155                 160

Ala Val Gly Thr Gln Ser Arg Gly Leu Ser Gln Glu Cys Ile Ser Leu
                165                 170                 175

Leu Pro Ile Thr Lys Tyr Lys Cys Gly Phe Phe Ser Arg Lys Lys Thr
            180                 185                 190

Arg Arg Glu Arg Cys Val Ile Cys Gln Met Glu Tyr Arg Arg Gly Asn
        195                 200                 205

Leu Gln Ile Thr Leu Pro Cys Lys His Val Tyr His Ala Ser Cys Val
210                 215                 220

Thr Arg Trp Leu Ser Ile Asn Lys Val Cys Pro Val Cys Phe Ala Glu
225                 230                 235                 240

Val Pro Gly Glu Asp Ser Leu Arg Gln
                245

<210> SEQ ID NO 77
<211> LENGTH: 272
<212> TYPE: PRT
<213> ORGANISM: Oryza sativa

<400> SEQUENCE: 77

Met Thr Glu Ser His Glu Arg Asp Thr Glu Val Thr Arg Trp Gln Val
1               5                   10                  15

His Asp Pro Ser Glu Gly Met Asn Gly Ser Arg Gln Met Glu Leu His
            20                  25                  30

Tyr Ile Asn Thr Gly Phe Pro Tyr Thr Ile Thr Glu Ser Phe Met Asp
        35                  40                  45

Phe Phe Glu Gly Leu Thr Tyr Ala His Ala Asp Phe Ala Ile Ala Asp
    50                  55                  60

Ala Phe His Asp Gln Ala Asn Pro Tyr Trp Ala Met Met His Thr Asn
65                  70                  75                  80

Ser Tyr Lys Tyr Gly Tyr Ser Gly Ala Gly Asn Tyr Ser Tyr Gly
                85                  90                  95

His Val Tyr Asp Met Asn Asp Tyr Met His Arg Ala Asp Gly Gly Arg
            100                 105                 110

Arg Ile Trp Asp Asn Ala Thr Pro Val Asn Asn Thr Glu Ser Pro Asn
        115                 120                 125

Val Val Leu Gln Gly Gly Glu Thr Pro His Ala Asn Thr Ser Ser Thr
130                 135                 140

Thr Glu Glu Cys Ile Gln Gln Val His Gln Asn Ser Ser Pro
145                 150                 155                 160

Gln Val Ile Trp Gln Asp Asn Ile Asp Pro Asn Met Thr Tyr Glu
                165                 170                 175

Glu Leu Leu Asp Leu Gly Glu Ala Val Gly Thr Gln Ser Arg Gly Leu
            180                 185                 190

Ser Gln Glu Arg Ile Ser Leu Leu Pro Val Thr Lys Tyr Lys Cys Gly
        195                 200                 205
```

Phe Phe Ser Arg Lys Lys Thr Arg Arg Glu Arg Cys Val Ile Cys Gln
            210                 215                 220

Met Glu Tyr Arg Arg Gly Asn Leu Gln Met Thr Leu Pro Cys Lys His
225                 230                 235                 240

Val Tyr His Ala Ser Cys Val Thr Arg Trp Leu Ser Ile Asn Lys Val
                245                 250                 255

Cys Pro Val Cys Phe Ala Glu Val Pro Gly Asp Glu Pro Lys Arg Gln
            260                 265                 270

<210> SEQ ID NO 78
<211> LENGTH: 250
<212> TYPE: PRT
<213> ORGANISM: Oryza sativa

<400> SEQUENCE: 78

Met Asn Gly Ser Arg Gln Met Glu Leu His Tyr Ile Asn Thr Gly Phe
1               5                   10                  15

Pro Tyr Thr Ile Thr Glu Ser Phe Met Asp Phe Phe Glu Gly Leu Thr
            20                  25                  30

Tyr Ala His Ala Asp Phe Ala Ile Ala Asp Ala Phe His Asp Gln Ala
        35                  40                  45

Asn Pro Tyr Trp Ala Met Met His Thr Asn Ser Tyr Lys Tyr Gly Tyr
    50                  55                  60

Ser Gly Ala Gly Asn Tyr Tyr Ser Tyr Gly His Val Tyr Asp Met Asn
65                  70                  75                  80

Asp Tyr Met His Arg Ala Asp Gly Gly Arg Arg Ile Trp Asp Asn Ala
                85                  90                  95

Thr Pro Val Asn Asn Thr Glu Ser Pro Asn Val Val Leu Gln Gly Gly
            100                 105                 110

Glu Thr Pro His Ala Asn Thr Ser Ser Thr Thr Glu Glu Cys Ile Gln
        115                 120                 125

Gln Gln Val His Gln Asn Ser Ser Ser Pro Val Ile Trp Gln Asp
    130                 135                 140

Asn Ile Asp Pro Asp Asn Met Thr Tyr Glu Glu Leu Leu Asp Leu Gly
145                 150                 155                 160

Glu Ala Val Gly Thr Gln Ser Arg Gly Leu Ser Gln Glu Arg Ile Ser
                165                 170                 175

Leu Leu Pro Val Thr Lys Tyr Lys Cys Gly Phe Phe Ser Arg Lys Lys
            180                 185                 190

Thr Arg Arg Glu Arg Cys Val Ile Cys Gln Met Glu Tyr Arg Arg Gly
        195                 200                 205

Asn Leu Gln Met Thr Leu Pro Cys Lys His Val Tyr His Ala Ser Cys
    210                 215                 220

Val Thr Arg Trp Leu Ser Ile Asn Lys Val Cys Pro Val Cys Phe Ala
225                 230                 235                 240

Glu Val Pro Gly Asp Glu Pro Lys Arg Gln
                245                 250

<210> SEQ ID NO 79
<211> LENGTH: 251
<212> TYPE: PRT
<213> ORGANISM: Brachypodium distachyon

<400> SEQUENCE: 79

Met Asn Gly Ser Arg Gln Met Glu Leu His Tyr Ile Asn Thr Gly Phe
1               5                   10                  15

```
Pro Tyr Thr Ile Thr Glu Ser Phe Met Asp Phe Phe Glu Gly Leu Thr
            20                  25                  30

Tyr Ala His Ala Asp Phe Ala Leu Ala Asp Ala Phe Gln Asp Gln Ala
        35                  40                  45

Asn Pro Tyr Trp Thr Met Met Gln Thr Asn Ser Tyr Lys Tyr Gly Tyr
 50                  55                  60

Ser Gly Ala Ser Asn Tyr Tyr Ser Tyr Gly His Val Tyr Asp Met Asn
 65                  70                  75                  80

Asp Tyr Met His Arg Ala Asp Gly Gly Arg Ile Trp Asp Asn Pro
                85                  90                  95

Thr Pro Ala Ser Asn Thr Asp Ser Pro Asn Val Val Leu Gln Gly Ala
                100                 105                 110

Ala Glu Ala Pro His Pro Arg Ala Ser Ser Thr Thr Glu Glu Cys Ile
            115                 120                 125

Gln Gln Pro Val His Gln Asn Ser Ser Ser Pro Gln Val Val Trp Gln
130                 135                 140

Asp Asn Val Asp Pro Asp Asn Met Thr Tyr Glu Leu Leu Asp Leu
145                 150                 155                 160

Gly Glu Ala Val Gly Thr Gln Ser Arg Gly Leu Ser Gln Glu Arg Ile
                165                 170                 175

Ser Ser Leu Pro Val Thr Lys Tyr Lys Cys Gly Phe Phe Ser Arg Lys
            180                 185                 190

Lys Thr Arg Arg Glu Arg Cys Val Ile Cys Gln Met Glu Tyr Arg Arg
            195                 200                 205

Gly Asp Leu Gln Met Ala Leu Pro Cys Lys His Val Tyr His Ala Ser
        210                 215                 220

Cys Val Thr Arg Trp Leu Ser Ile Asn Lys Val Cys Pro Val Cys Phe
225                 230                 235                 240

Ala Glu Val Pro Ser Glu Pro Ser Arg Gln
            245                 250

<210> SEQ ID NO 80
<211> LENGTH: 246
<212> TYPE: PRT
<213> ORGANISM: Solanum lycopersicum

<400> SEQUENCE: 80

Met Asn Trp Asn Gln Gln Thr Glu Ile Tyr Tyr Thr Asn Gly Ala Met
 1               5                   10                  15

Pro Tyr Asn Ser Ile Gly Ser Phe Met Asp Phe Phe Gly Gly Val Thr
            20                  25                  30

Tyr Asp His Val Asn Tyr Ile Phe Ala Asp Pro Pro Tyr Ala Gln Glu
        35                  40                  45

Ser Leu Tyr Pro Ser Ile Ser Thr Asn Pro Tyr Lys Phe Gly Tyr Ser
 50                  55                  60

Glu Ala Gly Ser Phe Ser Tyr Tyr Asp Tyr Arg Glu Tyr Val Val
 65                  70                  75                  80

Asn Asp His Val Ser Gly Ile Glu Glu His Asp Arg His Leu Glu Asn
                85                  90                  95

Pro Ser Thr Thr Thr Val Asn Val Ala Ala Asn Val His Arg Glu Glu
                100                 105                 110

Ile Ser Gly Ser Asn Ser Leu Thr Asn Ser Val Glu Cys Pro Arg Gly
            115                 120                 125

Gln Ile Asn Thr Arg Asp Ser Glu Val Val Trp Gln Asp Asn Ile Asp
```

```
                130             135                 140
Pro Asp Asn Met Thr Tyr Glu Glu Leu Leu Glu Leu Gly Glu Ala Val
145                 150                 155                 160

Gly Thr Gln Ser Arg Gly Leu Ser Gln Asn Gln Ile Ser Leu Leu Pro
                165                 170                 175

Val Thr Lys Phe Lys Cys Gly Phe Phe Ser Arg Lys Lys Ser Arg Lys
                180                 185                 190

Glu Arg Cys Val Ile Cys Gln Met Glu Tyr Lys Arg Lys Asp Gln Gln
                195                 200                 205

Val Thr Leu Pro Cys Lys His Val Tyr His Ala Gly Cys Gly Ser Arg
                210                 215                 220

Trp Leu Ser Ile Asn Lys Ala Cys Pro Ile Cys Tyr Thr Glu Val Val
225                 230                 235                 240

Ile Asn Thr Ser Lys Arg
                245

<210> SEQ ID NO 81
<211> LENGTH: 240
<212> TYPE: PRT
<213> ORGANISM: Ricinus communis

<400> SEQUENCE: 81

Met Glu Val His Tyr Ile Asn Thr Gly Phe Pro Tyr Thr Val Thr Glu
1               5                   10                  15

Ser Phe Leu Asp Phe Phe Glu Gly Leu Ser His Val Pro Val His Tyr
                20                  25                  30

Ala His Thr Gly Gln Val Leu Asp Gln Val Gln Glu Asn Ala Tyr Trp
                35                  40                  45

Ser Met Asn Met Asn Ala Tyr Lys Tyr Gly Phe Ser Gly Pro Gly Ser
50                  55                  60

Thr Tyr Tyr Asp Pro Tyr Glu Val Asn Asp Asn Leu Pro Arg Met Asp
65                  70                  75                  80

Val Ser Arg Ser Thr Trp Glu Tyr Pro Ser Val Val Asn Met Glu Glu
                85                  90                  95

Ala Thr Thr Thr Asp Thr Gln Ser Glu Gly Asp Ala Val Val Gly Val
                100                 105                 110

His Ala Ser Pro Glu Glu Cys Ile Pro Asn His Thr Ser Gly Asp Ser
                115                 120                 125

Pro Gln Gly Val Trp Gln Asp Asp Val Asp Pro Asp Asn Met Thr Tyr
                130                 135                 140

Glu Glu Leu Leu Asp Leu Gly Glu Thr Val Gly Thr Gln Ser Arg Gly
145                 150                 155                 160

Leu Ser Gln Glu Leu Ile Ser Leu Leu Pro Thr Ser Lys Cys Lys Phe
                165                 170                 175

Arg Ser Phe Phe Leu Arg Lys Lys Ala Gly Glu Arg Cys Val Ile Cys
                180                 185                 190

Gln Met Arg Tyr Lys Arg Gly Asp Lys Gln Met Lys Leu Pro Cys Lys
                195                 200                 205

His Val Tyr His Ser Glu Cys Ile Ser Lys Trp Leu Gly Ile Asn Lys
                210                 215                 220

Val Cys Pro Val Cys Asn Asn Glu Val Phe Gly Glu Asp Ser Arg His
225                 230                 235                 240

<210> SEQ ID NO 82
<211> LENGTH: 203
```

<212> TYPE: PRT
<213> ORGANISM: Populus trichocarpa

<400> SEQUENCE: 82

```
Met Glu Val His Tyr Met Asn Thr Asp Phe Pro Tyr Thr Thr Thr Glu
1               5                   10                  15

Ser Phe Met Asp Phe Phe Glu Gly Leu Thr His Ala Pro Val Asn Tyr
            20                  25                  30

Ala His Asn Gly Pro Met His Asp Gln Asp Asn Ala Tyr Trp Ser Met
        35                  40                  45

Asn Met Asn Ala Tyr Lys Phe Gly Phe Ser Gly Leu Gly Ser Thr Ser
    50                  55                  60

Tyr Tyr Ser Pro Tyr Glu Val Asn Asp Asn Leu Pro Arg Met Asp Val
65                  70                  75                  80

Ser Arg Met Ala Trp Glu Tyr Pro Ser Val Val Ile Lys Ala Leu Trp
                85                  90                  95

Gln Asp Asp Val Asp Pro Asp Thr Met Thr Tyr Glu Glu Leu Val Asp
            100                 105                 110

Leu Gly Glu Thr Val Gly Thr Gln Ser Lys Gly Leu Ser Pro Glu Leu
        115                 120                 125

Ile Ser Leu Leu Pro Thr Ser Lys Cys Lys Phe Gly Ser Phe Phe Ser
    130                 135                 140

Arg Lys Arg Ser Gly Glu Arg Cys Val Ile Cys Gln Met Lys Tyr Lys
145                 150                 155                 160

Arg Gly Asp Lys Gln Ile Lys Leu Leu Cys Lys His Ala Tyr His Ser
                165                 170                 175

Glu Cys Ile Thr Lys Trp Leu Gly Ile Asn Lys Val Cys Pro Val Cys
            180                 185                 190

Asn Asp Glu Val Phe Gly Glu Ser Arg Asn
        195                 200
```

<210> SEQ ID NO 83
<211> LENGTH: 247
<212> TYPE: PRT
<213> ORGANISM: Glycine max

<400> SEQUENCE: 83

```
Met Asn Asp Gly Arg Gln Met Gly Val His Tyr Val Asp Ala Gly Phe
1               5                   10                  15

Pro Tyr Ala Val Asn Asp Asn Phe Val Asp Phe Gln Gly Phe Thr
            20                  25                  30

His Val Pro Val Asn Tyr Ala Phe Ala Gly Ser Ile Pro Asp Gln Glu
        35                  40                  45

Ser Val Tyr Trp Ser Met Asn Met Asn Pro Tyr Lys Phe Gly Leu Ser
    50                  55                  60

Gly Pro Gly Ser Thr Ser Tyr Tyr Ser Tyr Glu Val Asn Gly His
65                  70                  75                  80

Leu Pro Arg Met Glu Ile Asp Arg Ala Glu Trp Glu Tyr Pro Ser Thr
                85                  90                  95

Ile Thr Thr Val Glu Glu Pro Ala Thr Thr Asp Ser Pro Pro Arg Arg
            100                 105                 110

Asp Gly Val Thr Ser Met Gln Thr Ile Pro Glu Glu Cys Ser Pro Asn
        115                 120                 125

His His Glu Ser Asn Ser Ser Ser Gln Val Ile Trp Gln Asp Asn Ile
    130                 135                 140
```

```
Tyr Pro Asp Asp Met Thr Tyr Glu Glu Leu Leu Asp Leu Gly Glu Ala
145                 150                 155                 160

Val Gly Thr Gln Ser Arg Gly Leu Ser Gln Glu Leu Ile Asp Met Leu
                165                 170                 175

Pro Thr Ser Lys Tyr Lys Phe Gly Ser Leu Phe Lys Arg Lys Asn Ser
            180                 185                 190

Gly Lys Arg Cys Val Ile Cys Gln Met Thr Tyr Arg Arg Gly Asp Gln
        195                 200                 205

Gln Met Lys Leu Pro Cys Ser His Val Tyr His Gly Glu Cys Ile Thr
    210                 215                 220

Lys Trp Leu Ser Ile Asn Lys Lys Cys Pro Val Cys Asn Thr Glu Val
225                 230                 235                 240

Phe Gly Glu Glu Ser Thr His
                245

<210> SEQ ID NO 84
<211> LENGTH: 247
<212> TYPE: PRT
<213> ORGANISM: Glycine max

<400> SEQUENCE: 84

Met Asn Asp Gly Arg Gln Met Gly Val Asn Tyr Val Asp Ala Gly Phe
1               5                   10                  15

Pro Tyr Ala Val Asn Glu Asn Phe Val Asp Phe Gln Gly Phe Thr
            20                  25                  30

Pro Val Pro Val Asn Tyr Ala Phe Ala Gly Ser Ile Pro Asp Gln Glu
            35                  40                  45

Ser Val Tyr Trp Ser Met Asn Met Asn Pro Tyr Lys Phe Gly Leu Ser
    50                  55                  60

Gly Pro Gly Ser Thr Ser Tyr Tyr Ser Ser Tyr Glu Val Asn Gly His
65                  70                  75                  80

Leu Pro Arg Met Glu Ile Asp Arg Ala Glu Trp Glu Tyr Pro Ser Thr
                85                  90                  95

Ile Thr Thr Val Glu Glu Pro Ala Thr Thr Asp Ser Pro Pro Arg Arg
            100                 105                 110

Asp Gly Val Thr Asn Met Gln Thr Ile Pro Glu Glu Cys Ser Pro Asn
        115                 120                 125

His His Glu Ser Asn Ser Ser Ser Gln Val Ile Trp Gln Asp Asn Ile
    130                 135                 140

Asp Pro Asp Asn Met Thr Tyr Glu Glu Leu Leu Asp Leu Gly Glu Ala
145                 150                 155                 160

Val Gly Thr Gln Ser Arg Gly Leu Ser Gln Glu Leu Ile Asp Met Leu
                165                 170                 175

Pro Thr Ser Lys Tyr Lys Phe Gly Asn Leu Phe Lys Arg Lys Asn Ser
            180                 185                 190

Gly Lys Arg Cys Val Ile Cys Gln Met Thr Tyr Arg Arg Gly Asp Gln
        195                 200                 205

Gln Met Lys Leu Pro Cys Ser His Val Tyr His Gly Glu Cys Ile Thr
    210                 215                 220

Lys Trp Leu Ser Ile Asn Lys Lys Cys Pro Val Cys Asn Thr Glu Val
225                 230                 235                 240

Phe Gly Glu Glu Ser Thr His
                245

<210> SEQ ID NO 85
```

<211> LENGTH: 247
<212> TYPE: PRT
<213> ORGANISM: Vitis vinifera

<400> SEQUENCE: 85

Met Asn Gly Asn Arg Gln Met Glu Val His Tyr Ile Asn Thr Gly Phe
1               5                   10                  15

Pro Tyr Thr Ile Thr Glu Ser Phe Met Asp Phe Phe Glu Gly Leu Gly
            20                  25                  30

His Val Pro Val Asn Tyr Ala Gln Ala Glu Ala Met His Asn Gln Ser
        35                  40                  45

Ile Gln Glu Asn Phe Tyr Trp Thr Met Asn Met Asn Ser Tyr Lys Phe
50                  55                  60

Gly Phe Ser Gly Pro Gly Ser Thr Tyr Tyr Gly Pro Tyr Asp Val Asn
65                  70                  75                  80

Glu His Val Pro Gly Ile Glu Val Ser Arg Arg Pro Trp Glu Tyr Pro
                85                  90                  95

Ser Ser Met Ile Val Glu Glu Pro Thr Thr Ile Glu Thr Gln Pro Thr
            100                 105                 110

Gly Asn Glu Val Met Asn Val His Ala Ile Pro Glu Glu Cys Ser Pro
        115                 120                 125

Asn His Tyr Ser Ala Thr Ser Ser Gln Ala Ile Trp Gln Asp Asn Val
130                 135                 140

Asp Pro Asp Asn Met Thr Tyr Glu Glu Leu Leu Asp Leu Gly Glu Ala
145                 150                 155                 160

Val Gly Thr Gln Ser Arg Gly Leu Ser Gln Glu His Ile Asn Leu Leu
                165                 170                 175

Pro Thr Cys Arg Tyr Lys Ser Gly Arg Leu Phe Ser Arg Lys Arg Ser
            180                 185                 190

Ala Glu Arg Cys Val Ile Cys Gln Met Gly Tyr Lys Arg Gly Asp Arg
        195                 200                 205

Gln Ile Lys Leu Pro Cys Lys His Val Tyr His Thr Asp Cys Gly Thr
210                 215                 220

Lys Trp Leu Thr Ile Asn Lys Val Cys Pro Val Cys Asn Ile Glu Val
225                 230                 235                 240

Phe Gly Glu Glu Ser Arg His
                245

<210> SEQ ID NO 86
<211> LENGTH: 242
<212> TYPE: PRT
<213> ORGANISM: Theobroma cacao

<400> SEQUENCE: 86

Met Asn Gly Asn Arg Gln Met Glu Val His Tyr Ile Asp Thr Gly Phe
1               5                   10                  15

Pro Tyr Thr Ala Thr Glu Ser Phe Met Asp Phe Phe Glu Gly Leu Thr
            20                  25                  30

His Val Pro Val Asn Tyr Thr His Thr Val Pro Met Gln Asp Gln Glu
        35                  40                  45

Asn Ile Tyr Trp Ser Met Ser Met Asn Ala Tyr Lys Phe Gly Phe Ser
50                  55                  60

Gly Pro Glu Ser Thr Phe Tyr Ser Pro Tyr Glu Val Ser Asp His Leu
65                  70                  75                  80

Pro Arg Met Asp Val Ser Arg Arg Thr Trp Asp Tyr Pro Ser Thr Leu
                85                  90                  95

```
Asn Ser Glu Glu Pro Ala Thr Ile Asp Met Gln Pro Gly Gly Glu Ala
            100                 105                 110

Val Val Gly Ile His Ala Ile Pro Glu Glu Cys Ile Thr Asn His Gln
            115                 120                 125

Ser Asn Ser Asn Ser Gln Val Val Trp Gln Asp Asn Ile Asp Pro Asp
            130                 135                 140

Asn Met Thr Tyr Glu Glu Leu Leu Asp Leu Gly Glu Thr Ile Gly Ser
145                 150                 155                 160

Gln Ser Arg Gly Leu Ser Gln Glu Leu Ile Asp Leu Pro Thr Ser
                165                 170                 175

Lys Cys Lys Phe Gly Ser Phe Phe Ser Thr Lys Arg Glu Arg Cys Val
                180                 185                 190

Ile Cys Gln Met Arg Tyr Lys Arg Gly Glu Gln Gln Met Lys Leu Pro
            195                 200                 205

Cys Lys His Val Tyr His Ser Gln Cys Ile Thr Lys Trp Leu Ser Ile
            210                 215                 220

Asn Lys Ile Cys Pro Val Cys Asn Asn Glu Val Phe Gly Glu Glu Ser
225                 230                 235                 240

Arg His

<210> SEQ ID NO 87
<211> LENGTH: 245
<212> TYPE: PRT
<213> ORGANISM: Prunus persica

<400> SEQUENCE: 87

Met Asn Gly Asn Gly Gln Met Asp Val His Tyr Ile Asp Thr Asp Phe
1               5                   10                  15

Pro Tyr Thr Pro Thr Glu Ser Phe Met Asp Phe Phe Gly Gly Val Thr
                20                  25                  30

His Val Pro Met Asn Tyr Gly His Ala Met Pro Met His Asp Gln Glu
            35                  40                  45

Thr Ala Tyr Trp Ser Met Asn Met His Ser Tyr Lys Phe Gly Pro Ser
50                  55                  60

Gly Pro Gly Ser Asn Ser Tyr Tyr Gly Asn Tyr Tyr Glu Val Asn Asp
65                  70                  75                  80

His Leu Pro Arg Met Asp Val Ser Arg Arg Thr Trp Glu His Pro Ser
                85                  90                  95

Val Met Asn Ser Glu Glu Pro Ala Asn Ile Asp Ser His Pro Glu Glu
            100                 105                 110

Glu Asp Ala Val Ala Glu Ala Ala Pro Glu Glu Cys Ile Gln Asn Gln
            115                 120                 125

Gln Asn Thr Asn Thr Ser Gln Val Val Trp Gln Glu Asp Ile Asp Pro
            130                 135                 140

Asp Asn Met Thr Tyr Glu Glu Leu Leu Asp Leu Gly Glu Ala Val Gly
145                 150                 155                 160

Thr Gln Ser Arg Gly Leu Ser Asp Glu Leu Ile Ser Leu Leu Pro Thr
                165                 170                 175

Ser Lys Tyr Lys Cys Gly Ser Phe Phe Ser Arg Lys Ser Gly Glu
                180                 185                 190

Arg Cys Val Ile Cys Gln Met Arg Tyr Lys Arg Gly Asp Arg Gln Ile
            195                 200                 205

Asn Leu Pro Cys Lys His Val Tyr His Ser Glu Cys Ile Ser Lys Trp
            210                 215                 220
```

```
Leu Gly Ile Asn Lys Val Cys Pro Val Cys Asn Leu Glu Val Ser Gly
225                 230                 235                 240

Glu Glu Ser Arg His
            245
```

<210> SEQ ID NO 88
<211> LENGTH: 243
<212> TYPE: PRT
<213> ORGANISM: Capsella rubella

<400> SEQUENCE: 88

```
Met Asn Gly Asp Arg Pro Val Glu Asp Ala His Tyr Thr Ala Glu
1               5                   10                  15

Phe Pro Tyr Ala Ala Ser Gly Ser Tyr Ile Asp Phe Tyr Gly Gly Ala
                20                  25                  30

Pro Gln Gly Pro Leu Asn Tyr Ala His Ala Gly Thr Met Asp Asn Leu
            35                  40                  45

Tyr Trp Thr Met Asn Thr Asn Ala Tyr Lys Phe Gly Phe Ser Gly Ser
    50                  55                  60

Asp Asn Pro Ser Phe Tyr Asn Ser Tyr Asp Met Thr Asp His Leu Ser
65                  70                  75                  80

Arg Met Ser Ile Gly Arg Thr Asn Trp Glu Tyr His Pro Met Val Asn
                85                  90                  95

Val Asp Asp Pro Asp Ile Thr Leu Ala Arg Ser Val Gln Ile Gly Asp
            100                 105                 110

Ser Asp Glu His Ser Glu Ala Glu Asp Cys Ile Ala Asn Glu His Asp
            115                 120                 125

Pro Asp Ser Pro Gln Val Ser Trp Gln Asp Asp Ile Asp Pro Asp Thr
            130                 135                 140

Met Thr Tyr Glu Glu Leu Val Glu Leu Gly Glu Ala Val Gly Thr Glu
145                 150                 155                 160

Ser Arg Gly Leu Ser Gln Glu Leu Ile Glu Thr Leu Pro Thr Arg Lys
                165                 170                 175

Phe Lys Phe Gly Ser Ile Phe Ser Arg Lys Arg Ala Gly Glu Arg Cys
            180                 185                 190

Val Ile Cys Gln Leu Lys Tyr Lys Ile Gly Glu Arg Gln Met Asn Leu
        195                 200                 205

Pro Cys Lys His Val Tyr His Ser Glu Cys Ile Ser Lys Trp Leu Ser
    210                 215                 220

Ile Asn Lys Val Cys Pro Val Cys Asn Thr Glu Val Phe Gly Asp Pro
225                 230                 235                 240

Ser Ile His
```

<210> SEQ ID NO 89
<211> LENGTH: 248
<212> TYPE: PRT
<213> ORGANISM: Arabidopsis thaliana

<400> SEQUENCE: 89

```
Met Asn Gly Asp Asn Arg Pro Val Glu Asp Ala His Tyr Thr Glu Thr
1               5                   10                  15

Gly Phe Pro Tyr Ala Ala Thr Gly Ser Tyr Met Asp Phe Tyr Gly Gly
                20                  25                  30

Ala Ala Gln Gly Pro Leu Asn Tyr Asp His Ala Ala Thr Met His Pro
            35                  40                  45
```

```
Gln Asp Asn Leu Tyr Trp Thr Met Asn Thr Asn Ala Tyr Lys Phe Gly
     50                  55                  60

Phe Ser Gly Ser Asp Asn Ala Ser Phe Tyr Gly Ser Tyr Asp Met Asn
65                  70                  75                  80

Asp His Leu Ser Arg Met Ser Ile Gly Arg Thr Asn Trp Asp Tyr His
                 85                  90                  95

Pro Met Val Asn Val Ala Asp Asp Pro Glu Asn Thr Val Ala Arg Ser
            100                 105                 110

Val Gln Ile Gly Asp Thr Asp Glu His Ser Glu Ala Glu Glu Cys Ile
            115                 120                 125

Ala Asn Glu His Asp Pro Asp Ser Pro Gln Val Ser Trp Gln Asp Asp
130                 135                 140

Ile Asp Pro Asp Thr Met Thr Tyr Glu Glu Leu Val Glu Leu Gly Glu
145                 150                 155                 160

Ala Val Gly Thr Glu Ser Arg Gly Leu Ser Gln Glu Leu Ile Glu Thr
                165                 170                 175

Leu Pro Thr Lys Lys Tyr Lys Phe Gly Ser Ile Phe Ser Arg Lys Arg
            180                 185                 190

Ala Gly Glu Arg Cys Val Ile Cys Gln Leu Lys Tyr Lys Ile Gly Glu
            195                 200                 205

Arg Gln Met Asn Leu Pro Cys Lys His Val Tyr His Ser Glu Cys Ile
    210                 215                 220

Ser Lys Trp Leu Ser Ile Asn Lys Val Cys Pro Val Cys Asn Ser Glu
225                 230                 235                 240

Val Phe Gly Glu Pro Ser Ile His
                245

<210> SEQ ID NO 90
<211> LENGTH: 243
<212> TYPE: PRT
<213> ORGANISM: Solanum lycopersicum

<400> SEQUENCE: 90

Met Ser Gly Asp Gln His Met Glu Ala Met His Tyr Met Asn Met Gly
1               5                   10                  15

Phe Pro Tyr Asn Val Pro Glu Ser Phe Pro Gly Phe Leu Asp Gly Val
            20                  25                  30

Ser Gln Ala Pro Ile Ile Gln Tyr His Asn Asn Pro Val Gln Ile Gln
        35                  40                  45

Asp Gln Glu Asn Ala Tyr Trp Ser Met Asn Met Ser Tyr Tyr Lys Tyr
    50                  55                  60

Glu His Ser Asn Leu Glu Ser Thr Ser Tyr His Ser Tyr Glu Thr Gly
65                  70                  75                  80

Asn Asn His Val Ser Arg Pro Asp Phe Ser Glu Arg Pro Trp Glu Tyr
                85                  90                  95

Ala Val Pro Met Asn Val His Glu Gly Val Ser Thr Asp Val Ile Tyr
            100                 105                 110

Glu Glu Asn Thr Val Pro Val Glu Asp Val Gly Thr Glu Glu Cys Val
            115                 120                 125

Leu Ser Asn Gln Asp Asp Ser Asn His Gln Asp Ile Leu Glu Asp Glu
        130                 135                 140

Ile Asp Leu Asp Asn Met Thr Tyr Glu Glu Leu Leu Asp Leu Gly Glu
145                 150                 155                 160

Thr Val Gly Thr Glu Ser Arg Gly Leu Ala Glu Glu Leu Ile Asn Leu
                165                 170                 175
```

```
Leu Pro Thr Thr Lys Tyr Lys Ser Asn Gly Ile Phe Ser Arg Lys Lys
            180                 185                 190

Ser Glu Glu Arg Cys Val Ile Cys Gln Met Arg Tyr Lys Arg Gly Asp
        195                 200                 205

Arg Gln Ile Asn Phe Pro Cys Lys His Ile Tyr His Thr Glu Cys Gly
        210                 215                 220

Ser Lys Trp Leu Ser Ile Asn Lys Arg Cys Ser Leu Met Asn Glu Val
225                 230                 235                 240

Val Gln Trp

<210> SEQ ID NO 91
<211> LENGTH: 10
<212> TYPE: PRT
<213> ORGANISM: Artificial sequence
<220> FEATURE:
<223> OTHER INFORMATION: Synthetic sequence: LIM domain
<220> FEATURE:
<221> NAME/KEY: VARIANT
<222> LOCATION: (2)..(3)
<223> OTHER INFORMATION: Xaa is any amino acid
<220> FEATURE:
<221> NAME/KEY: VARIANT
<222> LOCATION: (5)..(6)
<223> OTHER INFORMATION: Xaa is any amino acid
<220> FEATURE:
<221> NAME/KEY: VARIANT
<222> LOCATION: (8)..(9)
<223> OTHER INFORMATION: Xaa is any amino acid

<400> SEQUENCE: 91

His Xaa Xaa Cys Xaa Xaa Cys Xaa Xaa Cys
1               5                   10
```